United States Patent
Haabeth et al.

(10) Patent No.: US 12,102,675 B2
(45) Date of Patent: *Oct. 1, 2024

(54) MRNA THERAPEUTIC COMPOSITIONS

(71) Applicant: Nutcracker Therapeutics, Inc., Emeryville, CA (US)

(72) Inventors: Ole Haabeth, Emeryville, CA (US); Gunasekaran Kannan, Emeryville, CA (US)

(73) Assignee: Nutcracker Therapeutics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/605,049

(22) Filed: Mar. 14, 2024

(65) Prior Publication Data
US 2024/0277827 A1 Aug. 22, 2024

Related U.S. Application Data

(63) Continuation of application No. 18/505,881, filed on Nov. 9, 2023, now Pat. No. 12,011,478, which is a continuation of application No. PCT/US2023/076531, filed on Oct. 11, 2023.

(60) Provisional application No. 63/495,412, filed on Apr. 11, 2023, provisional application No. 63/444,195, filed on Feb. 8, 2023, provisional application No. 63/442,566, filed on Feb. 1, 2023, provisional application No. 63/434,219, filed on Dec. 21, 2022, provisional application No. 63/416,241, filed on Oct. 14, 2022.

(51) Int. Cl.
| | | |
|---|---|---|
| *A61K 39/12* | (2006.01) | |
| *A61K 9/50* | (2006.01) | |
| *A61K 39/39* | (2006.01) | |
| *A61P 31/20* | (2006.01) | |

(52) U.S. Cl.
CPC ............ *A61K 39/12* (2013.01); *A61K 9/5052* (2013.01); *A61K 39/39* (2013.01); *A61P 31/20* (2018.01)

(58) Field of Classification Search
None
See application file for complete search history.

(56) References Cited

PUBLICATIONS

Kanodia et al. "Expression of LIGHT/TNFSF14 combined with vaccination against human papillomavirus Type 16 E7 induces significant tumor regression", Cancer Res. May 15, 2010;70(10):3955-64 (Year: 2010).*
Da Silva, R.L., da Silva Batista, Z., Bastos, G.R. et al. Role of HPV 16 variants among cervical carcinoma samples from Northeastern Brazil. BMC Womens Health 20, 162 (2020).
Tao, L., Han, L., Li, X. et al. Prevalence and risk factors for cervical neoplasia: a cervical cancer screening program in Beijing. BMC Public Health 14, 1185 (2014).
Marielle Kocken , Theo J M Helmerhorst, Johannes Berkhof, Jacqueline A Louwers, Marielle A E Nobbenhuis, Aagje G Bais, Cornelis J A Hogewoning, Afra Zaal, Rene H M Verheijen, Peter J F Snijders, Chris J L M Meijer. Lancet Oncol May 2011;12(5):441-50.
Feltkamp MC, Smits HL, Vierboom MP, et al. Vaccination with cytotoxic T lymphocyte epitope-containing peptide protects against a tumor induced by human papillomavirus type 16-transformed cells. Eur J Immunol 1993;23:2242-9.
Arbyn M, Weiderpass E, Bruni L, et al. Estimates of incidence and mortality of cervical cancer in 2018: a worldwide analysis. Lancet Glob Health 2020; 8: e191-203.
Bjorge T, Skare GB, Bjorge L, et al. Adverse pregnancy outcomes after treatment for cervical intraepithelial neoplasia. Obstet Gynecol. 2016; 128(6):1265-1273.
Centers for Disease Control and Prevention (CDC). Estimated No. of cases of high-grade cervical lesions diagnosed among women—United States, 2008 and 2016. MMWR Morb Mortal Wkly Rep. 2019; 68(15):337-343.
Keytruda® (pembrolizumab) prescribing information. Aug. 2022. https://dailymed.nlm.nih.gov/dailymed/drugInfo.cfmsetid=9333c79b-d487-4538-a9f0-71b91a02b287.
Loopik DL, IntHout J, Ebisch RMF, et al. The risk of cervical cancer after cervical intraepithelial neoplasia grade 3: A population-based cohort study with 80,442 women. Gynecol Oncol. 2020;157(1):195-201.
Mirabello L., Clarke M. A., Nelson C. W., et al. The intersection of HPV epidemiology, genomics and mechanistic studies of HPV-mediated carcinogenesis. Viruses. 2018;10(2).
Moscicki AB, Schiffman M, Kjaer S, et al. Chapter 5: Updating the natural history of HPV and anogenital cancer. Vaccine. 2006;24 Suppl 3:S3/42-S3/51.
Narisawa-Saito M, Kiyono T. Basic mechanisms of high-risk human papillomavirus-induced carcinogenesis: roles of E6 and E7 proteins. Cancer Sci. 2007;98(10):1505-1511.
National Comprehensive Cancer Network (NCCN) Clinical Practice Guidelines in Oncology (NCCN Guidelines®). Cervical Cancer. Version 1. 2022.
Noehr B, Jensen A, Frederiksen K, Tabor A, Kjaer SK. Loop electrosurgical excision of the cervix and subsequent risk for spontaneous preterm delivery: a population-based study of singleton deliveries during a 9-year period. Am J Obstet Gynecol. 2009;201(1):33.e1-33.e336.
Pan XQ. The mechanism of the anticancer function of M1 macrophages and their use in the clinic. Chin J Cancer. 2012;31(12):557-563.
Smith JS, Lindsay L, Hoots B, et al. Human papillomavirus type distribution in invasive cervical cancer and high-grade cervical lesions: a meta-analysis update. Int J Cancer. 2007;121(3):621-632.
Spanos WC, Hoover A, Harris GF, et al. The PDZ binding motif of human papillomavirus type 16 E6 induces PTPN13 loss, which allows anchorage-independent growth and synergizes with RAS for invasive growth. J Virol. 2008;82(5):2493-2500.

(Continued)

*Primary Examiner* — Amy E Juedes
*Assistant Examiner* — Peter Johansen
(74) *Attorney, Agent, or Firm* — McAndrews, Held & Malloy, Ltd.

(57) ABSTRACT

The present disclosed and described technology are directed to multimodal mRNA-based immunotherapies that deliver both antigens and immunomodulators. Related formulations, method of administration, and kits are disclosed and described.

17 Claims, 40 Drawing Sheets
Specification includes a Sequence Listing.

(56) References Cited

PUBLICATIONS

Walboomers JM, Jacobs MV, Manos MM, et al. Human papillomavirus is a necessary cause of invasive cervical cancer worldwide. J Pathol. 1999;189(1):12-19.

Wieking BG, Vermeer DW, Spanos WC, et al. A non-oncogenic HPV 16 E6/E7 vaccine enhances treatment of HPV expressing tumors. Cancer Gene Ther. 2012;19(10):667-674.

Young N. The effect of loop electrosurgical excision procedure on the subsequent risk of preterm delivery. [scholarly project]. Toledo, OH: The University of Toledo; 2010.

\* cited by examiner

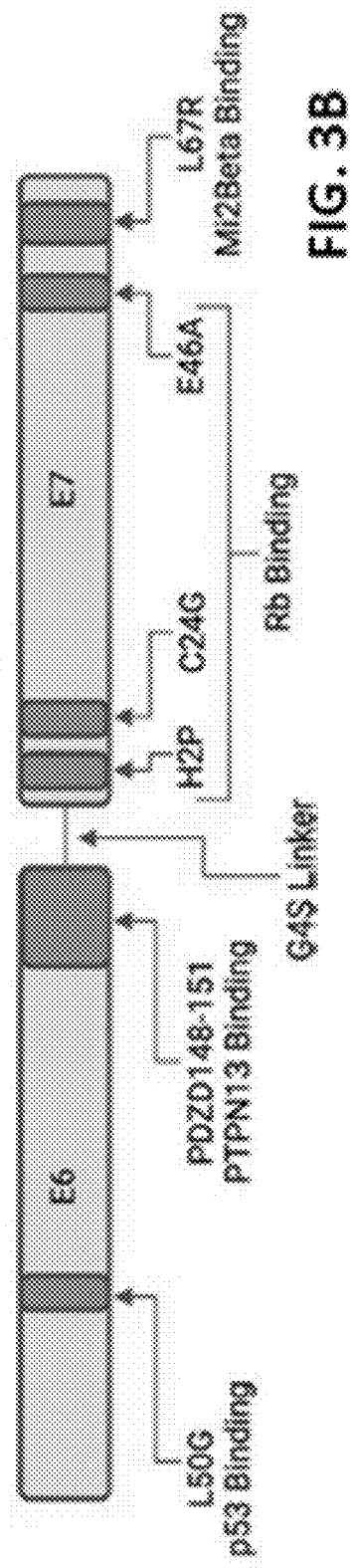
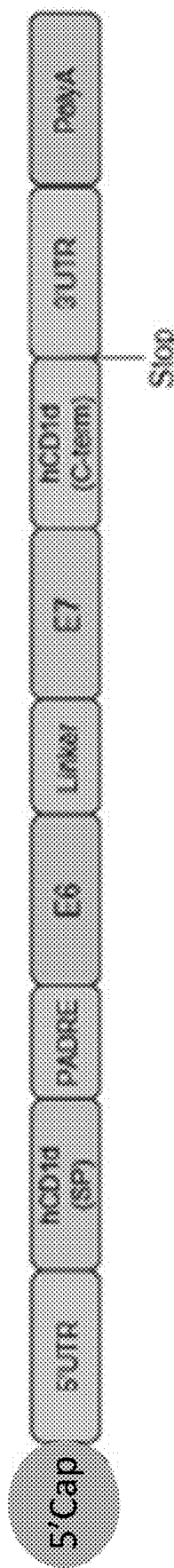

SEQUENCE LISTING

```
Sequence total quantity: 54
SEQ ID NO: 1            moltype = AA  length = 240
FEATURE                 Location/Qualifiers
source                  1..240
                        mol_type = protein
                        note = Human Wild Type LIGHT (786) aa
                        organism = synthetic construct
SEQUENCE: 1
MEESVVRPSV FVVDGQTDIP FTRLGRSHRR QSCSVARVGL GLLLLLMGAG LAVQGWFLLQ    60
LHWRLGEMVT RLPDGPAGSW EQLIQERRSH EVNPAAHLTG ANSSLTGSGG PLLWETQLGL   120
AFLRGLSYHD GALVVTKAGY YYIYSKVQLG GVGCPLGLAS TITHGLYKRT PRYPEELELL   180
VSQQSPCGRA TSSSRVWWDS SFLGGVVHLE AGEEVVVRVL DERLVRLRDG TRSYFGAFMV   240

SEQ ID NO: 2            moltype = RNA  length = 723
FEATURE                 Location/Qualifiers
source                  1..723
                        mol_type = other RNA
                        note = Wild Type 786 nt
                        organism = synthetic construct
SEQUENCE: 2
atggaggaga gtgtcgtacg gccctcagtg tttgtggtgg atggacagac cgacatccca    60
ttcacgaggc tgggacgaag ccaccggaga cagtcgtgca gtgtggcccg ggtgggtctg   120
ggactgttgc tgtttgctgat gggggctggg ctggccgtcc aaggctggtt cctcctgcag   180
ctgcactggc gtctaggaga gatggtcacc cgcctgcctg acggacctgc aggctcctgg   240
gagcagctga tacaagagcg aagaagccac gaggtcaacc cagcagcgca tctcacaggg   300
gccaactcca gcttgaccgg cagcgggggg ccgctgttat gggagactca gctgggcctg   360
gccttcctga ggggcctcag ctaccacgat gggggccttg tggtcaccaa agctggctac   420
tactacatct actccaaggt gcagctgggc ggtgtgggct gcccgctggg cctggccagc   480
accatcaccc acggcctcta caagcgcaca ccccgctacc ccgaggagct ggagctgttg   540
gtcagccagc agtcacctg cggacgggcc accagcagct cccgggtctg gtgggacagc   600
agcttcctgg gtggtgtggt acacctggag gctggggagg aggtggtcgt ccgtgtgctg   660
gatgaacgcc tggttcgact gcgtgatggt acccggtctt acttcggggc tttcatggtg   720
tga                                                                  723

SEQ ID NO: 3            moltype = AA  length = 238
FEATURE                 Location/Qualifiers
```

```
source                   1..238
                         mol_type = protein
                         note = LIGHT ICD TM 1-75 PDG Gly4Ser LIGHT 83-240 1352 aa
                         organism = synthetic construct
SEQUENCE: 3
MEESVVRPSV FVVDGQTDIP FTRLGRSHRR QSCSVARVGL GLLLLLMGAG LAVQGWFLLQ   60
LHWRLGEMVT RLPDGGGGGS LIQERRSHEV NPAAHLTGAN SSLTGSGGPL LWETQLGLAF  120
LRGLSYHDGA LVVTKAGYYY IYSKVQLGGV GCPLGLASTI THGLYKRTPR YPEELELLVS  180
QQSPCGRATS SSRVWWDSSF LGGVVHLEAG EKVVVRVLDE RLVRLRDGTR SYFGAFMV    238

SEQ ID NO: 4             moltype = RNA   length = 1033
FEATURE                  Location/Qualifiers
source                   1..1033
                         mol_type = other RNA
                         organism = synthetic construct
SEQUENCE: 4
aggcatagaa gtcgagacac agccactaag taagccacca tggaagagtc cgtggtgcgg   60
cctagcgtgt tcgtggtcga cggccagaca gatatcccct tcaccagact gggcagaagc  120
catagaagac agagctgcag cgtggccaga gttggactgg gcctgctgct gctcctgatg  180
ggcgccggac tggccgtgca gggctggttc ctgctgcagc tgcactggcg gctgggagaa  240
atggtcacca gactgcccga cggcggcggc ggcggcagcc tgatccagga gcggcggagc  300
cacgaggtga accctgccgc tcacctgaca ggagccaaca gctctctgac cggcagcggc  360
ggccctctgc tgtgggagac acagctgggc ctggcttttc tgagaggcct gagctaccac  420
gacggagccc tggtggtgac caaggccggc tactactaca tctacagcaa agtgcaactg  480
ggcggcgtgg gatgtcctct gggcctggcc tctacaatca cccacggcct ttataagcgg  540
acccctagat accccgagga actggaactg ctggtgtctc agcagtctcc atgcggcaga  600
gccaccagct cctctagagt gtggtgggac agcagctttc tcggcggagt ggtgcacctg  660
gaagccggcg agaaggtggt ggtcagagtc ctggatgaga gactggtgcg gctgcgcgac  720
ggcaccaggt cttacttcgg cgcttttatg gtgtgataag cgccgcctcc gggacagtgc  780
acccaggctg cggcccctcc cccgtcctgg aggttccaga gcccactta gccttaatg   840
cgccaataaa ccaatgaacg aagcaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa 1020
aaaaaaaaaa aaa                                                    1033

SEQ ID NO: 5             moltype = AA   length = 234
FEATURE                  Location/Qualifiers
source                   1..234
                         mol_type = protein
                         note = LIGHT ICD TM 1-75 PDG Gly4Ser 2  LIGHT 92-240 1353 aa
                         organism = synthetic construct
SEQUENCE: 5
MEESVVRPSV FVVDGQTDIP FTRLGRSHRR QSCSVARVGL GLLLLLMGAG LAVQGWFLLQ   60
LHWRLGEMVT RLPDGGGGGS GGGGSVNPAA HLTGANSSLT GSGGPLLWET QLGLAFLRGL  120
SYHDGALVVT KAGYYYIYSK VQLGGVGCPL GLASTITHGL YKRTPRYPEE LELLVSQQSP  180
CGRATSSSRV WWDSSFLGGV VHLEAGEKVV VRVLDERLVR LRDGTRSYFG AFMV        234

SEQ ID NO: 6             moltype = RNA   length = 1021
FEATURE                  Location/Qualifiers
source                   1..1021
                         mol_type = other RNA
                         note = LIGHT ICD TM 1-75 PDG Gly4Ser 2 LIGHT 92-240 1353 nt
                         organism = synthetic construct
SEQUENCE: 6
aggcatagaa gtcgagacac agccactaag taagccacca tggaagagag cgtggtgcgg   60
cctagcgttt tcgtggttga cggccagacc gacatccgat tcaccagact gggcagaagc  120
cacagaaggc agagctgcag cgtggccaga gtgggcctgg gactgctgct gctgctgatg  180
ggcgctggcc tcgccgtgca gggatggttc ctgttgcagc tgcattggag acttggggag  240
atggtcacac ggctgcctga tggcggcggc ggaggcagcg gaggaggcgg atctgtgaac  300
cccgccgccc acctgacagg cgctaacagc agcctgaccg gcagcggcgg tcctctgctg  360
tgggagacac agctgggcct ggcctttctg agaggcctga gctaccacga cggcgccctg  420
gtggtgacca aggccggcta ctactacatc tacagcaagg tgcaactggg cggcgtgggc  480
tgccccctgg gcctggcctc aacaatcacc cacggcctgt acaagcggac ccctagatac  540
cccgaggaac tggaactgct ggtgtcccag cagtctcctt gtggcagagc caccagcagc  600
tctagagtgt ggtgggacag ctccttcctg ggaggagtgg tgcacctgga agccggcgag  660
aaagtggtgg tgcgggtgct ggacgagcgg ctggtccgcc tcagagatgg caccagatct  720
tatttcggcg cttttatggt gtgataagcc cgcctccga cagtgcacca ccaggctgcg  780
gcccctcccc cgtcctggag gttcccagc cccacttacc gcttaatgcg ccaataaacc  840
aatgaacgaa gcaaaaaaaa aaaaaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa 1020
a                                                                 1021

SEQ ID NO: 7             moltype = AA   length = 234
FEATURE                  Location/Qualifiers
source                   1..234
                         mol_type = protein
```

```
                        note = LIGHT ICD   TM 1-66 RLG Gly4Ser 2   LIGHT 83-240 1354
                          aa
                        organism = synthetic construct
SEQUENCE: 7
MEESVVRPSV FVVDGQTDIP FTRLGRSHRR QSCSVARVGL GLLLLLMGAG LAVQGWFLLQ   60
LHWRLGGGGG SGGGGSLIQE RRSHEVNPAA HLTGANSSLT GSGGPLLWET QLGLAFLRGL  120
SYHDGALVVT KAGYYYIYSK VQLGGVGCPL GLASTITHGL YKRTPRYPEE LELLVSQQSP  180
CGRATSSSRV WWDSSFLGGV VHLEAGEKVV VRVLDERLVR LRDGTRSYFG AFMV        234

SEQ ID NO: 8            moltype = RNA   length = 1021
FEATURE                 Location/Qualifiers
source                  1..1021
                        mol_type = other RNA
                        note = LIGHT ICD   TM 1-66 RLG Gly4Ser 2   LIGHT 83-240 1354
                          nt
                        organism = synthetic construct
SEQUENCE: 8
aggcatagaa gtcgagacac agccactaag taagccacca tggaagagag cgtggtgcgg    60
ccttctgtct tcgtggtcga cggccagacc gatatcccct tcacaagact gggcagaagc   120
catagacgcc agagctgcag cgtggcccgg tgggcctgg gacttctgct gctgctgatg    180
ggagctggcc tggccgtgca gggctggttt ctgctccagc tgcactggcg gctgggagga   240
ggcggcggct ctggcggcgg aggaagcctg atccaggagc ggagatccca cgaggtgaac   300
cctgccgcca acctgaccgg cgccaacagc tccctgacag gcagcggcgg ccctctgctg   360
tgggagacac agctgggcct ggccttcctg cggggcctga gctaccacga cggcgctctg   420
gtcgtgacca aggccggata ctactacatc tacagcaagg tgcaactcgg cggcgtgggc   480
tgcccctgg gcctggcttc taccatcacc acggcgctgt acaaaagaac ccctagatac    540
cctgaggaac tggaactgct ggtgtcccag cagagcccat gtggcagagc caccagctct   600
agcagagtgt ggtgggacag cagcttcctg gcggagtgg tgcacctgga agccggcgag    660
aaggtggtgg ttagagtgct ggacgagaga ctggtgcggc tgagagatgg tacaaggtct   720
tatttcggcg cctttatggt gtgataagcc ccgcctccgg gacagtgcac ccaggctgcg   780
gcccctcccc cgtcctggag gttcccagc cccacttacc gcttaatgcg ccaataaacc    840
aatgaacgaa gcaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
a                                                                   1021

SEQ ID NO: 9            moltype = AA   length = 230
FEATURE                 Location/Qualifiers
source                  1..230
                        mol_type = protein
                        note = LIGHT ICD   TM 1-66 RLG Gly4Ser 3   LIGHT 92-240 1355 aa
                        organism = synthetic construct
SEQUENCE: 9
MEESVVRPSV FVVDGQTDIP FTRLGRSHRR QSCSVARVGL GLLLLLMGAG LAVQGWFLLQ   60
LHWRLGGGGG SGGGGSGGGG SVNPAAHLTG ANSSLTGSGG PLLWETQLGL AFLRGLSYHD  120
GALVVTKAGY YYIYSKVQLG GVGCPLGLAS TITHGLYKRT PRYPEELELL VSQQSPCGRA  180
TSSSRVWWDS SFLGGVVHLE AGEKVVVRVL DERLVRLRDG TRSYFGAFMV             230

SEQ ID NO: 10           moltype = RNA   length = 1009
FEATURE                 Location/Qualifiers
source                  1..1009
                        mol_type = other RNA
                        note = LIGHT ICD   TM 1-66 RLG Gly4Ser 3   LIGHT 92-240 1355
                          nt
                        organism = synthetic construct
SEQUENCE: 10
aggcatagaa gtcgagacac agccactaag taagccacca tggaagagag cgtggtgcgg    60
cctagcgtgt tcgtggtgga cggccagaca gatatcccct tcaccagact gggcagaagc   120
cacagaagac agagctgcag cgtggccaga gtgggactgg gcctgctgct gctgctgatg   180
ggcgccggac tggccgtgca aggctggttc ctgctccagc tgcactggcg gctgggcggc   240
ggcggcggat ctggcggagg cggctctggc ggcggcggct ccgtgaaccc cgccgctcat   300
ctgacaggcg ccaacagcag cctgacaggc agcggaggtc ctctgctgtg gaaacccag   360
ctgggcctgg ctttttctgag aggcttgtct taccacgacg gcgctctggt cgtgaccaag   420
gccggctact actatatcta cagcaaggtg cagctggatg gctgtgggaa                480
ctggccagca ccatcaccca cggcctgtac aagcggaccc ctagatacc tgaggaactg    540
gaactgctgt tgtcccagca gagccccatg ggcagagcca aagcagctc tagagtctgg   600
tgggattcta gcttcctggg cggcgtggtg cacctggagg ccggcgagaa agtggtcgtg   660
cgcgtgctgg acgagagact ggtgaggctg cgggacggga cccggtccta cttcggcgcc   720
tttatggtgt gataagcgcc gcctccggga cagtgcacc cctccccg                780
tcctggaggt tccccagccc cacttaccgc ttaatgcgcc aataaaccaa tgaacgaagc   840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaa                          1009

SEQ ID NO: 11           moltype = AA   length = 225
FEATURE                 Location/Qualifiers
source                  1..225
                        mol_type = protein
                        note = LIGHT ICD   TM 1-66 RLG Gly4Ser 2   LIGHT 92-240 1356
```

```
                        aa
                        organism = synthetic construct
SEQUENCE: 11
MEESVVRPSV  FVVDGQTDIP  FTRLGRSHRR  QSCSVARVGL  GLLLLLMGAG  LAVQGWFLLQ   60
LHWRLGGGGG  SGGGGSVNPA  AHLTGANSSL  TGSGGPLLWE  TQLGLAFLRG  LSYHDGALVV  120
TKAGYYYIYS  KVQLGGVGCP  LGLASTITHG  LYKRTPRYPE  ELELLVSQQS  PCGRATSSSR  180
VWWDSSFLGG  VVHLEAGEKV  VVRVLDERLV  RLRDGTRSYF  GAFMV                   225

SEQ ID NO: 12           moltype = RNA  length = 994
FEATURE                 Location/Qualifiers
source                  1..994
                        mol_type = other RNA
                        note = LIGHT ICD TM 1-66 RLG Gly4Ser 2  LIGHT 92-240 1356 nt
                        organism = synthetic construct
SEQUENCE: 12
aggcatagaa gtcgagacac agccactaag taagccacca tggaagagtc tgtggtcaga    60
cctagcgtgt tcgtggtcga cggccagacc gacatcccct tcaccagact gggaagaagc   120
catagaagac agagctgcag cgtggccaga gtgggcctgg gcctgctgct gctgctgatg   180
ggcgctggcc tggccgtgca aggctggttc ctgctgcagc tgcactggcg gctgggcgga   240
ggcggcggct ctggcggcgg aggctccgtg aaccccgccg ccacctgac cggcgccaac    300
agcagcctga caggcagcgg cggtcctctg ctgtgggaaa cccagctggg actggctttt   360
ctgagaggcc tgagctacca cgacggcgcc ctggtggtga ccaaggccgg ctattactac   420
atctacagca aggtgcagct gggcggcgtt ggatgtcctc tgggcctggc ttctacaatc   480
acccacggcc tgtacaagcg gacccctaga tacccgtagg aactggagct gctggtgtcc   540
cagcagtccc catgcggccg gccacaagc tcttctagag tgtggtggga tagcagcttc    600
ctgggcggag tggtgcacct cgaggccgga gagaaagtgg tggtgcgggt gctggatgag   660
agactggtta ggctgcgcga cggcacacgg agctacttcg gcgcctttat ggtgtgataa   720
gcgccgcctc cgggacagtg cacccaggct gcggcccctc cccgtcctg gaggttcccc     780
agccccactt accgcttaat gcgccaataa accaatgaac gaagcaaaaa aaaaaaaaaa   840
aaaaaaaaaa aaaaaaaaaa aaaaaaaaaa aaaaaaaaaa aaaaaaaaaa aaaaaaaaaa   900
aaaaaaaaaa aaaaaaaaaa aaaaaaaaaa aaaaaaaaaa aaaaaaaaaa aaaaaaaaaa   960
aaaaaaaaaa aaaaaaaaaa aaaaaaaaaa aaaa                                994

SEQ ID NO: 13           moltype = AA  length = 238
FEATURE                 Location/Qualifiers
source                  1..238
                        mol_type = protein
                        note = LIGHT ICD TM 1-75 PDG SSAST  LIGHT 83-240 1357 aa
                        organism = synthetic construct
SEQUENCE: 13
MEESVVRPSV  FVVDGQTDIP  FTRLGRSHRR  QSCSVARVGL  GLLLLLMGAG  LAVQGWFLLQ   60
LHWRLGEMVT  RLPDGSSAST  LIQERRSHEV  NPAAHLTGAN  SSLTGSGGPL  LWETQLGLAF  120
LRGLSYHDGA  LVVTKAGYYY  IYSKVQLGGV  GCPLGLASTI  THGLYKRTPR  YPEELELLVS  180
QQSPCGRATS  SSRVWWDSSF  LGGVVHLEAG  EKVVVRVLDE  RLVRLRDGTR  SYFGAFMV    238

SEQ ID NO: 14           moltype = RNA  length = 1033
FEATURE                 Location/Qualifiers
source                  1..1033
                        mol_type = other RNA
                        note = LIGHT ICD TM 1-75 PDG  SSAST LIGHT 83-240 1357 nt
                        organism = synthetic construct
SEQUENCE: 14
aggcatagaa gtcgagacac agccactaag taagccacca tggaagagag cgtggtgcgc    60
cccagcgtgt tcgtggtcga cggccagacc gacatcccct tcacccggct gggaagaagc   120
catagaaggc agagctgcag cgtggccaga gtcggcctgg gcctgctgct gctgctgatg   180
ggcgctggcc tggccgtgca gggctggttc ctgctccagc tgcactggcg gctgggagaa   240
atggtgacca gactgccaga tggcagctcc gcctctacca tgatccagga gcggagaagc   300
cacgaggtga accccgccgc ccacctgaca ggcgccaaca gcagcctgac cggctccgga   360
ggacctctgc tgtgggagac acagctggga ctggcttttc tgagaggact gagctaccac   420
gacggagccc tggtggttac aaaagccggc tactactaca tctacagcaa ggtgcaactg   480
ggcggcgtgg gctgtcctct gggcctggct tctacaatca cccacggcct gtacaagcgg   540
acccctagat accctgagga actcgagctg ctttgtgtcc agcagagccc ttgcggcgga   600
gccacaagct cttctagagt gtggtgggac agcagctttc tgggaggcgt tgtgcacctg   660
gaagccggcg aaaaggtggt ggtgcgggtg ctggacgaga gactggtgcg gctgagagat   720
ggcaccagat cttatttcgg cgccttcatg gtgtgataag cgccgcctcc gggacagtgc   780
acccaggctg cggcccctcc ccgtcctgga ggttcccca gccccactta ccgcttaatg    840
cgccaataaa ccaatgaacg aagcaaaaaa aaaaaaaaaa aaaaaaaaaa aaaaaaaaaa   900
aaaaaaaaaa aaaaaaaaaa aaaaaaaaaa aaaaaaaaaa aaaaaaaaaa aaaaaaaaaa   960
aaaaaaaaaa aaaaaaaaaa aaaaaaaaaa aaaaaaaaaa aaaaaaaaaa aaaaaaaaaa  1020
aaaaaaaaaa aaa                                                     1033

SEQ ID NO: 15           moltype = AA  length = 234
FEATURE                 Location/Qualifiers
source                  1..234
                        mol_type = protein
                        note = LIGHT ICD TM 1-75 PDG SSASTDKTHT  LIGHT 92-240 1358
                        aa
                        organism = synthetic construct
```

```
SEQUENCE: 15
MEESVVRPSV FVVDGQTDIP FTRLGRSHRR QSCSVARVGL GLLLLLMGAG LAVQGWFLLQ    60
LHWRLGEMVT RLPDGSSAST DKTHTVNPAA HLTGANSSLT GSGGPLLWET QLGLAFLRGL   120
SYHDGALVVT KAGYYYIYSK VQLGGVGCPL GLASTITHGL YKRTPRYPEE LELLVSQQSP   180
CGRATSSSRV WWDSSFLGGV VHLEAGEKVV VRVLDERLVR LRDGTRSYFG AFMV         234

SEQ ID NO: 16           moltype = RNA   length = 1021
FEATURE                 Location/Qualifiers
source                  1..1021
                        mol_type = other RNA
                        note = LIGHT ICD  TM 1-75 PDG + SSASTDKTHT + LIGHT 92-240
                         1358 nt
                        organism = synthetic construct
SEQUENCE: 16
aggcatagaa gtcgagacac agccactaag taagccacca tggaagagag cgtggtgcgg     60
cctagcgtgt tcgtggtgga cggccagacc gacatcccct tcaccagact gggaagatcc    120
cacagaaggc agtcctgcag cgtggccaga gtgggcctgg gctgctgct gctgctgatg     180
ggcgcggcc tcgccgtgca gggctggttc ctgctgcagc tgcactggcg gctgggcgag    240
atggtcacaa gactgcctga tggatcctagc gccagcaccg ataagacaca caccgtgaac  300
cccgccgctc acctgaccgg cgccaacagc agcctgacag gctctggcgg acctctgctg   360
tgggagacac agctgggact ggcctttctg agaggcctga gctatcacga cggcgccctg   420
gtggtgacaa aggccggcta ctactacatc tacagcaagg tgcaactggg cggcgtcgga   480
tgcccctgg gactggcttc taccatcacc cacggcctgt acaagcggac ccctagatac    540
cctgaggaac tggaactgct tgtttcccag cagtctccat gtggcagagc caccagcagc   600
agcagagtgt ggtgggatag ctccttcctg ggtggcgtgg tccatctgga agccggagag   660
aaagtggtgg tgcgcgtgct ggacgagaga ctcgtcggac gacaccggagc             720
tacttcggcg cttttatggt gtgataagcc ccgcctccgg gacagtgcac ccaggctgcg    780
gccccctccc cgtcctggag gttccccagc cccacttacc gcttaatgcg ccaataaacc   840
aatgaacgaa gcaaaaaaaa aaaaaaaaa aaaaaaaaa aaaaaaaaa aaaaaaaaa       900
aaaaaaaaa aaaaaaaaa aaaaaaaaa aaaaaaaaa aaaaaaaaa aaaaaaaaa         960
aaaaaaaaa aaaaaaaaa aaaaaaaaa aaaaaaaaa aaaaaaaaa aaaaaaaaa        1020
a                                                                  1021

SEQ ID NO: 17           moltype = AA   length = 225
FEATURE                 Location/Qualifiers
source                  1..225
                        mol_type = protein
                        note = LIGHT ICD TM 1-66 RLG   SSASTDKTHT   LIGHT 92-240
                         1359, aka 1495 aa
                        organism = synthetic construct
SEQUENCE: 17
MEESVVRPSV FVVDGQTDIP FTRLGRSHRR QSCSVARVGL GLLLLLMGAG LAVQGWFLLQ    60
LHWRLGSSAS TDKTHTVNPA AHLTGANSSL TGSGGPLLWE TQLGLAFLRG LSYHDGALVV   120
TKAGYYYIYS KVQLGGVGCP LGLASTITHG LYKRTPRYPE ELELLVSQQS PCGRATSSSR   180
VWWDSSFLGG VVHLEAGEKV VVRVLDERLV RLRDGTRSYF GAFMV                   225

SEQ ID NO: 18           moltype = RNA   length = 994
FEATURE                 Location/Qualifiers
source                  1..994
                        mol_type = other RNA
                        note = LIGHT ICD TM 1-66 RLG SSASTDKTHT LIGHT 92-240 1359,
                         aka 1495 nt
                        organism = synthetic construct
SEQUENCE: 18
aggcatagaa gtcgagacac agccactaag taagccacca tggaggagag cgtggtgcgg    60
cctagcgtgt tcgtggtcga cggccagacc gacatcccct tcaccagact gggaagaagc   120
cacagaaggc agtcttgctc cgtggccaga gtgggcctgg gctgctcct gctgctgatg    180
ggcgctggcc tggccgtgca aggctggttc ctgctgcagc tgcactggcg gctgggcagc   240
agcgcctcta ccgataagac ccacaccgtg aaccctgccg cccacctgac cggcgccaac   300
agctctctga ccggatctgg cggacctctg ctgtgggaga cacagctggg ccttgctttt   360
ctgcggggcc tgagctacca cgacggcgct ctggtggtta caaggccgg ctactactac   420
atctacagca aggtgcagct gggaggcgtg ggttgtccac tgggactggc cagcacaatc   480
acacacggcc tttataagcg gacccctaga taccccgagg aactggaact gctggtctcc   540
cagcagagcc cttgcggcag agccacaagc agcagcagag tgtggtggga cagctcattc   600
ctgggcggcg tggtgcatct ggaagccggc gagaaagtgg tggtcagagt gctggacgag   660
agactggtgc ggctgagaga tgggacccgc tcctacttcg gcgcctttat ggtgtgataa   720
gcgccgcctc cgggacagtg cacccaggct gcggcccctc ccccgtcctg gaggttccc  780
agccccactt accgcttaat gcgccaataa accaatgaac gaagcaaaaa aaaaaaaaa    840
aaaaaaaaa aaaaaaaaa aaaaaaaaa aaaaaaaaa aaaaaaaaa aaaaaaaaa         900
aaaaaaaaa aaaaaaaaa aaaaaaaaa aaaaaaaaa aaaaaaaaa aaaaaaaaa         960
aaaaaaaaa aaaaaaaaa aaaaaaaaa aaaa                                  994

SEQ ID NO: 19           moltype = DNA   length = 1958
FEATURE                 Location/Qualifiers
source                  1..1958
                        mol_type = other DNA
                        note = Human IL12 Fusion Single chain DNA-683
                        organism = synthetic construct
```

-continued

```
SEQUENCE: 19
aatcataata cgactcacta taaggcatag aagtcgagac acagccacta agtaagccac   60
catgtgccac cagcagctgg tcatcagctg gttcagcctg gtgttcctgg cctctcctct  120
ggtggccatc tgggagctga agaaagacgt gtacgtggtg aactggact ggtatcccga  180
tgctcctggc gagatggtgg tgctgacctg cgatacccct gaagaggacg gcatcaccty  240
gacactggat cagtctagcg aggtgctcgg cagcggcaag accctgacca tccaagtgaa  300
agagtttggc gacgccggcc agtacacctg tcacaaaggc ggagaagtgc tgagccacag  360
cctgctgctg ctccacaaga agaggatggc catttggagc accgacatcc tgaaggacca  420
gaaagagccc aagaacaaga ccttcctgag atgcgaggcc aagaactaca gcggccggtt  480
cacatgttgg tggctgacca ccatcagcac cgacctgacc ttcagcgtga agtccagcag  540
aggcagcagt gatcctcagg gcgttacatg tggcgccgct acactgtctg ccgaaagagt  600
gcggggcgac aacaaagaat acgagtacag cgtggaatgc aagaggaca cgcctgtcc   660
agccgccgaa gagtctctgc ctatcgaagt gatggtggac gccgtgcaca agctgaagta  720
cgagaactac acctccagct ttttcatccg ggacatcatc aagcccgatc ctccaaagaa  780
cctgcagctg aagcctctga agaacagcag acaggtggaa gtgtcctggg agtacccga  840
cacctggtct acaccccaca gctacttcag cctgaccttt tgcgtgcaag tgcagggcaa  900
gtccaagcgc gagaaaaagg accgggtgtt caccgacaag accagcgcca ccgtgatctg  960
cagaaagaac gccagcatca gcgtcagagc ccaggaccgg tactacagca gctcttggag 1020
cgaatgggcc agcgtgccat gttctgtgg cggaggatct ggcggaggtg aagcggcgg  1080
aggcggatct agaaatctgc ctgtggccac tcctgatcct ggcatgttcc cttgtctgca 1140
ccacagccag aacctgctga gagccgtgtc caacatgctg cagaaggcca gacagaccct 1200
ggaattctac ccctgcacca gcgaggaaat cgaccacgag gacatcacca aggataagac 1260
cagcaccgtg gaagcctgcc tgcctctgga actgaccaag aacgagagct gcctgaacag 1320
ccgggaaacc agcttcatca ccaacggctc ttgcctggcc agcagaaaga cctccttcat 1380
gatgccctg tgcctgagca gcatctacga ggacctgaag atgtaccagg tggaattcaa 1440
gaccatgaac gccaagctgc tgatggaccc caagcgacta atcttcctgg accagaatat 1500
gctggccgtg atcgacgagc tgatgcaggc cctgaacttc aacagcgaga cagtgcccca 1560
gaagtctagc ctggaagaac ccgacttcta caagaccaag atcaagctgt gcatcctgct 1620
gcacgccttc cggatcagag ccgtgaccat cgacagagtg atgagctacc tgaacgcctc 1680
ctgagcgccg cctccgggac agtgcaccca ggctgcgcc cctcccccgt cctggaggtt 1740
ccccagcccc acttaccgct taatgcgcca ataaaccaat gaacgaagca aaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaa                                   1958

SEQ ID NO: 20      moltype = RNA  length = 1936
FEATURE            Location/Qualifiers
source             1..1936
                   mol_type = other RNA
                   note = Human IL12 Fusion Single chain RNA-683
                   organism = synthetic construct
SEQUENCE: 20
aggcatagaa gtcgagacac agccactaag taagccacca tgtgccacca gcagctggtc   60
atcagctggt tcagcctggt gttcctggcc tctcctctgg tggccatctg ggagctgaag  120
aaaagacgtg tacgtggtgga actggactgg tatcccgatg ctcctggcga gatggtggtg  180
ctgacctgcg atacccctga gaggacggc atcacctgga cactggatca gtctagcgag  240
gtgctcggca gcggcaagac cctgaccatc aagtgaagt agtttggcga cgccggccag  300
tacacctgtc acaaaggcgg agaagtgctg agccacagcc tgctgctgct ccacaagaaa  360
gaggatggca tttggagcac cgacatcctg aaggaccaga agagcccaa gaacaagacc  420
ttcctgagat gcgaggccaa gaactacagc ggccggttca catgttggtg gctgaccacc  480
atcagcaccg acctgacctt cagcgtgaag tccagcagag gcagcagtga tcctcaggg  540
gttacatgtg gcgccgctac actgtctgcc gaaagagtgc ggggcgacaa caaagaatac  600
gagtacagc tggaatgcca agaggacagc cctgtccag ccgccgaaga gtctctgcct  660
atcgaagtga tggtggacgc cgtgcacaag ctgaagtacg agaactacac ctccagcttt  720
ttcatccggg acatcatcaa gcccgatcct ccaaagaacc tgcagctgaa gcctctgaag  780
aacagcagac aggtggaagt gtcctggag taccccgaca cctggtctac accccacagc  840
tacttcagcc tgacctttg cgtgcaagtg cagggcaagt ccaagcgcga gaaaaaggac  900
cgggtgttca ccgacaagac cagcgccacc gtgatctgca gaaagaacgc cagcatcagc  960
gtcagagccc aggaccggta ctacagcagc tcttggagcg aatgggccag cgtgccatgt 1020
tctgtggcg gaggatctgg cggaggtgga agcggcggag gcggatctag aaatctgcct 1080
gtggccactc ctgatcctgg catgttccct tgtctgcacc acagccagaa cctgctgaga 1140
gccgtgtcca acatgctgca gaaggccaga cagaccctgg aattctaccc ctgcaccagc 1200
gaggaaatcg accacgagga catcaccaag gataagacca gcaccgtgga agcctgcctg 1260
cctctggaac tgaccaagaa cgagagctgc ctgaacagcc gggaaaccag cttcatcacc 1320
aacggctctt gcctggccag cagaaagacc tccttcatga tggccctgtg cctgagcagc 1380
atctacgagg acctgaagat gtaccaggtg gaattcaagc ccatgaacgc caagctgctg 1440
atggacccca gcggcagat cttcctggac cagaatatgc tggccgtgat cgacgagctg 1500
atgcaggcc tgaacttcaa cagcgagaca gtgccccaga agtctagcct ggaagaaccc 1560
gacttctaca agaccaagat caagctgtgc atcctgctgc acgccttccg gatcagagcc 1620
gtgaccatcg acagagtgat gagctacctg aacgcctcct gagcgccgcc tccgggacag 1680
tgcacccagg ctgcggcccc tcccccgtcc tggaggttcc ccagccccac ttaccgctta 1740
atgcgccaat aaaccaatga acgaagcaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaa                                                 1936

SEQ ID NO: 21      moltype = AA  length = 540
FEATURE            Location/Qualifiers
source             1..540
```

```
                                    mol_type = protein
                                    note = Human IL12 Fusion Single chain AA-683
                                    organism = synthetic construct
SEQUENCE: 21
MCHQQLVISW FSLVFLASPL VAIWELKKDV YVVELDWYPD APGEMVVLTC DTPEEDGITW     60
TLDQSSEVLG SGKTLTIQVK EFGDAGQYTC HKGGEVLSHS LLLLHKKEDG IWSTDILKDQ    120
KEPKNKTFLR CEAKNYSGRF TCWWLTTIST DLTFSVKSSR GSSDPQGVTC GAATLSAERV    180
RGDNKEYEYS VECQEDSACP AAEESLPIEV MVDAVHKLKY ENYTSSFFIR DIIKPDPPKN    240
LQLKPLKNSR QVEVSWEYPD TWSTPHSYFS LTFCVQVQGK SKREKKDRVF TDKTSATVIC    300
RKNASISVRA QDRYYSSSWS EWASVPCSGG GGSGGGGSGG GGSRNLPVAT PDPGMFPCLH    360
HSQNLLRAVS NMLQKARQTL EFYPCTSEEI DHEDITKDKT STVEACLPLE LTKNESCLNS    420
RETSFITNGS CLASRKTSFM MALCLSSIYE DLKMYQVEFK TMNAKLLMDP KRQIFLDQNM    480
LAVIDELMQA LNFNSETVPQ KSSLEEPDFY KTKIKLCILL HAFRIRAVTI DRVMSYLNAS    540

SEQ ID NO: 22           moltype = DNA  length = 1002
FEATURE                 Location/Qualifiers
source                  1..1002
                        mol_type = other DNA
                        note = Sec-PADRE-HPV18E6E7-hCD1d
                        organism = synthetic construct
SEQUENCE: 22
atgggctgcc tgctgtttct gctgctttgg gctctgctgc aggcctgggg atctgccgcc     60
aagttcgtgg ctgcctggac cctgaaggct gccgctgcca gattcgagga ccctaccaga    120
agcggctaca agctgcctga cctgtgcacc gagctgaaca caagcctgca ggacatcgag    180
atcacctgtg tgtactgcaa gaccgtgctg gaactgaccg aggtgttcga gaaggacctg    240
ttcgtggtgt acagagacag catccctcac gccgcctgcc acaagtgcat cgacttctac    300
agcagaatca gagagctgag gcactacagc gacagcgtgt acggcgacac cctggaaaag    360
ctgaccaaca ccgcctgta caacctgctg atcagatgcc tgagatgcca gaagcctctg    420
ctgagacacc tgaacgagaa gaggcggttc acaatatcg ccggcactaca agaggccag    480
tgccacagct gttgtaacag agccagacaa gagaggctgc agagaaggcg cgaaacccag    540
gtgggcggag atctggcgg aggtggaagc ggcggaggcg gatctatgca cggccctaag    600
gccacactgc aggacatcgt gctgcacctg aacctcaga cgagatccc tgtggatctg    660
ctcggacacg gccagctgag cgatagcgag aagagaacg acgagatcga cggcgtgaac    720
caccagcatc tgcctgctag aagggccgag cctcagagac acaccatgct gtgcatgtgc    780
tgcaagtgcg aggccagaat caagctggtg gtggaaagca gcgccgacga cctgagagct    840
ttccagcagc tgttcctgaa caccctgagc ttcgtgtgtc cttggtgcgc ctctcagcaa    900
ggcctgatcg ccctggctgt tctggcctgt ctgttgttcc tgctgattgt gggcttcacc    960
agcagattca agagacagac cagctaccag ggcgtgctct ag                      1002

SEQ ID NO: 23           moltype = RNA  length = 1002
FEATURE                 Location/Qualifiers
source                  1..1002
                        mol_type = other RNA
                        note = SEC-PADRE-HPV18E6E7-HCD1D
                        organism = synthetic construct
SEQUENCE: 23
atgggctgcc tgctgtttct gctgctttgg gctctgctgc aggcctgggg atctgccgcc     60
aagttcgtgg ctgcctggac cctgaaggct gccgctgcca gattcgagga ccctaccaga    120
agcggctaca agctgcctga cctgtgcacc gagctgaaca caagcctgca ggacatcgag    180
atcacctgtg tgtactgcaa gaccgtgctg gaactgaccg aggtgttcga gaaggacctg    240
ttcgtggtgt acagagacag catccctcac gccgcctgcc acaagtgcat cgacttctac    300
agcagaatca gagagctgag gcactacagc gacagcgtgt acggcgacac cctggaaaag    360
ctgaccaaca ccgcctgta caacctgctg atcagatgcc tgagatgcca gaagcctctg    420
ctgagacacc tgaacgagaa gaggcggttc acaatatcg ccggcactaca agaggccag    480
tgccacagct gttgtaacag agccagacaa gagaggctgc agagaaggcg cgaaacccag    540
gtgggcggag atctggcgg aggtggaagc ggcggaggcg gatctatgca cggccctaag    600
gccacactgc aggacatcgt gctgcacctg aacctcaga cgagatccc tgtggatctg    660
ctcggacacg gccagctgag cgatagcgag aagagaacg acgagatcga cggcgtgaac    720
caccagcatc tgcctgctag aagggccgag cctcagagac acaccatgct gtgcatgtgc    780
tgcaagtgcg aggccagaat caagctggtg gtggaaagca gcgccgacga cctgagagct    840
ttccagcagc tgttcctgaa caccctgagc ttcgtgtgtc cttggtgcgc ctctcagcaa    900
ggcctgatcg ccctggctgt tctggcctgt ctgttgttcc tgctgattgt gggcttcacc    960
agcagattca agagacagac cagctaccag ggcgtgctct ag                      1002

SEQ ID NO: 24           moltype = AA  length = 333
FEATURE                 Location/Qualifiers
source                  1..333
                        mol_type = protein
                        note = Sec-PADRE-HPV18E6E7-hCD1d
                        organism = synthetic construct
SEQUENCE: 24
MGCLLFLLLW ALLQAWGSAA KFVAAWTLKA AAARFEDPTR SGYKLPDLCT ELNTSLQDIE     60
ITCVYCKTVL ELTEVFEKDL FVVYRDSIPH AACHKCIDFY SRIRELRHYS DSVYGDTLEK    120
LTNTGLYNLL IRCLRCQKPL LRHLNEKRRF HNIAGHYRGQ CHSCCNRARQ ERLQRRRETQ    180
VGGGSGGGGS GGGGSMHGPK ATLQDIVLHL EPQNEIPVDL LGHGQLSDSE EENDEIDGVN    240
HQHLPARRAE PQRHTMLCMC CKCEARIKLV VESSADDLRA FQQLFLNTLS FVCPWCASQQ    300
GLIALAVLAC LLFLLIVGFT SRFKRQTSYQ GVL                                 333
```

```
SEQ ID NO: 25          moltype = DNA  length = 1343
FEATURE                Location/Qualifiers
source                 1..1343
                       mol_type = other DNA
                       note = Sec-PADRE-HPV16E6E7-hCD1d (DNA-795)
                       organism = synthetic construct
SEQUENCE: 25
aatcataata cgactcacta taaggcatag aagtcgagac acagccacta agtaagccac    60
catgggctgc ctgctgtttc tgctgctttg ggctctgctg caggcctggg gatctgccgc   120
caagttcgtg gctgcctgga ccctgaaggc tgccgctcac cagaaaagaa ccgccatgtt   180
ccaggatcct caagagaggc cagaaagct gcctcagctg tgtaccgagc tgcagaccac   240
catccacgac atcatcctgg aatgcgtgta ctgcaagcag cagctcctga agagagggt   300
gtacgacttc gccttccgcg acggctgcat cgtgtacaga gatggcaacc cttacgccgt   360
gtgcgacaag tgcctgaagt tctacagcaa gatcagcgag taccggcact actgctacag   420
cctgtacggc accacactgg aacagcagta caacaagccc ctgtgcgacc tgctgatcag   480
atgcatcaac tgccagaaac tctgtgcccc gaggaaaag cagagacacc tggacaagaa    540
gcagcggttc cacaacatca gaggcagatg gaccggcaga tgcatgtcct gctgcagaag   600
ctccagaacc agaagggctg ctgcagctgg tggcggagga tctggcggag gtggaagcgg   660
cggaggcgga tctatgcctg gcgatacacc tacactgcac gagtacatgc tggacctgca   720
gcctgagaca accgatctgt acggctacga gcagctgaac gacagcagcg aggaagagga   780
cgagatcgac ggacctgctg gacaggctgc tcctgataga gcccactaca acatcgtgac   840
attctgctgc aagtgcgaca gcaccctgcg gagatgtgtg cagtctaccc acgtggacat   900
cagaaccctg gaagatctgc tgatgggcac cctgggcatc gtgtgcccta tctgttctca   960
gaagcctggc ctgatcgccc tggctgttct ggcctgtctg ttgttcctgc tgattgtggg  1020
cttcaccagc agattcaaga gacagaccag ctaccagggc tgctctaggg ccccactcc   1080
gggacagtgc acccaggctg cggcccctcc ccgtcctgga aggttcccca gccccactta  1140
ccgcttaatg cgccaataaa ccaatgaacg aagcaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaa                                          1343

SEQ ID NO: 26          moltype = RNA  length = 1321
FEATURE                Location/Qualifiers
source                 1..1321
                       mol_type = other RNA
                       note = Sec-PADRE-HPV16E6E7-hCD1d (RNA-795)
                       organism = synthetic construct
SEQUENCE: 26
aggcatagaa gtcgagacac agccactaag taagccacca tgggctgcct gctgtttctg    60
ctgctttggg ctctgctgca ggcctggga tctgccgcca agttcgtggc tgcctggacc   120
ctgaaggctg ccgctcacca gaaaagaacc gccatgttcc aggatcctca agagaggccc   180
agaaagctgc ctcagctgtg taccgagctg cagaccacca tccacgacat catcctggaa   240
tgcgtgtact gcaagcagca gctcctgaga gagaggtgt acgacttcgc cttccgcgac   300
ggctgcatcg tgtacagaga tggcaaccct tacgccgtgt gcgacaagtg cctgaagttc   360
tacagcaaga tcagcgagta ccggcactac tgctacagcc tgtacggcac cacactggaa   420
cagcagtaca acaagcccct gtgcgacctg ctgatcagat gcatcaactg ccagaaacct   480
ctgtgccccg aggaaaagca gagacacctg gacaagaag agcggttcca acatcagaa   540
ggcagatgga ccggcagatg catgtcctgc tgcagaagct ccagaaccag aagggctgct   600
gcagctggtg gcggaggatc tggcggaggt ggaagcggcg gaggcggatc tatgcctggc   660
gatacaccta cactgcacga gtacatgctg gacctgcag cctgagacaa ccgatctgta   720
cggctacgag cagctgaacg acagcagcga ggaagaggac gagatcgacg gacctgctgg   780
acaggctgct cctgatagag cccactacaa catcgtgaca ttctgctgca agtgcgacag   840
cacCctgcgg agatgtgtgca gtctaccac gtggacatca gaaccctgga agatctgctg   900
atgggcaccc tgggcatcgt gtgccctatc tgttctcaga agcctggcct gatcgccctg   960
gctgttctgg cctgtctgtt gttcctgctg attgtgggct tcaccagcag attcaagaga  1020
cagaccagct accagggcgt gctctaggcg ccgcctccgg gacagtgcac caggctgcgg  1080
gcccctcccc gtcctggagg ttccccagcc cacttaccgc ttaatgcgcc aataaaccaa  1140
atgaacgaag caaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
a                                                                  1321

SEQ ID NO: 27          moltype = AA  length = 335
FEATURE                Location/Qualifiers
source                 1..335
                       mol_type = protein
                       note = Sec-PADRE-HPV16E6E6-hCD1d (AA-795)
                       organism = synthetic construct
SEQUENCE: 27
MGCLLFLLLW ALLQAWGSAA KFVAAWTLKA AAHQKRTAMF QDPQERPRKL PQLCTELQTT    60
IHDIILECVY CKQQLLRREV YDFAFRDGCI VYRDGNPYAV CDKCLKFYSK ISEYRHYCYS   120
LYGTTLEQQY NKPLCDLLIR CINCQKPLCP EEKQRHLDKK QRFHNIRGRW TGRCMSCCRS   180
SRTRRAAAAG GGGSGGGGSG GGGSMPGDTP TLHEYMLDLQ PETTDLYGYE QLNDSSEEED   240
EIDGPAGQAA PDRAHYNIVT FCCKCDSTLR RCVQSTHVDI RTLEDLLMGT LGIVCPICSQ   300
KPGLIALAVL ACLLFLLIVG FTSRFKRQTS YQGVL                              335

SEQ ID NO: 28          moltype = RNA  length = 43
FEATURE                Location/Qualifiers
```

```
source                  1..43
                        mol_type = other RNA
                        organism = synthetic construct
SEQUENCE: 28
catcggcgct ttgccacttg tacccgagtt tttgattctc aac              43

SEQ ID NO: 29           moltype = RNA   length = 49
FEATURE                 Location/Qualifiers
source                  1..49
                        mol_type = other RNA
                        organism = synthetic construct
SEQUENCE: 29
catcggcgct ttgccacttg tacccgagtt tttgattctc aacgccacc         49

SEQ ID NO: 30           moltype = RNA   length = 49
FEATURE                 Location/Qualifiers
source                  1..49
                        mol_type = other RNA
                        organism = synthetic construct
SEQUENCE: 30
catcgacgct ttgccacttg tacccgagtt tttgattctc aacgccacc         49

SEQ ID NO: 31           moltype = RNA   length = 49
FEATURE                 Location/Qualifiers
source                  1..49
                        mol_type = other RNA
                        organism = synthetic construct
SEQUENCE: 31
catcgacact ttgccacttg tacccgagtt tttgattctc aacgccacc         49

SEQ ID NO: 32           moltype = RNA   length = 49
FEATURE                 Location/Qualifiers
source                  1..49
                        mol_type = other RNA
                        organism = synthetic construct
SEQUENCE: 32
catcgacact ttgccacttg tacccgggtt tttgattctc aacgccacc         49

SEQ ID NO: 33           moltype = RNA   length = 49
FEATURE                 Location/Qualifiers
source                  1..49
                        mol_type = other RNA
                        organism = synthetic construct
SEQUENCE: 33
catcgacact ttgccacttg tacccaagtt tttgattctc aacgccacc         49

SEQ ID NO: 34           moltype = RNA   length = 49
FEATURE                 Location/Qualifiers
source                  1..49
                        mol_type = other RNA
                        organism = synthetic construct
SEQUENCE: 34
catcgacact ttgccacttg tacccgaatt tttgattctc aacgccacc         49

SEQ ID NO: 35           moltype = RNA   length = 49
FEATURE                 Location/Qualifiers
source                  1..49
                        mol_type = other RNA
                        organism = synthetic construct
SEQUENCE: 35
cattcacact ttgccacttg tacccgaatt tttgactctc aacgccacc         49

SEQ ID NO: 36           moltype = RNA   length = 49
FEATURE                 Location/Qualifiers
source                  1..49
                        mol_type = other RNA
                        organism = synthetic construct
SEQUENCE: 36
catcgacact ttgccacttg tacccgaatt tttgatcctc aacgccacc         49

SEQ ID NO: 37           moltype = RNA   length = 49
FEATURE                 Location/Qualifiers
source                  1..49
                        mol_type = other RNA
                        organism = synthetic construct
SEQUENCE: 37
catcgacact ttgccacttg tacccgaatt tttgattttc aacgccacc         49

SEQ ID NO: 38           moltype = RNA   length = 49
```

```
FEATURE                 Location/Qualifiers
source                  1..49
                        mol_type = other RNA
                        organism = synthetic construct
SEQUENCE: 38
cattcacact ttgccacttg tacccgaatt ttcgactctc aacgccacc              49

SEQ ID NO: 39           moltype = RNA  length = 49
FEATURE                 Location/Qualifiers
source                  1..49
                        mol_type = other RNA
                        organism = synthetic construct
SEQUENCE: 39
cattcacact ttgccacttg tacccgaatt tccgactctc gccgccacc              49

SEQ ID NO: 40           moltype = RNA  length = 49
FEATURE                 Location/Qualifiers
source                  1..49
                        mol_type = other RNA
                        organism = synthetic construct
SEQUENCE: 40
cattcacact ttgccacttg taccgccatt tccgactctc gccgccacc              49

SEQ ID NO: 41           moltype = RNA  length = 49
FEATURE                 Location/Qualifiers
source                  1..49
                        mol_type = other RNA
                        organism = synthetic construct
SEQUENCE: 41
cattcacact ttgccacttg taccgccatt tccaactctc gccgccacc              49

SEQ ID NO: 42           moltype = RNA  length = 50
FEATURE                 Location/Qualifiers
source                  1..50
                        mol_type = other RNA
                        organism = synthetic construct
SEQUENCE: 42
gcatcgacac tttaccactt gtacccaaat ttttgactct caacgccacc             50

SEQ ID NO: 43           moltype = RNA  length = 36
FEATURE                 Location/Qualifiers
source                  1..36
                        mol_type = other RNA
                        organism = synthetic construct
SEQUENCE: 43
cctttccgtc tggcggcagc catcaggtaa gccaag                            36

SEQ ID NO: 44           moltype = RNA  length = 37
FEATURE                 Location/Qualifiers
source                  1..37
                        mol_type = other RNA
                        organism = synthetic construct
SEQUENCE: 44
gcatagaagt ctggcggcag ccatcaggta agccaag                           37

SEQ ID NO: 45           moltype = RNA  length = 37
FEATURE                 Location/Qualifiers
source                  1..37
                        mol_type = other RNA
                        organism = synthetic construct
SEQUENCE: 45
gcatagaagt ctggcggcag ccatcaggta agccacc                           37

SEQ ID NO: 46           moltype = RNA  length = 37
FEATURE                 Location/Qualifiers
source                  1..37
                        mol_type = other RNA
                        organism = synthetic construct
```

```
SEQUENCE: 46
gcatagaagt ctgatcgcag ccatcaggta agccacc                              37

SEQ ID NO: 47           moltype = RNA   length = 37
FEATURE                 Location/Qualifiers
source                  1..37
                        mol_type = other RNA
                        organism = synthetic construct
SEQUENCE: 47
gcatagaagt ttgatcgcag ccatcggata agccacc                              37

SEQ ID NO: 48           moltype = RNA   length = 37
FEATURE                 Location/Qualifiers
source                  1..37
                        mol_type = other RNA
                        organism = synthetic construct
SEQUENCE: 48
gcatagaagt ttgatcgcag ccattgaata agccacc                              37

SEQ ID NO: 49           moltype = RNA   length = 37
FEATURE                 Location/Qualifiers
source                  1..37
                        mol_type = other RNA
                        organism = synthetic construct
SEQUENCE: 49
gcatagaagt ccgatcgcag ccattgaata agccacc                              37

SEQ ID NO: 50           moltype = RNA   length = 36
FEATURE                 Location/Qualifiers
source                  1..36
                        mol_type = other RNA
                        organism = synthetic construct
SEQUENCE: 50
catagaagtc gagacacagc cactaagtaa gccacc                               36

SEQ ID NO: 51           moltype = RNA   length = 38
FEATURE                 Location/Qualifiers
source                  1..38
                        mol_type = other RNA
                        organism = synthetic construct
SEQUENCE: 51
gagagaaaag aagagtaaga agaaatataa gagccacc                             38

SEQ ID NO: 52           moltype = RNA   length = 36
FEATURE                 Location/Qualifiers
source                  1..36
                        mol_type = other RNA
                        organism = synthetic construct
SEQUENCE: 52
catagaagtc gagacacagc cactaagtaa gccacc                               36

SEQ ID NO: 53           moltype = RNA   length = 105
FEATURE                 Location/Qualifiers
source                  1..105
                        mol_type = other RNA
                        organism = synthetic construct
SEQUENCE: 53
gcgccgcctc cgggacagtg cacccaggct gcggcccctc cccgtcctg gaggttcccc      60
agccccactt accgcttaat gcgccaataa accaatgaac gaagc                    105

SEQ ID NO: 54           moltype = AA    length = 10
FEATURE                 Location/Qualifiers
source                  1..10
                        mol_type = protein
                        organism = synthetic construct
SEQUENCE: 54
SSASTDKTHT                                                            10
```

MRNA THERAPEUTIC COMPOSITIONS

RELATED APPLICATIONS

The present patent application is a continuation of U.S. patent application Ser. No. 18/505,881, filed Nov. 9, 2023, which is a continuation of International Application No. PCT/US2023/76531, filed Oct. 11, 2023 and claims the priority benefit of U.S. Provisional Patent Application Ser. No. 63/416,241, filed Oct. 14, 2022; U.S. Provisional Patent Application Ser. No. 63/434,219, filed Dec. 21, 2022; U.S. Provisional Patent Application Ser. No. 63/442,566, filed Feb. 1, 2023; U.S. Provisional Patent Application Ser. No. 63/444,195, filed Feb. 8, 2023; and U.S. Provisional Patent Application Ser. No. 63/495,412, filed Apr. 11, 2023, the content of each is hereby incorporated by reference in its entirety into this disclosure.

INCORPORATION BY REFERENCE OF SEQUENCE LISTING

This application contains a Sequence listing that has been submitted in a computer readable format and is hereby incorporated by reference in its entirety. The computer readable file, created on Oct. 20, 2023, is named 66633US08-1030-US_SequenceListing and is 74,822 bytes in size.

BACKGROUND

Human papillomavirus (HPV) is a contagious cause of anogenital and oropharyngeal cancers developing from persistently infected and subsequently transformed basal keratinocytes of mucosal epithelium. While more than 90% of cervical cancers and pre-cancerous cervical intraepithelial neoplasia (CIN) are linked to infections with high-risk HPV, with more than 50% of cancers linked to HPV16, (1, 2), other cancers caused by HPV include head and neck, oropharyngeal, anal, penile, vulvar cancers. For cervical cancer, at least 25% of women with high-grade CIN lesions progress to in situ or invasive cancer if untreated (3). Current treatments for HPV related cancers can remove abnormal tissue but do not address underlying HPV infection. In the case of cervical cancer, 15% of women treated develop residual or recurrent high-grade CIN or cervical cancer (4). Long-term efficacy of a HPV cancer therapeutic may require the induction of tumor-specific T cell responses combined with alleviated local immune suppression and increased tumor immune cell infiltration.

Infection with high-risk HPV types is the major etiological cause of cervical cancer and its pre-cancerous lesions (Walboomers, 1999) with Types 16 and 18 accounting for approximately 70% of cervical cancers and approximately 50% of high-grade lesions CIN2/3 (Smith, 2007). Persistent high grade HPV infection is considered necessary to promote progression of pre-malignant stages to invasive cancer (Moscicki, 2006). While prophylactic HPV vaccines are highly effective, there is still a large pool of women at risk for CIN due to ineligibility or who choose not to be vaccinated. In the US, the annual incidence of CIN2/3 is approximately 200000 (CDC, 2019). While loop electrosurgical excision procedure (LEEP) is an effective treatment in many patients with CIN2/3, the recurrence rate is 20% (Young, 2010). An observational study, consisting of 110 patients with high grade CIN lesions after LEEP between January 2010 and June 2015, indicates that LEEP does not completely eradicate HPV infection. The HPV persistence rate after LEEP is higher in infections with Type 16 and in women older than 36.5 years (Pirtea, 2016). In addition, treatment with major excisional procedures, including LEEP, was associated with increased risks of preterm birth and spontaneous abortion (Noehr, 2009; Bjorge, 2016). The risk of preterm birth was highest at early gestational ages and for those with the largest amount of tissue excised (Bjorge, 2016). Thus, there is an unmet medical need for non-surgical therapeutics for the treatment of high-grade CIN patients.

Women with CIN3 have a 2-fold increased risk of developing cervical cancer even post-treatment, and the risk increases with diagnosis at an older age (Loopik, 2020). In 2018, cervical cancer accounted for an estimated 570000 new cancer cases and 311000 deaths worldwide (Arbyn, 2020). Over 50% of cervical cancer is the result of infection by HPV16 (Mirabello, 2018). Standard of care treatment in early-stage cervical cancer consists of radical hysterectomy with or without lymphadenectomy followed by adjuvant chemotherapy in intermediate to high-risk patients. For women at a low risk of recurrence, fertility-sparing surgery may be considered. For high-risk women, adjuvant chemotherapy such as a single agent cisplatin with radiation therapy is used as the primary treatment of locally advanced cervical cancer (NCCN, 2022). Immunotherapy such as KEYTRUDA® (pembrolizumab) in combination with chemotherapy showed improvements in overall survival with or without bevacizumab in patients with persistent, recurrent, or metastatic cervical cancer whose tumors express PD-L1 (CPS≥1). However, objective response is only around 14% when KEYTRUDA® is used as a single agent for the treatment of recurrent or metastatic cervical cancer with disease progression on or after chemotherapy whose tumors express PD-L1 (CPS≥1) (KEYNOTE-158) (KEYTRUDA, 2022). Thus, new treatments for cervical cancer are still needed.

While cervical cancer is the most common HPV-associated cancer among women, oropharyngeal cancers (cancers of the back of the throat, including the base of the tongue and tonsils) are the most common among men. An estimate of 36500 cancers were attributable to HPV each year during 2014 to 2018. Of these, 29500 were caused by HPV Types 16 and 18, which included squamous cell carcinomas of the cervical, oropharynx, anus, penis, vagina, and vulva (CDC, 2021). Currently, there is a paucity of approved treatment options for HPV-associated cancers.

BRIEF SUMMARY

Multimodal mRNA-based immunotherapies that deliver both antigens and immunomodulators in a single therapeutic represent a promising new approach for the treatment of HPV-driven cancer or a disease associated with HPV that can address current disease as well as the underlying cause (HPV infection).

One aspect of the present disclosure is an isolated polypeptide comprising an amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17. Another aspect of the disclosure is an isolated polynucleotide that encodes a polypeptide of the disclosure.

One aspect of the present disclosure is an isolated polynucleotide comprising a first isolated messenger ribonucleic acid (mRNA), at least a portion of thereof encoding a membrane-stabilized LIGHT. One aspect is an isolated polynucleotide including a formula: 5'UTR-Signal/Leader mRNA coding region-3' UTR-PolyA, wherein the mRNA coding region encodes a membrane-stabilized LIGHT. In one aspect, the isolated polynucleotide comprises a modified 3'UTR, a modified 5'UTR, one or more modifications to a nucleobase-sugar-internucleoside linkage, or a combination thereof.

In one aspect, the isolated polynucleotide comprises a nucleobase-sugar-internucleoside linkage selected from the group consisting of pseudouridine-alpha-thio-MP, 1-methyl-pseudouridine-alpha-thio-MP, 1-ethyl-pseudouridine-MP, 1-propyl-pseudouridine-MP, 1-(2,2,2-trifluoroethyl)-pseudouridine-MP, 2-amino-adenine-MP, xanthosine-MP, 5-bromo-cytidine-MP, 5-aminoallyl-cytidine-MP, 2-aminopurine-riboside-MP, pseudouridine-alpha-thio-MP, 1-methyl-pseudouridine-alpha-thio-MP, 5-bromo-cytidine-MP, and combinations thereof.

In one aspect, the 5'UTR includes a sequence selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 48, SEQ ID NO: 50, SEQ ID NO: 51, and SEQ ID NO: 52. In one aspect, the 3'UTR has a sequence comprising SEQ ID NO: 53.

In one aspect, the membrane-stabilized LIGHT is a membrane-stabilized human LIGHT. In another aspect, the membrane-stabilized LIGHT includes replacement of a section of the transmembrane region of soluble LIGHT with a linker. In one aspect, the linker is an antibody variable region linker or a peptide linker. In another aspect, the linker comprises (Gly4Ser)n, wherein n is 1, 2, 3, 4, 5, 6, 7, 8, 9, or 10. In yet another aspect, the linker comprises the sequence SSASTDKTHT (SEQ ID NO: 54).

In one aspect, the membrane-stabilized LIGHT has at least about 70%, alternatively at least about 75%, alternatively at least about 80%, alternatively at least about 85%, alternatively at least about 90%, alternatively at least about 95% amino acid sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17.

In another aspect, the membrane-stabilized LIGHT has at least about 80%, alternatively at least about 85%, alternatively at least about 90%, alternatively at least about 93%, alternatively at least about 95%, alternatively at least about 96% alternatively at least about 97%, alternatively at least about 98%, alternatively at least about 99% amino acid sequence identity to SEQ ID NO: 11 or SEQ ID NO: 17.

In some aspects, the first isolated mRNA has at least about 50%, alternatively at least about 60%, alternatively at least about 65%, alternatively at least about 70%, alternatively at least about 75%, alternatively at least about 80%, alternatively at least about 85%, alternatively at least about 90%, alternatively at least about 95% nucleic acid sequence identity to SEQ ID NO: 4, SEQ ID NO: 6, SEQ ID NO: 9, SEQ ID NO: 10, SEQ ID NO: 12, SEQ ID NO: 14, SEQ ID NO: 16, or SEQ ID NO: 18.

In another aspect, the first isolated mRNA has at least about 80%, alternatively at least about 85%, alternatively at least about 90%, alternatively at least about 93%, alternatively at least about 95%, alternatively at least about 96% alternatively at least about 97%, alternatively at least about 98%, alternatively at least about 99% nucleic acid sequence identity to SEQ ID NO: 12 or SEQ ID NO: 18.

One aspect of the present disclosure is a composition including an isolated polynucleotide as described. In some aspects, the composition further includes at least a second isolated mRNA, at least a portion thereof encoding a checkpoint inhibitor, an immunosuppression antagonist, a pro-inflammatory agent, or a pro-inflammatory cytokine. In another aspect, the pro-inflammatory cytokine is interleukin-12. In yet another aspect, the pro-inflammatory cytokine has at least about 50%, alternatively at least about 60%, alternatively at least about 65%, alternatively at least about 70%, alternatively at least about 75%, alternatively at least about 80%, alternatively at least about 85%, alternatively at least about 90%, alternatively at least about 95% amino acid sequence identity to SEQ ID NO:21.

In one aspect of the composition the second isolated mRNA has a formula: 5'UTR Signal/Leader-mRNA coding region-3' UTR-PolyA, wherein the mRNA coding region encodes human interleukin-12. In another aspect, the second isolated mRNA comprises a modified 3'UTR, a modified 5'UTR, one or more modifications to a nucleobase-sugar-internucleoside linkage, or a combination thereof.

In an aspect, the second isolated mRNA comprises a nucleobase-sugar-internucleoside linkage selected from the group consisting of pseudouridine-alpha-thio-MP, 1-methyl-pseudouridine-alpha-thio-MP, 1-ethyl-pseudouridine-MP, 1-propyl-pseudouridine-MP, 1-(2,2,2-trifluoroethyl)-pseudouridine-MP, 2-amino-adenine-MP, xanthosine-MP, 5-bromo-cytidine-MP, 5-aminoallyl-cytidine-MP, 2-aminopurine-riboside-MP, pseudouridine-alpha-thio-MP, 1-methyl-pseudouridine-alpha-thio-MP, 5-bromo-cytidine-MP, and combinations thereof.

In another aspect, the mRNA coding region encodes at least two heterodimers of human interleukin-12. In a further aspect, the first interleukin-12 heterodimer connected to the second interleukin-12 heterodimer via a linker. In yet a further aspect, the linker is an antibody variable region linker, a peptide linker, and/or a (Gly4Ser)n linker wherein n is 1, 2, 3, 4, 5, 6, 7, 8, 9, or 10. In a particular aspect, the linker is a (Gly4Ser)n linker wherein n is 3.

In an aspect, the second isolated mRNA has at least about 50%, alternatively at least about 60%, alternatively at least about 65%, alternatively at least about 70%, alternatively at least about 75%, alternatively at least about 80%, alternatively at least about 85%, alternatively at least about 90%, alternatively at least about 95% nucleic acid sequence identity to SEQ ID NO:20.

In another aspect of the disclosure, the composition further includes at least a third isolated mRNA, wherein the third isolated mRNA comprises a first region encoding a first antigen and a second region encoding a second antigen. In an aspect, the first region and/or the second region encodes all or a portion of an antigen specific to cervical cancer, HPV-driven cancer, or a disease associated with HPV. In another aspect the third isolated mRNA encodes HPV16 E6 E7 or HPV18 E6 E7. In yet another aspect, the third isolated mRNA encodes HPV16 E6 E7.

In an aspect, third isolated mRNA has a formula of 5'UTR—Signal/Leader—(An1)n-Xo-(An2)p—3' UTR-PolyA, wherein An1 encodes HPV16 E6, An2 encodes HPV16 E7, X is a spacer or linker, and n is 1, 2, 3, 4, 5, 6, 7, 8, 9, or 10; o is 0, 1, 2, 3, 4, 5, 6, 7, 8, 9, or 10; and p is 1, 2, 3, 4, 5, 6, 7, 8, 9, or 10. In another aspect, the linker is an antibody variable region linker, a peptide linker, and/or a (Gly4Ser)n linker wherein n is 1, 2, 3, 4, 5, 6, 7, 8, 9, or 10. In a particular aspect, the linker is a (Gly4Ser)n linker wherein n is 3.

In an aspect, the third isolated mRNA comprises a modified 3'UTR, a modified 5'UTR, one or more modifications to a nucleobase-sugar-internucleoside linkage, or a combination thereof.

In an aspect, the third isolated mRNA comprises a nucleobase-sugar-internucleoside linkage selected from the group consisting of pseudouridine-alpha-thio-MP, 1-methyl-pseudouridine-alpha-thio-MP, 1-ethyl-pseudouridine-MP, 1-propyl-pseudouridine-MP, 1-(2,2,2-trifluoroethyl)-pseudouridine-MP, 2-amino-adenine-MP, xanthosine-MP, 5-bromo-cytidine-MP, 5-aminoallyl-cytidine-MP, 2-aminopurine-riboside-MP, pseudouridine-alpha-thio-MP, 1-methyl-pseudouridine-alpha-thio-MP, 5-bromo-cytidine-MP, and combinations thereof.

In an aspect, the third isolated mRNA encodes an antigen, wherein the antigen has at least about 50%, alternatively at least about 60%, alternatively at least about 65%, alternatively at least about 70%, alternatively at least about 75%, alternatively at least about 80%, alternatively at least about 85%, alternatively at least about 90%, alternatively at least about 95% amino acid sequence identity to SEQ ID NO: 24 or SEQ ID NO: 27.

In another aspect, the third isolated mRNA has at least about 50%, alternatively at least about 60%, alternatively at least about 65%, alternatively at least about 70%, alternatively at least about 75%, alternatively at least about 80%, alternatively at least about 85%, alternatively at least about 90%, alternatively at least about 95% nucleic acid sequence identity to SEQ ID NO: 23 or SEQ ID NO: 26.

In an aspect, at least the first isolated mRNA, second isolated mRNA and/or third isolated mRNA are formulated and/or in communication with a delivery vehicle. In another aspect, at least the first isolated mRNA, second isolated mRNA and/or third isolated mRNA are at least partially encapsulated with the delivery vehicle. In an aspect, the delivery vehicle is selected from the group including amphipathic molecules, amino-lipidated peptides, and tertiary amino lipidated cationic peptides. In another aspect, the delivery vehicle has a particle size less than or equal to about 200 nm.

In certain aspects, the polynucleotides, mRNAs and/or compositions described herein are formulated with a delivery agent or vehicle or delivery vehicle composition to make delivery vehicle complexes or pharmaceutical formulations. Such polyanionic compounds may also be referred to as polyanionic cargo compounds or cargos of a delivery vehicle complex (also referred to as a multicomponent delivery system), which complex or system also includes delivery vehicle compositions.

In some aspects, the delivery vehicle or delivery vehicle composition includes a peptoid, a lipoid, a liposome, a lipoplex, a lipid nanoparticle, a polymeric compound, or a conjugate.

In some aspects, the delivery vehicle or delivery vehicle composition includes lipid nanoparticles (LNPs), such as cationic lipid nanoparticles. Exemplary cationic lipid nanoparticles are described in, for example, WO2020/219941 and WO2020/097548. In some aspects, the delivery vehicle or delivery vehicle composition includes peptoids, such as tertiary amino lipidated and/or PEGylated cationic peptoids. Exemplary cationic peptoids are described in, for example, WO 2020/069442, WO 2020/069445, WO 2021/030218, and WO 2022/32058, each of which is incorporated herein by reference.

In some aspects, the delivery vehicle or delivery vehicle composition is a cationic peptoid. In some aspects, the cationic peptoid is a hydroxyethyl-capped tertiary amino lipidated cationic peptoid. In some aspects, the cationic peptoid complexes with polyanionic compounds, such as nucleic acids, including, but not limited to, mRNA (including, but not limited to the first isolated mRNA, the second isolated mRNA or third isolated mRNA described herein), an isolated polynucleotide, a polynucleotide encoding a polypeptide, polynucleotides, and nucleic acids encoding polypeptides, including those described herein.

In some aspects, the delivery vehicle includes a compound having formula (I)

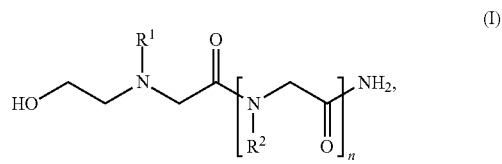

wherein n is 1, 2, 3, 4, 5, or 6; $R^1$ is H, $C_{1-3}$alkyl, or hydroxyethyl; and each $R^2$ independently is $C_{8-24}$alkyl or $C_{8-24}$alkenyl. In some aspects, n is 3. In various aspects, n is 4. In some aspects, $R^1$ is H. In some aspects, $R^1$ is ethyl or hydroxyethyl. In various cases, $R^2$ independently is $C_{8-18}$alkyl or $C_{8-18}$alkenyl. In some aspects, each $R^2$ is selected from the group consisting of

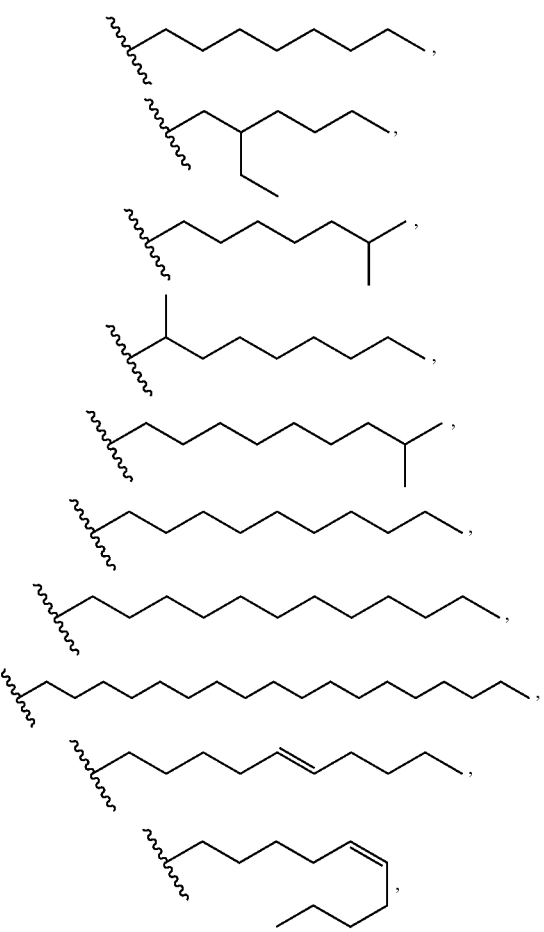

-continued
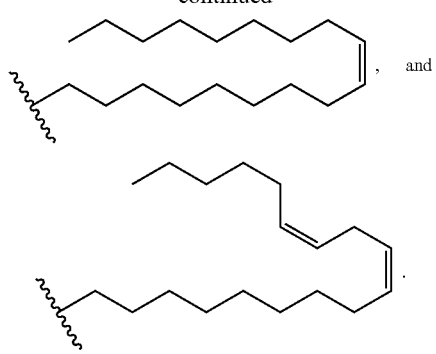
In various aspects, each R² independently is selected from the group consisting of
In some aspects, R² independently is selected from the group consisting of
In various aspects, each R² is
In some aspects, the compound of Formula (I) has a structure selected from the group consisting of:
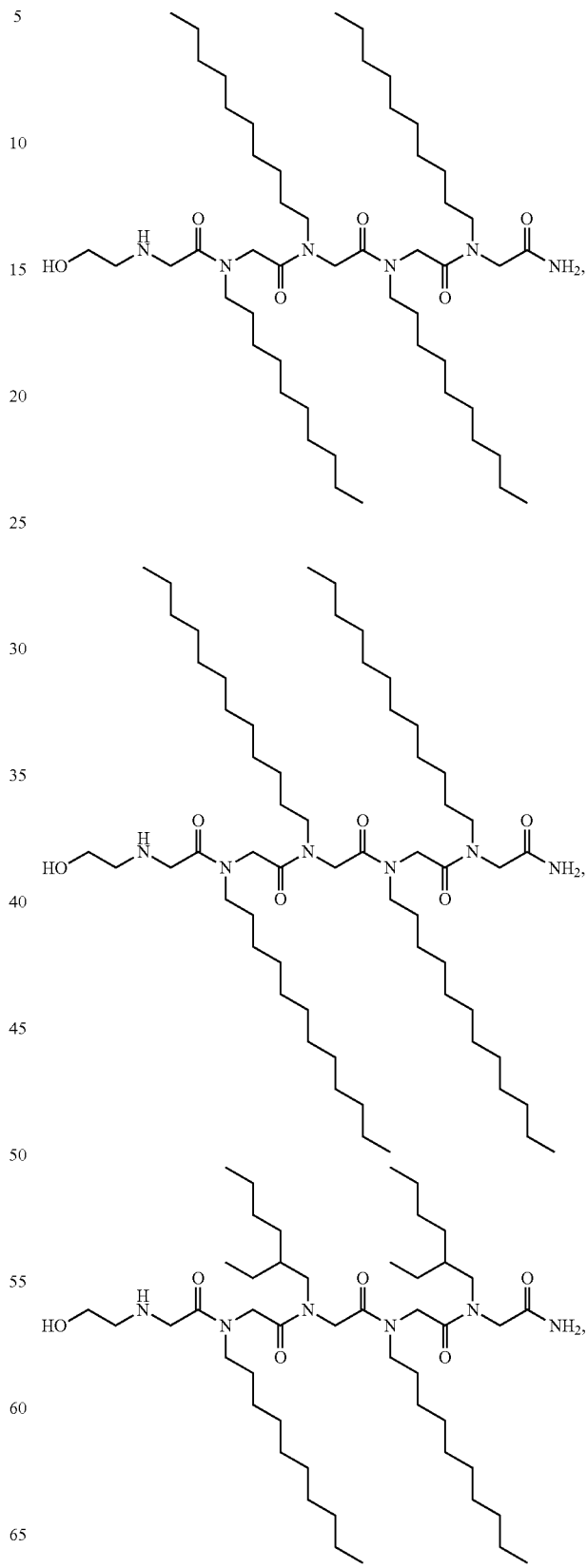

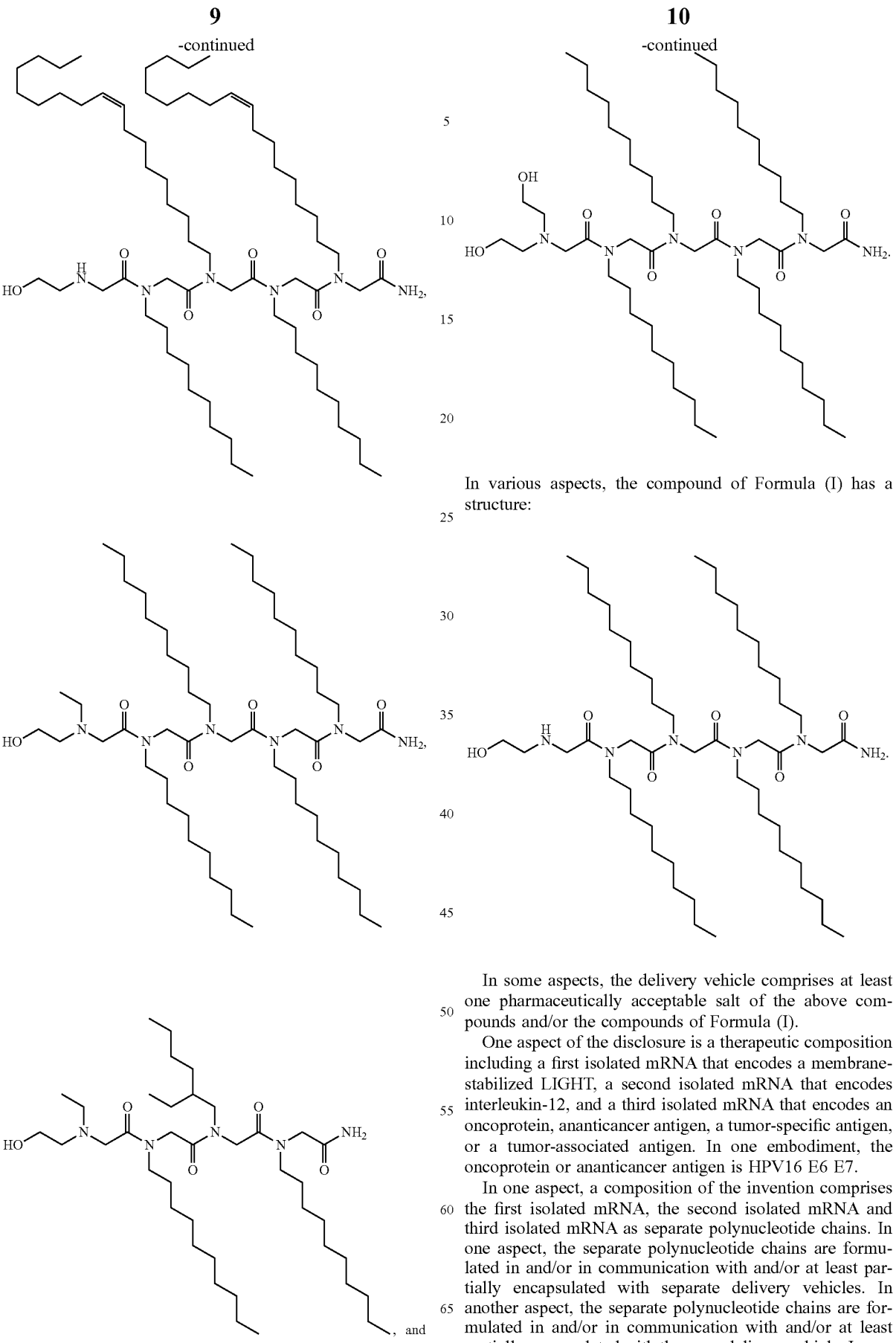

In various aspects, the compound of Formula (I) has a structure:

In some aspects, the delivery vehicle comprises at least one pharmaceutically acceptable salt of the above compounds and/or the compounds of Formula (I).

One aspect of the disclosure is a therapeutic composition including a first isolated mRNA that encodes a membrane-stabilized LIGHT, a second isolated mRNA that encodes interleukin-12, and a third isolated mRNA that encodes an oncoprotein, ananticancer antigen, a tumor-specific antigen, or a tumor-associated antigen. In one embodiment, the oncoprotein or anancancer antigen is HPV16 E6 E7.

In one aspect, a composition of the invention comprises the first isolated mRNA, the second isolated mRNA and third isolated mRNA as separate polynucleotide chains. In one aspect, the separate polynucleotide chains are formulated in and/or in communication with and/or at least partially encapsulated with separate delivery vehicles. In another aspect, the separate polynucleotide chains are formulated in and/or in communication with and/or at least partially encapsulated with the same delivery vehicle. In one aspect, the first isolated mRNA, second isolated mRNA and third isolated mRNA are part of a single polynucleotide chain. In one aspect, the first isolated mRNA and second isolated mRNA are part of a single polynucleotide chain. In one aspect, the first isolated mRNA and third isolated mRNA are part of a single polynucleotide chain. In one aspect, the second isolated mRNA and third isolated mRNA are part of a single polynucleotide chain. In one aspect, any of the polynucleotide chains described above may be formulated in and/or in communication with and/or at least partially encapsulated with a delivery vehicle. In any of the above aspects, the delivery vehicle may be selected from the group including amphipathic molecules, amino-lipidated peptides, and tertiary amino lipidated cationic peptides. In another aspect, the delivery vehicle has a particle size less than or equal to about 200 nm.

One aspect of the disclosure is a composition including a first isolated mRNA has at least about 80% nucleic acid sequence identity to SEQ ID NO: 12 or SEQ ID NO: 18; a second isolated mRNA that has at least about 80% nucleic acid sequence identity to SEQ ID NO:20; and a third isolated mRNA has at least about 80% nucleic acid sequence identity to SEQ ID NO:23 or SEQ ID NO:26, wherein the first isolated mRNA, second isolated mRNA and third isolated mRNA are at least partially encapsulated with a delivery vehicle. In another aspect of the composition, the first isolated mRNA has at least about 80% nucleic acid sequence identity to SEQ ID NO:18 and the third isolated mRNA has at least about 80% nucleic acid sequence identity to SEQ ID NO:26.

One aspect of the disclosure is a composition including a first isolated mRNA that encodes a membrane-stabilized LIGHT, a second isolated mRNA that encodes interleukin-12, a third isolated mRNA that encodes HPV16 E6 E7, and wherein the first isolated mRNA, second isolated mRNA and third isolated mRNA are at least partially encapsulated with a delivery vehicle.

In an aspect, the composition is a therapeutic composition or a vaccine. In another aspect, the composition is a human papillomavirus (HPV) mRNA vaccine. In a yet a further aspect, the composition is used in a cancer immunotherapy. In an aspect, the composition is configured to be administered to a subject known to have cervical cancer, HPV-driven cancer, or a disease associated with HPV.

Another aspect of the disclosure provides mRNA therapeutic formulations in delivery vehicle compositions including the compounds disclosed above or a pharmaceutically acceptable salts thereof. In some aspects, the delivery vehicle composition further includes one or more of a phospholipid, a sterol, and a PEGylated lipid. In some aspects, the compound or salt of Formula (I) is present in the delivery vehicle composition in an amount of about 30 mol % to about 60 mol %. In some aspects, the compound or salt of Formula (I) is present in the delivery vehicle composition in an amount of about 35 mol % to about 55 mol %. In various aspects, the compound or salt of Formula (I) is present in the delivery vehicle composition in an amount of about 30 mol % to about 45 mol %. In various aspects, the compound or salt of Formula (I) is present in the delivery vehicle composition in an amount of about 35 mol % to about 39 mol %. In some aspects, the compound or salt of Formula (I) is present in the delivery vehicle composition in an amount of about 39 mol % to about 52 mol %. In various aspects, the compound or salt of Formula (I) is present in the delivery vehicle composition in an amount of about 30 mol % to about 35 mol %. In various aspects, the compound or salt of Formula (I) is present in the delivery vehicle composition in an amount of about 40 mol % to about 45 mol %. In various aspects, the compound or salt of Formula (I) is present in an amount of about 42 mol % to about 49 mol %. In some aspects, the compound or salt of Formula (I) is present in an amount of about 50 mol % to about 52 mol %.

In various aspects, the delivery vehicle composition includes a phospholipid, a sterol, and a PEGylated lipid. In some cases, the delivery vehicle composition includes a compound disclosed herein or a salt thereof, a phospholipid, a sterol, and a PEGylated lipid. In some cases, the delivery vehicle composition includes about 30 mol % to about 60 mol % of the compound of Formula (I); about 3 mol % to about 20 mol % of the phospholipid, about 25 mol % to about 60 mol % of the sterol, and about 1 mol % to about 5 mol % of the PEGylated lipid. In various aspects, the delivery vehicle composition comprises about 35 mol % to about 55 mol % of the compound or salt of Formula (I); about 5 mol % to about 15 mol % of the phospholipid, about 30 mol % to about 55 mol % of the sterol, and about 1 mol % to about 3 mol % of the PEGylated lipid. In some implementations, the delivery vehicle composition comprises about 38 mol % to about 52 mol % of the compound or salt of Formula (I); about 9 mol % to about 12 mol % of the phospholipid, about 35 mol % to about 50 mol % of the sterol, and about 1 mol % to about 2 mol % of the PEGylated lipid. In various implementations, the delivery vehicle composition comprises about 30 mol % to about 49 mol % of the compound of Formula (I); about 5 mol % to about 15 mol % of the phospholipid, about 30 mol % to about 55 mol % of the sterol, and about 1 mol % to about 3 mol % of the PEGylated lipid. In some cases, the delivery vehicle composition comprises about 35 mol % to about 49 mol % of the compound or salt of Formula (I); about 7 mol % to about 12 mol % of the phospholipid, about 35 mol % to about 50 mol % of the sterol, and about 1 mol % to about 2 mol % of the PEGylated lipid. In some cases, the delivery vehicle composition comprises about 30 mol % to about 45 mol % of the compound or salt of Formula (I); about 7 mol % to about 12 mol % of the phospholipid, about 40 mol % to about 55 mol % of the sterol, and about 1 mol % to about 3 mol % of the PEGylated lipid. In some cases, the delivery vehicle composition comprises about 30 mol % to about 35 mol % of the compound or salt of Formula (I); about 7 mol % to about 12 mol % of the phospholipid, about 50 mol % to about 55 mol % of the sterol, and about 2 mol % to about 3 mol % of the PEGylated lipid. In some cases, the delivery vehicle composition comprises about 40 mol % to about 45 mol % of the compound or salt of Formula (I); about 7 mol % to about 12 mol % of the phospholipid, about 40 mol % to about 45 mol % of the sterol, and about 1 mol % to about 2 mol % of the PEGylated lipid. In some aspects, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C 16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE),1,2-dipalmitoyl-sn-glycero-3-phosphoethanolamine (DPPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and combinations thereof. In some aspects, the phospholipid is DOPE, DSPC, or a combination thereof. In various aspects, the phospholipid is DSPC. In some aspects, the sterol is selected from the group consisting of cholesterol, fecosterol, sitosterol, ergosterol, campesterol, stigmasterol, brassicasterol, tomatidine, ursolic acid, alpha-tocopherol, and mixtures thereof. In some cases, the sterol is cholesterol. In some aspects, the PEGylated lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, a PEG-modified sterol, and a PEG-modified phospholipid. In various implementations, the PEG-modified lipid is selected from the group consisting of PEG-modified cholesterol, N-octanoyl-sphingosine-1-{succinyl[methoxy(polyethylene glycol)]}, N-palmitoyl-sphingosine-1-{succinyl[methoxy (polyethylene glycol)]}, PEG-modified DMPE (DMPE-PEG), PEG-modified DSPE (DSPE-PEG), PEG-modified DPPE (DPPE-PEG), PEG-modified DOPE (DOPE-PEG), dimyristoylglycerol-polyethylene glycol (DMG-PEG), distearoylglycerol-polyethylene glycol (DSG-PEG), dipalmitoylglycerol-polyethylene glycol (DPG-PEG), dioleoylglycerol-polyethylene glycol (DOG-PEG), and a combination thereof. In some aspects, the PEG-modified lipid is dimyristoylglycerol-polyethylene glycol 2000 (DMG-PEG 2000). In various cases, the delivery vehicle composition comprises about 38.2 mol % of Compound 140, about 11.8 mol % of DSPC, about 48.2 mol % of cholesterol, and about 1.9 mol % of DMG-PEG 2000. In some aspects, the delivery vehicle composition comprises about 42.6 mol % of Compound 140, about 10.9 mol % of DSPC, about 44.7 mol % of cholesterol, and about 1.7 mol % of DMG-PEG 2000. In some aspects, the delivery vehicle composition comprises about 48.2 mol % of Compound 140, about 9.9 mol % of DSPC, about 40.4 mol % of cholesterol, and about 1.6 mol % of DMG-PEG 2000. In various aspects, the delivery vehicle composition comprises about 51.3 mol % of Compound 140, about 9.3 mol % of DSPC, about 38 mol % of cholesterol, and about 1.5 mol % of DMG-PEG 2000. In various aspects, the delivery vehicle composition comprises about 44.4 mol % of Compound 140, about 10.6 mol % of DSPC, about 43.3 mol % of cholesterol, and about 1.7 mol % of DMG-PEG 2000. In various aspects, the delivery vehicle composition comprises about 44.4 mol % of Compound 140, about 10.6 mol % of DSPC, about 43.4 mol % of cholesterol, and about 1.7 mol % of DMG-PEG 2000. In various aspects, the delivery vehicle composition comprises about 33.1 mol % of Compound 140, about 10.6 mol % of DSPC, about 53.8 mol % of cholesterol, and about 2.5 mol % of DMG-PEG 2000.

Further disclosed herein is a therapeutic formulation including one or more polyanionic compounds (e.g., mRNA (including, but not limited to the first isolated mRNA, the second isolated mRNA or third isolated mRNA described herein), an isolated polynucleotide, or a polynucleotide encoding a polypeptide described herein) with a delivery vehicle complex including the delivery vehicle composition described herein and a polyanionic compound. In some aspects, the compound of Formula (I) or salt thereof is complexed to the polyanionic compound. In various aspects, the compound or salt of Formula (I) and the polyanionic compound are present in a mass ratio of about 5:1 to about 25:1. In some aspects, the compound or salt of Formula (I) and the polyanionic compound are present in a mass ratio of about 7:1 to about 20:1. In various aspects, the compound or salt of Formula (I) and the polyanionic compound are present in a mass ratio of about 10:1 to about 17:1. In some aspects, the compound or salt of Formula (I) and the polyanionic compound are present in a mass ratio of about 19:1. In some aspects, the compound or salt of Formula (I) and the polyanionic compound are present in a mass ratio of about 20:1. In some aspects, the compound or salt of Formula (I) and the polyanionic compound are present in a mass ratio of about 10:1. In various aspects, the compound or salt of Formula (I) and the polyanionic compound are present in a mass ratio of about 12:1. In another aspect, the compound or salt of Formula (I) and the polyanionic compound are present in a mass ratio of about 13:1. In some aspects, the compound or salt of Formula (I) and the polyanionic compound are present in a mass ratio of about 15:1. In various aspects, the compound or salt of Formula (I) and the polyanionic compound are present in a mass ratio of about 17:1. In some aspects, the phospholipid and the polyanionic compound are present in a mass ratio of about 2:1 to about 10:1. In some aspects, the phospholipid and the polyanionic compound are present in a mass ratio of about 2:1 to about 4:1. In various aspects, the phospholipid and the polyanionic compound are present in a mass ratio of about 2:1 to about 3:1. In various aspects, the phospholipid and the polyanionic compound are present in a mass ratio of about 4.0:1. In various aspects, the phospholipid and the polyanionic compound are present in a mass ratio of about 2.7:1. In some aspects, the sterol and the polyanionic compound are present in a mass ratio of about 5:1 to about 8:1. In some aspects, the sterol and the polyanionic compound are present in a mass ratio of about 5:1 to about 6:1. In various aspects, the sterol and the polyanionic compound are present in a mass ratio of about 5.4:1. In some aspects, the sterol and the polyanionic compound are present in a mass ratio of about 8.1:1. In some aspects, the sterol and the polyanionic compound are present in a mass ratio of about 6.7:1. In some aspects, the PEGylated lipid and the polyanionic compound are present in a mass ratio of about 0.5:1 to about 2.5:1. In various aspects, the PEGylated lipid and the polyanionic compound are present in a mass ratio of about 1:1 to about 2:1. In some aspects, the phospholipid and the polyanionic compound are present in a mass ratio of about 2.1:1. In some aspects, the phospholipid and the polyanionic compound are present in a mass ratio of about 1.4:1. In various aspects the delivery vehicle complex includes Compound 140 having about a 10:1 mass ratio to the polyanionic compound, DSPC having about a 2.7:1 mass ratio to the polyanionic compound, cholesterol having about a 5.4:1 mass ratio to the polyanionic compound, and DMG-PEG 2000 having about a 1.4:1 mass ratio to the polyanionic compound. In various aspects, the delivery vehicle complex includes Compound 140 having about a 12:1 mass ratio to the polyanionic compound, DSPC having about a 2.7:1 mass ratio to the polyanionic compound, cholesterol having about a 5.4:1 mass ratio to the polyanionic compound, and DMG-PEG 2000 having about a 1.4:1 mass ratio to the polyanionic compound. In some aspects, the delivery vehicle complex includes Compound 140 having about a 15:1 mass ratio to the polyanionic compound, DSPC having about a 2.7:1 mass ratio to the polyanionic compound, and cholesterol having about a 5.4:1 mass ratio to the polyanionic compound, and DMG-PEG 2000 having about a 1.4:1 mass ratio to the polyanionic compound. In various aspects, the delivery vehicle complex comprises Compound 140 having about a 17:1 mass ratio to the polyanionic compound, DSPC having about a 2.7:1 mass ratio to the polyanionic compound, cholesterol having about a 5.4:1 mass ratio to the polyanionic compound, and DMG-PEG 2000 having about a 1.4:1 mass ratio to the polyanionic compound. In various aspects, the delivery vehicle complex comprises Compound 140 having about a 13:1 mass ratio to the polyanionic compound, DSPC having about a 2.7:1 mass ratio to the polyanionic compound, cholesterol having about a 5.4:1 mass ratio to the polyanionic compound, and DMG-PEG 2000 having about a 1.4:1 mass ratio to the polyanionic compound. In various aspects, the delivery vehicle complex comprises Compound 140 having about a 19:1 mass ratio to the polyanionic compound, DSPC having about a 4.0:1 mass ratio to the polyanionic compound, cholesterol having about a 5.4:1 mass ratio to the polyanionic compound, and DMG-PEG 2000 having about a 2.1:1 mass ratio to the polyanionic compound. In various aspects, the delivery vehicle complex comprises Compound 140 having about a 9.7:1 mass ratio to the polyanionic compound, DSPC having about a 2.7:1 mass ratio to the polyanionic compound, cholesterol having about a 6.7:1 mass ratio to the polyanionic compound, and DMG-PEG 2000 having about a 2.1:1 mass ratio to the polyanionic compound.

In some aspects, a pharmaceutical formulation including one or more mRNA (including, but not limited to, the first isolated mRNA, the second isolated mRNA or third isolated mRNA described herein), an isolated polynucleotide, a polynucleotide encoding a polypeptide, polynucleotides, and nucleic acids encoding polypeptides, including those described herein and a delivery vehicle composition, said delivery vehicle composition comprising Compound 140, DSPC, cholesterol, and DMG-PEG2000, is suspended in a sucrose-containing citrate buffer at a pH between pH 5.0 and pH 6.0, e.g., at pH 5.5. In some aspects, the pharmaceutical formulation comprises the above delivery vehicle composition and an isolated polynucleotide encoding a polypeptide comprising an amino acid sequence having at least about 70%, alternatively at least about 75%, alternatively at least about 80%, alternatively at least about 85%, alternatively at least about 90%, alternatively at least about 95% amino acid sequence identity with a sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17. In some aspects, the pharmaceutical formulation comprises the above delivery vehicle composition and an isolated polynucleotide encoding a polypeptide comprising an amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17. In some aspects, the pharmaceutical formulation includes the above delivery vehicle composition and an isolated mRNA comprising a sequence that has at least about 70%, alternatively at least about 75%, alternatively at least about 80%, alternatively at least about 85%, alternatively at least about 90%, alternatively at least about 95% nucleic acid sequence identity to SEQ ID NO: 4, SEQ ID NO: 6, SEQ ID NO: 9, SEQ ID NO: 10, SEQ ID NO: 12, SEQ ID NO: 14, SEQ ID NO: 16, or SEQ ID NO: 18.

In some aspects, the mRNA encodes for a human papillomavirus (HPV) protein or a functional fragment thereof. In various cases, the mRNA encodes for the HPV E6 protein and/or the HPV E7 protein, a variant thereof, or a functional fragment of any of the foregoing. In some aspects, the HPV protein is from HPV subtype HPV 16, 18, 31, 33, 35, 39, 45, 51, 52, 56, 58, 59, 66, and/or 68. In various ca aspects ses, the HPV protein is from HPV subtype HPV 16 and/or HPV 18.

In some aspects, the pharmaceutical formulation includes the above delivery vehicle composition and a first isolated mRNA has at least about 80% nucleic acid sequence identity to SEQ ID NO: 12 or SEQ ID NO: 18; a second isolated mRNA that has at least about 80% nucleic acid sequence identity to SEQ ID NO:20; and a third isolated mRNA has at least about 80% nucleic acid sequence identity to SEQ ID NO:23 or SEQ ID NO:26. In another aspect, the first isolated mRNA has at least about 80% nucleic acid sequence identity to SEQ ID NO:18 and the third isolated mRNA has at least about 80% nucleic acid sequence identity to SEQ ID NO:26.

In some aspects, the pharmaceutical formulation includes the above delivery vehicle composition and a first isolated mRNA that encodes a membrane-stabilized LIGHT, a second isolated mRNA that encodes interleukin-12, a third isolated mRNA that encodes HPV16 E6 E7.

Further disclosed herein is a pharmaceutical composition or formulation comprising the delivery vehicle complexes or multicomponent delivery systems described herein and a pharmaceutically acceptable excipient. In some cases, the pharmaceutical composition is suitable for intramuscular (IM), intratumoral (IT), intracervical, paracervical and/or endocervical administration, e.g., E-CERVIC route of administration, as well as intravulval, intravaginal, intrapenile, intra-anal, and intraoropharyngeal.

Also disclosed herein is a method of delivering one or more polyanionic compounds, e.g., one or more mRNA (including, but not limited to the first isolated mRNA, the second isolated mRNA or third isolated mRNA described herein), an isolated polynucleotide, a polynucleotide encoding a polypeptide, polynucleotides, and nucleic acids encoding polypeptides, including those described herein, to a cell, including contacting the cell with a pharmaceutical formulation or multicomponent delivery system comprising a delivery vehicle complex described herein. In some aspects, the cell is a muscle cell, an epithelial cell, a tumor cell, or a combination of two or all three. In some aspects, the cell is a cervical cell. In some aspects, the cell is a cervical epithelial cell. In some aspects, the cell is a cervical squamous intraepithelial neoplasia cell. In some aspects, the cell is a cervical dysplasia. In some aspects, the polyanionic compound is an mRNA that encodes for a peptide, a protein, or a fragment of any of the foregoing, and the cell expresses the peptide, the protein, or the fragment after being contacted with the delivery vehicle complex.

Also disclosed herein is a method of forming the delivery vehicle complex disclosed herein, including contacting a compound or salt of Formula (I) with the polyanionic compound (such as an mRNA). In some cases, the method includes admixing a solution comprising the compound or salt of Formula (I) with a solution comprising the polyanionic compound (e.g., an mRNA).

Also disclosed herein are vaccines including a delivery vehicle complex disclosed herein or a pharmaceutical composition disclosed herein. Also disclosed are vaccines including a delivery vehicle complex disclosed herein or a pharmaceutical composition disclosed herein for use in the treatment or prevention of cancer. Also disclosed are methods of treating or preventing cancer in a patient, comprising administering to the patient a delivery vehicle complex disclosed herein or a pharmaceutical composition disclosed herein. In some aspects, the administering is to treat cervical dysplasia (cervical intraepithelial neoplasia, or CIN), a precancerous condition in which abnormal cells grow on the surface of the cervix. In some cases, the cancer is cervical cancer, head and neck cancer, B-cell lymphoma, T-cell lymphoma, prostate In another aspect, the composition is configured to be administered as an injectable preparation. In another aspect, the composition further includes one or more one or more therapeutically acceptable carriers, therapeutically acceptable diluents, therapeutically acceptable excipients or other therapeutic agents. In yet another aspect, the therapeutically acceptable excipients are selected from the group including of salts, buffering agents, preservatives, antiadherents, antioxidants, binders, coatings, compression aids, disintegrants, dyes, emollients, emulsifiers, fillers, film formers, coatings, flavors, fragrances, glidants, lubricants, sorbents, suspending or dispersing agents, sweeteners, and waters of hydration.

One aspect of the disclosure is a method of administering to a subject in need thereof, a therapeutically effective amount of a composition of the disclosure. In an aspect, the composition is administered as an injectable. In another aspect, the composition is configured to be administered intratumorally to the subject in need thereof.

One aspect of the disclosure is a kit including any one of the disclosed compositions and instructions for use. In another aspect, the instructions for use include instructions for intratumoral administration and/or intratumoral administration in combination with injection at another site. In yet another aspect, the kit further includes at least one of a therapeutic nucleic acid, drug, therapeutic agent, diagnostic agent, or prophylactic agent.

BRIEF DESCRIPTION OF THE DRAWINGS

Various aspects of the present disclosure will now be described, by way of example only, with reference to the attached Figures, wherein:

FIG. 3A is an illustration of an isolated mRNA according to an aspect of the disclosure. FIG. 3B is an illustration of an isolated mRNA that may encode a tumor associated antigen according to an aspect of the disclosure. FIG. 3C is an illustration of an isolated mRNA that may encode a tumor associated antigen according to an aspect of the disclosure.

FIG. 19A shows IFNg ELISpot responses in HPV16E7 peptide mix pulsed splenocytes from nanoparticle formulated HPV16E6E7 mRNA vaccinated mice. FIG. 19B shows tetramer positive (E7-specific) CD8 T cell frequency in splenocytes from nanoparticle formulated HPV16E6E7 mRNA vaccinated mice. FIG. 19C shows anti-E7 immunoglobulin responses in HPV16E6E7 mRNA vaccinated mice.

DETAILED DESCRIPTION

Figure 1A:
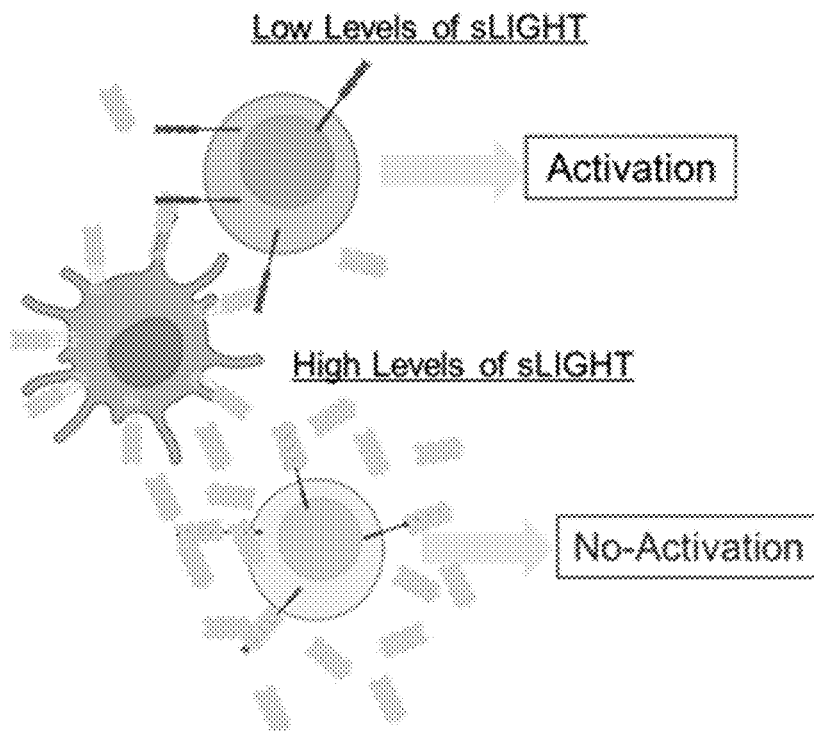
FIGS. 1A and 1B depict the inhibition of the activation of membrane-stabilized LIGHT by soluble LIGHT.

Unless otherwise defined, all technical and scientific terms used herein have the same meaning as commonly understood by one of ordinary skill in the art to which the methods described herein belong. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

The singular form "a", "an" and "the" include plural referents unless the context clearly dictates otherwise. These articles refer to one or to more than one (i.e., to at least one). The term "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z".

The term "about" as used in connection with a numerical value throughout the specification and the claims denotes an interval of accuracy, familiar and acceptable to a person skilled in the art. In general, such interval of accuracy is +/−10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

The term "exemplary" means serving as a non-limiting example, instance, or illustration. As utilized herein, the terms "e.g.," and "for example" set off lists of one or more non-limiting aspects, examples, instances, or illustrations.

As used herein, the term "similarity" refers to the overall relatedness between polymeric molecules, e.g., between polynucleotide molecules (e.g., DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions.

As used herein, the term "substantially" refers to the qualitative condition of exhibiting total or near-total extent or degree of a characteristic or property of interest. Biological and chemical phenomena rarely, if ever, go to completion and/or proceed to completeness or achieve or avoid an absolute result. The term "substantially" is therefore used herein to capture the potential lack of completeness inherent in many biological and chemical phenomena. For example, "substantially" may refer to being within at least about 20%, alternatively at least about 10%, alternatively at least about 5% of a characteristic or property of interest.

The terms "nucleic acid sequence," "nucleotide sequence," or "polynucleotide sequence" are used interchangeably and refer to a continuous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Example nucleic acids or polynucleotides of the disclosure include, but are not limited to, ribonucleic acids (RNAs) or deoxyribonucleic acids (DNAs).

The phrase "nucleotide sequence encoding" or "encoding" refers to the nucleic acid (e.g., an mRNA or DNA molecule) coding sequence that encodes a polypeptide. As used herein, the terms "coding region" and "coding sequence", refer to an Open Reading Frame (ORF) in a polynucleotide that upon expression, yields a polypeptide or protein. The coding sequence can further include initiation and termination signals operably linked to regulatory elements, including a promoter and polyadenylation signal capable of directing expression in the cells of an individual or mammal to which the nucleic acid is administered. The coding sequence can further include sequences that encode signal peptides.

The term "polynucleotide" as used herein refers to polymers of nucleotides of any length, including ribonucleotides, deoxyribonucleotides, analogs thereof, or mixtures thereof. Aspects of this disclosure include compositions including polynucleotides having a length of 18-25 nucleotides (e.g., 18-mers, 19-mers, 20-mers, 21-mers, 22-mers, 23-mers, 24-mers, or 25-mers), or medium-length polynucleotides having a length of 26 or more nucleotides (e.g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e.g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length.

Where a polynucleotide is double-stranded, its length may be similarly described in terms of base pairs. This term refers to the primary structure of the molecule. Thus, the term includes triple-, double- and single-stranded deoxyribonucleic acid ("DNA"), as well as triple-, double- and single-stranded ribonucleic acid ("RNA"). More particularly, the term "polynucleotide" includes polydeoxyribonucleotides (containing 2-deoxy-D-ribose), polyribonucleotides (containing D-ribose), including tRNA, rRNA, hRNA, siRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA.

Nucleotides are referred to by their commonly accepted single-letter codes. Unless otherwise indicated, nucleic acids are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, and U represents uracil.

The T bases in the codon maps disclosed herein are present in DNA, whereas the T bases may be replaced by U bases in corresponding RNAs. For example, a codon-nucleotide sequence disclosed herein in DNA form, e.g., a vector or an in vitro translation (IVT) template, may have its T bases transcribed as U based in its corresponding transcribed mRNA. In this respect, both codon-optimized DNA sequences (comprising T) and their corresponding RNA sequences (comprising U) are considered codon-optimized nucleotide sequences of the present disclosure. Equivalent codon-maps can be generated by replacing one or more bases with non-natural bases. Thus, e.g., a TTC codon (DNA map) may correspond to a UUC codon (RNA map), which in turn may correspond to a 'P'C codon (RNA map in which U has been replaced with pseudouridine).

Standard A-T and G-C base pairs form under conditions that allow the formation of hydrogen bonds between the N3-H and C4-oxy of thymidine and the N1 and C6-NH2, respectively, of adenosine and between the C2-oxy, N3, and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base, which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine.

Usually RNA may be obtainable by transcription of a DNA sequence, e.g., inside a cell. In eukaryotic cells, transcription is typically performed inside the nucleus or the mitochondria. In vivo, transcription of DNA usually results in the so-called premature RNA (also called pre-mRNA, precursor mRNA or heterogeneous nuclear RNA) which has to be processed into so-called messenger RNA, usually abbreviated as mRNA. Processing of the premature RNA, e.g. in eukaryotic organisms, comprises a variety of different posttranscriptional modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5' untranslated region ("5'UTR"), an open reading frame, optionally a 3' untranslated region ("3'UTR") and a poly(A) tail.

As used herein, the term "messenger RNA" (mRNA) refers to any polynucleotide that encodes a polypeptide of interest and is capable of being translated to produce the encoded polypeptide in vitro, in vivo, in situ, or ex vivo.

In addition to messenger RNA, several non-coding types of RNA exist which may be involved in regulation of transcription and/or translation, and immunostimulation. Within the present disclosure the term "RNA" further encompasses any type of single stranded (ssRNA) or double stranded RNA (dsRNA) molecule known in the art, such as viral RNA, retroviral RNA and replicon RNA, small interfering RNA (siRNA), antisense RNA (asRNA), circular RNA (circRNA), ribozymes, aptamers, riboswitches, immunostimulating/immunostimulatory RNA, transfer RNA (tRNA), ribosomal RNA (rRNA), small nuclear RNA (snRNA), small nucleolar RNA (snoRNA), microRNA (miRNA), and Piwi-interacting RNA (piRNA).

As used herein "5'-CAP" (or a 5'-CAP-Structure) is typically a modified nucleotide (CAP analogue), particularly a guanine nucleotide, added to the 5' end of an mRNA molecule. In certain implementations, the 5'-CAP is added using a 5'-5'-triphosphate linkage (also named m7GpppN). Further examples of 5'-CAP structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures may be used in the context of the present disclosure to modify the RNA sequence of the present disclosure. Further modified 5'-CAP structures which may be used in the context of the present disclosure are CAP1 (additional methylation of the ribose of the adjacent nucleotide of m7GpppN), CAP2 (additional methylation of the ribose of the 2nd nucleotide downstream of the m7GpppN), CAP3 (additional methylation of the ribose of the 3rdnucleotide downstream of the m7GpppN), CAP4 (additional methylation of the ribose of the 4thnucleotide downstream of the m7GpppN), ARCA (anti-reverse CAP analogue), modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

In the context of the present disclosure, a 5' Cap structure may also be formed in chemical RNA synthesis or RNA in vitro transcription (co-transcriptional capping) using cap analogues, or a cap structure may be formed in vitro using capping enzymes (e.g., commercially available capping kits).

A cap analogue refers to a non-polymerizable di-nucleotide that has cap functionality in that it facilitates translation or localization, and/or prevents degradation of the RNA molecule when incorporated at the 5' end of the RNA molecule. Non-polymerizable means that the cap analogue will be incorporated only at the 5'terminus because it does not have a 5' triphosphate and therefore cannot be extended in the 3' direction by a template-dependent RNA polymerase.

Cap analogues include, but are not limited to, a chemical structure selected from the group consisting of m7GpppG, m7GpppA, m7GpppC; unmethylated cap analogues (e.g., GpppG); dimethylated cap analogue (e.g., m2,7GpppG), trimethylated cap analogue (e.g., m2,2,7GpppG), dimethylated symmetrical cap analogues (e.g., m7Gpppm7G), or anti reverse cap analogues (e.g., ARCA; m7,2'OmeGpppG, m7,2'dGpppG, m7,3'OmeGpppG, m7,3'dGpppG and their tetraphosphate derivatives) The synthesis of N7-(4-chlorophenoxyethyl) substituted dinucleotide cap analogues has been described recently.

As used herein, a "poly(A) tail" also called "3'-poly(A) tail" or "Poly(A) sequence" is typically a long homopolymeric sequence of adenosine nucleotides of up to about 400 adenosine nucleotides, e.g. from about 25 to about 400, from about 50 to about 400, from about 50 to about 300, from about 50 to about 250, or from about 60 to about 250 adenosine nucleotides, added to the 3' end of an mRNA. In certain implementations of the present disclosure, the poly (A) tail of an mRNA or srRNA is derived from a DNA template by RNA in vitro transcription. Alternatively, the poly(A) sequence may also be obtained in vitro by common methods of chemical synthesis without being necessarily transcribed from a DNA-progenitor. Moreover, poly(A) sequences, or poly(A) tails may be generated by enzymatic polyadenylation of the RNA.

A stabilized nucleic acid, typically, exhibits a modification increasing resistance to in vivo degradation (e.g. degradation by an exo- or endo-nuclease) and/or ex vivo degradation (e.g. by the manufacturing process prior to composition administration, e.g. in the course of the preparation of the composition to be administered). Stabilization of RNA can, e.g., be achieved by providing a 5'-CAP-Structure, a poly(A) tail, or any other UTR-modification. Stabilization can also be achieved by backbone-modification (e.g., use of synthetic backbones such as phosphorothioate) or modification of the G/C-content or the C-content of the nucleic acid. Various other methods are known in the art and conceivable in the context of the disclosure, to stabilize or otherwise improve the function of the nucleic acid. Provided herein, therefore, are polynucleotides which have been designed to improve one or more of the stability and/or clearance in tissues, receptor uptake and/or kinetics, cellular access, engagement with translational machinery, RNA half-life, translation efficiency, immune evasion, immune induction (for vaccines), protein production capacity, secretion efficiency (when applicable), accessibility to circulation, protein half-life and/or modulation of a cell's status, function and/or activity.

As used herein, a "therapeutic polynucleotide" refers to a polynucleotide (e.g., an mRNA) that may be part of a therapeutic polynucleotide composition for delivery to a subject to treat a symptom, disease, or condition in a subject; prevent a symptom, disease, or condition in a subject; or to improve or otherwise modify the subject's health.

As used herein, a "therapeutic polynucleotide composition" (or "therapeutic composition" for short) may refer to a composition including one or more therapeutic polynucleotides (e.g., mRNA) encapsulated by a delivery vehicle, which composition may be administered to a subject in need thereof using any suitable administration routes, such as intratumoral, intramuscular, etc. injection. An example of a therapeutic polynucleotide composition is an mRNA (therapeutic) nanoparticle comprising at least one mRNA encapsulated by a delivery vehicle molecule. An mRNA vaccine is one example of a therapeutic polynucleotide composition. A therapeutic composition may be administered in an "effective amount". An "effective amount" includes a "therapeutically effective amount" and a "prophylactically effective amount." The term "therapeutically effective amount" refers to an amount effective in treating and/or ameliorating a disease or condition in a subject. The term "prophylactically effective amount" refers to an amount effective in preventing and/or substantially lessening the chances of a disease or condition in a subject.

As used herein, "delivery vehicle" refers to any substance that facilitates, at least in part, the in vivo, in vitro, or ex vivo delivery of a polynucleotide (e.g., therapeutic polynucleotide) to targeted cells or tissues (e.g., tumors, etc.). Referring to something as a delivery vehicle need not exclude the possibility of the delivery vehicle also having therapeutic effects. Some versions of a delivery vehicle may provide additional therapeutic effects. In some versions, a delivery vehicle may be a peptoid molecule, such as an amino-lipidated peptoid molecule, that may be used to at least partially encapsulate mRNA. The term "DV" may also be used herein as a shorthand for "delivery vehicle." In some aspects, the mRNA for use in the delivery vehicle complexes herein comprise an mRNA comprising at least one region encoding a peptide (e.g., a polypeptide), or protein, or functional fragment of the foregoing. As used herein, "functional fragment" refers to a fragment of a peptide, (e.g., a polypeptide), or protein that retains the ability to induce an immune response.

As used herein, "multimodal" refers to a therapeutic composition that includes at least two different therapeutic polynucleotides, alternatively at least three different therapeutic polynucleotides.

As used herein, the term "identity" refers to the overall monomer conservation between polymeric molecules, e.g., between polynucleotide molecules (e.g., DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequence for optimal alignment and non-identical sequences can be disregarded for comparison purposes). In certain aspects, the length of a sequence aligned for comparison purposes is at least about 30%, at least about 40%, at least about 50%, at least about 60%, at least about 70%, at least about 80%, at least about 90%, at least about 95%, at least about 96% at least about 97%, at least about 98%, at least about 99% or at least about 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources and for alignment of both protein and nucleotide sequences. One suitable program to determine percent sequence identity is bl2seq, part of the BLAST suite of programs available from the U.S. government's National Center for Biotechnology Information BLAST website (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI).

Sequence alignments can be conducted using methods such as, but not limited to, MAFFT, Clustal (ClustalW, Clustal X or Clustal Omega), or MUSCLE.

Different regions within a single polynucleotide or polypeptide target sequence that aligns with a polynucleotide or polypeptide reference sequence can each have their own percent sequence identity.

As used herein, the term "isolated" refers to a substance or entity that has been separated from at least some of the components with which it was associated (whether in nature or in an experimental setting). Isolated substances (e.g., nucleotide sequence or protein sequence) can have varying levels of purity in reference to the substances from which they have been associated. Isolated substances and/or entities can be separated from at least about 10%, about 20%, about 30%, about 40%, about 50%, about 60%, about 70%, about 80%, about 90%, or more of the other components with which they were initially associated. In some aspects, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The term "substantially isolated" means that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those that have been purified to the degree that they are no longer in a form in which they are found in nature. In some aspects, a polynucleotide, vector, polypeptide, or composition that is isolated is substantially pure.

As used herein, a "native" or "naturally occurring" polynucleotide sequence means a polynucleotide sequence existing in nature without artificial aid. A synthetic polynucleotide sequence that is identical to a wild polynucleotide sequence is, for the purposes of this disclosure, considered a naturally occurring sequence. For example, a wild type polynucleotide sequence is a naturally occurring polynucleotide sequence, but not limited thereto. A naturally occurring polynucleotide sequence also refers to variant polynucleotide sequences as found in nature that differ from wild type. For example, allelic variants and naturally occurring recombinant polynucleotide sequences due to hybridization or horizontal gene transfer, but not limited thereto. The term, "wild type" when used herein with reference to a polynucleotide refers to a naturally occurring, non-mutant form of a polynucleotide.

The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine). The term, as used herein, refers to proteins, polypeptides, and peptides of any size, structure, or function. Polypeptides include gene products, naturally occurring polypeptides, synthetic polypeptides, homologs, orthologs, paralogs, fragments and other equivalents, variants, and analogs of the foregoing. A polypeptide can be a single polypeptide or can be a multi-molecular complex such as a dimer, trimer, or tetramer. They can also comprise single chain or multichain polypeptides. Most commonly, disulfide linkages are found in multichain polypeptides. The term polypeptide can also apply to amino acid polymers in which one or more amino acid residues are an artificial chemical analogue of a corresponding naturally occurring amino acid. In some aspects, a "peptide" can be less than or equal to about 50 amino acids long, e.g., about 5, 10, 15, 20, 25, 30, 35, 40, 45, or 50 amino acids long.

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues.

LIGHT is a multi-domain protein that belongs to the TNF superfamily members. LIGHT consists of intracellular, transmembrane, and receptor binding domains, as well as linker region connecting the transmembrane to the receptor binding domain and plays an important role in innate immunity and adaptive immunity.

LIGHT is expressed by activated T cells, NK cells, and immature dendritic cells. Herpes Virus Entry Mediator (HVEM) and Lymphotoxin-β Receptor (LTOR) are the two different receptors LIGHT primarily binds and elicits different functions in cell-type dependent manner. LIGHT binds to HVEM and LTOR by its homotrimeric form and also functions soluble and membrane-stabilized forms. These proteases are reported to be overexpressed in many tumors including HPV-driven cancers (e.g., cervical cancer).

Figure 1B:
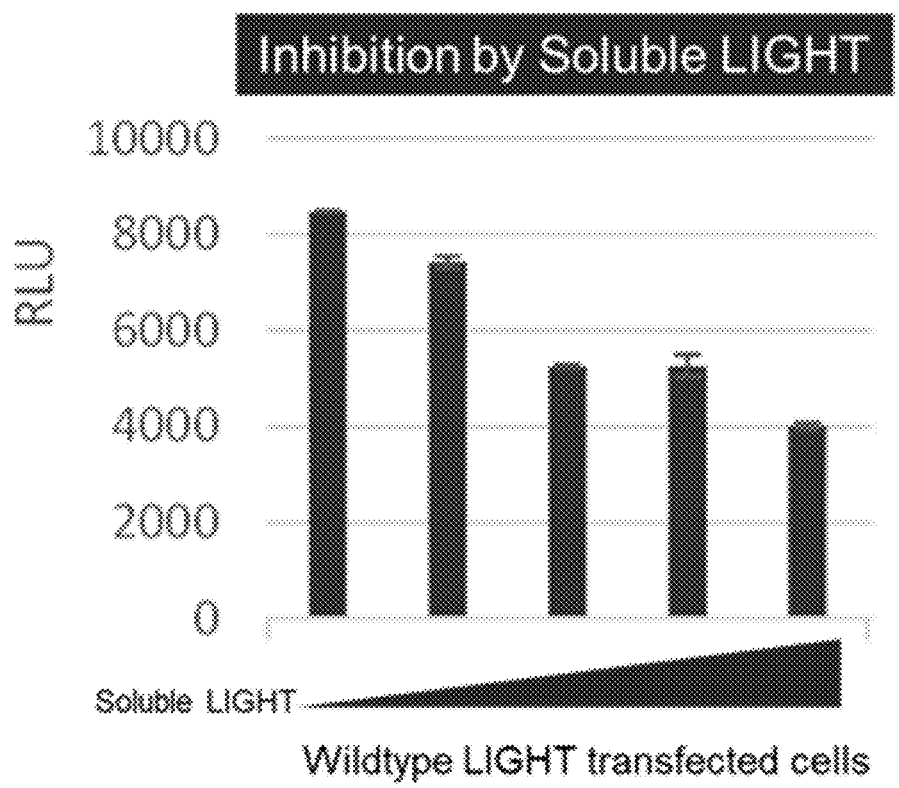
Figure 2A:
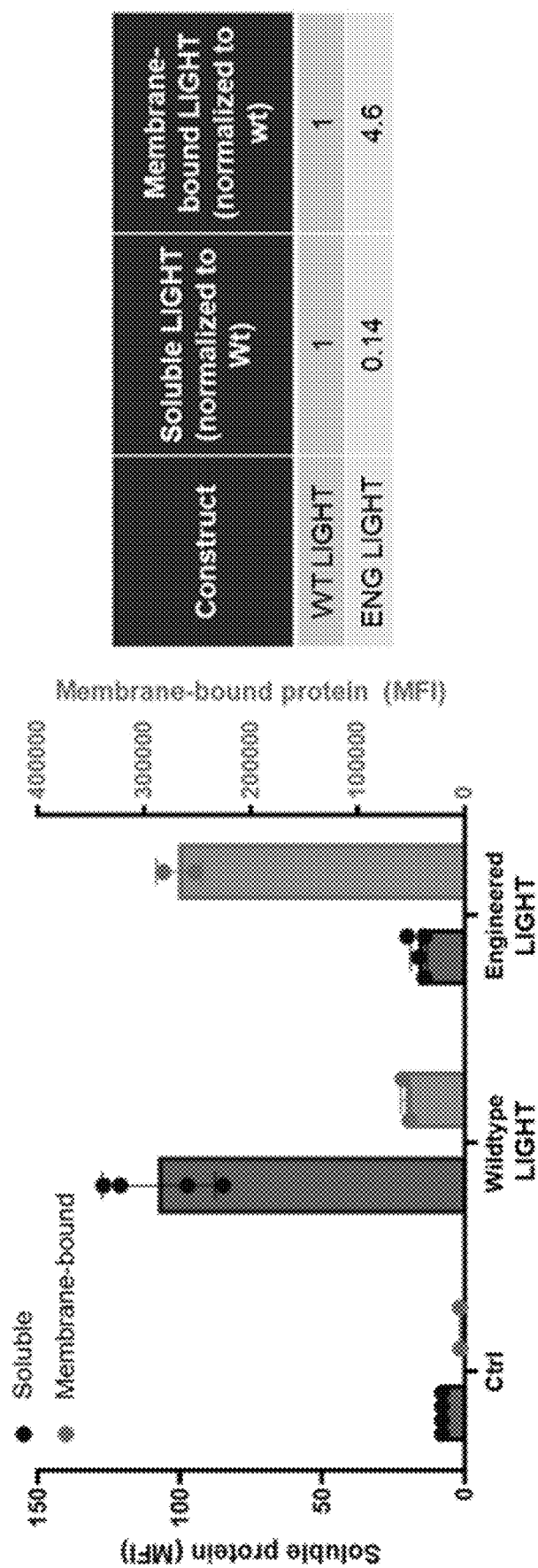
FIG. 2A-2D are graphs illustrating the membrane-bound protein produced by the membrane-stabilized LIGHT generated according to an aspect of this disclosure as compared to soluble LIGHT.
Figure 2B:
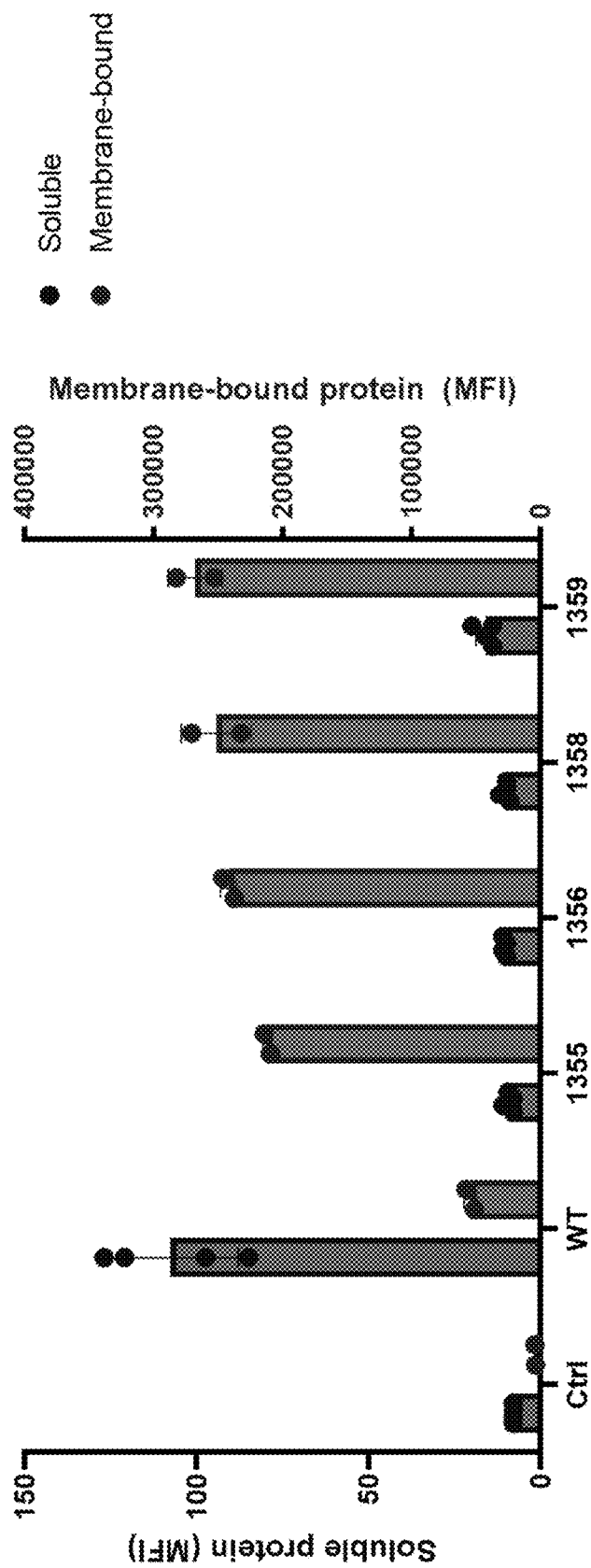
Figure 2C:
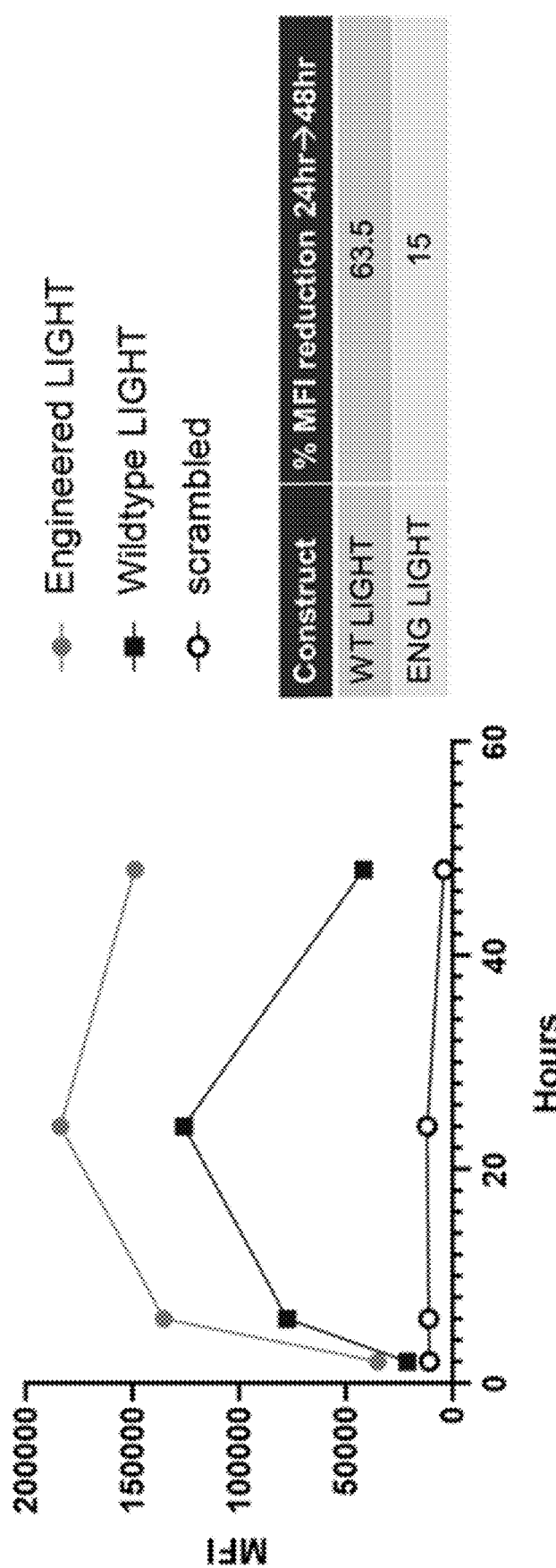
Figure 2D:
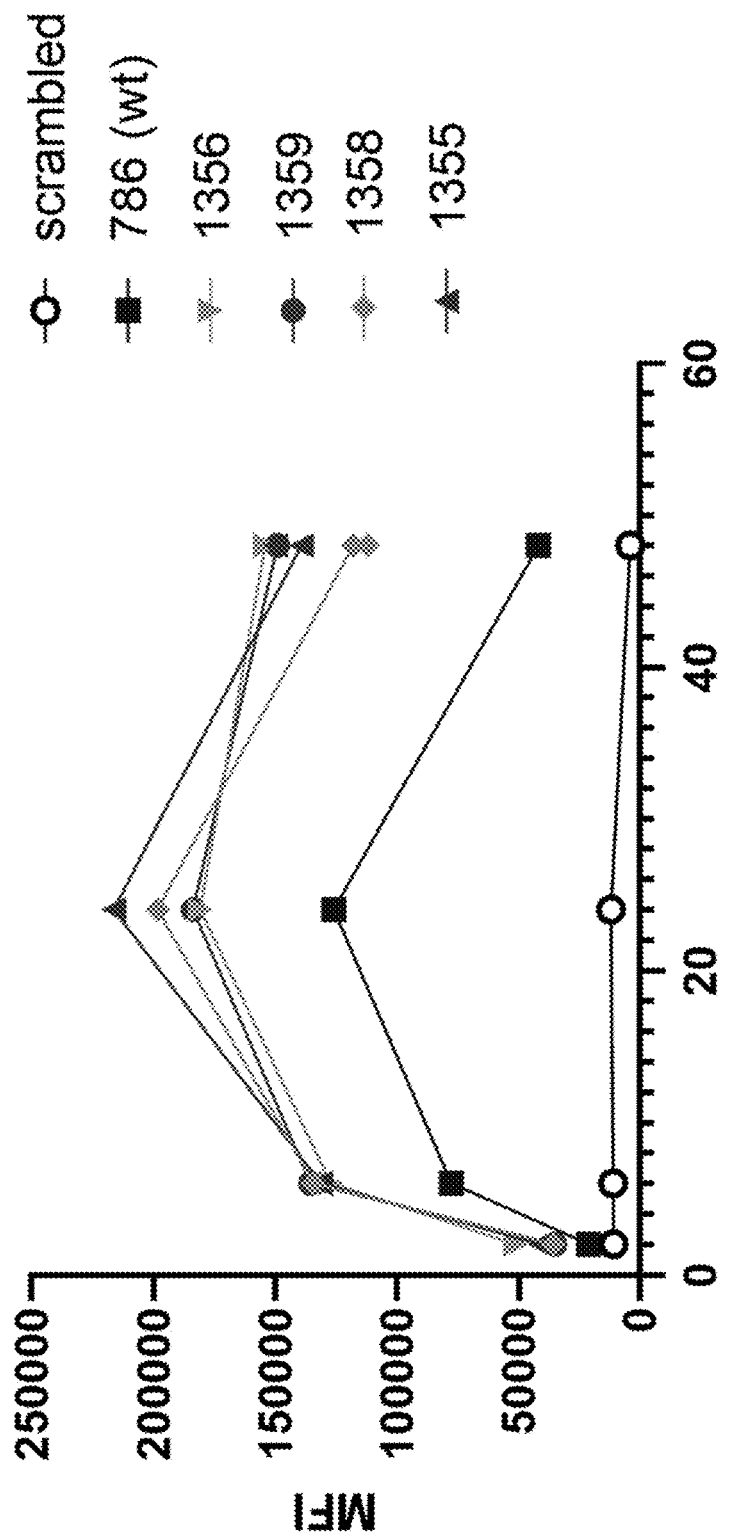

It has been surprisingly found that novel membrane-stabilized LIGHT constructs as described herein have superior activity as compared to wild-type ("soluble") LIGHT, in the activation of HVEM in a dose-dependent manner. Therapeutics that comprise membrane-stabilized LIGHT ("engineered" or "ENG") also cause increased T cell proliferation as compared to soluble (wild-type) LIGHT and are more functional as a co-stimulant. As shown in FIGS. 1A and 1B, the presence of soluble LIGHT decreases the ability of membrane-stabilized LIGHT to activate HVEM. The incorporation of a modified membrane-stabilized LIGHT into a cancer immunotherapy allows for the effective targeting cancers, such as HPV-driven cancers.

In some aspects of the disclosure, suitable membrane-stabilized LIGHT proteins, protein fragments, peptides, or polypeptides (collectively "membrane-stabilized LIGHT")

can be generated by modifying soluble LIGHT. In a non-limiting example, a section of the transmembrane region of soluble LIGHT can be replaced by a linker or modified trimerization domains to generate membrane-stabilized LIGHT. In one aspect, this membrane-stabilized LIGHT comprises modified trimerization domains, such as Collagen, Foldon and Leucine Zipper. In some aspects, the linker may be, but is not limited to, an antibody linker or a peptide linker.

In some aspects, to generate the novel membrane-stabilized LIGHT described herein, the soluble LIGHT primary amino acid sequence was examined for the potential transmembrane region and identified positions occupied by glycine, as it can serve as helix terminating residues. This resulted in potential sites for the N-terminus of the linker to be either position 66 or 75. In order to identify the C-terminus of the linker region, the crystal structure of the receptor binding domain of the LIGHT was examined. Although the protein sequence utilized for the crystal structure determination starts with residue 83, structured region in the structure starts with residue 92 only. Therefore, the positions 83 and 92 were identified as being the C-terminus of the linker region connecting the transmembrane and the receptor binding domain. With this linker region prediction information, the segment in the LIGHT from residues 66 or 75 to 83 or 92 were replaced by linker. RNA-1495 corresponds to a single mRNA sequence (SEQ ID NO: 18) encoding the native secreted human LIGHT engineered to replace amino acids #66-92 with a novel 10 amino acid linker sequence to enhance membrane stability and expression, and is presented herein as SEQ ID NO: 17. This construct, also referred to as "ENG hLIGHT" is designed to be a surface-bound Type II membrane protein. It will be understood that any suitable polynucleotide sequence encoding SEQ ID NO: 17 is contemplated as useful in the embodiments described herein.

As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can also be comprised of amino acids, peptides, proteins, antibodies, and/or polynucleotides.

Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Other examples include, but are not limited to, cleavable moieties within the linker, such as, for example, a disulfide bond (—S—S—) or an azo bond (—N=N—), which can be cleaved using a reducing agent or photolysis.

In some aspects a (Gly4Ser)n linker was used. In some examples, n is an integer greater than 1. For example, n can be 1, 2, 3, 4, 5, 6, 7, 8, 9, or 10. In some examples, n can be greater than 10. In some examples, the linker sequence is an antibody, connecting the IgG1 variable domain and the constant domain (CH1) as well as that of CH1 and CH2. In some aspects, the linker comprises the sequence SSAS-TDKTHT (SEQ ID NO:54).

Non-limiting examples of membrane-stabilized human LIGHT made in accordance with this disclosure are disclosed in Table 1. Wild-type soluble human LIGHT (SEQ ID NO: 1) is also included for reference.

TABLE 1

| SEQ ID NO | Descriptor | Amino Acid Sequence |
|---|---|---|
| 1 | Human Wild Type LIGHT (786) aa | MEESVVRPSVFVVDGQTDIPFTRLGRSHRRQSCSVARV GLGLLLLLMGAGLAVQGWFLLQLHWRLGEMVTRLPD GPAGSWEQLIQERRSHEVNPAAHLTGANSSLTGSGGPL LWETQLGLAFLRGLSYHDGALVVTKAGYYYIYSKVQL GGVGCPLGLASTITHGLYKRTPRYPEELELLVSQQSPCG RATSSSRVWWDSSFLGGVVHLEAGEEVVVRVLDERLV RLRDGTRSYFGAFMV |
| 3 | LIGHT ICD + TM (1-75; . . . PDG) + Gly4Ser + LIGHT 83-240 (1352) aa | MEESVVRPSVFVVDGQTDIPFTRLGRSHRRQSCSVARV GLGLLLLLMGAGLAVQGWFLLQLHWRLGEMVTRLPD GGGGGSLIQERRSHEVNPAAHLTGANSSLTGSGGPLLW ETQLGLAFLRGLSYHDGALVVTKAGYYYIYSKVQLGG VGCPLGLASTITHGLYKRTPRYPEELELLVSQQSPCGRA TSSSRVWWDSSFLGGVVHLEAGEKVVVRVLDERLVRL RDGTRSYFGAFMV |
| 5 | LIGHT ICD + TM (1-75; . . . PDG) + (Gly4Ser)2 + LIGHT 92-240 (1353) aa | MEESVVRPSVFVVDGQTDIPFTRLGRSHRRQSCSVARV GLGLLLLLMGAGLAVQGWFLLQLHWRLGEMVTRLPD GGGGGSGGGGSVNPAAHLTGANSSLTGSGGPLLWETQ LGLAFLRGLSYHDGALVVTKAGYYYIYSKVQLGGVGC PLGLASTITHGLYKRTPRYPEELELLVSQQSPCGRATSSS RVWWDSSFLGGVVHLEAGEKVVVRVLDERLVRLRDG TRSYFGAFMV |
| 7 | LIGHT ICD + TM (1-66; . . . RLG) + (Gly4Ser)2 + LIGHT 83-240 (1354) aa | MEESVVRPSVFVVDGQTDIPFTRLGRSHRRQSCSVARV GLGLLLLLMGAGLAVQGWFLLQLHWRLGGGGSGGG GSLIQERRSHEVNPAAHLTGANSSLTGSGGPLLWETQL GLAFLRGLSYHDGALVVTKAGYYYIYSKVQLGGVGCP LGLASTITHGLYKRTPRYPEELELLVSQQSPCGRATSSSR VWWDSSFLGGVVHLEAGEKVVVRVLDERLVRLRDGT RSYFGAFMV |
| 9 | LIGHT ICD + TM (1-66; . . . RLG) + (Gly4Ser)3 + LIGHT 92-240 | MEESVVRPSVFVVDGQTDIPFTRLGRSHRRQSCSVARV GLGLLLLLMGAGLAVQGWELLQLHWRLGGGGSGGG GSGGGGSVNPAAHLTGANSSLTGSGGPLLWETQLGLAF LRGLSYHDGALVVTKAGYYYIYSKVQLGGVGCPLGLA |

TABLE 1-continued

| SEQ ID NO | Descriptor | Amino Acid Sequence |
|---|---|---|
| | (1355) aa | STITHGLYKRTPRYPEELELLVSQQSPCGRATSSSRVWW DSSFLGGVVHLEAGEKVVVRVLDERLVRLRDGTRSYF GAFMV |
| 11 | LIGHT ICD + TM (1-66; . . . RLG) + (Gly4Ser)$_2$ + LIGHT 92-240 (1356) aa | MEESVVRPSVFVVDGQTDIPFTRLGRSHRRQSCSVARV GLGLLLLLMGAGLAVQGWELLQLHWRLGGGGSGGG GSVNPAAHLTGANSSLTGSGGPLLWETQLGLAFLRGLS YHDGALVVTKAGYYYIYSKVQLGGVGCPLGLASTITH GLYKRTPRYPEELELLVSQQSPCGRATSSSRVWWDSSF LGGVVHLEAGEKVVVRVLDERLVRLRDGTRSYFGAFM V |
| 13 | LIGHT ICD + TM (1-75; . . . PDG) + SSAST + LIGHT 83-240 (1357) aa | MEESVVRPSVFVVDGQTDIPFTRLGRSHRRQSCSVARV GLGLLLLLMGAGLAVQGWFLLQLHWRLGEMVTRLPD GSSASTLIQERRSHEVNPAAHLTGANSSLTGSGGPLLWE TQLGLAFLRGLSYHDGALVVTKAGYYYIYSKVQLGGV GCPLGLASTITHGLYKRTPRYPEELELLVSQQSPCGRAT SSSRVWWDSSFLGGVVHLEAGEKVVVRVLDERLVRLR DGTRSYFGAFMV |
| 15 | LIGHT ICD + TM (1-75; . . . PDG) + SSASTDKTHT + LIGHT 92-240 (1358) aa | MEESVVRPSVFVVDGQTDIPFTRLGRSHRRQSCSVARV GLGLLLLLMGAGLAVQGWFLLQLHWRLGEMVTRLPD GSSASTDKTHTVNPAAHLTGANSSLTGSGGPLLWETQL GLAFLRGLSYHDGALVVTKAGYYYIYSKVQLGGVGCP LGLASTITHGLYKRTPRYPEELELLVSQQSPCGRATSSSR VWWDSSFLGGVVHLEAGEKVVVRVLDERLVRLRDGT RSYFGAFMV |
| 17 | LIGHT ICD + TM (1-66; . . . RLG) + SSASTDKTHT + LIGHT 92-240 (1359, aka 1495) aa | MEESVVRPSVFVVDGQTDIPFTRLGRSHRRQSCSVARV GLGLLLLLMGAGLAVQGWFLLQLHWRLGSSASTDKTH TVNPAAHLTGANSSLTGSGGPLLWETQLGLAFLRGLSY HDGALVVTKAGYYYIYSKVQLGGVGCPLGLASTITHGL YKRTPRYPEELELLVSQQSPCGRATSSSRVWWDSSFLG GVVHLEAGEKVVVRVLDERLVRLRDGTRSYFGAFMV |

ICD—Intracellular Domain of the LIGHT
TM—Transmembrane region

As shown in FIGS. 2A-2D, it has been surprisingly found that the membrane-stabilized LIGHT ("Engineered LIGHT") generated according to this disclosure has significantly higher cell-surface expression of membrane-bound protein and a significantly lower soluble fraction compared to soluble (wild type) LIGHT. This enhanced membrane stability for the disclosed membrane-stabilized LIGHT may increase the beneficial activity of LIGHT.

In some examples, an isolated polynucleotide may encode a membrane-stabilized LIGHT according to an aspect of this disclosure. In a non-limiting examples, the isolated polynucleotide includes at least a first isolated messenger ribonucleic acid (mRNA), at least a portion of thereof encoding a membrane-stabilized LIGHT.

The isolated polynucleotide may be configured for administration directly, configured for administration in a composition including other isolated mRNA, be encoded in one or more polynucleotides for expression in a cell, and/or may be encoded in DNA, RNA, or mRNA for administration. According to the present disclosure, a first isolated mRNA (FIG. 3A) may have the following formula:

5'UTR—Signal/Leader—mRNA coding region—
3'UTR—PolyA where "UTRs" are the untranslated regions located at the 5' and 3' ends of an mRNA construct, and "PolyA" refers to the polyadenylation site of the mRNA.

A 5'-UTR is typically understood to be a particular section of RNA. It is located 5' of the open reading frame of the mRNA. In the case of srRNA, the open reading frame encodes the viral non-structural proteins while the sequence of interest is encoded in the subgenomic fragment of the viral RNA. Thus, the 5'UTR is upstream of nsP1 open reading frame. In addition, the subgenomic RNA of the srRNA has a 5'UTR. Thus, the subgenomic RNA containing a sequence of interest encoding a protein of interest contains a 5'UTR. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'-UTR may be posttranscriptionally modified, for example by addition of a 5'-CAP. In the context of the present disclosure, a 5'UTR corresponds to the sequence of a mature mRNA or srRNA which is located between the 5'-CAP and the start codon. In one implementations, the 5'-UTR corresponds to the sequence which extends from a nucleotide located 3' to the 5'-CAP, and in certain implementations from the nucleotide located immediately 3' to the 5'-CAP, to a nucleotide located 5' to the start codon of the protein coding region and in some cases to the nucleotide located immediately 5' to the start codon of the protein coding region. The nucleotide located immediately 3' to the 5'-CAP of a mature mRNA or srRNA typically corresponds to the transcriptional start site. The term "corresponds to" means that the 5'-UTR sequence may be an RNA sequence, such as in the mRNA sequence used for defining the 5'-UTR sequence, or a DNA sequence which corresponds to such RNA sequence. In the context of the present disclosure, the term "a 5'-UTR of a gene", such as "a 5'-UTR of a NYESO1 gene", is the sequence which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence of the 5'-UTR.

Generally, the term "3'-UTR" refers to a part of the nucleic acid molecule which is located 3' (i.e. "downstream") of an open reading frame and which is not translated into protein. Typically, a 3'-UTR is the part of an RNA which is located between the protein coding region (open reading frame (ORF) or coding sequence (CDS)) and the poly(A) sequence of the mRNA. In the context of the present disclosure, the term 3'-UTR may also comprise elements, which are not encoded in the template, from which an RNA is transcribed, but which are added after transcription during maturation, e.g. a poly(A) sequence. A 3'-UTR of the RNA is not translated into an amino acid sequence.

With respect to srRNA, the 3'-UTR sequence is generally encoded by the viral genomic RNA, which is transcribed into the respective mRNA during the gene expression process. The genomic sequence is first transcribed into pre-mature mRNA. The pre-mature mRNA is then further processed into mature mRNA in a maturation process. This maturation process comprises 5'capping. In the context of the present disclosure, a 3'-UTR corresponds to the sequence of a mature mRNA or srRNA (and the srRNA subgenomic RNA), which is located between the stop codon of the protein coding region, preferably immediately 3' to the stop codon of the protein coding region for the sequence of interest, and the poly(A) sequence of the mRNA. The term "corresponds to" means that the 3'-UTR sequence may be an RNA sequence, such as in the mRNA sequence used for defining the 3'-UTR sequence, or a DNA sequence, which corresponds to such RNA sequence. In the context of the present disclosure, the term "a 3'-UTR of a gene", is the sequence, which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence (both sense and antisense strand and both mature and immature) of the 3'-UTR.

In some aspects, the 3'UTR is a modified 3'UTR and refers to a 3' UTR sequence resulting from sequence optimization. In some aspects, the 5'UTR is a modified 5'UTR and refers to a 5'UTR sequence resulting from sequence optimization. As used herein, "sequence optimization" refers to a process or series of processes by which nucleobases in a reference nucleic acid sequence are replaced with alternative nucleobases, resulting in a nucleic acid sequence with improved properties.

A non-limiting example of modified 3'UTRs (wild-type and modified) is listed in Table 2.

TABLE 2

| 3'UTR Sequence | SEQ ID NO |
|---|---|
| GCGCCGCCUCCGGGACAGUGCACCCAGGCUGCGGCCCCU CCCCCGUCCUGGAGGUUCCCCAGCCCCACUUACCGCUUA AUGCGCCAAUAAACCAAUGAACGAAGC | SEQ ID NO: 53 |

Non-limiting examples of 5'UTRs (wild-type and modified) are listed in Table 3.

TABLE 3

| 5'UTR Sequences | SEQ ID NO |
|---|---|
| CATCGGCGCTTTGCCACTTGTACCCGAGTTTTTGATTCTCAAC | SEQ ID NO: 28 |
| CATCGGCGCTTTGCCACTTGTACCCGAGTTTTTGATTCTCAACGCCACC | SEQ ID NO: 29 |
| CATCGACGCTTTGCCACTTGTACCCGAGTTTTTGATTCTCAACGCCACC | SEQ ID NO: 30 |
| CATCGACACTTTGCCACTTGTACCCGAGTTTTTGATTCTCAACGCCACC | SEQ ID NO: 31 |
| CATCGACACTTTGCCACTTGTACCCGGGTTTTTGATTCTCAACGCCACC | SEQ ID NO: 32 |
| CATCGACACTTTGCCACTTGTACCCAAGTTTTTGATTCTCAACGCCACC | SEQ ID NO: 33 |
| CATCGACACTTTGCCACTTGTACCCGAATTTTTGATTCTCAACGCCACC | SEQ ID NO: 34 |
| CATTCACACTTTGCCACTTGTACCCGAATTTTTGACTCTCAACGCCACC | SEQ ID NO: 35 |
| CATCGACACTTTGCCACTTGTACCCGAATTTTTGATCCTCAACGCCACC | SEQ ID NO: 36 |
| CATCGACACTTTGCCACTTGTACCCGAATTTTTGATTTCAACGCCACC | SEQ ID NO: 37 |
| CATTCACACTTTGCCACTTGTACCCGAATTTTCGACTCTCAACGCCACC | SEQ ID NO: 38 |
| CATTCACACTTTGCCACTTGTACCCGAATTTCCGACTCTCGCCGCCACC | SEQ ID NO: 39 |

TABLE 3-continued

| 5'UTR Sequences | SEQ ID NO |
|---|---|
| CATTCACACTTTGCCACTTGTACCGCCATTTCCGACTCTCGCCGCCACC | SEQ ID NO: 40 |
| CATTCACACTTTGCCACTTGTACCGCCATTTCCAACTCTCGCCGCCACC | SEQ ID NO: 41 |
| GCATCGACACTTTACCACTTGTACCCAAATTTTTGACTCTCAACGCCACC | SEQ ID NO: 42 |
| CCTTTCCGTCTGGCGGCAGCCATCAGGTAAGCCAAG | SEQ ID NO: 43 |
| GCATAGAAGTCTGGCGGCAGCCATCAGGTAAGCCAAG | SEQ ID NO: 44 |
| GCATAGAAGTCTGGCGGCAGCCATCAGGTAAGCCACC | SEQ ID NO: 45 |
| GCATAGAAGTCTGATCGCAGCCATCAGGTAAGCCACC | SEQ ID NO: 46 |
| GCATAGAAGTTTGATCGCAGCCATCGGATAAGCCACC | SEQ ID NO: 47 |
| GCATAGAAGTTTGATCGCAGCCATTGAATAAGCCACC | SEQ ID NO: 48 |
| GCATAGAAGTCCGATCGCAGCCATTGAATAAGCCACC | SEQ ID NO: 48 |
| CATAGAAGTCGAGACACAGCCACTAAGTAAGCCACC | SEQ ID NO: 50 |
| GAGAGAAAAGAAGAGTAAGAAGAAATATAAGAGCCACC | SEQ ID NO: 51 |
| CAUAGAAGUCGAGACACAGCCACUAAGUAAGCCACC | SEQ ID NO: 52 |

Signal/Leader refers to a suitable signal sequence, leader sequence, sorting sequence, in frame with and upstream of the mRNA coding region.

As used herein, the terms "mRNA coding region" and "mRNA coding sequence", refer to an Open Reading Frame (ORF)—a sequence that does not contain a stop codon in a given reading frame—in a polynucleotide that upon expression, yields a polypeptide or protein. The mRNA coding sequence can further include initiation and termination signals operably linked to regulatory elements, including a promoter and polyadenylation signal capable of directing expression in the cells of an individual or mammal to which the nucleic acid is administered. The coding sequence can further include sequences that encode signal peptides. In some aspects, the formula may further include a 5' cap. In some aspects, the formula may further include a PolyA tail.

In a non-limiting example, the RNA sequences for encoding membrane-stabilized human LIGHT have the following formula (See e.g., FIG. 3D):

5'UTR—Signal/Leader—mRNA membrane-stabilized human LIGHT coding region—3'UTR—PolyA In one example, the 3'UTR is modified. In another example, the 5'UTR is modified. In a further example, both the 3'UTR and 5'UTR are modified. In an example, the Signal/Leader is a secretion signal.

Non-limiting examples of the RNA sequences for encoding membrane-stabilized human LIGHT made in accordance with this disclosure are disclosed in Table 4. Wild-type soluble human LIGHT (SEQ ID NO: 2) is also included for reference.

TABLE 4

| SEQ ID NO | Descriptor | Polynucleotide Sequence: RNA |
|---|---|---|
| 2 | Wild Type (786) nt | AUGGAGGAGAGUGUCGUACGGCCCUCAGUGUUUGU<br>GGUGGAUGGACAGACCGACAUCCCAUUCACGAGGC<br>UGGGACGAAGCCACCGGAGACAGUCGUGCAGUGUG<br>GCCCGGGUGGGUCUGGGACUGUUGCUGUUGCUGAU<br>GGGGGCUGGGCUGGCCGUCCAAGGCUGGUUCCUCC<br>UGCAGCUGCACUGGCGUCUAGGAGAGAUGGUCACC<br>CGCCUGCCUGACGGACCUGCAGGCUCCUGGGAGCAG<br>CUGAUACAAGAGCGAAGAAGCCACGAGGUCAACCC<br>AGCAGCGCAUCUCACAGGGGCCAACUCCAGCUUGAC<br>CGGCAGCGGGGGGCCGCUGUUAUGGGAGACUCAGC |

TABLE 4-continued

| SEQ ID NO | Descriptor | Polynucleotide Sequence: RNA |
|---|---|---|
| | | UGGGCCUGGCCUUCCUGAGGGGCCUCAGCUACCACG<br>AUGGGGCCCUUGUGGUCACCAAAGCUGGCUACUAC<br>UACAUCUACUCCAAGGUGCAGCUGGGCGGUGUGGG<br>CUGCCCGCUGGGCCUGGCCAGCACCAUCACCCACGG<br>CCUCUACAAGCGCACACCCCGCUACCCCGAGGAGCU<br>GGAGCUGUUGGUCAGCCAGCAGUCACCCUGCGGAC<br>GGGCCACCAGCAGCUCCCGGGUCUGGUGGGACAGCA<br>GCUUCCUGGGUGGUGUGGUACACCUGGAGGCUGGG<br>GAGGAGGUGGUCGUCCGUGUGCUGGAUGAACGCCU<br>GGUUCGACUGCGUGAUGGUACCCGGUCUUACUUCG<br>GGGCUUUCAUGGUGUGA |
| 4 | LIGHT ICD + TM (1-75; . . . PDG) + Gly4Ser + LIGHT 83-240 (1352) nt | AGGCAUAGAAGUCGAGACACAGCCACUAAGUAAGC<br>CACCAUGGAAGAGUCCGUGGUGCGGCCUAGCGUGU<br>UCGUGGUCGACGGCCAGACAGAUAUCCCCUUCACCA<br>GACUGGGCAGAAGCCAUAGAAGACAGAGCUGCAGC<br>GUGGCCAGAGUUGGACUGGGCCUGCUGCUGCUCCU<br>GAUGGGCGCCGGACUGGCCGUGCAGGGCUGGUUCC<br>UGCUGCAGCUGCACUGGCGGCUGGGAGAAAUGGUC<br>ACCAGACUGCCCGACGGCGGCGGCGGCGGCAGCCUG<br>AUCCAGGAGCGGCGGAGCCACGAGGUGAACCCUGCC<br>GCUCACCUGACAGGAGCCAACAGCUCUCUGACCGGC<br>AGCGGCGGCCCCUCUGCUGUGGGAGACACAGCUGGG<br>UCUGGCUUUCCUGAGAGGCCUGAGCUACCACGACG<br>GAGCCCUGGUGGUGACCAAGGCCGGCUACUACUAC<br>AUCUACAGCAAAGUGCAACUGGGCGGCGUGGGAUG<br>UCCUCUGGGCCUGGCCUCUACAAUCACCCACGGCCU<br>UUAUAAGCGGACCCCUAGAUACCCCGAGGAACUGG<br>AACUGCUGGUGUCCCAGCAGUCUCCAUGCGGCAGA<br>GCCACCAGCUCCUCUAGAGUGUGGUGGGACAGCAG<br>CUUUCUCGGCGGAGUGGUGCACCUGGAAGCCGGCG<br>AGAAGGUGGUGGUCAGAGUGCUGGAUGAGAGACUG<br>GUGCGGCUGCGCGACGGCACCAGGUCUUACUUCGGC<br>GCUUUUAUGGUGUGAUAAGCGCCGCCUCCGGGACA<br>GUGCACCCAGGCUGCGGCCCCUCCCCCGUCCUGGAG<br>GUUCCCCAGCCCCACUUACCGCUUAAUGCGCCAAUA<br>AACCAAUGAACGAAGCAAAAAAAAAAAAAAAAAA<br>AAAAAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAAAAAAAAAAAAA<br>AAAAAAAAA |
| 6 | LIGHT ICD + TM (1-75; . . . PDG) + (Gly4Ser)$_2$ + LIGHT 92-240 (1353) nt | AGGCAUAGAAGUCGAGACACAGCCACUAAGUAAGC<br>CACCAUGGAAGAGAGCGUGGUGCGGCCUAGCGUUU<br>UCGUGGUUGACGGCCAGACCGACAUCCCAUUCACCA<br>GACUGGGCAGAAGCCACAGAAGGCAGAGCUGCAGC<br>GUGGCCAGAGUGGGCCUGGACUGCUGCUGCUGCU<br>GAUGGGCGCUGGCCUCGCCGUGCAGGGAUGGUUCC<br>UGUUGCAGCUGCAUUGGAGACUUGGGAGAUGGUC<br>ACACGGCUGCCUGAUGGCGGCGGCGGAGGCAGCGG<br>AGGAGGCGGAUCUGUGAACCCCGCCGCCACCUGAC<br>AGGCGCUAACAGCAGCCUGACCGGCAGCGGCGGUCC<br>UCUGCUGUGGGAGACACAGCUGGGCCUGGCCUUUC<br>UGAGAGGCCUGAGCUACCACGACGGCGCCCUGGUG<br>GUGACCAAGGCCGCUACUACUACAUCUACAGCAA<br>GGUGCAACUGGGCGGCGUGGGCUGCCCCUGGGCCU<br>GGCCUCAACAAUCACCCACGGCCUGUACAAGCGGAC<br>CCCUAGAUACCCCGAGGAACUGGAACUGCUGGUGU<br>CCCAGCAGUCUCCUUGUGGCAGAGCCACCAGCAGCU<br>CUAGAGUGUGGUGGGACAGCUCCUUCCUGGGAGGA<br>GUGGUGCACCUGGAAGCCGGCGAGAAGUGGUGGU<br>GCGGGUGCUGGACGAGCGGCUGGUCCGCCUCAGAG<br>AUGGCACCAGAUCUUAUUUCGGCGCUUUUAUGGUG<br>UGAUAAGCGCCGCCUCCGGGACAGUGCACCCAGGCU<br>GCGGCCCCUCCCCCGUCCUGGAGGUUCCCCAGCCCC<br>ACUUACCGCUUAAUGCGCCAAUAAACCAAUGAACG<br>AAGCAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAAAAAAAAAA |
| 8 | LIGHT ICD + TM (1-66; . . . RLG) + (Gly4Ser)$_2$ + LIGHT 83-240 | AGGCAUAGAAGUCGAGACACAGCCACUAAGUAAGC<br>CACCAUGGAAGAGAGCGUGGUGCGGCCUUCUGUCU<br>UCGUGGUCGACGGCCAGACCGAUAUCCCCUUCACAA<br>GACUGGGCAGAAGCCAUAGACGCCAGAGCUGCAGC |

TABLE 4-continued

| SEQ ID NO | Descriptor | Polynucleotide Sequence: RNA |
|---|---|---|
| | (1354) nt | GUGGCCCGGGUGGGCCUGGGACUUCUGCUGCUGCU<br>GAUGGGAGCUGGCCUGGCCGUGCAGGGCUGGUUUC<br>UGCUCCAGCUGCACUGGCGGCUGGGAGGAGGCGGC<br>GGCUCUGGCGGCGGAGGAAGCCUGAUCCAGGAGCG<br>GAGAUCCCACGAGGUGAACCCUGCCGCCCACCUGAC<br>CGGCGCCAACAGCUCCCUGACAGGCAGCGGCGGCCC<br>UCUGCUGUGGGAGACACAGCUGGGCCUGGCCUUCC<br>UGCGGGGCCUGAGCUACCACGACGGCGCUCUGGUCG<br>UGACCAAGGCCGGAUACUACUACAUCUACAGCAAG<br>GUGCAACUCGGCGGCGUGGGCUGCCCCCUGGGCCUG<br>GCUUCUACCAUCACCCACGGCCUGUACAAAGAACC<br>CCUAGAUACCCUGAGGAACUGGAACUGCUGGUGUC<br>CCAGCAGAGCCCAUGUGGCAGAGCCACCAGCUCUAG<br>CAGAGUGUGGUGGGACAGCAGCUUCCUGGGCGGAG<br>UGGUGCACCUGGAAGCCGGCGAGAAGGUGGUGGUU<br>AGAGUGCUGGACGAGAGACUGGUGCGGCUGAGAGA<br>UGGUACAAGGUCUUAUUUCGGCGCCUUUAUGGUGU<br>GAUAAGCGCCGCCUCCGGGACAGUGCACCCAGGCUG<br>CGGCCCCUCCCCCCGUCCUGGAGGUUCCCCAGCCCCA<br>CUUACCGCUUAAUGCGCCAAUAAACCAAUGAACGA<br>AGCAAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAAAAAAAAA |
| 10 | LIGHT ICD + TM (1-66; . . . RLG) + (Gly4Ser)₃ + LIGHT 92-240 (1355) nt | AGGCAUAGAAGUCGAGACACAGCCACUAAGUAAGC<br>CACCAUGGAAGAGAGCGUGGUGCGGCCUAGCGUGU<br>UCGUGGUGGACGGCCAGACAGAUAUCCCCUUCACCA<br>GACUGGGCAGAAGCCACAGAAGACAGAGCUGCAGC<br>GUGGCCAGAGUGGGACUGGGCCUGCUGCUGCUGCU<br>GAUGGGCGCCGGACUGGCCGUGCAAGGCUGGUUCC<br>UGCUCCAGCUGCACUGGCGGCUGGGCGGCGGCGGCG<br>GAUCUGGCGGAGGCGGCUCUGGCGGCGGCGGCUCC<br>GUGAACCCCGCCGCUCAUCUGACAGGCGCCAACAGC<br>AGCCUGACAGGCAGCGGAGGUCCUCUGCUGUGGGA<br>AACCCAGCUGGGCCUGGCUUUUCUGAGAGGCUUGU<br>CUUACCACGACGGCGCUCUGGUCGUGACCAAGGCCG<br>GCUACUACUAUAUCUACAGCAAGGUGCAGCUGGGA<br>GGCGUUGGAUGUCCUCUGGGACUGGCCAGCACCAU<br>CACCCACGGCCUGUACAAGCGGACCCCUAGAUACCC<br>UGAGGAACUGGAACUGCUGGUGUCCCAGCAGAGCC<br>CAUGCGGCAGAGCCACAAGCAGCUCUAGAGUCUGG<br>UGGGAUUCUAGCUUCCUGGGCGGCGUGGUGCACCU<br>GGAGGCCGGCGAGAAAGUGGUCGUGCGCGUGCUGG<br>ACGAGAGACUGGUGAGGCUGCGGGACGGGACCCGG<br>UCCUACUUCGGCGCCUUUAUGGUGUGAUAAGCGCC<br>GCCUCCGGGACAGUGCACCCAGGCUGCGGCCCCUCC<br>CCCGUCCUGGAGGUUCCCCAGCCCCACUUACCGCUU<br>AAUGCGCCAAUAAACCAAUGAACGAAGCAAAAAAA<br>AAAAAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAAAAAAAAAAAAA<br>AAAAAAAAAAAAAAAAAAAAAAA |
| 12 | LIGHT ICD + TM (1-66; . . . RLG) + (Gly4Ser)₂ + LIGHT 92-240 (1356) nt | AGGCAUAGAAGUCGAGACACAGCCACUAAGUAAGC<br>CACCAUGGAAGAGUCUGUGGUCAGACCUAGCGUGU<br>UCGUGGUCGACGGCCAGACCGACAUCCCCUUCACCA<br>GACUGGGAAGAAGCCAUAGAAGACAGAGCUGCAGC<br>GUGGCCAGAGUGGGCCUCGGCCUGCUGCUGCUGCU<br>GAUGGGCGCUGGCCUGGCCGUGCAAGGCUGGUUCC<br>UGCUGCAGCUGCACUGGCGGCUGGGCGGAGGCGGC<br>GGCUCUGGCGGCGGAGGCUCCGUGAACCCCGCCGCC<br>CACCUGACCGGCGCCAACAGCAGCCUGACAGGCAGC<br>GGCGGUCCUCUGCUGUGGGAAACCCAGCUGGGACU<br>GGCUUUUCUGAGAGGCCUGAGCUACCACGACGGCG<br>CCCUGGUGGUGACCAAGGCCGGCUAUUACUACAUC<br>UACAGCAAGGUGCAGCUGGGCGGCGUUGGAUGUCC<br>UCUGGGCCUGGCUUCUACAAUCACCCACGGCCUGUA<br>CAAGCGGACCCCUAGAUACCCUGAGGAACUGGAGC<br>UGCUGGUGUCCCAGCAGUCCCCAUGCGGCCGGGCCA<br>CAAGCUCUUCUAGAGUGUGGGGAUAGCAGCUUC<br>CUGGGCGGAGUGGUGCACCUCGAGGCCGGAGAGAA<br>AGUGGUGGUGCGGGUGCUGGAUGAGAGACUGGUUA<br>GGCUGCGCGACGGCACACGGAGCUACUUCGGCGCCU<br>UUAUGGUGUGAUAAGCGCCGCCUCCGGGACAGUGC |

TABLE 4-continued

| SEQ ID NO | Descriptor | Polynucleotide Sequence: RNA |
|---|---|---|
| | | ACCCAGGCUGCGGCCCCUCCCCCGUCCUGGAGGUUC CCCAGCCCCACUUACCGCUUAAUGCGCCAAUAAACC AAUGAACGAAGCAAAAAAAAAAAAAAAAAAAAAAA AAAAAAAAAAAAAAAAAAAAAAAAAAAAAAAAAAA AAAAAAAAAAAAAAAAAAAAAAAAAAAAAAAAAAA AAAAAAAAAAAAAAAAAAAAAAAAAAAAAAAAAAA AAAAAAAAAAAAAAAAAAAAAAAAAAAAAAAAAAA AAAAAA |
| 14 | LIGHT ICD + TM (1-75; . . . PDG) + SSAST + LIGHT 83-240 (1357) nt | AGGCAUAGAAGUCGAGACACAGCCACUAAGUAAGC CACCAUGGAAGAGAGCGUGGUGCGCCCCAGCGUGU UCGUGGUCGACGGCCAGACCGACAUCCCCUUCACCC GGCUGGGAAGAAGCCAUAGAAGGCAGAGCUGCAGC GUGGCCAGAGUCGGCCUGGGCCUGCUGCUGCUGCU GAUGGGCGCUGGCCUGGCCGUGCAGGGCUGGUUCC UGCUCCAGCUGCACUGGCGGCUGGGAGAAAUGGUG ACCAGACUGCCAGAUGGCAGCUCCGCCUCUACCCUG AUCCAGGAGCGGAGAAGCCACGAGGUGAACCCCGCC GCCCACCUGACAGGCGCCAACAGCAGCCUGACCGGC UCCGGCGGACCUCUGCUGUGGGAGACACAGCUGGG ACUGGCUUUUCUGAGAGGACUGAGCUACCACGACG GAGCCCUGGUGGUUUACAAAAGCCGGCUACUACUAC AUCUACAGCAAGGUGCAACUGGGCGGCGUGGGCUG UCCUCUGGGCCUGGCUUCUACAAUCACCCACGGCCU GUACAAGCGGACCCCUAGAUACCCUGAGGAACUCG AGCUGCUUGUGUCCCAGCAGAGCCCUUGCGGCAGA GCCACAAGCUCUUCUAGAGUGUGGUGGGACAGCAG CUUUCUGGGAGGCGUUGUGCACCUGGAAGCCGGCG AAAAGGUGGUGGUGCGGGUGCUGGACGAGAGACUG GUGCGGCUGAGAGAUGGCACCAGAUCUUUAUUUCGG CGCCUUCAUGGUGUGAUAAGCGCCGCCUCCGGGACA GUGCACCCAGGCUGCGGCCCCUCCCCCGUCCUGGAG GUUCCCCAGCCCCACUUACCGCUUAAUGCGCCAAUA AACCAAUGAACGAAGCAAAAAAAAAAAAAAAAAAA AAAAAAAAAAAAAAAAAAAAAAAAAAAAAAAAAAA AAAAAAAAAAAAAAAAAAAAAAAAAAAAAAAAAAA AAAAAAAAAAAAAAAAAAAAAAAAAAAAAAAAAAA AAAAAAAAAAAAAAAAAAAAAAAAAAAAAAAAAAA AAAAAAAAA |
| 16 | LIGHT ICD + TM (1-75; . . . PDG) + SSASTDKTHT + LIGHT 92-240 (1358) nt | AGGCAUAGAAGUCGAGACACAGCCACUAAGUAAGC CACCAUGGAAGAGAGCGUGGUGCGGCCUAGCGUGU UCGUGGUGGACGGCCAGACCGACAUCCCCUUCACCA GACUGGGAAGAUCCCACAGAAGGCAGUCCUGCAGC GUGGCCAGAGUGGGCCUGGGCCUGCUGCUGCUGCU GAUGGGCGCCGGCCUCGCCGUGCAGGGCUGGUUCCU GCUGCAGCUGCACUGGCGGCUGGGCGAGAUGGUCA CAAGACUGCCUGAUGGAUCUAGCGCCAGCACCGAU AAGACACACACCGUGAACCCCGCCGCUCACCUGACC GGCGCCAACAGCAGCCUGACAGGCUCUGGCGGACCU CUGCUGUGGGAGACACAGCUGGGACUGGCCUUUCU GAGAGGCCUGAGCUAUCACGACGGCGCCCUGGUGG UGACAAAGGCCGGCUACUACUACAUCUACAGCAAG GUGCAACUGGGCGGCGUCGGCUGCCCCUGGGACUG GCUUCUACCAUCACCCACGGCCUGUACAAGCGGACC CCUAGAUACCCUGAGGAACUGGAACUGCUUGUUUC CCAGCAGUCUCCAUGUGGCAGAGCCACCAGCAGCAG CAGAGUGUGGUGGGAUAGCUCCUUCCUGGGUUGGCG UGGUCCAUCUGGAAGCCGGAGAAAGUGGUGGUG CGCGUGCUGGACGAGAGACUCGUGCGGCUGCGGGA CGGCACCCGGAGCUACUUCGGCGCUUUUAUGGUGU GAUAAGCGCCGCCUCCGGGACAGUGCACCCAGGCUG CGGCCCCUCCCCCGUCCUGGAGGUUCCCCAGCCCCA CUUACCGCUUAAUGCGCCAAUAAACCAAUGAACGA AGCAAAAAAAAAAAAAAAAAAAAAAAAAAAAAAAA AAAAAAAAAAAAAAAAAAAAAAAAAAAAAAAAAAA AAAAAAAAAAAAAAAAAAAAAAAAAAAAAAAAAAA AAAAAAAAAAAAAAAAAAAAAAAAAAAAAAAAAAA AAAAAAAAAAAAAAAAAAAAAAAAAAAA |
| 18 | LIGHT ICD + TM (1-66; . . . RLG) + SSASTDKTHT + LIGHT 92-240 (1359, aka 1495) nt | AGGCAUAGAAGUCGAGACACAGCCACUAAGUAAGC CACCAUGGAGGAGAGCGUGGUGCGGCCUAGCGUGU UCGUGGUCGACGGCCAGACCGACAUCCCCUUCACCA GACUGGGAAGAAGCCACAGAAGGCAGUCUUGCUCC GUGGCCAGAGUGGGCCUGGGCCUGCUCCUGCUGCU GAUGGGCGCUGGCCUGGCCGUGCAAGGCUGGUUCC UGCUGCAGCUGCACUGGCGGCUGGGCAGCAGCGCCU |

TABLE 4-continued

| SEQ ID NO | Descriptor | Polynucleotide Sequence: RNA |
|---|---|---|
| | | CUACCGAUAAGACCCACACCGUGAACCCUGCCGCCC<br>ACCUGACCGGCGCCAACAGCUCUCUGACCGGAUCUG<br>GCGGACCUCUGCUGUGGGAGACACAGCUGGGCCUU<br>GCUUUUCUGCGGGGCCUGAGCUACCACGACGGCGCU<br>CUGGUGGUUACAAAGGCCGGCUACUACUACAUCUA<br>CAGCAAGGUGCAGCUGGGAGGCGUGGGUUGUCCAC<br>UGGGACUGGCCAGCACAAUCACACACGGCCUUUAU<br>AAGCGGACCCCUAGAUACCCCGAGGAACUGGAACU<br>GCUGGUCUCCCAGCAGAGCCCUUGCGGCAGAGCCAC<br>AAGCAGCAGCAGAGUGUGGUGGGACAGCUCAUUCC<br>UGGGCGGCGUGGUGCAUCUGGAAGCCGGCGAGAAA<br>GUGGUGGUCAGAGUGCUGGACGAGAGACUGGUGCG<br>GCUGAGAGAUGGGACCCGCUCCUACUUCGGCGCCUU<br>UAUGGUGUGAUAAGCGCCGCCUCCGGGACAGUGCA<br>CCCAGGCUGCGGCCCCUCCCCCGUCCUGGAGGUUCC<br>CCAGCCCCACUUACCGCUUAAUGCGCCAAUAAACCA<br>AUGAACGAAGCAAAAAAAAAAAAAAAAAAAAAAAA<br>AAAAAAAAAAAAAAAAAAAAAAAAAAAAAAAAAAA<br>AAAAAAAAAAAAAAAAAAAAAAAAAAAAAAAAAAA<br>AAAAAAAAAAAAAAAAAAAAAAAAAAAAAAAAAAA<br>AAAAAAAAAAAAAAAAAAAAAAAAAAAAAAAAAAA<br>AAAAA |

ICD—Intracellular Domain of the LIGHT
TM—Transmembrane region

In some non-limiting aspects, the isolated mRNA encodes a membrane-stabilized LIGHT that has at least about 50%, alternatively at least about 60%, alternatively at least about 65%, alternatively at least about 70%, alternatively at least about 75%, alternatively at least about 80%, alternatively at least about 85%, alternatively at least about 90%, alternatively at least about 95% amino acid sequence identity to SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17. In another non-limiting aspect, the membrane-stabilized LIGHT has at least about 80%, alternatively at least about 85%, alternatively at least about 90%, alternatively at least about 93%, alternatively at least about 95%, alternatively at least about 96% alternatively at least about 97%, alternatively at least about 98%, alternatively at least about 99% amino acid sequence identity to SEQ ID NO: 11 or SEQ ID NO: 17.

In other non-limiting examples, the isolated mRNA that encodes a membrane-stabilized LIGHT has at least about 50%, alternatively at least about 60%, alternatively at least about 65%, alternatively at least about 70%, alternatively at least about 75%, alternatively at least about 80%, alternatively at least about 85%, alternatively at least about 90%, alternatively at least about 95% nucleic acid sequence identity to SEQ ID NO: 4, SEQ ID NO: 6, SEQ ID NO: 9, SEQ ID NO: 10, SEQ ID NO: 12, SEQ ID NO: 14, SEQ ID NO: 16, or SEQ ID NO: 18. In another aspect, isolated mRNA has at least about 80%, alternatively at least about 85%, alternatively at least about 90%, alternatively at least about 93%, alternatively at least about 95%, alternatively at least about 96% alternatively at least about 97%, alternatively at least about 98%, alternatively at least about 99% nucleic acid sequence identity to SEQ ID NO: 12 or SEQ ID NO: 18.

A feature of the universal genetic code is its redundancy. Most amino acids are encoded by more than one codon (the exceptions being the amino acids methionine and tryptophan, which each has only one corresponding codon). Therefore, within the constraints of this degeneracy, a polynucleotide sequence can be altered without affecting the sequence of amino acids in the encoded polypeptide.

For example, the amino acid alanine has four possible codons (GCT, GCC, GCA, and GCG) that differ from each other in only one nucleotide position, meaning that each time an alanine codon appears within a polynucleotide, the third nucleotide in the codon can be exchanged for another nucleotide without changing the encoded polypeptide.

mRNA-based therapeutics that combine an mRNA-encoded membrane-stabilized LIGHT with mRNA-encoded effector molecules, mRNA-encoded immunomodulators, and/or mRNA-encoded tumor associated antigens may function as an effective cancer immunotherapy. The prevention or treatment of disease with substances that stimulate the immune response is generally referred to as immunotherapy. Immunotherapy, sometimes also referred to as immuno-oncology, introduces therapies that target not the tumor, but the host immune system. These therapies may possess unique pharmacological response profiles, and thus represent therapies that might cure many distinct types of cancer. In one example, cancers of the lungs, kidney, bladder and skin are among those that derive substantial efficacy from treatment with immuno-oncology in terms of survival or tumor response, as does, in particular, melanoma. Immunotherapy often features checkpoint inhibitor treatment with biologic drugs known as checkpoint inhibitor antibodies.

The disclosed mRNA-based therapeutics are particularly well-suited for cancer immunotherapies as the technology provides for the delivery of both tumor-specific antigen mRNA and, for example, one or more mRNA encoding immunomodulators or an immunomodulatory agent, allowing de novo synthesis of functional proteins within target cells, e.g., within target cells in tumors. Immunomodulators or immunomodulatory agents include, but are not limited to, oncology-related polypeptides, checkpoint inhibitors, immunosuppression antagonists, pro-inflammatory agents, pro-inflammatory cytokines, and other agents that would be useful in immuno-oncology ("IO"). These cancer immunotherapies leverage the ability of the mRNA to deliver genetic information and initiate immunostimulatory activity. The disclosed mRNA-based therapeutics may have modified nucleotides to minimize unwanted immune activation (e.g., the innate immune response associated with in vivo introduction of foreign nucleic acids) and optimize the translation efficiency of mRNA to protein. As shown in FIGS. 4A-4E, the membrane-stabilized LIGHT (ENG-LIGHT) displays anti-tumor efficacy.

A non-limiting aspect of the disclosure is an mRNA-based therapeutic that is able to target cervical cancer, HPV-driven cancer, or a disease associated with HPV. HPV-driven cancers include, but are not limited to, cervical cancer, oropharyngeal cancers, which typically develop in the throat (usually the tonsils or the back of the tongue), anal cancer, penile cancer, vaginal cancer, and vulvar cancer. Cervical cancer is the leading genital cancer among women worldwide, with almost half a million new cases per year (GLOBOCAN, 2012). In 2015, 526,000 women developed cervical cancer worldwide and caused 239,000 deaths. In addition to the risk of death, cervical cancer is associated with increased morbidity, including bleeding, pain, and kidney failure, which are difficult to treat.

Figure 5:
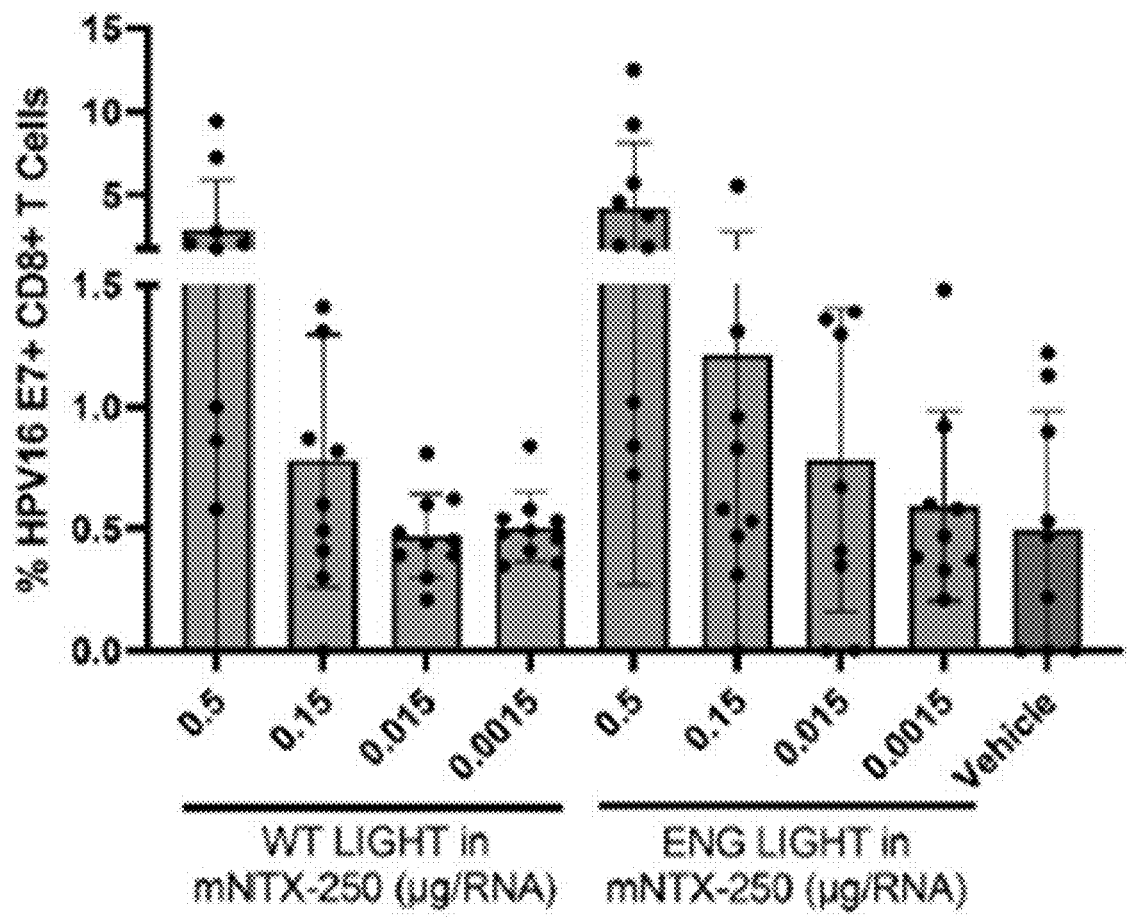
FIG. 5 shows the dose-response of mNTX-250 (containing either WT or ENG mLIGHT) on HPV16 tetramer-positive T cell generation in vivo.

In a non-limiting aspect, an mRNA-based therapeutic that is able to target cervical cancer, HPV-driven cancer, or a disease associated with HPV may include a first isolated mRNA that encodes a membrane-stabilized LIGHT, a second isolated mRNA that encodes an immunomodulatory agent, and a third isolated mRNA that encodes at least one tumor associated antigen. As shown in FIG. 5, membrane-stabilized LIGHT generates HPV-specific T cell responses.

In some examples, the mRNA-based therapeutic may further include additional isolated mRNA that encode additional immunomodulatory agents, including immune checkpoint modulators, checkpoint inhibitors, and/or other antibody therapeutics.

Non-limiting examples of checkpoint inhibitors include proteins that target and inhibit one or more immune system checkpoint proteins. Examples include proteins that inhibit one more of CTLA4, PD-1, and PD-L1. In some variations the checkpoint inhibitor refers to a protein that inhibits CTLA-4. For example, a checkpoint inhibitor protein may include a protein that binds to CTLA-4, such as an antibody or antibody fragment, e.g., antigen-binding fragments (Fab), single chain variable fragments (scFv), aptamer, and the like. An mRNA encoding checkpoint inhibitors encodes, for example, anti-PD-L1 antibody (such as atezolizumab, avelumab, or durvalumab), an anti-CTLA-4 antibody (such as tremelimumab or ipilimumab), an anti-PD1 antibody (such as nivolumab or pembrolizumab), or combinations thereof.

An immunosuppression antagonist may include a protein that prevents or limits immunosuppression, blocking a pathway for suppression of the immune system. For example, antagonists against Transforming Growth Factor Beta (TGF-β-RII) is a cytokine that may act as an immunosuppression antagonist. A pro-inflammatory agent typically induces an inflammatory response itself and may cause a local inflammation. For example, interleukin-12 is a pro-inflammatory, pleiotropic cytokine widely accepted as an important regulator of Th1 responses. It also promotes the expansion and survival of activated T-cells and NK cells and modulates the cytotoxic activity of CTLs and NK cells. Thus, as used herein, an immunomodulatory agent (immunomodulator) may include interleukins (e.g., IL-2, IL-7, IL-12), other cytokines (interferons, GM-CSF), chemokines (CCL3, CCL26, CXCL-7), or the like.

In some examples, the additional isolated mRNA may have the following formula:

5'UTR—Signal/Leader—mRNA coding region—
3'UTR—PolyA

In a non-limiting example, an isolated mRNA that encodes human IL-12 has the following formula:

5'UTR—Signal/Leader—mRNA coding region—
3'UTR—PolyA

In one example, the 3'UTR is modified. In another example, the 5'UTR is modified. In a further example, both the 3'UTR and 5'UTR are modified. In an example, the Signal/Leader is a secretion signal.

In some aspects, the mRNA human IL-12 coding region may encode at least two heterodimers of IL-12, with the first IL-12 heterodimer connected to the second IL-12 heterodimer via a linker. See e.g., FIG. 3E. The linker may be any linked know in the art including, an antibody variable region linker, a peptide linker, and/or a (Gly4Ser)n linker wherein n is 1, 2, 3, 4, 5, 6, 7, 8, 9, or 10.

As shown in FIGS. 6A-6D, an mRNA based therapeutic that includes both the membrane-stabilized LIGHT and a proinflammatory cytokine, like IL-12, may promote increased beneficial Th1, M1 and overall proinflammatory tumor microenvironment changes compared to soluble LIGHT.

A non-limiting example of the sequence of an isolated mRNA that encodes a human IL-12 fusion and the human IL-12 fusion amino acid sequence is in Table 5.

TABLE 5

```
SEQ ID NO: 19
Human IL12 Fusion Single chain DNA-683:
Polynucleotide Sequence: DNA
AATCATAATACGACTCACTATAAGGCATAGAAGTCGAGACACAGCCACTA
AGTAAGCCACCATGTGCCACCAGCAGCTGGTCATCAGCTGGTTCAGCCTGG
TGTTCCTGGCCTCTCCTCTGGTGGCCATCTGGGAGCTGAAGAAAGACGTGT
ACGTGGTGGAACTGGACTGGTATCCCGATGCTCCTGGCGAGATGGTGGTGC
TGACCTGCGATACCCCTGAAGAGGACGGCATCACCTGGACACTGGATCAGT
CTAGCGAGGTGCTCGGCAGCGGCAAGACCCTGACCATCCAAGTGAAAGAG
TTTGGCGACGCCGGCCAGTACACCTGTCACAAAGGCGGAGAAGTGCTGAG
CCACAGCCTGCTGCTGCTCCACAAGAAAGAGGATGGCATTTGGAGCACCG
ACATCCTGAAGGACCAGAAAGAGCCCAAGAACAAGACCTTCCTGAGATGC
GAGGCCAAGAACTACAGCGGCCGGTTCACATGTTGGTGGCTGACCACCATC
AGCACCGACCTGACCTTCAGCGTGAAGTCCAGCAGAGGCAGCAGTGATCCT
CAGGGCGTTACATGTGGCGCCGCTACACTGTCTGCCGAAAGAGTGCGGGGC
GACAACAAAGAATACGAGTACAGCGTGGAATGCCAAGAGGACAGCGCCTG
TCCAGCCGCCGAAGAGTCTCTGCCTATCGAAGTGATGGTGGACGCCGTGCA
CAAGCTGAAGTACGAGAACTACACCTCCAGCTTTTTCATCGGGACATCAT
CAAGCCCGATCCTCCAAAGAACCTGCAGCTGAAGCCTCTGAAGAACAGCA
GACAGGTGGAAGTGTCCTGGGAGTACCCCGACACCTGGTCTACACCCCACA
```

TABLE 5-continued

```
GCTACTTCAGCCTGACCTTTTGCGTGCAAGTGCAGGGCAAGTCCAAGCGCG
AGAAAAAGGACCGGGTGTTCACCGACAAGACCAGCGCCACCGTGATCTGC
AGAAAGAACGCCAGCATCAGCGTCAGAGCCCAGGACCGGTACTACAGCAG
CTCTTGGAGCGAATGGGCCAGCGTGCCATGTTCTGGTGGCGGAGGATCTGG
CGGAGGTGGAAGCGGCGGAGGCGGATCTAGAAATCTGCCTGTGGCCACTC
CTGATCCTGGCATGTTCCCTTGTCTGCACCACAGCCAGAACCTGCTGAGAG
CCGTGTCCAACATGCTGCAGAAGGCCAGACAGACCCTGGAATTCTACCCCT
GCACCAGCGAGGAAATCGACCACGAGGACATCACCAAGGATAAGACCAGC
ACCGTGGAAGCCTGCCTGCCTCTGGAACTGACCAAGAACGAGAGCTGCCTG
AACAGCCGGGAAACCAGCTTCATCACCAACGGCTCTTGCCTGGCCAGCAGA
AAGACCTCCTTCATGATGGCCCTGTGCCTGAGCAGCATCTACGAGGACCTG
AAGATGTACCAGGTGGAATTCAAGACCATGAACGCCAAGCTGCTGATGGA
CCCCAAGCGGCAGATCTTCCTGGACCAGAATATGCTGGCCGTGATCGACGA
GCTGATGCAGGCCCTGAACTTCAACAGCGAGACAGTGCCCCAGAAGTCTA
GCCTGGAAGAACCCGACTTCTACAAGACCAAGATCAAGCTGTGCATCCTGC
TGCACGCCTTCCGGATCAGAGCCGTGACCATCGACAGAGTGATGAGCTACC
TGAACGCCTCCTGAGCGCCGCCTCCGGGACAGTGCACCCAGGCTGCGGCCC
CTCCCCCGTCCTGGAGGTTCCCCAGCCCCACTTACCGCTTAATGCGCCAAT
AAACCAATGAACGAAGCAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAA

SEQ ID NO: 20
Human IL12 Fusion Single chain RNA-683:
Polynucleotide Sequence: RNA
AGGCAUAGAAGUCGAGACACAGCCACUAAGUAAGCCACCAUGUGCCACCAGCA
GCUGGUCAUCAGCUGGUUCAGCCUGGUGUUCCUGGCCUCUCCUCUGGUGGCCA
UCUGGGAGCUGAAGAAAGACGUGUACGUGGUGGAACUGGACUGGUAUCCCGAU
GCUCCUGGCGAGAUGGUGGUGCUGACCUGCGAUACCCCUGAAGAGGACGGCAU
CACCUGGACACUGGAUCAGUCUAGCGAGGUGCUCGGCAGCGGCAAGACCCUGA
CCAUCCAAGUGAAAGAGUUUGGCGACGCCGGCCAGUACACCUGUCACAAGGC
GGGAGAAGUGCUGAGCCACAGCCUGCUGCUGCUCCACAAGAAGGAUGGCAU
UUGGAGCACCGACAUCCUGAAGGACCAGAAAGAGCCCAAGAACAAGACCUUCC
UGAGAUGCGAGGCCAAGAACUACAGCGGCCGGUUCACAUGUUGGUGGCUGACC
ACCAUCAGCACCGACCUGACCUUCAGCGUGAAGUCCAGCAGAGGCAGCAGUGA
UCCUCAGGGCGUUACAUGUGGCGCCGCUACACUGUCUGCCGAAAGAGUGCGGG
GCGACAACAAAGAAUACGAGUACAGCGUGGAAUGCCAAGAGGACAGCGCCUGU
CCAGCCGCCGAAGAGUCUCUGCCAUCGAAGUGAUGGUGGACGCCGUGCACAA
GCUGAAGUACGAGAACUACACCUCCAGCUUUUUCAUCCGGGACAUCAUCAAGC
CCGAUCCUCCAAAGAACCUGCAGCUGAAGCCUCUGAAGAACAGCAGACAGGUG
GAAGUGUCCUGGGAGUACCCCGACACCUGGUCUACACCCCACAGCUACUUCAGC
CUGACCUUUUGCGUGCAAGUGCAGGGCAAGUCCAAGCGCGAGAAAAAGGACCG
GGUGUUCACCGACAAGACCAGCGCCACCGUGAUCUGCAGAAAGAACGCCAGCA
UCAGCGUCAGAGCCCAGGACCGGUACUACAGCAGCUCUUGGAGCGAAUGGGCC
AGCGUGCCAUGUUCUGGUGGCGGAGGAUCUGGCGGAGGUGGAAGCGGCGGAGG
CGGAUCUAGAAAUCUGCCUGUGGCCACUCCUGAUCCUGGCAUGUUCCCUUGUC
UGCACCACAGCCAGAACCUGCUGAGAGCCGUGUCCAACAUGCUGCAGAAGGCCA
GACAGACCCUGGAAUUCUACCCCUGCACCAGCGAGGAAAUCGACCACGAGGACA
UCACCAAGGAUAAGACCAGCACCGUGGAAGCCUGCCUGCCUCUGGAACUGACCA
AGAACGAGAGCUGCCUGAACAGCCGGGAAACCAGCUUCAUCACCAACGGCUCU
UGCCUGGCCAGCAGAAAGACCUCCUUCAUGAUGGCCCUGUGCCUGAGCAGCAUC
UACGAGGACCUGAAGAUGUACCAGGUGGAAUUCAAGACCAUGAACGCCAAGCU
GCUGAUGGACCCCAAGCGGCAGAUCUUCCUGGACCAGAAUAUGCUGGCCGUGA
UCGACGAGCUGAUGCAGGCCCUGAACUUCAACAGCGAGACAGUGCCCCAGAAG
UCUAGCCUGGAAGAACCCGACUUCUACAAGACCAAGAUCAAGCUGUGCAUCCU
GCUGCACGCCUUCCGGAUCAGAGCCGUGACCAUCGACAGAGUGAUGAGCUACC
UGAACGCCUCCUGAGCGCCGCCUCCGGGACAGUGCACCCAGGCUGCGGCCCCUC
CCCCGUCCUGGAGGUUCCCCAGCCCCACUUACCGCUUAAUGCGCCAAUAAACCA
AUGAACGAAGCAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAA SEQ ID NO: 21
Human IL12 Fusion Single chain AA-683:
Amino Acid Sequence:
MCHQQLVISWFSLVFLASPLVAIWELKKDVYVVELDWYPDAPGEMVVLTCDTPEED
GITWTLDQSSEVLGSGKTLTIQVKEFGDAGQYTCHKGGEVLSHSLLLLHKKEDGIWST
DILKDQKEPKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYENYTSSFFIR
DIIKPDPPKNLQLKPLKNSRQVEVSWEYPDTWSTPHSYFSLTFCVQVQGKSKREKKDR
VFTDKTSATVICRKNASISVRAQDRYYSSSWSEWASVPCSGGGGSGGGGSGGGGSRN
LPVATPDPGMFPCLHHSQNLLRAVSNMLQKARQTLEFYPCTSEEIDHEDITKDKTSTV
EACLPLELTKNESCLNSRETSFITNGSCLASRKTSFMMALCLSSIYEDLKMYQVEFKT
MNAKLLMDPKRQIFLDQNMLAVIDELMQALNFNSETVPQKSSLEEPDFYKTKIKLCIL
LHAFRIRAVTIDRVMSYLNAS
```

In an aspect, the second isolated mRNA encodes a proinflammatory cytokine has at least about 50%, alternatively at least about 60%, alternatively at least about 65%, alternatively at least about 70%, alternatively at least about 75%, 70%, alternatively at least about 75%, alternatively at least about 80%, alternatively at least about 85%, alternatively at least about 90%, alternatively at least about 95% amino acid sequence identity to SEQ ID NO:21. In a different, non-limiting aspect, the pro-inflammatory cytokine has at least about 80%, alternatively at least about 85%, alternatively at least about 90%, alternatively at least about 93%, alternatively at least about 95%, alternatively at least about 96% alternatively at least about 97%, alternatively at least about 98%, alternatively at least about 99% amino acid sequence identity to SEQ ID NO:21.

In an aspect, the second isolated mRNA has at least 50%, alternatively at least about 60%, alternatively at least about 65%, alternatively at least about 70%, alternatively at least about 75%, alternatively at least about 80%, alternatively at least about 85%, alternatively at least about 90%, alternatively at least about 95% nucleic acid sequence identity to SEQ ID NO:20. In a different, non-limiting aspect, the second isolated mRNA has at least about 80%, alternatively at least about 85%, alternatively at least about 90%, alternatively at least about 93%, alternatively at least about 95%, alternatively at least about 96% alternatively at least about 97%, alternatively at least about 98%, alternatively at least about 99% nucleic acid sequence identity to SEQ ID NO:20.

The most carcinogenic HPV type is HPV16, and 50% of all cervical cancers are associated with HPV16. The second most carcinogenic HPV type is HPV18, and 15-20% of all cervical cancers are associated with HPV18. HPV replication is encoded on the E region of the virus, notably containing the viral genes E6 and E7 that are associated with deregulated cell proliferation, and initiation of tumorigenesis, and ultimately progression of cancer in the host. Additionally, E6 and E7 viral genes are retained and integrated into the host genome, and constitutively expressed, providing target antigens specific to HPV-infected cells and major histocompatibility complex class I-restricted CD8+ T-cell responses in patients with cervical cancer.

In some aspects, the third isolated mRNA may encode a tumor associated antigen may have the following formula:

5'UTR—Signal/Leader—(An1)n-Xo-(An2)p—
3'UTR—PolyA where "UTRs" are the untranslated regions located at the 5' and 3' ends of an mRNA construct, and "PolyA" refers to the polyadenylation site of the mRNA. In one example, the 3'UTR is modified. In another example, the 5'UTR is modified. In a further example, both the 3'UTR and 5'UTR are modified.

Signal/Leader refers to a suitable signal sequence, leader sequence, sorting sequence, in frame with and upstream of the antigenic region. In an example, the Signal/Leader is a secretion signal and/or a helper epitope.

(An1)n-Xo-(An2)p refers to any suitable antigenic region comprising a first antigen (An1), a spacer or linker region (X), and a second antigen (An2). In some examples, n is an integer greater than 1. For example, n can be 1, 2, 3, 4, 5, 6, 7, 8, 9, or 10. In some examples, n can be greater than 10. In some examples, o is 0, In other examples, o is an integer greater than 0. For example, o can be 0, 1, 2, 3, 4, 5, 6, 7, 8, 9, or 10. In some examples, o can be greater than 10. In some examples, p is an integer greater than 0. For example, p can be 0, 1, 2, 3, 4, 5, 6, 7, 8, 9, or 10. In some examples, p can be greater than 10.

There are several HPV related antigens including HPV16, 18, 31, 33, 35, 39, 45, 51, 52, 56, 58, 59, 66, and 68. HPV16 and HPV18 are responsible for most HPV-related diseases. In a non-limiting example, the polynucleotide comprising an mRNA-encoded tumor associated antigen encodes HPV16 E6 and E7 or HPV18 E6 and E7 oncoproteins linked by a short Gly4Ser linker to make one continuous protein antigen. See. e.g., FIG. 3B, FIG. 3C.

In a non-limiting example, the third isolated mRNA has a formula of:

5'UTR—Signal/Leader—(An1)n-Xo-(An2)p—
3'UTR—PolyA wherein An1 encodes HPV16 E6, An2 encodes HPV16 E7, X is a spacer or linker, and n is 1, 2, 3, 4, 5, 6, 7, 8, 9, or 10;

is 0, 1, 2, 3, 4, 5, 6, 7, 8, 9, or 10; and p is 1, 2, 3, 4, 5, 6, 7, 8, 9, or 10.

Several mutations in the E6 and E7 sequences may be created to reduce the oncogenic function of the E6 and E7 proteins. In some aspects, the mRNA-encoded tumor associated antigen cassette may additionally include PADRE T helper epitope to enhance adaptive immune responses and/or hCD1d scaffold to enhance CD4 T cell responses and cross presentation of antigens.

After synthesis in the endoplasmic reticulum (ER), CD1d traverse the secretory pathway (Trans Golgi Network TGM) to the cell surface or directly to the multivesicular bodies/Antigen processing compartments. The cytoplasmic tail of the CD1d isoform interact with adaptor-protein complexes, leading to distinct patterns of steady-state distribution in subcompartments of the endosomal network.

By piggybacking on the intracellular trafficking of CD1d molecules, mRNAs encoding antigens flanked by CD1d signal peptide (Sec) and the CD1d cytoplasmic tail (Antigen-CD1d) were designed. Upon transfection of the cells, the mRNAs are translated and the resulting antigen protein is directed towards the antigen-processing compartment by the CD1d endolysosomal trafficking signals. The endolysosomal trafficking domain, CD1d, enhances antigen antigenicity and cross-presentation. By taking advantage of the CD1d endolysosomal trafficking signals, antigen processing and cross-presentation on both MHC class I (endogenously derived antigens) and MHC class II (exogenously derived antigens) is facilitated.

Figure 19A:
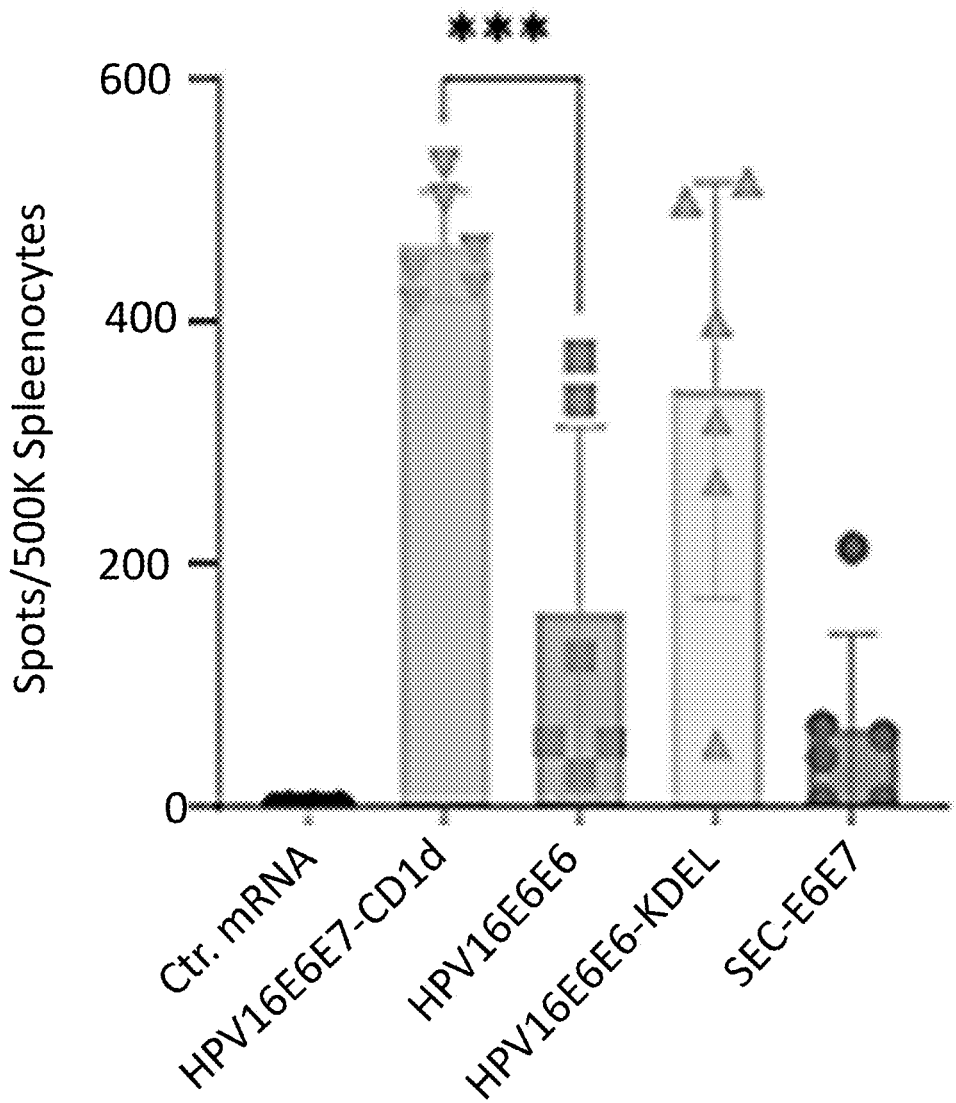
FIGS. 19A-19C are graphs showing that CD1d endolysosomal trafficking domain significantly improves antigen-specific immune responses in vivo.
Figure 19B:
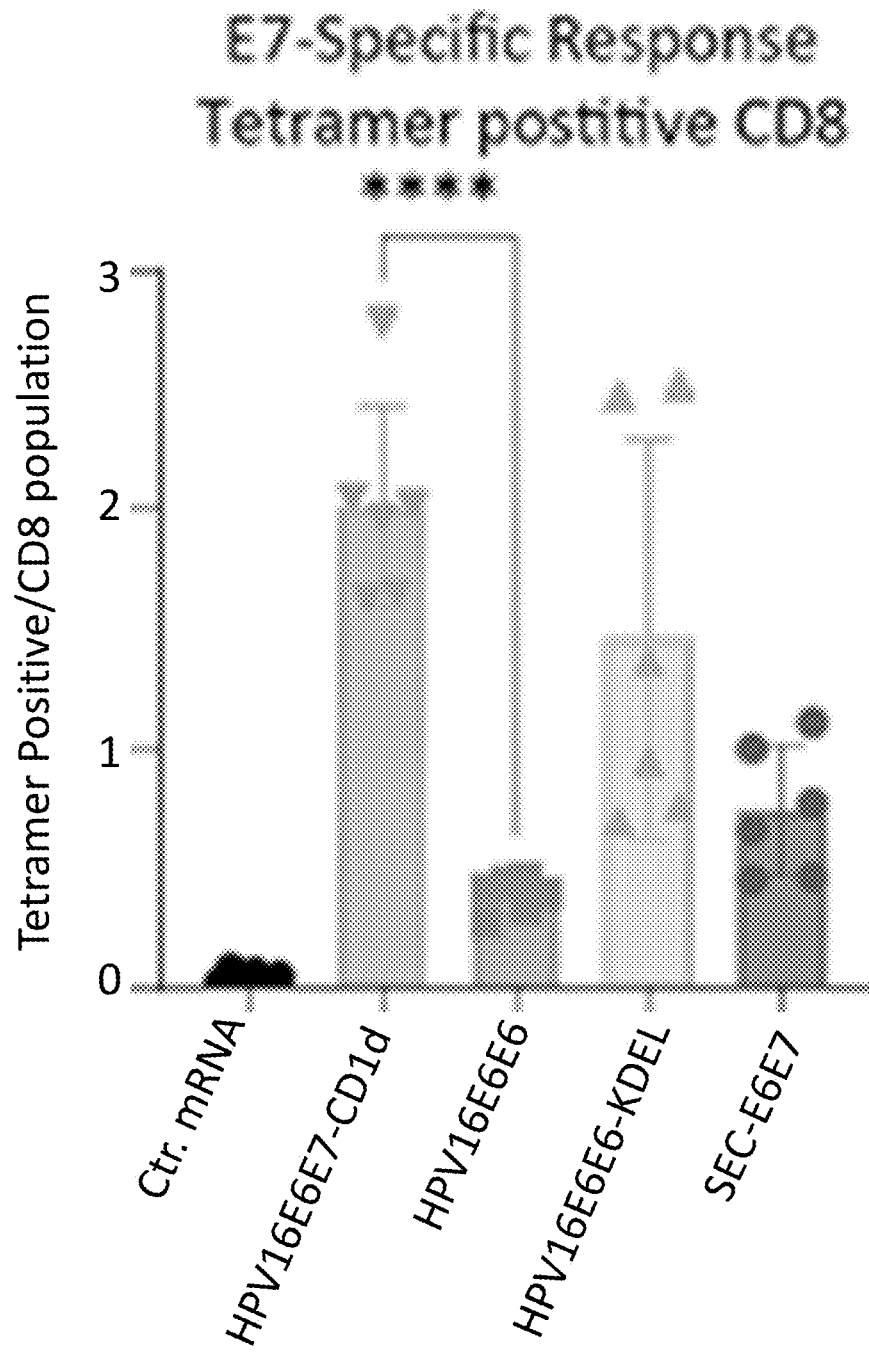
Figure 19C:
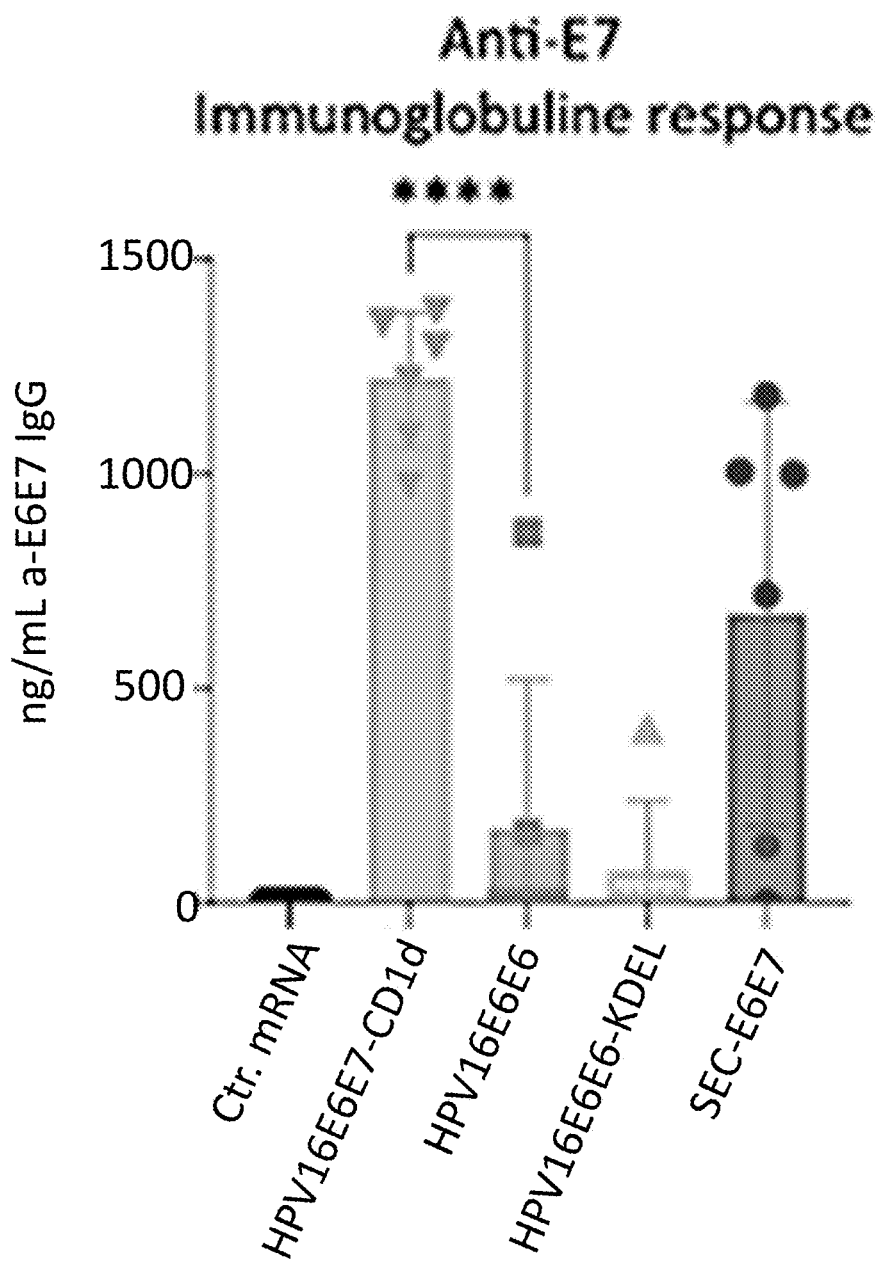

CD1d endolysosomal trafficking domain linked antigens show sustained intracellular expression in multivesicular bodies that results in improved CD4 and CD8 antigen-specific engagement. In vivo, the antigen-CD1d mRNAs significantly improves the antigen-specific CD8 T cells responses and enhances the immunoglobulin response. FIGS. 19A-19C. Improved immunoglobulin responses is indicative of a more productive antigen presentation to both B and T cells. This further shows how antigenicity of vaccines can be improved by leveraging the unique feature of mRNA drugs to facilitate intracellular protein subcellular expression Non-limiting examples of the nucleic acid sequence of an isolated mRNA that encodes tumor associated antigens and amino acid sequences of the tumor associated antigens according to an aspect of this disclosure are listed in Table 6.

TABLE 6

```
SEQ ID NO: 22
Sec-PADRE-HPV18E6E7-hCD1d
>Polynucleotide Sequence: DNA
ATGGGCTGCCTGCTGTTTCTGCTGCTTTGGGCTCTGCTGCAGGCCTGGGGATCTGC
CGCCAAGTTCGTGGCTGCCTGGACCCTGAAGGCTGCCGCTGCCAGATTCGAGGAC
CCTACCAGAAGCGGCTACAAGCTGCCTGACCTGTGCACCGAGCTGAACACAAGCC
TGCAGGACATCGAGATCACCTGTGTGTACTGCAAGACCGTGCTGGAACTGACCGA
GGTGTTCGAGAAGGACCTGTTCGTGGTGTACAGAGACAGCATCCCTCACGCCGCC
TGCCACAAGTGCATCGACTTCTACAGCAGAATCAGAGAGCTGAGGCACTACAGCG
ACAGCGTGTACGGCGACACCCTGGAAAAGCTGACCAACACCGGCCTGTACAACCT
GCTGATCAGATGCCTGAGATGCCAGAAGCCTCTGCTGAGACACCTGAACGAGAAG
AGGCGGTTCCACAATATCGCCGGCCACTACAGAGGCCAGTGCCACAGCTGTTGTA
ACAGAGCCAGACAAGAGAGGCTGCAGAGAAGGCGCGAAACCCAGGTGGGCGGA
GGATCTGGCGGAGGTGGAAGCGGCGGAGGCGGATCTATGCACGGCCCTAAGGCC
ACACTGCAGGACATCGTGCTGCACCTGGAACCTCAGAACGAGATCCCTGTGGATC
TGCTCGGACACGGCCAGCTGAGCGATAGCGAGGAAGAGAACGACGAGATCGACG
GCGTGAACCACCAGCATCTGCCTGCTAGAAGGGCCGAGCCTCAGAGACACACCAT
GCTGTGCATGTGCTGCAAGTGCGAGGCCAGAATCAAGCTGGTGGTGGAAAGCAGC
GCCGACGACCTGAGAGCTTTCCAGCAGCTGTTCCTGAACACCCTGAGCTTCGTGTG
TCCTTGGTGCGCCTCTCAGCAAGGCCTGATCGCCCTGGCTGTTCTGGCCTGTCTGT
TGTTCCTGCTGATTGTGGGCTTCACCAGCAGATTCAAGAGACAGACCAGCTACCA
GGGCGTGCTCTAG SEQ ID NO: 23
SEC-PADRE-HPV18E6E7-HCD1D
>Polynucleotide Sequence: RNA
AUGGGCUGCCUGCUGUUUCUGCUGCUUUGGGCUCUGCUGCAGGCCUGGGGAUC
UGCCGCCAAGUUCGUGGCUGCCUGGACCCUGAAGGCUGCCGCUGCCAGAUUCGA
GGACCCUACCAGAAGCGGCUACAAGCUGCCUGACCUGUGCACCGAGCUGAACAC
AAGCCUGCAGGACAUCGAGAUCACCUGUGUGUACUGCAAGACCGUGCUGGAAC
UGACCGAGGUGUUCGAGAAGGACCUGUUCGUGGUGUACAGAGACAGCAUCCCU
CACGCCGCCUGCCACAAGUGCAUCGACUUCUACAGCAGAAUCAGAGAGCUGAG
GCACUACAGCGACAGCGUGUACGGCGACACCCUGGAAAAGCUGACCAACACCGG
CCUGUACAACCUGCUGAUCAGAUGCCUGAGAUGCCAGAAGCCUCUGCUGAGAC
ACCUGAACGAGAAGAGGCGGUUCCACAAUAUCGCCGGCCACUACAGAGGCCAG
UGCCACAGCUGUUGUAACAGAGCCAGACAAGAGAGGCUGCAGAGAAGGCGCGA
AACCCAGGUGGGCGGAGGAUCUGGCGGAGGUGGAAGCGGCGGAGGCGGAUCUA
UGCACGGCCCUAAGGCCACACUGCAGGACAUCGUGCUGCACCUGGAACCUCAGA
ACGAGAUCCCUGUGGAUCUGCUCGGACACGGCCAGCUGAGCGAUAGCGAGGAA
GAGAACGACGAGAUCGACGGCGUGAACCACCAGCAUCUGCCUGCUAGAAGGGC
CGAGCCUCAGAGACACACCAUGCUGUGCAUGUGCUGCAAGUGCGAGGCCAGAA
UCAAGCUGGUGGUGGAAAGCAGCGCCGACGACCUGAGAGCUUUCCAGCAGCUG
UUCCUGAACACCCUGAGCUUCGUGUGUCCUUGGUGCGCCUCUCAGCAAGGCCUG
AUCGCCCUGGCUGUUCUGGCCUGUCUGUUGUUCCUGCUGAUUGUGGGCUUCAC
CAGCAGAUUCAAGAGACAGACCAGCUACCAGGGCGUGCUCUAG SEQ ID NO: 24
Sec-PADRE-HPV18E6E7-hCD1d
>Protein Sequence
MGCLLFLLLWALLQAWGSAAKFVAAWTLKAAAARFEDPTRSGYKLPDLCTELNTSL
QDIEITCVYCKTVLELTEVFEKDLFVVYRDSIPHAACHKCIDFYSRIRELRHYSDSVYG
DTLEKLTNTGLYNLLIRCLRCQKPLLRHLNEKRRFHNIAGHYRGQCHSCCNRARQERL
QRRRETQVGGGSGGGGSGGGGSMHGPKATLQDIVLHLEPQNEIPVDLLGHGQLSDSE
EENDEIDGVNHQHLPARRAEPQRHTMLCMCCKCEARIKLVVESSADDLRAFQQLFLN
TLSFVCPWCASQQGLIALAVLACLLFLLIVGFTSRFKRQTSYQGVL SEQ ID NO: 25
Sec-PADRE-HPV16E6E7-hCD1d (DNA-795)
>Polynucleotide Sequence: DNA
AATCATAATACGACTCACTATAAGGCATAGAAGTCGAGACACAGCCACTAAGTAA
GCCACCATGGGCTGCCTGCTGTTTCTGCTGCTTTGGGCTCTGCTGCAGGCCTGGGG
ATCTGCCGCCAAGTTCGTGGCTGCCTGGACCCTGAAGGCTGCCGCTGCCACCAGAAA
AGAACCGCCATGTTCCAGGATCCTCAAGAGAGGCCCAGAAAGCTGCCTCAGCTGT
GTACCGAGCTGCAGACCACCATCCACGACATCATCCTGGAATGCGTGTACTGCAA
GCAGCAGCTCCTGAGAAGAGAGGTGTACGACTTCGCCTTCCGCGACGGCTGCATC
GTGTACAGAGATGGCAACCCTTACGCCGTGTGCGACAAGTGCCTGAAGTTCTACA
GCAAGATACAGCGAGTACCGGCACTACTGCTACAGCCTGTACGGCACCACACTGGA
ACAGCAGTACAACAAGCCCCTGTGCGACCTGCTGATCAGATGCATCAACTGCCAG
AAACCTCTGTGCCCCGAGGAAAAGCAGAGACACCTGGACAAGAAGCAGCGGTTC
CACAACATCAGAGGCAGATGGACCGGCAGATGCATGTCCTGCTGCAGAAGCTCCA
GAACCAGAAGGGCTGCTGCAGCTGGTGGCGGAGGATCTGGCGGAGGTGGAAGCG
GCGGAGGCGGATCTATGCCTGGCGATACACCTACACTGCACGAGTACATGCTGGA
CCTGCAGCCTGAGACAACCGATCTGTACGGCTACGAGCAGCTGAACGACAGCAGC
GAGGAAGAGGACGAGATCGACGGACCTGCTGGACAGGCTGCTCCTGATAGAGCC
CACTACAACATCGTGACATTCTGCTGCAAGTGCGACAGCACCCTGCGGGAGATGTG
TGCAGTCTACCCACGTGGACATCAGAACCCTGGAAGATCTGCTGATGGGCACCCT
GGGCATCGTGTGCCCTATCTGTTCTCAGAAGCCTGGCCTGATCGCCCTGGCTGTTC
TGGCCTGTCTGTTGTTCCTGCTGATTGTGGGCTTCACCAGCAGATTCAAGAGACAG
ACCAGCTACCAGGGCGTGCTCTAGGCGCCGCCTCCGGGACAGTGCACCCAGGCTG
CGGCCCCTCCCCCGTCCTGGAGGTTCCCCAGCCCCACTTACCGCTTAATGCGCCAA
```

TABLE 6-continued

```
TAAACCAATGAACGAAGCAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAA

SEQ ID NO: 26
Sec-PADRE-HPV16E6E7-hCD1d (RNA-795)
>Polynucleotide Sequence: RNA
AGGCAUAGAAGUCGAGACACAGCCACUAAGUAAGCCACCAUGGGCUGCCUGCU
GUUUCUGCUGCUUUGGGCUCUGCUGCAGGCCUGGGGAUCUGCCGCCAAGUUCG
UGGCUGCCUGGACCCUGAAGGCUGCCGCUCACCAGAAAAGAACCGCCAUGUUCC
AGGAUCCUCAAGAGAGGCCCAGAAAGCUGCCUCAGCUGUGUACCGAGCUGCAG
ACCACCAUCCACGACAUCAUCCUGGAAUGCGUGUACUGCAAGCAGCAGCUCCUG
AGAAGAGAGGUGUACGACUUCGCCUUCCGCGACGGCUGCAUCGUGUACAGAGA
UGGCAACCCUUACGCCGUGUGCGACAAGUGCCUGAAGUUCUACAGCAAGAUCA
GCGAGUACCGGCACUACUGCUACAGCCUGUACGGCACCACACUGGAACAGCAGU
ACAACAAGCCCCUGUGCGACCUGCUGAUCAGAUGCAUCAACUGCCAGAAACCUC
UGUGCCCCGAGGAAAAGCAGAGACACCUGGACAAGAAGCAGCGGUUCCACAAC
AUCAGAGGCAGAUGGACCGGCAGAUGCAUGUCCUGCUGCAGAAGCUCCAGAAC
CAGAAGGGCUGCUGCAGCUGGUGGCGGAGGAUCUGGCGGAGGUGGAAGCGGCG
GAGGCGGAUCUAUGCCUGGCGAUACACCUACACUGCACGAGUACAUGCUGGAC
CUGCAGCCUGAGACAACCGAUCUGUACGGCUACGAGCAGCUGAACGACAGCAG
CGAGGAAGAGGACGAGAUCGACGGACCCUGCUGGACAGGCUGCUCCUGAUAGAG
CCCACUACAACAUCGUGACAUUCUGCUGCAAGUGCGACAGCACCCUGCGGAGAU
GUGUGCAGUCUACCCACGUGGACAUCAGAACCCUGGAAGAUCUGCUGAUGGGC
ACCCUGGGCAUCGUGUGCCCUAUCUGUUCUCAGAAGCCUGGCCUGAUCGCCCUG
GCUGUUCUGGCCUGUCUGUUGUUCCUGCUGAUUGUGGGCUUCACCAGCAGAUU
CAAGAGACAGACCAGCUACCAGGGCGUGCUCUAGGCGCCGCCUCCGGGACAGUG
CACCCAGGCUGCGGCCCCUCCCCCGUCCUGGAGGUUCCCCAGCCCCACUUACCG
CUUAAUGCGCCAAUAAACCAAUGAACGAAGCAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAA SEQ ID NO: 27
Sec-PADRE-HPV16E6E6-hCD1d (AA-795)
>Amino Acid Sequence:
MGCLLFLLLWALLQAWGSAAKFVAAWTLKAAAHQKRTAMFQDPQERPRKLPQLCT
ELQTTIHDIILECVYCKQQLLRREVYDFAFRDGCIVYRDGNPYAVCDKCLKFYSKISEY
RHYCYSLYGTTLEQQYNKPLCDLLIRCINCQKPLCPEEKQRHLDKKQRFHNIRGRWTG
RCMSCCRSSRTRRAAAAGGGGGGGSGGGGSMPGDTPTLHEYMLDLQPETTDLYG
YEQLNDSSEEEDEIDGPAGQAAPDRAHYNIVTFCCKCDSTLRRCVQSTHVDIRTLEDL
LMGTLGIVCPICSQKPGLIALAVLACLLFLLIVGFTSRFKRQTSYQGVL
```

In an aspect, the third isolated mRNA encodes an antigen has at least about 50%, alternatively at least about 60%, alternatively at least about 65%, alternatively at least about 70%, alternatively at least about 75%, alternatively at least about 80%, alternatively at least about 85%, alternatively at least about 90%, alternatively at least about 95% amino acid sequence identity to SEQ ID NO:24 or SEQ ID NO:27. In a different, non-limiting aspect, the antigen has at least about 80%, alternatively at least about 85%, alternatively at least about 90%, alternatively at least about 93%, alternatively at least about 95%, alternatively at least about 96% alternatively at least about 97%, alternatively at least about 98%, alternatively at least about 99% amino acid sequence identity to SEQ ID NO:24 or SEQ ID NO:27.

In an aspect, the third isolated mRNA has at least about 50%, alternatively at least about 60%, alternatively at least about 65%, alternatively at least about 70%, alternatively at least about 75%, alternatively at least about 80%, alternatively at least about 85%, alternatively at least about 90%, alternatively at least about 95% nucleic acid sequence identity to SEQ ID NO:23 or SEQ ID NO:26. In a different, non-limiting aspect, the third isolated mRNA has at least about 80%, alternatively at least about 85%, alternatively at least about 90%, alternatively at least about 93%, alternatively at least about 95%, alternatively at least about 96% alternatively at least about 97%, alternatively at least about 98%, alternatively at least about 99% nucleic acid sequence identity to SEQ ID NO:23 or SEQ ID NO:26.

Methods of making polynucleotides of a predetermined sequence are well-known. Solid-phase synthesis methods are known for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well.

Any method known in the art for making RNA, including, but not limited to making mRNA, is contemplated herein. Illustrative methods for making RNA include but are not limited to, chemical synthesis and in vitro transcription.

In certain aspects, the RNA for use in the methods herein is chemically synthesized. Chemical synthesis of relatively short fragments of oligonucleotides with defined chemical structure provides a rapid and inexpensive access to custom-made oligonucleotides of any desired sequence. Whereas enzymes synthesize DNA, RNA, and mRNA only in the 5' to 3' direction, chemical oligonucleotide synthesis does not have this limitation, although it is most often carried out in the opposite, i.e. the 3' to 5' direction. In certain implementations, the process is implemented as solid-phase synthesis using the phosphoramidite method and phosphoramidite building blocks derived from protected nucleosides (A, C, G, and U), or chemically modified nucleosides.

In some aspects, modifications are included in the modified nucleic acid or in one or more individual nucleoside or nucleotide. For example, modifications to a nucleoside may include one or more modifications to the nucleobase, the sugar, and/or the internucleoside linkage. In some implementations having at least one modification, the polynucleotide includes a backbone moiety containing the nucleobase, sugar, and internucleoside linkage of: pseudouridine-alpha-thio-MP, 1-methyl-pseudouridine-alpha-thio-MP, 1-ethyl-pseudouridine-MP, 1-propyl-pseudouridine-MP, 1-(2,2,2-trifluoroethyl)-pseudouridine-MP, 2-amino-adenine-MP, xanthosine-MP, 5-bromo-cytidine-MP, 5-aminoallyl-cytidine-MP, or 2-aminopurine-riboside-MP.

In other aspects having at least one modification, the polynucleotide includes a backbone moiety containing the nucleobase, sugar, and internucleoside linkage of: pseudouridine-alpha-thio-MP, 1-methyl-pseudouridine-alpha-thio-MP, or 5-bromo-cytidine-MP. Examples of such nucleoside and nucleotide modifications contemplated for use in the present disclosure are provided in PCT Publication No. WO2022/232087 which is incorporated by reference in its entirety.

To obtain the desired oligonucleotide, the building blocks are sequentially coupled to the growing oligonucleotide chain on a solid phase in the order required by the sequence of the product in a fully automated process. Upon the completion of the chain assembly, the product is released from the solid phase to the solution, deprotected, and collected. The occurrence of side reactions sets practical limits for the length of synthetic oligonucleotides (up to about 200 nucleotide residues), because the number of errors increases with the length of the oligonucleotide being synthesized. Products are often isolated by HPLC to obtain the desired oligonucleotides in high purity.

In certain aspects, RNA is made using in vitro transcription. The terms "RNA in vitro transcription" or "in vitro transcription" relate to a process wherein RNA is synthesized in a cell-free system (in vitro). DNA, particularly plasmid DNA, is used as template for the generation of RNA and/or mRNA transcripts. RNA may be obtained by DNA-dependent in vitro transcription of an appropriate DNA template, which in certain implementations is a linearized plasmid DNA template. The promoter for controlling in vitro transcription can be any promoter for any DNA-dependent mRNA polymerase. Particular examples of DNA-dependent RNA polymerases are the T7, T3, and SP6 RNA polymerases. A DNA template for in vitro RNA transcription may be obtained by cloning of a nucleic acid, in particular cDNA corresponding to the respective RNA to be in vitro transcribed, and introducing it into an appropriate vector for in vitro transcription, for example into plasmid DNA. In one aspect of the present disclosure, the DNA template is linearized with a suitable restriction enzyme, before it is transcribed in vitro. The cDNA may be obtained by reverse transcription of mRNA or chemical synthesis. Moreover, the DNA template for in vitro RNA synthesis may also be obtained by gene synthesis.

Methods for in vitro transcription are known in the art for example in PCT Publication Nos. WO 2022/170228 and WO2022/232087, which are incorporated by reference in their entirety. Reagents used in the methods typically include: 1) a linearized DNA template with a promoter sequence that has a high binding affinity for its respective RNA polymerase such as bacteriophage-encoded RNA polymerases; 2) ribonucleoside triphosphates (NTPs) for the four bases (adenine, cytosine, guanine and uracil); 3) in some cases, a cap analogue as defined above (e.g. m7G(5')ppp (5')G (m7G)); 4) a DNA-dependent RNA polymerase capable of binding to the promoter sequence within the linearized DNA template (e.g. T7, T3 or SP6 RNA polymerase); 5) optionally a ribonuclease (RNase) inhibitor to inactivate any contaminating RNase; 6) optionally a pyrophosphatase to degrade pyrophosphate, which may inhibit transcription; 7) MgCl2, which supplies Mg2+ ions as a co-factor for the polymerase; 8) a buffer to maintain a suitable pH value, which can also contain antioxidants (e.g. DTT), and/or polyamines such as spermidine at optimal concentrations.

In some aspects, all or some of the processing steps (including by not limited to template generation, mRNA synthesis, and or drug product formulation) may be performed in an unbroken fluid processing pathway, which may be configured as one or a series of consumable microfluidic path device(s)—in some instances also referred to as a process chip or a biochip (though the chip need not necessarily be used in bio-related applications). The entire production may proceed as a sterile-by-design, closed-path process without contact with the atmosphere. All the production operations may be automated, controlled by the control system to achieve a copy-exact process, regardless of the attributes of the facility housing the system. The production parameters, raw materials and environment data (including a full visual record) may become a part of an extensive, encrypted electronic file secured in the cloud and associated with each production run. In addition, purification operations, as well as a number of QC assays may be performed in-line during the production process in a single fluid flow, allowing anomalies to be detected at an early stage, through process control concepts developed in the semi-conductor industry.

In one specific aspect, the mRNA-based therapeutic composition includes a first isolated mRNA that encodes a membrane-stabilized LIGHT, a second isolated mRNA that encodes interleukin-12, and a third isolated mRNA that encodes HPV16 E6 E7. In another specific aspect, this mRNA-based therapeutic composition is a multimodal mRNA therapeutic.

In some aspects, the mRNA-based therapeutic composition is formulated with and/or in communication with a delivery vehicle. A "delivery vehicle" refers to any substance that facilitates, at least in part, the in vivo, in vitro, or ex vivo delivery of a polynucleotide to targeted cells or tissues (e.g., tumors, etc.). Referring to something as a delivery vehicle does not mean that it may not also have therapeutic effects. Delivery vehicles include, but are not limited to, viral vectors and particles such as lentivirus, adenovirus, adeno-associated virus, herpes simplex virus, retrovirus, and the like. Other modalities may also be used such as mRNA, plasmids, and recombinant proteins.

Disclosed herein are delivery vehicle compositions comprising hydroxyethyl-capped cationic peptoids, including, for example, hydroxyethyl-capped tertiary amino lipidated cationic peptoids. The delivery vehicle compositions of the disclosure can form an electrostatic interaction between the hydroxyethyl-capped tertiary amino lipidated cationic peptoids of the delivery vehicle composition and a polyanionic compound, such as a nucleic acid, to form a delivery vehicle complex, wherein the polyanionic compound functions as the cargo of the complex. The delivery vehicle complex is useful for the delivery of polyanionic compounds, such as nucleic acids (e.g., mRNA), into cells. Delivery vehicle complexes of the disclosure that include mRNA as the polyanionic cargo unexpectedly exhibit superior mRNA expression both in vitro and in vivo. When the mRNA of the delivery vehicle complex encodes, e.g., for a viral antigen, the delivery vehicle complexes can elicit humoral and cellular immune responses in vivo, thus functioning as a vaccine. The delivery vehicle complexes disclosed herein are further advantages in that they are stable, and demonstrate good tolerability and low toxicity.

As used herein, "peptoid" refers to a peptidomimetic compound in which one or more of the nitrogen atoms of the peptide backbone are substituted with side chains. As used herein, "lipidated peptoid" refers to a peptoid in which one or more of the side chains on the nitrogen atom comprises a lipid. As used herein, "polyanionic" refers to a compound having at least two negative charges, such as nucleic acids.

Some example delivery vehicle compositions of the disclosure comprise one or more hydroxyethyl-capped tertiary amino lipidated cationic peptoids. These positively charged peptoids can associate with a polyanionic compound, such as a nucleic acid, to form a delivery vehicle complex. In some aspects, the delivery vehicle compositions further comprise one or more of an anionic or zwitterionic component, such as a phospholipid; a neutral lipid, such as a sterol; and a shielding lipid, such as a PEGylated lipid. In various aspects, the delivery vehicle compositions further comprise an anionic or zwitterionic component (e.g., a phospholipid), a neutral lipid (e.g., a sterol), and a shielding lipid (e.g., a PEGylated lipid). In some aspects, the delivery vehicle compositions consist essentially of a hydroxyethyl-capped tertiary amino lipidated cationic peptoid, an anionic or zwitterionic component (e.g., a phospholipid), a neutral lipid (e.g., a sterol), and a shielding lipid (e.g., a PEGylated lipid).

Hydroxyethyl-Capped Tertiary Amino Lipidated Cationic Peptoid Component

The delivery vehicle compositions of the disclosure comprise a hydroxyethyl-capped tertiary amino lipidated cationic peptoid ("cationic component", sometimes referred to as an "ionizable lipid"). In some aspects, the hydroxyethyl-capped tertiary amino lipidated cationic peptoids comprise a compound of Formula (I):

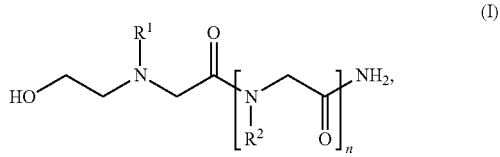

wherein n is 1, 2, 3, 4, 5, or 6; $R^1$ is H, $C_{1-3}$alkyl, or $C_{2-3}$hydroxyalkyl; and each $R^2$ independently is $C_{8-24}$alkyl or $C_{8-24}$alkenyl. As used herein, "alkyl" refers to straight chained and branched saturated hydrocarbon groups containing one to thirty carbon atoms, for example, one to four carbon atoms (e.g., 1, 2, 3, or 4). The term $C_1$ means the alkyl group has "n" carbon atoms. For example, $C_3$ alkyl refers to an alkyl group that has 3 carbon atoms. $C_{1-4}$alkyl refers to an alkyl group having a number of carbon atoms encompassing the entire range (i.e., 1 to 4 carbon atoms), as well as all subgroups (e.g., 1-2, 1-3, 2-3, 2-4, 1, 2, 3, and 4 carbon atoms). Nonlimiting examples of alkyl groups include, methyl, ethyl, n-propyl, isopropyl, n-butyl, sec-butyl (2-methylpropyl), and t-butyl (1,1-dimethylethyl). Unless otherwise indicated, an alkyl group can be an unsubstituted alkyl group or a substituted alkyl group. As used herein, "hydroxyalkyl" refers to an alkyl group, as defined herein, that is substituted with a hydroxyl group. For example, "$C_2$hydroxyalkyl" or "hydroxyethyl" has a structure:

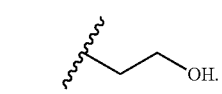 [SMILES: *CCO]

As used herein, "alkenyl" refers to straight chained and branched hydrocarbon groups having a double bond and containing two to thirty carbon atoms, for example, two to four carbon atoms (e.g., 2, 3, or 4). The term $C_1$ means the alkenyl group has "n" carbon atoms. For example, $C_3$ alkenyl refers to an alkenyl group that has 3 carbon atoms. $C_2$-$C_4$ alkenyl refers to an alkenyl group having a number of carbon atoms encompassing the entire range (i.e., 2 to 4 carbon atoms), as well as all subgroups (e.g., 2-3, 2-4, 2, 3, and 4 carbon atoms). Nonlimiting examples of alkenyl groups include, ethenyl, propenyl, and butenyl. Unless otherwise indicated, an alkenyl group can be an unsubstituted alkenyl group or a substituted alkenyl group.

In some aspects, n is 2 to 5. In various aspects, n is 3 to 4. In some aspects, n is 1. In various aspects, n is 2. In some aspects, n is 3. In various aspects, n is 4. In some aspects n is 5. In various aspects, n is 6.

In some aspects, $R^1$ is H. In various aspects, $R^1$ is $C_{1-3}$alkyl. In some aspects, $R^1$ is methyl or ethyl. In some aspects, $R^1$ is ethyl. In various aspects, $R^1$ is $C_{2-3}$hydroxyalkyl, In some aspects, $R^1$ is

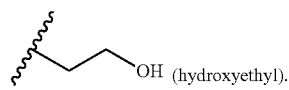 [SMILES: *CCO]

In various aspects, $R^1$ is ethyl or hydroxyethyl.

In some aspects, each $R^2$ independently is $C_{8-18}$alkyl or $C_{8-18}$alkenyl. In various aspects, each $R^2$ independently is $C_{8-16}$alkyl or $C_{10-18}$alkenyl. In some aspects, each $R^2$ independently is $C_{10-12}$ alkyl or $C_{10-18}$alkenyl. In some aspects, each $R^2$ independently is: $C_{8-18}$alkyl, or $C_{8-16}$alkyl, or $C_{8-14}$alkyl, or $C_{8-12}$alkyl. In various aspects, each $R^2$ independently is selected from the group consisting of

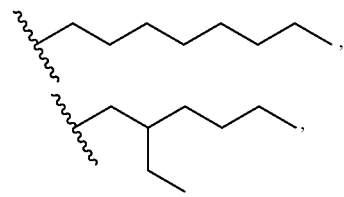

-continued
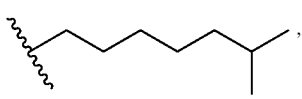
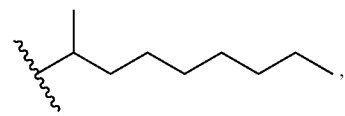
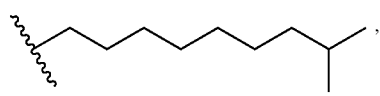
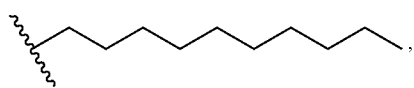
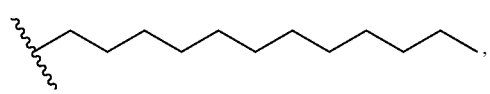
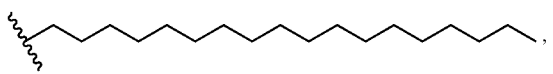
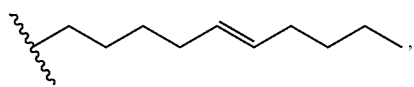
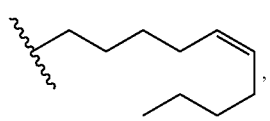
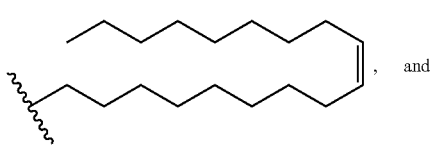, and
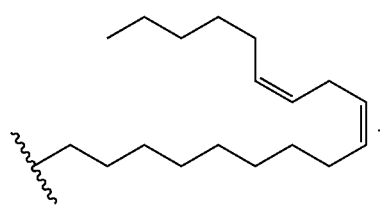
In some aspects, each $R^2$ independently is selected from the group consisting of
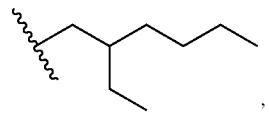
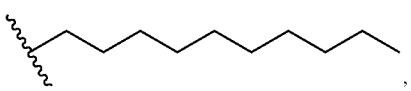
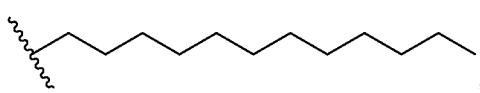, and
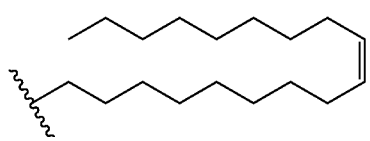
In various aspects, each $R^2$ independently is selected from the group consisting of
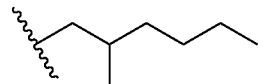
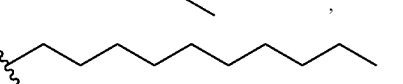, and
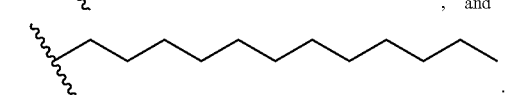
In some aspects, each $R^2$ independently is
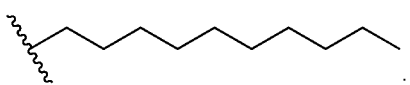 [SMILES: *CCCCCCCCCC]
In some aspects, n is 4, $R^1$ is H, and each $R^2$ is
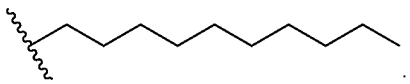 [SMILES: *CCCCCCCCCC]

Contemplated compounds of Formula (I) include, but are not limited to, the compounds listed in Table 7.

TABLE 7

Examples of hydroxyethyl-capped tertiary amino lipidated cationic peptoids.

| Compound | Structure |
|---|---|
| 140 | 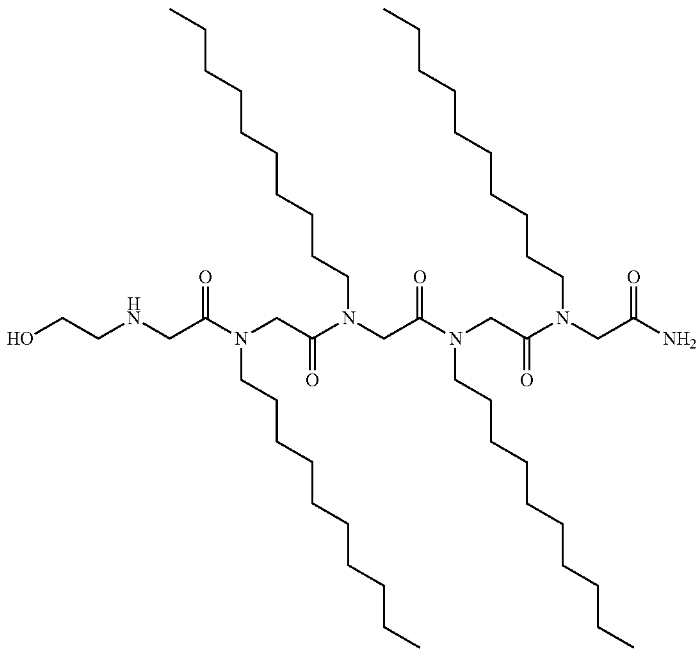 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CNCCO] |
| 146 | 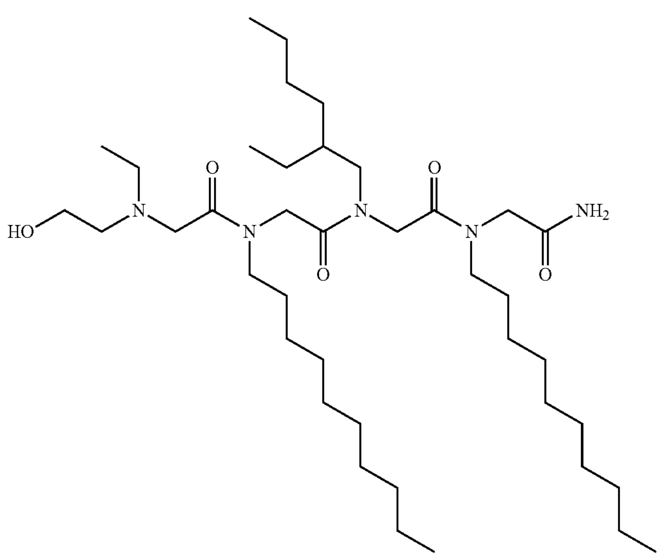 [SMILES: CCCCCCCCCCN(CC(N)=O)C(=O)CN(CC(CC)CCCC)C(=O)CN(CCCCCCCCCC)C(=O)CN(CC)CCO] |

TABLE 7-continued
Examples of hydroxyethyl-capped tertiary amino lipidated cationic peptoids.
| Compound | Structure |
|---|---|
| 151 | 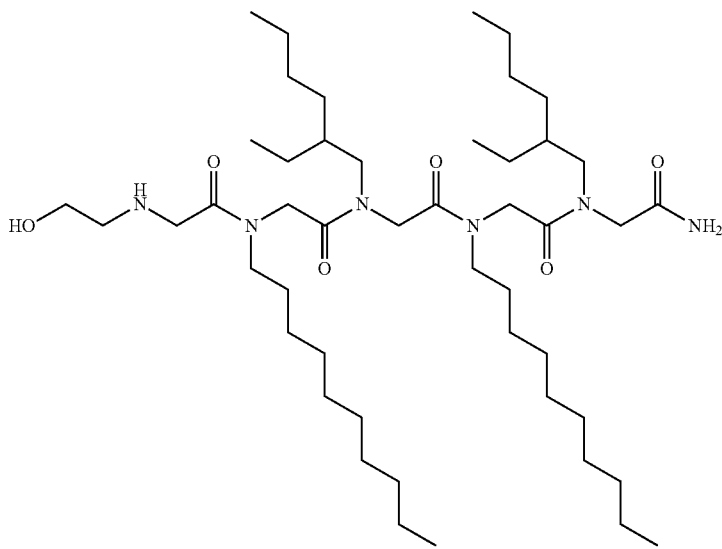 [SMILES: CCCCCCCCCCN(CC(=O)N(CC(=O)N(CCCCCCCCCC)CC(=O)N(CC(N)=O)CC(CC)CCCC)CC(CC)CCCC)C(=O)CNCCO] |
| 152 | 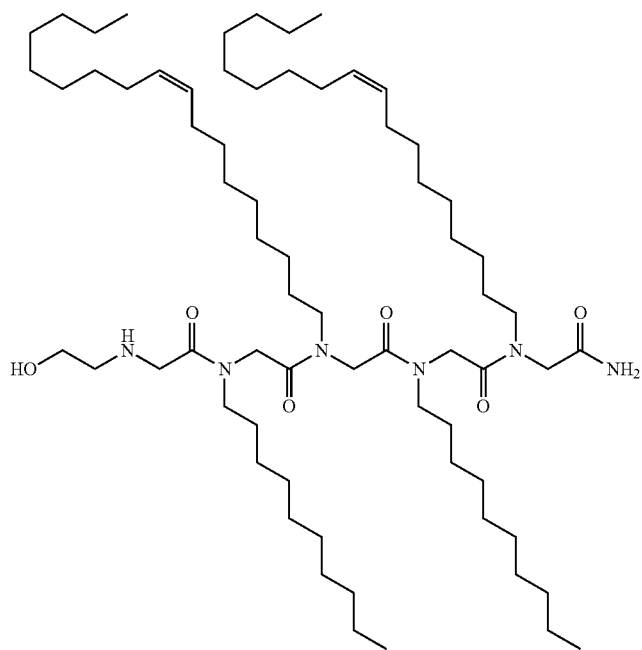 [SMILES: CCCCCCCC/C=C\CCCCCCCCN(CC(N)=O)C(=O)CN(CCCCCCCCCC)C(=O)CN(CCCCCCCC/C=C\CCCCCCCC)C(=O)CN(CCCCCCCCCC)C(=O)CNCCO] |

TABLE 7-continued
Examples of hydroxyethyl-capped tertiary amino lipidated cationic peptoids.
| Compound | Structure |
|---|---|
| 160 | 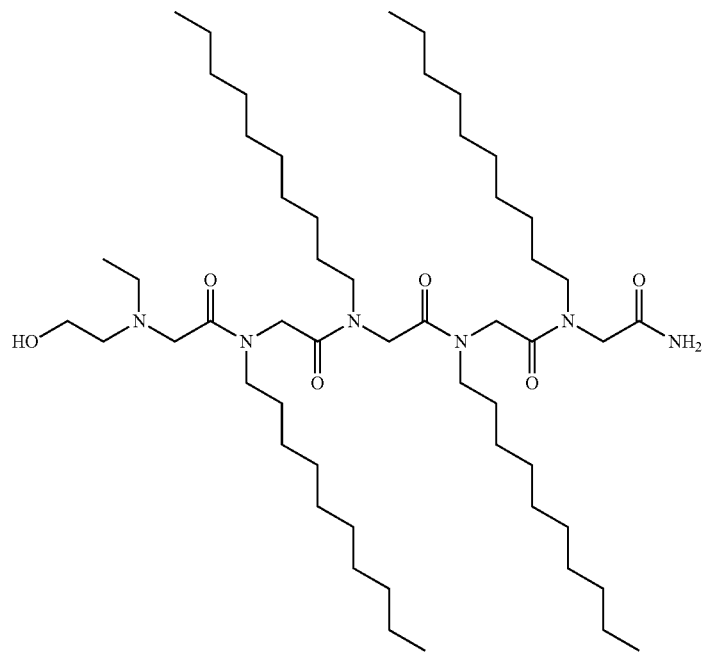 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CC)CCO] |
| 161 | 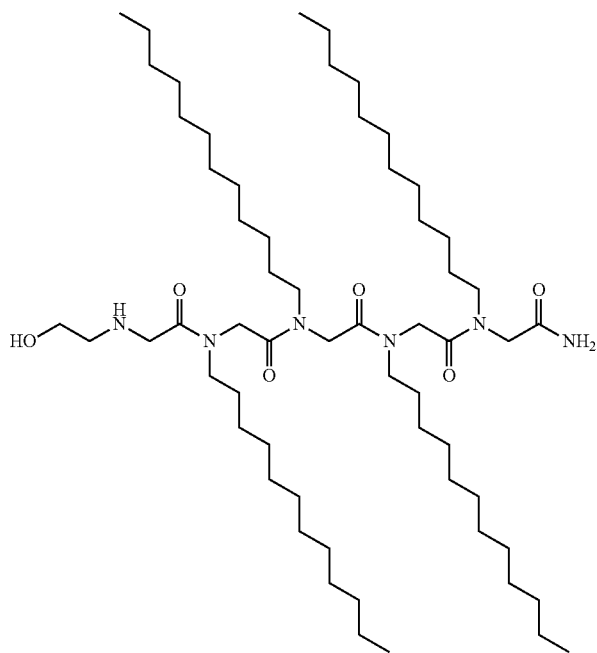 [SMILES: CCCCCCCCCCCCN(CC(N)=O)C(=O)CN(CCCCCCCCCCCC)C(=O)CN(CCCCCCCCCCCC)C(=O)CN(CCCCCCCCCCCC)C(=O)CNCCO] |

TABLE 7-continued

Examples of hydroxyethyl-capped tertiary amino lipidated cationic peptoids.

| Compound | Structure |
|---|---|
| 162 | 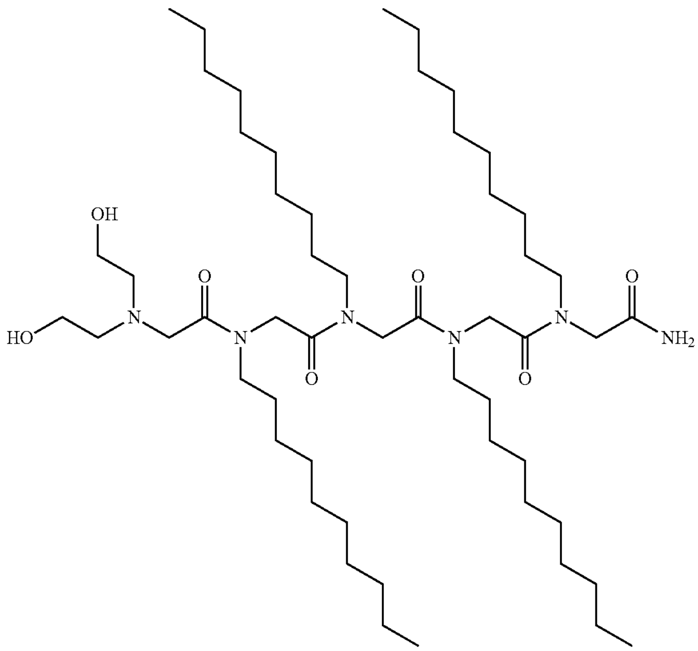 [SMILES: CCCCCCCCCCN(CC(N)=O)C(=O)CN(CCCCCCCCCC)C(=O)CN(CCCCCCCCCC)C(=O)CN(CCCCCCCCCC)C(=O)CN(CCO)CCO] |

In some aspects the compound of Formula (I) is Compound 140.

The compounds of the disclosure are defined herein by their chemical structures and/or chemical names. Where a compound is referred to by both a chemical structure and a chemical name, and the chemical structure and chemical name conflict, the chemical structure is determinative of the compound's identity.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this disclosure, unless only one of the isomers is specifically indicated. Therefore, single stereochemical isomers as well as enantiomeric, diastereomeric, cis/trans, conformational, and rotational mixtures of the present compounds are within the scope of the disclosure. In some aspects, the compounds disclosed herein are stereoisomers. "Stereoisomers" refer to compounds that differ in the chirality of one or more stereocenters. Stereoisomers include enantiomers and diastereomers. The compounds disclosed herein can exist as a single stereoisomer, or as a mixture of stereoisomers. Stereochemistry of the compounds shown herein indicate a relative stereochemistry, not absolute, unless discussed otherwise. As indicated herein, a single stereoisomer, diastereomer, or enantiomer refers to a compound that is at least more than 50% of the indicated stereoisomer, diastereomer, or enantiomer, and in some aspects, at least 90% or 95% of the indicated stereoisomer, diastereomer, or enantiomer.

The compounds described herein can exist in free form, or where appropriate, as a pharmaceutically acceptable salt. As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio. Pharmaceutically acceptable salts are well known in the art. Pharmaceutically acceptable salts of the compounds described herein include those derived from suitable inorganic and organic acids and bases. These salts can be prepared in situ during the final isolation and purification of the compounds. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine. This disclosure also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate and aryl sulfonate.

In aspects, the delivery vehicle composition comprises between about 25 mol % to about 70 mol % of the hydroxyethyl-capped tertiary amino lipidated cationic peptoid (e.g., a compound of Formula (I), such as Compound 140), based on the total number of moles of components in the delivery vehicle composition. The unit "mol %" or "molar percentage" refers to the number of moles of a particular component of the delivery vehicle composition divided by the total number of moles of all components in the delivery vehicle composition, times 100%. The polyanionic cargo is not calculated as part of the total number of moles of the delivery vehicle composition. In some aspects, the delivery vehicle composition comprises between about 30 mol % to about 60 mol %, or about 35 mol % to about 55 mol %, or about 30 mol % to about 45 mol %, or about 35 mol % to about 40 mol %, or about 45 mol % to about 60 mol %, or about 50 mol % to about 55 mol %, or about 38 mol % to about 52 mol %, or about 38 mol %, or about 52 mol % of the hydroxyethyl-capped tertiary amino lipidated cationic peptoid (e.g., a compound of Formula (I), such as Compound 140), based on the total number of moles of components in the delivery vehicle composition. In some aspects, the delivery vehicle composition comprises less than about 50 mol % of the hydroxyethyl-capped tertiary amino lipidated cationic peptoid, such as less than about 49 mol %, less than about 48 mol %, less than about 47 mol %, less than about 46 mol %, less than about 45 mol %, less than about 44 mol %, less than about 43 mol %, less than about 42 mol %, less than about 41 mol %, less than about 40 mol %, less than about 39 mol %, less than about 38 mol %, less than about 37 mol %, less than about 36 mol %, less than about 35 mol %, less than about 34 mol %, less than about 33 mol %, less than about 32 mol %, less than about 31 mol %, less than about 30 mol %; and greater than about 20 mol % of the hydroxyethyl-capped tertiary amino lipidated cationic peptoid, such as greater than about 21 mol %, greater than about 22 mol %, greater than about 23 mol %, greater than about 24 mol %, greater than about 25 mol %, greater than about 26 mol %, greater than about 27 mol %, greater than about 28 mol %, greater than about 29 mol %, greater than about 30 mol %, greater than about 31 mol %, greater than about 33 mol %, greater than about 34 mol %, greater than about 35 mol %, greater than about 36 mol %, greater than about 38 mol %, greater than about 39 mol %, or greater than about 40 mol % of the hydroxyethyl-capped tertiary amino lipidated cationic peptoid, based on the total number of moles of components in the delivery vehicle composition.

In aspects, the delivery vehicle composition comprises less than about 50 mol % of the hydroxyethyl-capped tertiary amino lipidated cationic peptoid, such as less than about 49 mol %, less than about 48 mol %, less than about 47 mol %, less than about 46 mol %, less than about 45 mol %, less than about 44 mol %, less than about 43 mol %, less than about 42 mol %, less than about 41 mol %, less than about 40 mol %, less than about 39 mol %, less than about 38 mol %, less than about 37 mol %, less than about 36 mol %, less than about 35 mol %, less than about 34 mol %, less than about 33 mol %, less than about 32 mol %, less than about 31 mol %, less than about 30 mol %; and greater than about 20 mol % of the hydroxyethyl-capped tertiary amino lipidated cationic peptoid, such as greater than about 21 mol %, greater than about 22 mol %, greater than about 23 mol %, greater than about 24 mol %, greater than about 25 mol %, greater than about 26 mol %, greater than about 27 mol %, greater than about 28 mol %, greater than about 29 mol %, greater than about 30 mol %, greater than about 31 mol %, greater than about 33 mol %, greater than about 34 mol %, greater than about 35 mol %, greater than about 36 mol %, greater than about 38 mol %, greater than about 39 mol %, greater than about 40 mol %, greater than about 41 mol %, greater than about 42 mol %, greater than about 43 mol %, or greater than about 44 mol % of the hydroxyethyl-capped tertiary amino lipidated cationic peptoid, based on the total number of moles of components in the delivery vehicle composition. In some aspects, the delivery vehicle composition comprises about 30 mol % to about 49.5 mol %, or about 30 mol % to about 45 mol %, or about 30 mol % to about 35 mol %, or about 40 mol % to about 45 mol %, or about 35 mol % to about 49 mol %, or about 36 mol % to about 48 mol %, or about 38 mol % to about 45 mol %, or about 38 mol % to about 42 mol % of the hydroxyethyl-capped tertiary amino lipidated cationic peptoid (e.g., a compound of Formula (I), such as Compound 140), based on the total number of moles of components in the delivery vehicle composition. In some aspects, the delivery vehicle composition comprises about 30 mol % to about 49.5 mol % or about 35 mol % to about 49 mol %, or about 36 mol % to about 48 mol %, or about 38 mol % to about 45 mol %, or about 38 mol % to about 42 mol % of the hydroxyethyl-capped tertiary amino lipidated cationic peptoid (e.g., a compound of Formula (I), such as Compound 140), based on the total number of moles of components in the delivery vehicle composition. In some aspects, the delivery vehicle composition comprises about 30 mol % to about 35 mol % of the hydroxyethyl-capped tertiary amino lipidated cationic peptoid (e.g., a compound of Formula (I), such as Compound 140), based on the total number of moles of components in the delivery vehicle composition. In some aspects, the delivery vehicle composition comprises about 40 mol % to about 45 mol % of the hydroxyethyl-capped tertiary amino lipidated cationic peptoid (e.g., a compound of Formula (I), such as Compound 140), based on the total number of moles of components in the delivery vehicle composition. In some aspects, the delivery vehicle composition comprises about 35 mol % to about 39 mol % of the hydroxyethyl-capped tertiary amino lipidated cationic peptoid (e.g., a compound of Formula (I), such as Compound 140), based on the total number of moles of components in the delivery vehicle composition. In various aspects, the delivery vehicle composition comprises about 39 mol % to about 52 mol % of the hydroxyethyl-capped tertiary amino lipidated cationic peptoid (e.g., a compound of Formula (I), such as Compound 140), based on the total number of moles of components in the delivery vehicle composition. In some aspects, the delivery vehicle composition comprises about 42 mol % to about 49 mol % of the hydroxyethyl-capped tertiary amino lipidated cationic peptoid (e.g., a compound of Formula (I), such as Compound 140), based on the total number of moles of components in the delivery vehicle composition. In various aspects, the delivery vehicle composition comprises about 50 mol % to about 52 mol % of the hydroxyethyl-capped tertiary amino lipidated cationic peptoid (e.g., a compound of Formula (I), such as Compound 140), based on the total number of moles of components in the delivery vehicle composition. In some aspects, the delivery vehicle composition comprises about 30 mol %, about 31 mol %, about 32 mol %, about 33 mol %, about 34 mol %, about 35 mol %, about 36 mol %, about 37 mol %, about 38 mol %, about 39 mol %, about 40 mol %, about 41 mol %, about 42 mol %, about 43 mol %, about 44 mol %, or about 45 mol % of the hydroxyethyl-capped tertiary amino lipidated cationic peptoid (e.g., a compound of Formula (I), such as Compound 140), based on the total number of moles of components in the delivery vehicle composition.

Anionic/Zwitterionic Component

In some aspects, the delivery vehicle composition further includes a component that is anionic or zwitterionic ("anionic/zwitterionic component"). The anionic/zwitterionic component can buffer the zeta potential of a particle or a delivery vehicle complex formed from the delivery vehicle composition, without affecting the ratio of the cargo and/or contributing to particle or delivery vehicle endosomal escape through protonation at low pH in the endosome. Zwitterionic components can serve a further function of holding particles together by interacting with both the hydroxyethyl-capped tertiary amino lipidated cationic peptoid and the polyanionic cargo compounds. Anionic components can also allow for the formation of a core-shell structure of the particle or delivery vehicle, where first a net positive zeta potential particle is made (e.g., by mixing the hydroxyethyl-capped tertiary amino lipidated cationic peptoid and the cargo at a positive+/−charge ratio), which is then coated with the anionic components. These negatively charged multicomponent system particles would avoid reticuloendothelial system (RES) clearance better than positively charged ones.

Example of suitable anionic and zwitterionic components of the delivery vehicle composition are described in WO2020/069442 and WO2020/069445, each of which is incorporated herein by reference in its entirety. In some aspects, the zwitterionic component comprises one or more phospholipids. Phospholipids can provide further stabilization to complexes in solution, as well as facilitate cell endocytosis, by virtue of their amphipathic character and ability to disrupt the cell membrane.

In some aspects, the one or more phospholipids are selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C 16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE),1,2-dipalmitoyl-sn-glycero-3-phosphoethanolamine (DPPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof. In some aspects, the phospholipid is DSPC, DOPE, or a combination thereof. In various aspects, the phospholipid is DSPC. In various aspects, the phospholipid is DOPE.

In aspects, the delivery vehicle composition comprises between about 1 mol % to about 40 mol % of the phospholipid (e.g., DSPC or DOPE), based on the total number of moles of components in the delivery vehicle composition. In some aspects, the delivery vehicle composition comprises between about 3 mol % to about 30 mol %, or about 5 mol % to about 15 mol %, or about 5 mol % to about 10 mol %, or about 10 mol % to about 15 mol %, or about 9 mol % to about 12 mol %, or about 7 mol % to about 11 mol %, or about 7 mol % to about 12 mol %, or about 10 mol % to about 14 mol %, or about 9 mol %, or about 12 mol % of the phospholipid (e.g., DSPC or DOPE), based on the total number of moles of components in the delivery vehicle composition. In some aspects, the delivery vehicle composition comprises between about 10 mol % to about 11 mol % of the phospholipid (e.g., DSPC or DOPE), based on the total number of moles of components in the delivery vehicle composition. In some aspects, the delivery vehicle composition comprises about 10.0 mol %, about 10.1 mol %, about 10.2 mol %, about 10.3 mol %, about 10.4 mol %, about 10.5 mol %, about 10.6 mol %, about 10.7 mol %, about 10.8 mol %, about 10.9 mol %, or about 11.0 mol % of the phospholipid (e.g., DSPC or DOPE), based on the total number of moles of components in the delivery vehicle composition.

Neutral Lipid Component

In some aspects, the delivery vehicle composition further includes a component that is a neutral lipid ("neutral lipid component"). The neutral lipid component can be designed to degrade or hydrolyze to facilitate in vivo clearance of the multicomponent delivery system. Contemplated neutral lipid components include, for example, naturally-occurring lipids and lipidated peptoids comprising lipid moieties at the N-position of the peptoid. Further examples of lipidated petoids are described in WO2020/069442 and WO2020/069445, each of which is incorporated herein by reference in its entirety.

In some aspects, the neutral lipid component of the delivery vehicle composition comprises one or more sterols. In some aspects, the one more sterols are selected from the group consisting of cholesterol, fecosterol, sitosterol, ergosterol, campesterol, stigmasterol, brassicasterol, tomatidine, ursolic acid, alpha-tocopherol, and mixtures thereof. In some aspects, the sterol comprises cholesterol. In aspects, the delivery vehicle composition comprises between about 10 mol % to about 80 mol % of the sterol (e.g., cholesterol), based on the total number of moles of components in the delivery vehicle composition. In some aspects, the delivery vehicle composition comprises between about 20 mol % to about 70 mol %, or about 25 mol % to about 60 mol %, or about 30 mol % to about 55 mol %, or about 35 mol % to about 50 mol %, or about 25 mol % to about 45 mol %, or about 40 mol % to about 60 mol %, or about 30 mol % to about 40 mol %, or about 45 mol % to about 55 mol %, or about 35 mol %, or about 50 mol % of the sterol (e.g., cholesterol), based on the total number of moles of components in the delivery vehicle composition. In some aspects, the delivery vehicle composition comprises between about 40 mol % to about 55 mol %, or about 40 mol % to about 45 mol %, or about 50 mol % to about 55 mol % of the sterol (e.g., cholesterol), based on the total number of moles of components in the delivery vehicle composition. In some aspects, the delivery vehicle composition comprises about 40 mol %, about 41 mol %, about 42 mol %, about 43 mol %, about 44 mol %, about 45 mol %, about 46 mol %, about 47 mol %, about 48 mol %, about 49 mol %, about 50 mol %, about 51 mol %, about 52 mol %, about 53 mol %, about 54 mol %, or about 55 mol % of the sterol (e.g., cholesterol), based on the total number of moles of components in the delivery vehicle composition.

Shielding Component

In some aspects, the delivery vehicle composition further comprises a shielding component. The shielding component can increase the stability of the particle or delivery vehicle in vivo by serving as a steric barrier, thus improving circulation half-life. Examples of suitable shielding components are described in WO2020/069442 and WO2020/069445, each of which is incorporated herein by reference in its entirety.

In some aspects, the shielding component comprises one or more PEGylated lipids. As used herein, a "PEGylated lipid" includes any lipid or lipid-like compound covalently bound to a polyethylene glycol moiety. Suitable lipid moieties for the PEGylated lipid can include, for example, branched or straight chain aliphatic moieties that can be unsubstituted or substituted, or moieties derived from natural lipid compounds, including fatty acids, sterols, and isoprenoids, that either be unsubstituted or substituted.

In some aspects, the lipid moieties may include branched or straight chain aliphatic moieties having from about 6 to about 50 carbon atoms or from about 10 to about 50 carbon atoms. The aliphatic moieties can comprise, in some aspects, one or more heteroatoms, and/or one or more double or triple bonds (i.e., saturated or mono- or poly-unsaturated). In some aspects, the lipid moieties may include aliphatic, straight chain or branched moieties, each hydrophobic tail independently having from about 8 to about 30 carbon atoms or from about 6 to about 30 carbon atoms, wherein the aliphatic moieties can be unsubstituted or substituted. In various aspects, the lipid moieties may include, for example, aliphatic carbon chains derived from fatty acids and fatty alcohols. In some aspects, each lipid moiety is independently $C_8$-$C_{24}$-alkyl or $C_8$-$C_{24}$-alkenyl, wherein the $C_8$-$C_{24}$-alkenyl can be, in some aspects, mono- or poly-unsaturated.

Natural lipid moieties employed in the practice of the present disclosure can be derived from, for example, phospholipids, glycerides (such as di- or tri-glycerides), glycosylglycerides, sphingolipids, ceramides, and saturated and unsaturated sterols, isoprenoids, and other like natural lipids.

Other suitable lipid moieties may include lipophilic aromatic groups such as optionally substituted aryl or arylalkyl moieties, including for example naphthalenyl or ethylbenzyl, or lipids comprising ester functional groups including, for example, sterol esters and wax esters.

In some aspects, the one or more PEGylated lipids are selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any combinations thereof. In some aspects, the PEGylated lipids comprise a PEG-modified sterol. In various aspects, the PEGylated lipids comprise PEG-modified cholesterol. In some aspects, the PEGylated lipid is a PEG-modified ceramide. In some aspects, the PEG-modified ceramine is selected from the group consisting of N-octanoyl-sphingosine-1-{succinyl[methoxy(polyethylene glycol)]} and N-palmitoyl-sphingosine-1-{succinyl[methoxy (polyethylene glycol)]}, and any combination thereof.

In some aspects, the PEGylated lipids are PEG-modified phospholipids, wherein the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C 16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE),1,2-dipalmitoyl-sn-glycero-3-phosphoethanolamine (DPPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof. In various aspects, the phospholipid is DOPE.

In some aspects, the one or more PEGylated lipids comprise a PEG-modified phosphatidylethanol. In some aspects, the PEGylated lipid is a PEG-modified phosphatidylethanol selected from the group consisting of PEG-modified DMPE (DMPE-PEG), PEG-modified DSPE (DSPE-PEG), PEG-modified DPPE (DPPE-PEG), and PEG-modified DOPE (DOPE-PEG).

In various aspects, the PEGylated lipid is selected from the group consisting of dimyristoylglycerol-polyethylene glycol (DMG-PEG), distearoylglycerol-polyethylene glycol (DSG-PEG), dipalmitoylglycerol-polyethylene glycol (DPG-PEG), and dioleoylglycerol-polyethylene glycol (DOG-PEG). In some aspects, the PEG lipid is DMG-PEG.

The molecular weights of the PEG chain in the foregoing PEGylated lipids can be tuned, as desired, to optimize the properties of the delivery vehicle compositions. In some aspects, the PEG chain has a molecular weight between 350 and 6,000 g/mol, between 1,000 and 5,000 g/mol, or between 2,000 and 5,000 g/mol, or between about 1,000 and 3,000 g/mol, or between abut 1,500 and 4,000 g/mol. In some aspects, the PEG chain of the PEG lipid has a molecular weight of about 350 g/mol, 500 g/mol, 600 g/mol, 750 g/mol, 1,000 g/mol, 2,000 g/mol, 3,000 g/mol, 5,000 g/mol, or 10,000 g/mol. In some aspects, the PEG chain of the PEGylated lipid has a molecular weight of about 500 g/mol, 750 g/mol, 1,000 g/mol, 2,000 g/mol or 5,000 g/mol. The PEG chain can be branched or linear. In some aspects, the PEGylated lipid is dimyristoylglycerol-polyethylene glycol 2000 (DMG-PEG 2000).

In aspects, the delivery vehicle composition comprises between about 1 mol % to about 5 mol % of the PEGylated lipid (e.g., DMG-PEG 2000), based on the total number of moles of components in the delivery vehicle composition. In some aspects, the delivery vehicle composition comprises between about 1 mol % to about 3 mol %, or about 1 mol % to about 2 mol %, or about 2 mol % to about 5 mol %, or about 0.5 mol % to about 1.5 mol %, or about 1.5 mol % to about 2.5 mol %, or about 1.5 mol % to about 2.0 mol %, or about 2.0 mol % to about 2.5 mol %, or about 1 mol %, or about 1.5 mol %, or about 2 mol %, or about 2.5 mol %, or about 3 mol %, or about 3.5 mol %, or about 4 mol %, or about 5 mol % of the PEGylated lipid (e.g., DMG-PEG 2000), based on the total number of moles of components in the delivery vehicle composition. In some aspects, the delivery vehicle composition comprises between about 1 mol % to about 3 mol %, or about 1 mol % to about 2 mol %, or about 2 mol % to about 5 mol %, or about 0.5 mol % to about 1.5 mol %, or about 1.5 mol % to about 2.5 mol %, or about 1 mol %, or about 1.5 mol %, or about 2 mol %, or about 2.5 mol %, or about 3 mol %, or about 3.5 mol %, or about 4 mol %, or about 5 mol % of the PEGylated lipid (e.g., DMG-PEG 2000), based on the total number of moles of components in the delivery vehicle composition. In some aspects, the delivery vehicle composition comprises about 1.5 mol %, 1.6 mol %, 1.7 mol %, 1.8 mol %, 1.9 mol %, 2.0 mol %, 2.1 mol %, 2.2 mol %, 2.3 mol %, 2.4 mol %, or about 2.5 mol % of the PEGylated lipid (e.g., DMG-PEG 2000), based on the total number of moles of components in the delivery vehicle composition.

Representative Examples

Non-limiting delivery vehicle combinations are described below. As previously described, the unit "mol %" or "molar percentage" refers to the number of moles of a particular component of the delivery vehicle composition divided by the total number of moles of all components in the delivery vehicle composition, times 100%.

In some aspects, the delivery vehicle composition comprises at least 99 mol % the cationic component and less than about 1 mol % shielding component (e.g., Formula F1A in Table 2). In some aspects, the delivery vehicle composition comprises less than about 20 mol % of the cationic component, less than about 5 mol % of a shielding component, and more than about 75 mol % of a mixture of the anionic/zwitterionic component and the neutral lipid component (e.g., Formula F2A and Formula F4A in Table 2). In some aspects, the delivery vehicle composition comprises about 30 to about 45 mol % of the cationic component, about 50 to about 70 mol % of a mixture of the anionic/zwitterionic component and the neutral lipid component, and about 1.5 to about 4.5 mol % of the shielding component (e.g., Formula F3A and Formula F5A in Table 2). In various aspects, the delivery vehicle composition comprises about 15 to about 35 mol % of the cationic component, about 60 to about 80 mol % of a mixture of the anionic/zwitterionic component and the neutral lipid component, and about 1.5 to about 3.0 mol % of a shielding component (e.g., Formula F2A and Formula F3A in Table 2). In some aspects, the delivery vehicle composition comprises about 15 to about 35 mol % of the cationic component, about 10—about 20 mol % of an anionic/zwitterionic component, about 50 to about 65 mol % of a neutral lipid component, and about 1.5 to about 3.0 mol % of a shielding component (e.g., Formula F2A and Formula F3A in Table 2). In various aspects, the delivery vehicle composition comprises about 10 to about 20 mol % of the cationic component, about 75 to about 89 mol % of a lipid component, and about 1 to about 5 mol % of a shielding component (e.g., Formula F4A in Table 2). In some aspects, the delivery vehicle composition comprises about 40 to about 50 mol % of the cationic component, about 50 to about 59 mol % of an anionic/zwitterionic component, and about 1 to about 5 mol % shielding component (e.g., Formula F5A in Table 2). In various aspects, the delivery vehicle composition comprises about 30 to about 50 mol % of the cationic component, about 50 to about 70 mol % of a neutral lipid component, and about 1 to about 5 mol % shielding component (e.g., Formula F6A in Table 2). In various aspects, the delivery vehicle composition comprises about 40 to about 45 mol % of the cationic component, about 50 to about 60 mol % of a mixture of the anionic/zwitterionic component and the neutral lipid component, and about 1.5 to about 2.0 mol % of a shielding component (e.g., Formula F6.1 and Formula F6.2 in Table 2). In some aspects, the delivery vehicle composition comprises about 40 to about 45 mol % of the cationic component, about 10 to about 15 mol % of an anionic/zwitterionic component, about 40 to about 45 mol % of a neutral lipid component, and about 1.5 to about 2.0 mol % of a shielding component (e.g., Formula F6.1 and Formula F6.2 in Table 2). In various aspects, the delivery vehicle composition comprises about 30 to about 35 mol % of the cationic component, about 60 to about 70 mol % of a mixture of the anionic/zwitterionic component and the neutral lipid component, and about 2.0 to about 3.0 mol % of a shielding component (e.g., Formula F6.3 in Table 2). In some aspects, the delivery vehicle composition comprises about 30 to about 35 mol % of the cationic component, about 10 to about 15 mol % of an anionic/zwitterionic component, about 50 to about 55 mol % of a neutral lipid component, and about 2.0 to about 3.0 mol % of a shielding component (e.g., Formula F6.3 in Table 2). The cationic component can be any cationic component described herein, such as any of the compounds of Formula (I) (e.g., the compounds listed in Table 7, such as compound 140, 146, 151, 152, 160, 161, and 162). In some aspects, the cationic compound is Compound 140. The anionic/zwitterionic component can be any anionic/zwitterionic component described herein (e.g., a phospholipid). In some aspects, the anionic/zwitterionic component is DSPC or DOPE. The neutral lipid component can be any neutral lipid described herein (e.g., a sterol). In some aspects, the neutral lipid component is cholesterol. The shielding component can be any shielding component described herein (e.g., PEGylated lipids). In some aspects, the shielding component is DMG-PEG2000.

In some aspects, the delivery vehicle composition comprises about 30 mol % to about 60 mol % (e.g., about 35 mol % to about 39 mol %, or about 39 mol % to about 52 mol %, or about 42 mol % to about 49 mol %, or about 50 mol % to about 52 mol %) of the cationic component; about 3 mol % to about 20 mol % of the anionic/zwitterionic component, about 25 mol % to about 60 mol % of the neutral lipid compound, and about 1 mol % to about 5 mol % of the shielding component. In various aspects, the delivery vehicle composition comprises about 35 to about 55 mol % of the cationic component; about 5 mol % to about 15 mol % of the anionic/zwitterionic component, about 30 mol % to about 55 mol % of the neutral lipid compound, and about 1 mol % to about 3 mol % of the shielding component. In various aspects, the delivery vehicle composition comprises about 38 to about 52 mol % of the cationic component; about 9—about 12 mol % of the anionic/zwitterionic component, about 35 mol % to about 50 mol % of the neutral lipid compound, and about 1 mol % to about 2 mol % of the shielding component. In some aspects, the delivery vehicle composition comprises about 30 mol % to about 49 mol % of the compound of Formula (I); about 5 mol % to about 15 mol % of the phospholipid, about 30 mol % to about 55 mol % of the sterol, and about 1 mol % to about 3 mol % of the PEGylated lipid. In some aspects, the composition comprises about 35 mol % to about 49 mol % of the compound or salt of Formula (I); about 7 mol % to about 12 mol % of the phospholipid, about 35 mol % to about 50 mol % of the sterol, and about 1 mol % to about 2 mol % of the PEGylated lipid. The cationic component can be any cationic component described herein, such as any of the compounds of Formula (I) (e.g., the compounds listed in Table 7, such as compound 140, 146, 151, 152, 160, 161, and 162). In some aspects, the cationic compound is Compound 140. The anionic/zwitterionic component can be any anionic/zwitterionic component described herein (e.g., a phospholipid). In some aspects, the anionic/zwitterionic component is DSPC or DOPE. The neutral lipid component can be any neutral lipid described herein (e.g., a sterol). In some aspects, the neutral lipid component is cholesterol. The shielding component can be any shielding component described herein (e.g., PEGylated lipids). In some aspects, the shielding component is DMG-PEG2000.

In some aspects, the delivery vehicle composition comprises about 30 mol % to about 45 mol % of the cationic component; about 5 mol % to about 15 mol % of the anionic/zwitterionic component, about 40 mol % to about 60 mol % of the neutral lipid compound, and about 1 mol % to about 5 mol % of the shielding component. In various aspects, the delivery vehicle composition comprises about 35 mol % to about 40 mol % of the cationic component; about 8 mol % to about 12 mol % of the anionic/zwitterionic component, about 45 mol % to about 50 mol % of the neutral lipid compound, and about 1 mol % to about 3 mol % of the shielding component. In various aspects, the delivery vehicle composition comprises about 38.2 mol % of the cationic component; about 11.8 mol % of the anionic/zwitterionic component, about 48.2 mol % of the neutral lipid compound, and about 1.9 mol % of the shielding component ("Form F2"). The cationic component can be any cationic component described herein, such as any of the compounds of Formula (I) (e.g., the compounds listed in Table 7, such as compound 140, 146, 151, 152, 160, 161, and 162). In some aspects, the cationic compound is Compound 140. The anionic/zwitterionic component can be any anionic/zwitterionic component described herein (e.g., a phospholipid). In some aspects, the anionic/zwitterionic component is DSPC or DOPE. The neutral lipid component can be any neutral lipid described herein (e.g., a sterol). In some aspects, the neutral lipid component is cholesterol. The shielding component can be any shielding component described herein (e.g., PEGylated lipids). In some aspects, the shielding component is DMG-PEG-2000. In some aspects, the delivery vehicle composition comprises Form F2, as shown in Table 8, below. In some aspects, the delivery vehicle composition comprises about 38.2 mol % of Compound 140, about 11.8 mol % of DSPC, about 48.2 mol % of cholesterol, and about 1.9 mol % of DMG-PEG-2000 ("DV-140-F2").

In some aspects, the delivery vehicle composition comprises about 45 to about 55 mol % of the cationic component; about 5 mol % to about 15 mol % of the anionic/zwitterionic component, about 35 mol % to about 55 mol % of the neutral lipid compound, and about 1 mol % to about 5 mol % of the shielding component. In various aspects, the delivery vehicle composition comprises about 48 mol % to about 52 mol % of the cationic component; about 5 mol % to about 12 mol % of the anionic/zwitterionic component, about 38 mol % to about 42 mol % of the neutral lipid compound, and about 1 mol % to about 3 mol % of the shielding component. In various aspects, the delivery vehicle composition comprises about 51.3 mol % of the cationic component; about 9.3 mol % of the anionic/zwitterionic component, about 38.0 mol % of the neutral lipid compound, and about 1.5 mol % of the shielding component ("Form F6/17"). The cationic component can be any cationic component described herein, such as any of the compounds of Formula (I) (e.g., the compounds listed in Table 7, such as compound 140, 146, 151, 152, 160, 161, and 162). In some aspects, the cationic compound is Compound 140. The anionic/zwitterionic component can be any anionic/zwitterionic component described herein (e.g., a phospholipid). In some aspects, the anionic/zwitterionic component is DSPC or DOPE. The neutral lipid component can be any neutral lipid described herein (e.g., a sterol). In some aspects, the neutral lipid component is cholesterol. The shielding component can be any shielding component described herein (e.g., PEGylated lipids). In some aspects, the shielding component is DMG-PEG 2000. In some aspects, the delivery vehicle composition comprises Form F6/17, as shown in Table 8, below. In some aspects, the delivery vehicle composition comprises about 51.3 mol % of Compound 140, about 9.3 mol % of DSPC, about 38.0 mol % of cholesterol, and about 1.5 mol % of DMG-PEG 2000 ("DV-140-F6/17").

In some aspects, the delivery vehicle composition comprises about 30 mol % to about 49 mol % of the cationic component; about 5 mol % to about 15 mol % of the anionic/zwitterionic component, about 30 mol % to about 55 mol % of the neutral lipid compound, and about 1 mol % to about 3 mol % of the shielding component. In various aspects, the delivery vehicle composition comprises about 48 mol % to about 52 mol % of the cationic component; about 5 mol % to about 12 mol % of the anionic/zwitterionic component, about 38 mol % to about 42 mol % of the neutral lipid compound, and about 1 mol % to about 3 mol % of the shielding component. In various aspects, the delivery vehicle composition comprises about 42.6 mol % of the cationic component; about 10.0 mol % of the anionic/zwitterionic component, about 44.7 mol % of the neutral lipid compound, and about 1.7 mol % of the shielding component. The cationic component can be any cationic component described herein, such as any of the compounds of Formula (I) (e.g., the compounds listed in Table 7, such as compound 140, 146, 151, 152, 160, 161, and 162). In some aspects, the cationic compound is Compound 140. The anionic/zwitterionic component can be any anionic/zwitterionic component described herein (e.g., a phospholipid). In some aspects, the anionic/zwitterionic component is DSPC or DOPE. The neutral lipid component can be any neutral lipid described herein (e.g., a sterol). In some aspects, the neutral lipid component is cholesterol. The shielding component can be any shielding component described herein (e.g., PEGylated lipids). In some aspects, the shielding component is DMG-PEG 2000. In some aspects, the delivery vehicle composition comprises Form F6/12 or Form F6/15, as shown in Table 8, below. In some aspects, the delivery vehicle composition comprises about 42.6 mol % of Compound 140, about 10.9 mol % of DSPC, about 44.7 mol % of cholesterol, and about 1.7 mol % of DMG-PEG 2000 ("DV-140-F6/12"). In some aspects, the delivery vehicle composition comprises about 48.1 mol % of Compound 140, about 9.9 mol % of DSPC, about 40.4 mol % of cholesterol, and about 1.6 mol % of DMG-PEG 2000 ("DV-140-F6/15").

In some aspects, the delivery vehicle composition comprises about 40 mol % to about 49 mol % of the cationic component; about 5 mol % to about 15 mol % of the anionic/zwitterionic component, about 30 mol % to about 55 mol % of the neutral lipid compound, and about 1 mol % to about 3 mol % of the shielding component. In various aspects, the delivery vehicle composition comprises about 42 mol % to about 46 mol % of the cationic component; about 7 mol % to about 12 mol % of the anionic/zwitterionic component, about 41 mol % to about 45 mol % of the neutral lipid compound, and about 1 mol % to about 2 mol % of the shielding component. In various aspects, the delivery vehicle composition comprises about 44.4 mol % of the cationic component; about 10.6 mol % of the anionic/ zwitterionic component, about 43.3 mol % of the neutral lipid compound, and about 1.7 mol % of the shielding component. In various aspects, the delivery vehicle composition comprises about 44.4 mol % of the cationic component; about 10.6 mol % of the anionic/zwitterionic component, about 43.4 mol % of the neutral lipid compound, and about 1.7 mol % of the shielding component. The cationic component can be any cationic component described herein, such as any of the compounds of Formula (I) (e.g., the compounds listed in Table 7, such as compound 140, 146, 151, 152, 160, 161, and 162). In some aspects, the cationic compound is Compound 140. The anionic/zwitterionic component can be any anionic/zwitterionic component described herein (e.g., a phospholipid). In some aspects, the anionic/ zwitterionic component is DSPC or DOPE. The neutral lipid component can be any neutral lipid described herein (e.g., a sterol). In some aspects, the neutral lipid component is cholesterol. The shielding component can be any shielding component described herein (e.g., PEGylated lipids). In some aspects, the shielding component is DMG-PEG 2000. In some aspects, the delivery vehicle composition comprises F6.1 or F6.2, as shown in Table 8, below. In some aspects, the delivery vehicle composition comprises about 44.4 mol % of Compound 140, about 10.6 mol % of DSPC, about 43.3 mol % of cholesterol, and about 1.7 mol % of DMG-PEG 2000 ("DV-140-F6.1"). In some aspects, the delivery vehicle composition comprises about 44.4 mol % of Compound 140, about 10.6 mol % of DSPC, about 43.4 mol % of cholesterol, and about 1.7 mol % of DMG-PEG 2000 ("DV-140-F6.2").

In some aspects, the delivery vehicle composition comprises about 30 mol % to about 39 mol % of the cationic component; about 5 mol % to about 15 mol % of the anionic/zwitterionic component, about 30 mol % to about 55 mol % of the neutral lipid compound, and about 1 mol % to about 3 mol % of the shielding component. In various aspects, the delivery vehicle composition comprises about 30 mol % to about 35 mol % of the cationic component; about 7 mol % to about 12 mol % of the anionic/zwitterionic component, about 50 mol % to about 55 mol % of the neutral lipid compound, and about 2 mol % to about 3 mol % of the shielding component. In various aspects, the delivery vehicle composition comprises about 33.1 mol % of the cationic component; about 10.5 mol % of the anionic/ zwitterionic component, about 53.8 mol % of the neutral lipid compound, and about 2.5 mol % of the shielding component. The cationic component can be any cationic component described herein, such as any of the compounds of Formula (I) (e.g., the compounds listed in Table 7, such as compound 140, 146, 151, 152, 160, 161, and 162). In some aspects, the cationic compound is Compound 140. The anionic/zwitterionic component can be any anionic/zwitterionic component described herein (e.g., a phospholipid). In some aspects, the anionic/zwitterionic component is DSPC or DOPE. The neutral lipid component can be any neutral lipid described herein (e.g., a sterol). In some aspects, the neutral lipid component is cholesterol. The shielding component can be any shielding component described herein (e.g., PEGylated lipids). In some aspects, the shielding component is DMG-PEG 2000. In some aspects, the delivery vehicle composition comprises F6.3, as shown in Table 8, below. In some aspects, the delivery vehicle composition comprises about 33.1 mol % of Compound 140, about 10.5 mol % of DSPC, about 53.8 mol % of cholesterol, and about 2.5 mol % of DMG-PEG 2000 ("DV-140-F6.1").

TABLE 8

Delivery Vehicle Compositions

| Molecular Percentages (mol %) | Cationic component | Anionic or Zwitterionic component | Non-cationic lipid component | Shielding component |
|---|---|---|---|---|
| F1A | 99.1 | 0 | 0 | 0.9 |
| F2A | 17.9 | 16.4 | 62.9 | 2.8 |
| F3A | 32.9 | 13.4 | 51.7 | 2.0 |
| F4A | 17.1 | 0 | 80.2 | 2.7 |
| F5A | 42.3 | 53.3 | 0 | 4.4 |
| F6A | 38.0 | 0 | 59.7 | 2.3 |
| F1 | 21.4 | 15.7 | 60.3 | 2.7 |
| F2 | 38.2 | 11.8 | 48.2 | 1.9 |
| F3 | 36.0 | 10.0 | 51.7 | 2.4 |
| F4 | 30.2 | 29.6 | 39.5 | 0.7 |
| F5 | 32.0 | 16.7 | 48.7 | 2.6 |
| F6/12 | 42.6 | 10.9 | 44.7 | 1.7 |
| F6/15 | 48.1 | 9.9 | 40.4 | 1.6 |
| F6/17 | 51.3 | 9.3 | 38.0 | 1.5 |
| F6.1 | 44.4 | 10.6 | 43.3 | 1.7 |
| F6.2 | 44.4 | 10.6 | 43.4 | 1.7 |
| F6.3 | 33.1 | 10.5 | 53.8 | 2.5 |

In some aspects, the delivery vehicle composition is F6.1, F6.2, or F6.3. In some aspects, the delivery vehicle composition is F1A, F2A, F3A, F4A, F5A, F6A, F1, F2, F3, F4, F5, F6/12, F6/15, or F6/17.

The delivery vehicle compositions disclosed herein can form complexes with one or more polyanionic compounds (e.g., nucleic acids) through an electrostatic interaction between the cationic component of the delivery vehicle composition and the polyanionic compound. Thus, a delivery vehicle complex refers to a mixture comprising a delivery vehicle composition, as disclosed herein, and a polyanionic compound. The complexes, in some instances, permit a high amount of cargo encapsulation, are stable, and demonstrate excellent efficiency and tolerability in vivo. The delivery vehicle complexes, therefore, are useful as delivery vehicles for the transportation of the polyanionic cargo encapsulated therein to a target cell. Additionally or alternatively, the delivery vehicle complexes can include a non-anionic cargo. Accordingly, another aspect of the disclosure relates to a delivery vehicle complex comprising: (1) a delivery vehicle composition, as previously described herein, and (2) a polyanionic compound (or cargo). In some aspects, the delivery vehicle composition complexes with one polyanionic compound (e.g., one RNA). In various aspects, the delivery vehicle composition complexes with two different polyanionic compound (e.g., two different RNAs or an RNA and a DNA). In some aspects, the delivery vehicle composition complexes with three or more different polyanionic compounds (e.g., 3, 4, or 5 different RNAs).

The delivery vehicle complexes described herein may be characterized by the relative mass ratio of one of the components of the delivery vehicle composition to the cargo (e.g., a polyanionic compound) in the complex. Mass ratios of the components in the delivery vehicle complex can be readily calculated based upon the known concentrations and volumes of stock solutions of each component used in preparing the complex. Moreover, if non-anionic cargoes are present in the delivery vehicle complex, mass ratios may provide a more accurate representation of the relative amounts of delivery vehicle components to the overall cargo than cation:anion charge ratios, which do not account for non-anionic material. Specifically, the mass ratio of a component refers to the ratio of the mass of this particular component in the system to the mass of the "cargo" in the system. "Cargo" may refer to the total polyanionic compound(s) present in the system. In one example, the polyanionic compound(s) may refer to nucleic acid(s). In one example, the polyanionic compound(s) refer to mRNA(s) encoding at least one protein.

In some aspects, the cationic component and the polyanionic compound of the delivery vehicle complex have a mass ratio between about 0.5:1 and about 20:1, between about 0.5:1 and about 10:1, between about 0.5:1 and about 5:1, between about 1:1 and about 20:1, between about 1:1 and about 10:1, between about 1:1 and about 5:1, between about 2:1 and about 20:1, between about 2:1 and about 10:1, or between about 2:1 and about 5:1. In some aspects, the cationic component and the polyanionic compound of the delivery vehicle complex have a mass ratio between about 2:1 and about 5:1. In still yet other aspects, the cationic component and the polyanionic compound of the delivery vehicle complex have a mass ratio of about 3:1. In other aspects, the cationic component and the polyanionic compound of the delivery vehicle complex have a mass ratio of about 19:1. In other aspects, the cationic component and the polyanionic compound of the delivery vehicle complex have a mass ratio of about 20:1. In other aspects, the cationic component and the polyanionic compound of the delivery vehicle complex have a mass ratio of about 13:1. In other aspects, the cationic component and the polyanionic compound of the delivery vehicle complex have a mass ratio of about 10:1. In some aspects, the cationic component can be a compound of Formula (I), such as a compound listed in Table 7 (e.g., Compound 140).

In certain aspects wherein the delivery vehicle complex comprises a nucleic acid as the polyanionic compound, or cargo, the mass ratio of the cationic component and the nucleic acid is between about 0.5:1 and about 20:1, or between about 0.5:1 and about 10:1, or between about 0.5:1 and about 5:1, or between about 1:1 and about 20:1, or between about 1:1 and about 10:1, or between about 1:1 and about 5:1, or between about 2:1 and about 20:1, or between about 2:1 and about 10:1, or between about 2:1 and about 5:1. In certain aspects, the mass ratio of the cationic component and the nucleic acid is between about 2:1 and about 5:1. In still yet other aspects, the mass ratio of the cationic component and the nucleic acid is about 3:1. In other aspects, the mass ratio of the cationic component and the nucleic acid is about 19:1. In other aspects, the mass ratio of the cationic component and the nucleic acid is about 20:1. In other aspects, the mass ratio of the cationic component and the nucleic acid is about 13:1. In other aspects, the mass ratio of the cationic component and the nucleic acid is about 10:1. In some aspects, the cationic component can be a compound of Formula (I), such as a compound listed in Table 7 (e.g., Compound 140).

In some aspects, the mass ratio of the cationic component and the nucleic acid is between about 5:1 to about 25:1, or about 7:1 to about 20:1, or about 10:1 to about 17:1, or about 9.5:1 to about 10.5:1, or about 11:1 to about 17:1. In various aspects, the mass ratio of the cationic component and the nucleic acid is about 20:1. In various aspects, the mass ratio of the cationic component and the nucleic acid is about 19:1. In some aspects, the mass ratio of the cationic component and the nucleic acid is about 17:1. In various aspects, the mass ratio of the cationic component and the nucleic acid is about 15:1. In various aspects, the mass ratio of the cationic component and the nucleic acid is about 13:1. In various aspects, the mass ratio of the cationic component and the nucleic acid is about 12:1. In various aspects, the mass ratio of the cationic component and the nucleic acid is about 10:1. In some aspects, the cationic component can be a compound of Formula (I), as previously described herein, such as a compound listed in Table 7. In various aspects, the cationic component is Compound 140. In some aspects, the polyanionic cargo is a nucleic acid, such as RNA.

In some aspects, the mass ratio of the anionic/zwitterionic component and the polyanionic compound is about 2:1 to about 10:1, or about 2:1 to about 3:1, or about 2:1 to about 4:1, or about 5:1 to about 10:1. In some aspects, the mass ratio of the anionic/zwitterionic component and the polyanionic compound is about 2:1 to about 10:1, or about 2:1 to about 3:1, or about 5:1 to about 10:1. In some aspects, the mass ratio of the anionic/zwitterionic component and the polyanionic compound is about 4:1. In some aspects, the mass ratio of the anionic/zwitterionic component and the polyanionic compound is about 2.7:1. In some aspects, the anionic/zwitterionic component can be a phospholipid, as previously described herein. In various aspects, the anionic/zwitterionic component is DOPE, DSPC, or a combination thereof. In some aspects, the anionic/zwitterionic component is DSPC. In some aspects, the polyanionic cargo is a nucleic acid, such as RNA.

In some aspects, the mass ratio of the neutral lipid component and the polyanionic compound is between about 5:1 to about 8:1, or about 4:1 to about 7:1, or about 5:1 to about 6:1, or about 1:1 to about 5:1. In some aspects, the mass ratio of the neutral lipid component and the polyanionic compound is between about 4:1 to about 7:1, or about 5:1 to about 6:1, or about 1:1 to about 5:1. In some aspects, the mass ratio of the neutral lipid component and the polyanionic compound is about 5.4:1. In some aspects, the mass ratio of the neutral lipid component and the polyanionic compound is about 8.1:1. In some aspects, the mass ratio of the neutral lipid component and the polyanionic compound is about 6.7:1. In some aspects, the neutral lipid component can be a sterol, as previously described herein. In various aspects, the neutral lipid component is cholesterol. In some aspects, the polyanionic cargo is a nucleic acid, such as RNA.

In some aspects, the mass ratio of the shielding component and the polyanionic compound is between about 0.5:1 to about 2.5:1, or about 1:1 to about 2:1, or about 2:1 to about 3:1. In some aspects, the mass ratio of the neutral lipid component and the polyanionic compound is about 2.1:1. In some aspects, the mass ratio of the neutral lipid component and the polyanionic compound is about 1.4:1. In some aspects, the shielding component can be a PEGylated lipid, as previously described herein. In various aspects, the shielding component is DMG-PEG 2000. In some aspects, the polyanionic cargo is a nucleic acid, such as RNA.

In some aspects, the delivery vehicle complex comprises the cationic component and the polyanionic cargo at a mass ratio of about 10:1, the anionic/zwitterionic component and the polyanionic cargo at a mass ratio of about 2.7:1, the neutral lipid component and the polyanionic cargo at a mass ratio of about 5.4:1, and the shielding component and the polyanionic cargo at a mass ratio of about 1.4:1 ("Form F2"). In some aspects, the cationic component is a compound of Formula (I), the anionic/zwitterionic component is a phospholipid, the neutral lipid component is cholesterol, and the shielding component is a PEGylated lipid. In some aspects, the polyanionic compound is a nucleic acid, such as RNA. In various aspects, the delivery vehicle complex comprises Compound 140 at a mass ratio of about 10:1 with the nucleic acid, DSPC at a mass ratio of about 2.7:1 with the nucleic acid, cholesterol at a mass ratio of about 5.4:1 with the nucleic acid, and DMG-PEG 2000 at a mass ratio of about 1.4 with the nucleic acid ("DV-140-F2").

In some aspects, the delivery vehicle complex comprises the cationic component and the polyanionic cargo at a mass ratio of about 17:1, the anionic/zwitterionic component and the polyanionic cargo at a mass ratio of about 2.7:1, the neutral lipid component and the polyanionic cargo at a mass ratio of about 5.4:1, and the shielding component and the polyanionic cargo at a mass ratio of about 1.4:1 ("Form F6/17"). In some aspects, the cationic component is a compound of Formula (I), the anionic/zwitterionic component is a phospholipid, the neutral lipid component is cholesterol, and the shielding component is a PEGylated lipid. In some aspects, the polyanionic cargo is a nucleic acid, such as RNA. In various aspects, the delivery vehicle complex comprises Compound 140 at a mass ratio of about 17:1 with the nucleic acid, DSPC at a mass ratio of about 2.7:1 with the nucleic acid, cholesterol at a mass ratio of about 5.4:1 with the nucleic acid, and DMG-PEG 2000 at a mass ratio of about 1.4 with the nucleic acid ("DV-140-F6/17").

In some aspects, the delivery vehicle complex comprises the cationic component and the polyanionic cargo at a mass ratio of about 12:1, the anionic/zwitterionic component and the polyanionic cargo at a mass ratio of about 2.7:1, the neutral lipid component and the polyanionic cargo at a mass ratio of about 5.4:1, and the shielding component and the polyanionic cargo at a mass ratio of about 1.4:1 ("Form F6/12"). In some aspects, the cationic component is a compound of Formula (I), the anionic/zwitterionic component is a phospholipid, the neutral lipid component is cholesterol, and the shielding component is a PEGylated lipid. In some aspects, the polyanionic cargo is a nucleic acid, such as RNA. In various aspects, the delivery vehicle complex comprises Compound 140 at a mass ratio of about 12:1 with the nucleic acid, DSPC at a mass ratio of about 2.7:1 with the nucleic acid, cholesterol at a mass ratio of about 5.4:1 with the nucleic acid, and DMG-PEG 2000 at a mass ratio of about 1.4 with the nucleic acid ("DV-140-F6/12").

In some aspects, the delivery vehicle complex comprises the cationic component and the polyanionic cargo at a mass ratio of about 15:1, the anionic/zwitterionic component and the polyanionic cargo at a mass ratio of about 2.7:1, the neutral lipid component and the polyanionic cargo at a mass ratio of about 5.4:1, and the shielding component and the polyanionic cargo at a mass ratio of about 1.4:1 ("Form F6/15"). In some aspects, the cationic component is a compound of Formula (I), the anionic/zwitterionic component is a phospholipid, the neutral lipid component is cholesterol, and the shielding component is a PEGylated lipid. In some aspects, the polyanionic cargo is a nucleic acid, such as RNA. In various aspects, the delivery vehicle complex comprises Compound 140 at a mass ratio of about 15:1 with the nucleic acid, DSPC at a mass ratio of about 2.7:1 with the nucleic acid, cholesterol at a mass ratio of about 5.4:1 with the nucleic acid, and DMG-PEG 2000 at a mass ratio of about 1.4 with the nucleic acid ("DV-140-F6/15").

In some aspects, the delivery vehicle complex comprises the cationic component and the polyanionic cargo at a mass ratio of about 13:1, the anionic/zwitterionic component and the polyanionic cargo at a mass ratio of about 2.7:1, the neutral lipid component and the polyanionic cargo at a mass ratio of about 5.4:1, and the shielding component and the polyanionic cargo at a mass ratio of about 1.4:1 ("F6.1"). In some aspects, the cationic component is a compound of Formula (I), the anionic/zwitterionic component is a phospholipid, the neutral lipid component is cholesterol, and the shielding component is a PEGylated lipid. In some aspects, the polyanionic cargo is a nucleic acid, such as RNA. In various aspects, the delivery vehicle complex comprises Compound 140 at a mass ratio of about 13:1 with the nucleic acid, DSPC at a mass ratio of about 2.7:1 with the nucleic acid, cholesterol at a mass ratio of about 5.4:1 with the nucleic acid, and DMG-PEG 2000 at a mass ratio of about 1.4 with the nucleic acid ("DV-140-F6.1").

In some aspects, the delivery vehicle complex comprises the cationic component and the polyanionic cargo at a mass ratio of about 19:1, the anionic/zwitterionic component and the polyanionic cargo at a mass ratio of about 4.0:1, the neutral lipid component and the polyanionic cargo at a mass ratio of about 8.1:1, and the shielding component and the polyanionic cargo at a mass ratio of about 2.1:1 ("F6.2"). In some aspects, the cationic component is a compound of Formula (I), the anionic/zwitterionic component is a phospholipid, the neutral lipid component is cholesterol, and the shielding component is a PEGylated lipid. In some aspects, the polyanionic cargo is a nucleic acid, such as RNA. In various aspects, the delivery vehicle complex comprises Compound 140 at a mass ratio of about 19:1 with the nucleic acid, DSPC at a mass ratio of about 4.0:1 with the nucleic acid, cholesterol at a mass ratio of about 8.1:1 with the nucleic acid, and DMG-PEG 2000 at a mass ratio of about 2.1 with the nucleic acid ("DV-140-F6.2").

In some aspects, the delivery vehicle complex comprises the cationic component and the polyanionic cargo at a mass ratio of about 9.7, the anionic/zwitterionic component and the polyanionic cargo at a mass ratio of about 2.7:1, the neutral lipid component and the polyanionic cargo at a mass ratio of about 6.7:1, and the shielding component and the polyanionic cargo at a mass ratio of about 2.1:1 ("F6.3"). In some aspects, the cationic component is a compound of Formula (I), the anionic/zwitterionic component is a phospholipid, the neutral lipid component is cholesterol, and the shielding component is a PEGylated lipid. In some aspects, the polyanionic cargo is a nucleic acid, such as RNA. In various aspects, the delivery vehicle complex comprises Compound 140 at a mass ratio of about 9.7:1 with the nucleic acid, DSPC at a mass ratio of about 2.7:1 with the nucleic acid, cholesterol at a mass ratio of about 6.7:1 with the nucleic acid, and DMG-PEG 2000 at a mass ratio of about 2.1 with the nucleic acid ("DV-140-F6.3").

In still other aspects, the amount of polyanionic cargo present in the delivery vehicle complexes may be characterized by a mass ratio of delivery vehicle composition (e.g., hydroxyethyl capped lipidated cationic peptoids, phospholipid, cholesterol, and/or the shielding component in total) to the one or more polyanionic cargo compounds. In some aspects, the mass ratio of the delivery vehicle composition to the one or more polyanionic cargo compounds is between about 0.5:1 and about 20:1, between about 0.5:1 and about 10:1, between about 0.5:1 and about 5:1, between about 1:1 and about 20:1, between about 1:1 and about 10:1, between about 1:1 and about 5:1, between about 2:1 and about 20:1, between about 2:1 and about 10:1, or between about 2:1 and about 5:1. In certain aspects, the mass ratio of the delivery vehicle composition to the one or more polyanionic cargo compounds is between about 5:1 and about 8:1 or between about 6:1 and about 7:1.

In one non-limiting example, the mRNA-based therapeutic composition may comprise the first isolated mRNA, second isolated mRNA and/or third isolated mRNA at least partially encapsulated by a delivery vehicle molecule that has a formulation that may be, but not limited to, poly(lactic-co-glycolic acid)(PLGA) microspheres, lipidoids, lipoplex, liposome, polymers, carbohydrates (including simple sugars), cationic lipids, and combinations thereof.

In one aspect, the delivery vehicle molecule formulation may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, and PEGylated lipids. In another aspect, the lipid may be a cationic lipid such as, but not limited to, DLin-DMA, DLin-D-DMA, DLin-MC3-DMA, DLin-KC2-DMA, and DODMA.

In one aspect, the delivery vehicle molecule may have a geometry of a nanoparticle. The delivery vehicle may be, for example, an amino lipidated peptide that may include tertiary amino lipidated cationic peptides, such as any of those described in PCT application, PCT/US19/53661, titled "LIPID NANOPARTICLE FORMULATIONS COMPRISING LIPIDATED CATIONIC PEPTIDE COMPOUNDS FOR NUCLEIC ACID DELIVERY", filed on Sep. 27, 2019, and in PCT/US19/53655, titled "TERTIARY AMINO LIPIDATED CATIONIC PEPTIDES FOR NUCLEIC ACID DELIVERY" filed on Sep. 27, 2019, the contents of each of which are incorporated herein by reference in their entirety. The nanoparticle delivery vehicle may comprise additional lipids/components. For example, the amino lipidated peptides can include one or more phospholipids, e.g., MSPC or DSPC. The lipid composition can also comprise a quaternary amine compound such as DOTAP. In some aspects, the delivery vehicle has a particle size less than or equal to about 200 nm.

The mRNA-based therapeutic may be formulated using any of the delivery vehicles taught in, for example, US Publication No. US2018/0028688, the contents of which are incorporated herein by reference in their entirety.

Components of the delivery vehicle complex can be prepared through a variety of physical and/or chemical methods to modulate their physical, chemical, and biological properties. These may involve rapid combination of the hydroxyethyl-capped tertiary amino lipidated cationic peptoids in water or a water-miscible organic solvent with the desired polyanionic cargo compound (e.g., oligonucleotides or nucleic acids) in water or an aqueous buffer solution. These methods can include simple mixing of the components by pipetting, or microfluidic mixing processes such as those involving T-mixers, vortex mixers, or other chaotic mixing structures. In some aspects, the multicomponent delivery system is prepared on a microfluidic platform.

It is to be understood that the particular process conditions for preparing the delivery vehicle complexes described herein may be adjusted or selected accordingly to provide the desired physical properties of the complexes. For example, parameters for mixing the components of the delivery system complex that may influence the final compositions may include, but are not limited to, order of mixing, temperature of mixing, mixing speed/rate, flow rate, physical dimensions of the mixing structure, concentrations of starting solutions, molar ratio of components, and solvents used.

Formulation of the delivery vehicle complexes can be accomplished in many ways. In some aspects, all components can be pre-mixed prior to addition of the nucleic acid cargo, which can result in a uniform distribution of components throughout the delivery particle.

Exemplary mixing methods are detailed in, e.g., U.S. Pat. Nos. 11,278,895 and 11,325,122, incorporated herein by reference.

In other aspects, the components can be added sequentially to produce a core-shell type structure. For example, a cationic component could be added first to begin particle condensation, followed by a lipid component to allow the particle's surface to associate with target cells, followed by a shielding component to prevent particle aggregation. For example, the hydroxyethyl-capped tertiary amino lipidated cationic peptoid can be premixed with the nucleic acid cargo to form a core structure. Then, the lipid components (such as lipid components comprising phospholipids and cholesterol) can be added to influence cell/endosomal membrane association. Because the shielding component is primarily useful on the outside of the multicomponent delivery system, this component can be introduced last, so that it does not disrupt the internal structure of the system, but rather provides a coating of the system after it is formed.

Additional components in the complexes and composition, such as the additional components of polymers, surface-active agents, targeting moieties, and/or excipients, may be admixed and combined with the rest of the components before, during, or after the principal components of the nucleic acid cargo, the cationic component, the lipid component and the shielding component have been combined.

Accordingly, also provided herein is a method of forming the delivery vehicle complex disclosed herein, comprising contacting the compound or salt of Formula (I) with the polyanionic compound. In some aspects, the method comprises admixing a solution comprising the compound or salt of Formula (I) with a solution comprising the polyanionic compound.

The delivery vehicle complexes disclosed herein can be used to deliver the polyanionic compound of the complex (or cargo) to a cell. Accordingly, disclosed herein are methods of delivering a polyanionic compound, such as a nucleic acid (e.g., RNA) to a cell comprising contacting the cell with the delivery vehicle complex or pharmaceutical composition disclosed herein. In some aspects, the cell is obtained from a subject. In some aspects, the cell is a tumor cell. In some aspects, the cell is a muscle cell.

In some aspects, the one or more polyanionic cargo compounds may be delivered for therapeutic uses. Non-limiting therapeutic uses include CIN and cancer, e.g., as a vaccine.

Figure 18B:
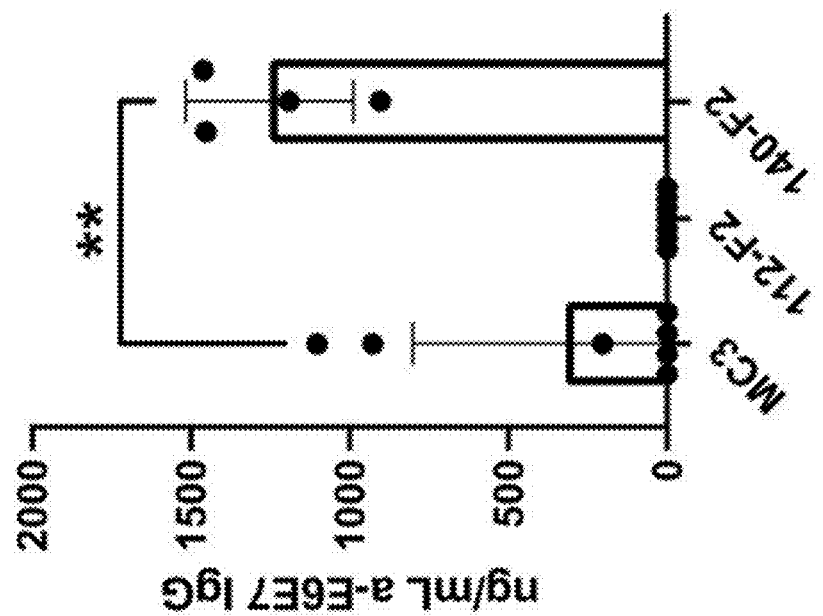
FIG. 18B depicts the humoral response of a delivery vehicle complex comprising DV-140-F2 according to an aspect of the disclosure.
Figure 18A:
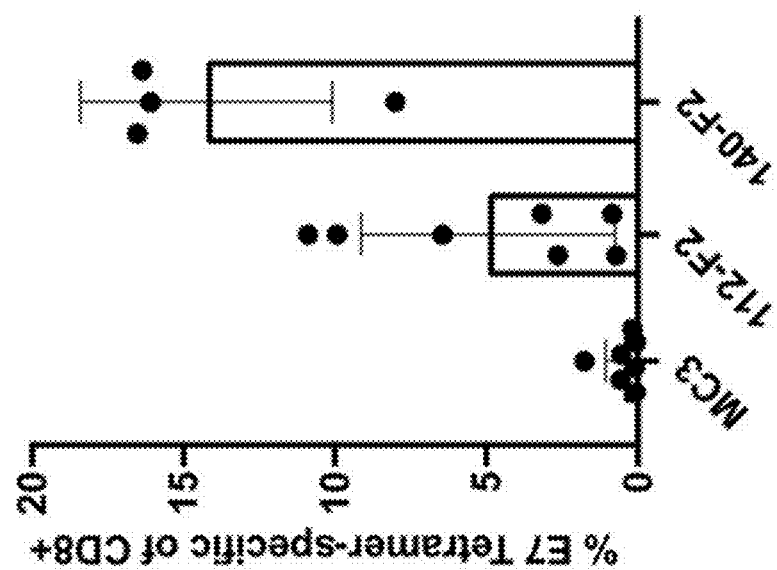
FIG. 18A depicts the cellular response of a delivery vehicle complex comprising DV-140-F2 according to an aspect of the disclosure.

The delivery vehicle complexes of the disclosure are useful as vaccines, in which the polyanionic compound is an RNA encoding a polypeptide as described herein. The immune system of a host provides the means for quickly and specifically mounting a protective response to pathogenic microorganisms and also for contributing to rejection of malignant tumors. Immune responses have been generally described as including humoral responses, in which antibodies specific for antigens are produced by differentiated B lymphocytes, and cell mediated responses, in which various types of T lymphocytes eliminate antigens by a variety of mechanisms. For example, CD4 (also called CD4+) helper T cells that are capable of recognizing specific antigens may respond by releasing soluble mediators such as cytokines to recruit additional cells of the immune system to participate in an immune response. CD8 (also called CD8+) cytotoxic T cells are also capable of recognizing specific antigens and may bind to and destroy or damage an antigen-bearing cell or particle. In particular, cell mediated immune responses that include a cytotoxic T lymphocyte (CTL) response can be important for elimination of tumor cells and cells infected by a microorganism, such as virus, bacteria, or parasite. The delivery vehicle complexes of the disclosure have been found to induce immune responses when one or more of the polyanionic compound of the complex encodes a viral peptide (e.g. a viral polypeptide), a viral protein, or functional fragment of the foregoing. For example, delivery vehicle complexes comprising either DV-140-F2 or DV-140-F6/17 complexed with mRNA encoding the HPV E6/E7 (e.g., from HPV 16 and/or HPV 18) oncogene elicited strong humoral and cellular immune responses. See, e.g., Example 7 and FIGS. 18A and 18B Thus, the disclosure includes methods for inducing an immune response in a subject in need thereof, comprising administering to the subject an effective amount of the delivery vehicle complex (e.g., formulated as an antigenic composition) of the disclosure. Also disclosed herein is a method of treating CIN, squamous cell carcinoma and adenocarcinoma, for example cancers of the cervix, vulva, vagina, penis, anus, oropharynx and head & neck, in a subject in need thereof, comprising administering to the subject an effective amount of the delivery vehicle complex of the disclosure. In some aspects, the administering is by intramuscular, intratumoral, intravenous, intraperitoneal, or subcutaneous delivery.

In various aspects, administering the delivery vehicle complexes of the disclosure (e.g., formulated as a composition, pharmaceutical formulation, or antigenic composition) to a subject can result in an increase in the amount of antibodies (e.g., neutralizing antibodies) against the viral antigen that is produced in the subject relative to the amount of antibodies that is produced in a subject who was not administered the delivery vehicle complex. In some aspects, the increase is a 2-fold increase, a 5-fold increase, a 10-fold increase, a 50-fold increase, a 100-fold increase, a 200-fold increase, a 500-fold increase, a 700-fold increase, or a 1000-fold increase.

The immune response raised by the methods of the present disclosure generally includes an antibody response, preferably a neutralizing antibody response, maturation and memory of T and B cells, antibody dependent cell-mediated cytotoxicity (ADCC), antibody cell-mediated phagocytosis (ADCP), complement dependent cytotoxicity (CDC), and T cell-mediated response such as CD4+, CD8+. The immune response generated by the delivery vehicle complexes comprising RNA that encodes a viral antigen as disclosed herein generates an immune response that recognizes, and preferably ameliorates and/or neutralizes, a viral infection as described herein. Methods for assessing antibody responses after administration of an antigenic composition (immunization or vaccination) are known in the art and/or described herein. In some aspects, the immune response comprises a T cell-mediated response (e.g., peptide-specific response such as a proliferative response or a cytokine response). In some aspects, the immune response comprises both a B cell and a T cell response. Antigenic compositions can be administered in a number of suitable ways, such as intramuscular injection, intratumoral injection, subcutaneous injection, intradermal administration and mucosal administration such as oral or intranasal. Additional modes of administration include but are not limited to intravenous, intraperitoneal, intranasal administration, intra-vaginal, intra-rectal, and oral administration. A combination of different routes of administration in the immunized subject, for example intramuscular and intranasal administration at the same time, is also contemplated by the disclosure.

Various cancers (e.g., cervical cancer, vulval cancer, vaginal cancer, penile cancer, anal cancer, oropharynxal cancer and head & neck cancer), as well as CIN, may be treated with the polyanionic cargo compounds delivered by the delivery vehicle complexes of the present disclosure. As shown in Example 7, DV-140-F2 complexed to an mRNA encoding for HPV E6/E7 (from HPV 16 and/or HPV 18) eliciting both strong cellular and humoral immune responses, illustrating the ability of the delivery vehicle complexes of the disclosure to treat cancer. As used herein, the term "cancer" refers to any of various malignant neoplasms characterized by the proliferation of anaplastic cells that tend to invade surrounding tissue and metastasize to new body sites and also refers to the pathological condition characterized by such malignant neoplastic growths. Cancers may be tumors or hematological malignancies, and include but are not limited to, all types of lymphomas/leukemias, carcinomas and sarcomas, such as those cancers or tumors found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid, uterus, vagina, and vulva.

As a non-limiting example, the carcinoma which may be treated may be anal cancer, cervical cancer, esophageal cancer, head and neck cancer, laryngeal cancer, lip cancer, metastatic squamous neck cancer, mouth cancer, nasal cavity cancer, nasopharyngeal cancer, neck cancer, oral cancer, oral cavity cancer, oropharyngeal cancer, penile cancer, pharyngeal cancer, rectal cancer, squamous cell carcinoma, tongue cancer, tonsil cancer, vaginal cancer, and vulvar cancer.

In some aspects, the delivery vehicle complexes of the disclosure are used to treat a cancer is selected from the group consisting of cervical cancer, head and neck cancer, B-cell lymphoma, T-cell lymphoma, prostate cancer, and lung cancer. In some aspects, the delivery vehicle complexes can be used to treat cervical cancer.

In some aspects, the mRNA-based composition is configured to be administered to a subject in need thereof. "Subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters, and guinea pigs; and so on. In certain aspects, the mammal is a human subject. In other aspects, a subject is a human patient. As used herein, "patient" refers to a subject who may seek or be in need of treatment, requires treatment, is receiving treatment, will receive treatment, or a subject who is under care by a trained professional for a particular disease or condition.

In some non-limiting aspects, the composition is a therapeutic composition, such as an mRNA-based therapeutic composition. The therapeutic composition may optionally include one or more therapeutically acceptable carriers, diluents, or excipients such as salts, buffering agents, preservatives, antiadherents, antioxidants, binders, coatings, compression aids, disintegrants, dyes, emollients, emulsifiers, fillers, film formers or coatings, flavors, fragrances, glidants, lubricants, sorbents, suspending or dispersing agents, sweeteners, waters of hydration, and/or other therapeutic agents. As used herein, the term "excipient" means any pharmaceutically acceptable additive, carrier, diluent, adjuvant, or other ingredient, other than the active pharmaceutical ingredient (API) (and typically in addition to components of the delivery vehicle compositions), suitably selected with respect to the intended form of administration, and consistent with conventional pharmaceutical practices. The disclosed compounds can be administered to a subject or patient in a therapeutically effective amount. The complexes can be administered alone or as part of a pharmaceutically acceptable composition or formulation. In addition, the compositions can be administered all at once, as for example, by a bolus injection, multiple times, or delivered substantially uniformly over a period of time. It is also noted that the dose of the compound can be varied over time.

In some aspects, the composition is a vaccine. A vaccine may be referred to as a substance used to stimulate the production of antibodies and provide immunity against one or several diseases, prepared from the causative agent of a disease, its products, or a synthetic substitute. In a non-limiting example, the composition may be a human papillomavirus (HPV) mRNA vaccine. The vaccine may further comprise one or more immunologic adjuvants. As used herein, the term "immunologic adjuvant" refers to a compound or a mixture of compounds that acts to accelerate, prolong, enhance or modify immune responses when used in conjugation with an immunogen (e.g., neoantigens). Adjuvant may be non-immunogenic when administered to a host alone, but that augments the host's immune response to another antigen when administered conjointly with that antigen. Specifically, the terms "adjuvant" and "immunologic adjuvant" are used interchangeably in the present disclosure. Adjuvant-mediated enhancement and/or extension of the duration of the immune response can be assessed by any method known in the art including without limitation one or more of the following: (i) an increase in the number of antibodies produced in response to immunization with the adjuvant/antigen combination versus those produced in response to immunization with the antigen alone; (ii) an increase in the number of T cells recognizing the antigen or the adjuvant; and (iii) an increase in the level of one or more cytokines. Adjuvants may be aluminum based adjuvants including but not limiting to aluminum hydroxide and aluminum phosphate; saponins such as steroid saponins and triterpenoid saponins; bacterial flagellin and some cytokines such as GM-CSF. Adjuvants selection may depend on antigens, vaccines, and routes of administrations.

In some aspects, adjuvants improve the adaptive immune response to a vaccine antigen by modulating innate immunity or facilitating transport and presentation. Adjuvants act directly or indirectly on antigen presenting cells (APCs) including dendritic cells (DCs). Adjuvants may be ligands for toll-like receptors (TLRs) and can directly affect DCs to alter the strength, potency, speed, duration, bias, breadth, and scope of adaptive immunity. In other instances, adjuvants may signal via proinflammatory pathways and promote immune cell infiltration, antigen presentation, and effector cell maturation. This class of adjuvants includes mineral salts, oil emulsions, nanoparticles, and polyelectrolytes and comprises colloids and molecular assemblies exhibiting complex, heterogeneous structures. In one example, the composition further comprises pidotimod as an adjuvant. In another example, the composition further comprises CpG as an adjuvant.

Figure 7A:
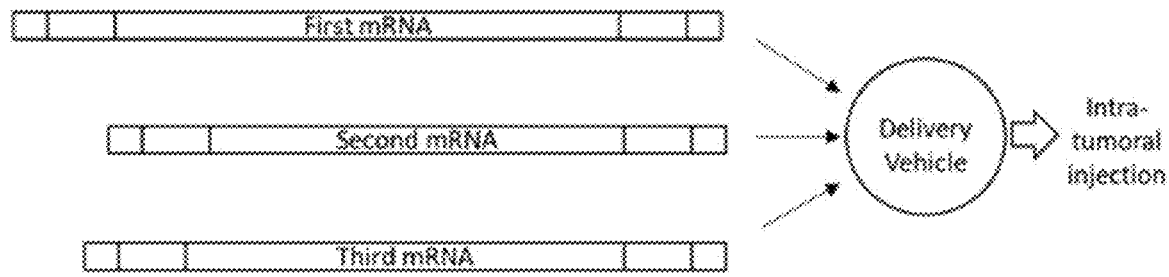
FIG. 7A is an illustration of a composition including three isolated mRNAs formulated into a delivery vehicle according to an aspect of this disclosure and subsequent administration.
Figure 7B:
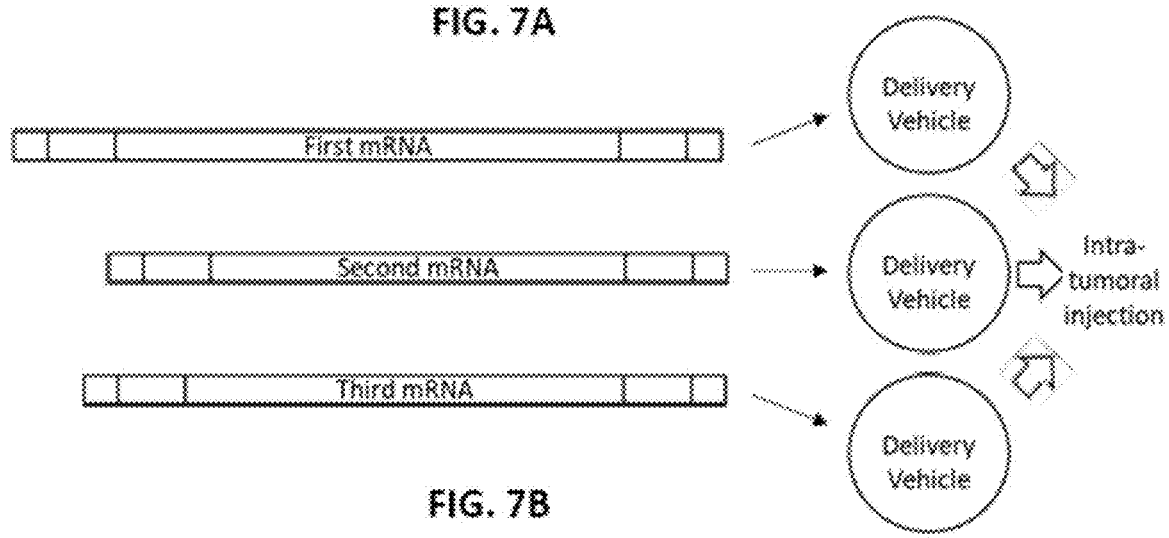
FIG. 7B is an illustration of a composition including three isolated mRNAs formulated into separate delivery vehicles according to an aspect of this disclosure and subsequent administration.
Figure 7C:
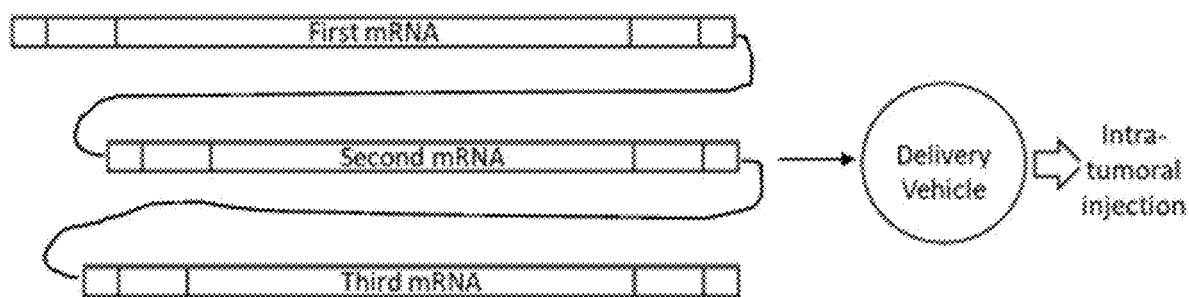
FIG. 7C is an illustration of a composition including an isolated polynucleotide comprising three mRNAs formulated into a delivery vehicle according to an aspect of this disclosure and subsequent administration.

In non-limiting aspects, the subject may be known to have cervical cancer, HPV-driven cancer, or a disease associated with HPV. FIGS. 7A-7C illustrate a formulation of multiple isolated mRNA with a delivery vehicle according to an aspect of this disclosure and subsequent administration. The mRNA-based therapeutic may be administered to a subject in need thereof by any route to achieve a therapeutically effective outcome. These include, but are not limited to, injectable preparations. In some aspects, the injectable preparation is configured to be administered intratumorally. The exact amount required to achieve a therapeutically effective outcome will vary from subject to subject, depending on the species, age, and general condition of the subject, the severity of the disease, the particular composition, its mode of administration, its mode of activity, and the like. The term "therapeutically effective" refers to an amount effective in treating and/or ameliorating a disease or condition in a subject.

Some non-limiting aspects include an expression cassette. As used herein, an expression cassette includes a promoter sequence, an open reading frame, and a termination sequence. Expression cassettes may be configured for administration directly or to be encoded in one or more polynucleotides for expression in a cell and may be encoded in DNA, RNA, or mRNA for administration. In some examples, the cassette may include a first mRNA encoding a membrane-stabilized LIGHT, a second mRNA encoding interleukin-12, and/or a third mRNA encoding HPV16 E6 E7. In some examples, the cassette may include a first isolated mRNA has at least about 80% nucleic acid sequence identity to SEQ ID NO: 18; a second isolated mRNA that has at least about 80% nucleic acid sequence identity to SEQ ID NO:20; and a third isolated mRNA has at least about 80% nucleic acid sequence identity to SEQ ID NO:26. In some aspects, cassette including the first isolated mRNA, second isolated mRNA or third isolated mRNA is at least partially encapsulated with a delivery vehicle. In another example, a multimodal mRNA therapeutic may include at least two or three of the disclosed cassettes.

The delivery vehicle complexes disclosed herein and the pharmaceutically active compounds described herein can be administered to a subject or patient by any suitable route, for example, by parenteral injection(s), e.g., intramuscularly (IM), intratumorally (IT), intracervically, paracervically, endocervically, intravulvally, intravaginally, intrapenilely, intra-anally, and intraoropharyngeally. All methods that can be used by those skilled in the art to administer a pharmaceutically active agent are contemplated.

Injectable preparations, for example, sterile injectable aqueous or oleaginous suspensions, may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose, any bland fixed oil can be employed, including synthetic mono- or diglycerides. Fatty acids such as oleic acid can be used in the preparation of injectables. Exemplary buffers include citrate, succinate, acetate, malate, succinate, histidine. In addition, stabilizers such as sucrose, may be included. For example, the therapeutic compositions may be suspended in a sucrose-containing citrate buffer at a pH between pH 5 and pH 6, e.g., at about pH 5.5.

Injectable formulations may be sterilized, for example, by filtration through a bacterial-retaining filter and/or by incorporating sterilizing agents in the form of sterile solid compositions, which can be dissolved or dispersed in sterile water or other sterile injectable media prior to use. Adjuvants such as local anesthetics, preservatives and buffering agents can also be added to the compositions.

In order to prolong the effect of active ingredients, it is often desirable to slow the absorption of active ingredients from subcutaneous or intramuscular injections. This may be accomplished by the use of liquid suspensions of crystalline or amorphous material with poor water solubility. The rate of absorption of active ingredients depends upon the rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are prepared by entrapping the drug in liposomes or microemulsions that are compatible with body tissues. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like.

The compounds and/or compositions of the disclosure can be administered to a subject or patient at dosage levels in the range of about 0.1 to about 100 mg per day. For weight-based dosing a normal adult human having a body weight of about 70 kg, a dosage in the range of about 0.001 to about 1 mg per kilogram body weight is contemplated to be sufficient. The specific dosage and dosage range that will be used can potentially depend on a number of factors, including the requirements of the subject or patient, the severity of the condition or disease being treated, and the pharmacological activity of the compound being administered. The determination of dosage ranges and optimal dosages for a particular subject or patient is within the ordinary skill in the art.

In some aspects, the mRNA-based therapeutic may be part of a kit. The kit may include a pharmaceutically acceptable carrier and/or a package insert comprising instructions for intratumoral administration (e.g., injection) of the mRNA-based therapeutic composition. The kit may further include instructions for treating or delaying progression of cancer in a subject. In some aspects, the package insert further comprises instructions for administration of the composition by intratumoral administration in combination with injection in another site (e.g., systemic injection) for treating or delaying progression of cancer in a subject. The kit may also include additional therapeutic nucleic acids, drug, therapeutic agent, diagnostic agent, prophylactic agent, and/or any other agent that, when administered to a subject, has a therapeutic, diagnostic, and/or prophylactic effect and/or elicits a desired biological and/or pharmacological effect.

In some aspects, a mRNA-based therapeutic that includes an isolated mRNA that encodes a membrane-stabilized LIGHT may result in durable tumor regression and long term CD8+ T-cell mediated cancer immunity as compared to wild type (soluble) LIGHT.

In some aspects, embodiments of the invention comprise RNA sequences encoding human papillomavirus 16 (hHPV16) E6/E7 antigen, the human version of Interleukin 12 (hIL-12), and the herein-described engineered human version of LIGHT (ENG hLIGHT), based on wild-type hLIGHT, which is also known as tumor necrosis factor superfamily member 14 (TNFSF14).

Figure 3D:
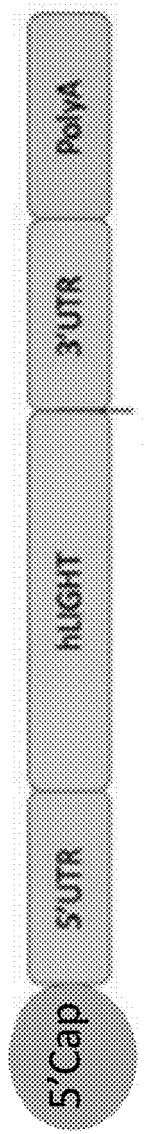
FIG. 3D is an illustration of an isolated mRNA that may encode a human LIGHT polypeptide according to an aspect of the disclosure.
Figure 3E:
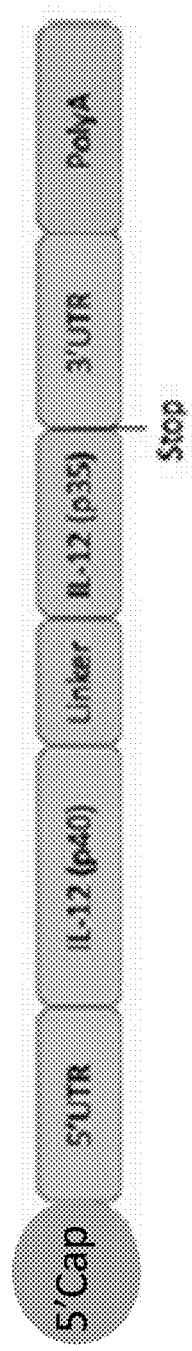
FIG. 3E is an illustration of an isolated mRNA that may encode a human IL-12 polypeptide or fusion protein according to an aspect of the disclosure.

FIGS. 3C, 3D and 3E are schematic representations showing an arrangement of RNA elements that, in some aspects, are part of RNA sequences encoding each of the hHPV16 E6/E7 antigen, ENG hLIGHT, and hIL-12 (fusion), respectively. The elements include a 5'Cap, a 5'UTR, coding sequences for hHPV16 E6/E7 antigen, ENG hLIGHT, or hIL-12 fusion, a 3'UTR, and a poly-A tail.

Figure 3F:
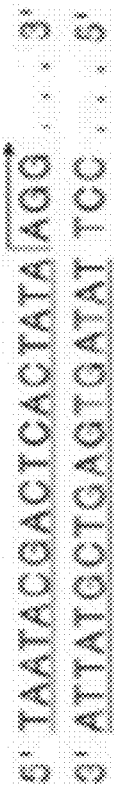
FIG. 3F shows the sequence of a template DNA and synthesized RNA with a T7 promoter sequence (underlined) and a 5' Cap initiation sequence (AGG). Arrow indicates transcription start site with nucleotide positions shown above.

In some aspects, the 5' cap consists of a naturally occurring 5' N7-methylguanosine linked by a 5' to 5' triphosphate bridge to the first 2 transcribed nucleotides, an A methylated on the ribose 0-2 position and guanine (G) nucleotide in the +1 and +2 positions. An embodiment of a template DNA and synthesized RNA with a T7 promoter sequence (underlined) and a 5' Cap initiation sequence is illustrated in FIG. 3F.

In one embodiment, termed "NTX-250", the hHPV16 antigen is encoded by RNA-795 (SEQ ID NO: 26), hIL-12 is encoded by RNA-683 (SEQ ID NO: 20), and ENG hLIGHT is encoded by RNA-1495 (SEQ ID NO: 18).

hHPV16 Antigen mRNA (RNA-795)

RNA-795 corresponds to a single mRNA sequence encoding a protein consisting of a vaccine scaffold, pan human leukocyte antigen (HLA) DR-binding epitope (PADRE), and derivatives of the E6 and E7 (E6/E7) antigenic sequences from HPV16. The nucleotide sequence which has been codon-optimized for increased expression, is comprised of 1321 nucleotides and has a molecular weight of 429037 g/mol. The construct follows the schematic illustrated in FIG. 3C The vaccine scaffold consists of the signal sequence as well as C terminal membrane and intracellular regions of the cluster of differentiation 1 (CD1d) gene, a member of the family of glycoproteins expressed on the surface of various antigen-presenting cells. The linking of the antigen to the CD1d trafficking signal sequence routes the antigen into processing compartments, resulting in improvement of T cell responses. The PADRE epitope is a peptide sequence that has been shown to activate antigen specific-CD4+ T cells (Wieking, 2012).

The antigenic E6/E7 sequences are connected by a flexible glycine-serine $(G_4S)_3$ linker to enable expression of the full length fusion protein. In addition, the following mutations were made to the natural human papillomavirus (HPV) E6/E7 protein sequence to alleviate the known oncogenic functions of E6/E7:

Leucine (UUA) to glycine (GGC) at construct nucleotide sequence #301-303, which encompasses the p53 binding and telomerase activation site.

Four mutations on the C-terminal PDZ-binding domain of E6; glutamic acid (Glu, GAG), threonine (ACU), glutamine (CGA), and leucine (CUU) at construct nucleotide sequence #595-606, were mutated to 4 alanines (GCU-GCU-GCA-GCU). The PDZ-binding domain participates in transformation by inactivating the tumor suppressor protein PTPN13 and other proteins with PDZ domain interactions (Spanos, 2008).

Three single point mutations in HPV16 E7 at the retinoblastoma (Rb) protein-binding sites, Histidine (CAA) to proline (CCU) at construct nucleotide sequence #655-657.

Cysteine (UGC) to glycine (GGC) at construct nucleotide sequence #721-723.

Glutamic acid (GAG) to alanine (GCU) at construct nucleotide sequence #787-789.

These mutations prevent E7 from binding and inactivating Rb protein and other proteins and from associating with Mi2Beta that enhances cellular growth (Narisawa-Saito, 2007).

Single point mutation of leucine (CUG) to arginine (AGA) at construct nucleotide sequence #850-853, was generated to disrupt Mi2Beta binding.

hIL-12 mRNA (RNA-683)

RNA-683 corresponds to a single mRNA sequence encoding the hIL-12 protein in which the 2 subunits, p40 and p35, have been linked into a single chain construct using a flexible $(G_4S)_3$ linker. The nucleotide sequence which has been codon-optimized for increased expression, is comprised of 1936 nucleotides, and has a molecular weight of 628446 g/mol. The construct follows the schematic illustrated in FIG. 3E.

ENG hLIGHT mRNA (RNA-1495)

RNA-1495 corresponds to a single mRNA sequence encoding the native secreted LIGHT engineered to replace amino acids #66-92 with a novel 10 amino acid linker sequence to enhance membrane stability and expression. ENG hLIGHT is designed to be a surface-bound Type II membrane protein. The nucleotide sequence which has been codon-optimized for increased expression, is comprised of 994 nucleotides and has a molecular weight of 323476 g/mol. The construct follows the schematic illustrated in FIG. 3D.

Formulation

In some aspects, formulated drug product is presented as white to off-white colloidal frozen suspension for injection. In one aspect, a vial of drug product may contain 1.0 mg mRNAs with 1:1:1 mass ratio for hHPV16 antigen:hIL-12: ENG hLIGHT mRNAs (1.0 mg/mL). For example, in one embodiment, NTX-250 finished product may contain aforementioned mRNAs encapsulated into a proprietary Lipid Nanoparticle (LNP) formulation dispersed in a sucrose-containing citrate buffer at pH 5.5. In some aspects, the sucrose-containing citrate buffer comprises 14.07 mM sodium citrate dihydrate, 5.93 mM citric acid, 300 mM sucrose, pH 5.5. In some aspects, the four lipids utilized to create the LNP are proprietary peptoid lipid N-(2-amino-2-oxoethyl)-N-decyl-2-(N-decyl-2-(N-decyl-2-(N-decyl-2-((2-hydroxyethyl) amino)acetamido)acetamido)acetamido) acetamide (DVI-0140, described in detail above), 1,2-distearoyl-sn-glycero-3-phosphocholine (DSPC), cholesterol, and 1,2-dimyristoyl-rac-glycero-3-methoxy-polyethylene glycol-2000 (DMG-PEG2000). In some aspects, the formulation is a 140-F2 formulation. In some aspects, the formulation is a 140-F6.1 formulation. In some aspects, the formulation is a 140-F6.2 formulation. In some aspects, the formulation is a 140-F6.3 formulation.

Nonclinical Studies on NTX-250

Nonclinical pharmacology studies performed in support of the present invention included in vitro and in vivo pharmacology studies to characterize the bioactivities and antitumor effect of NTX-250 or its murine surrogate, mNTX-250, and their respective mRNA components. The battery of nonclinical pharmacology studies included NTX-250 containing either the native wildtype (WT) LIGHT mRNA or ENG LIGHT mRNA. In vitro, treatment with NTX-250 or combinations of its mRNA components effectively induced IFN-γ secretion and T cell activation in HPV16-positive CIN and healthy donor PBMCs. Compared to WT LIGHT mRNA, ENG LIGHT mRNA resulted in higher surface expression and bioactivity on transfected cells, leading to increased T cell proliferation. In vivo, mNTX-250 effectively eradicated C3.43 tumors in a mouse syngeneic tumor model and improved survival in a dose-dependent manner, and synergistic antitumor effect of the 3 mRNA components of NTX-250 was demonstrated regardless of WT or ENG mLIGHT mRNA. mNTX-250 was also associated with HPV16-specific T cell generation, T cell infiltration into tumors, and proinflammatory cytokine induction. Rechallenge evaluation of HPV16 E7-expressing TC-1 tumor in mNTX-250 treated tumor free mice previously inoculated with C3.43 tumors showed immunologic memory and persistent tumor growth inhibition (TGI). In a subcutaneous (SC) MC38 colon cancer model in mice, treatment with ENG LIGHT resulted in higher levels of cytokines in the TME compared to WT LIGHT. HPV16-specific T cell immune responses were observed in both rats and monkeys administered intramuscular (IM) doses of mNTX-250 or NTX-250, respectively.

EXAMPLES

The presently described technology and its advantages will be better understood by reference to the following examples. These examples are provided to describe specific implementations of the present technology. By providing these specific examples, it is not intended limit the scope and spirit of the present technology.

Some of the experiments described below were performed using human sequence constructs, which are typically identified with an "h" preceding the name of the construct, for example, hLIGHT for human LIGHT. Some of the experiments described below were performed using murine surrogate constructs, which are typically identified with an "m" preceding the name of the construct, for example, mLIGHT for murine LIGHT.

Example 1: Comparative Analysis of Soluble LIGHT and Membrane-Stabilized LIGHT

Figure 8A:
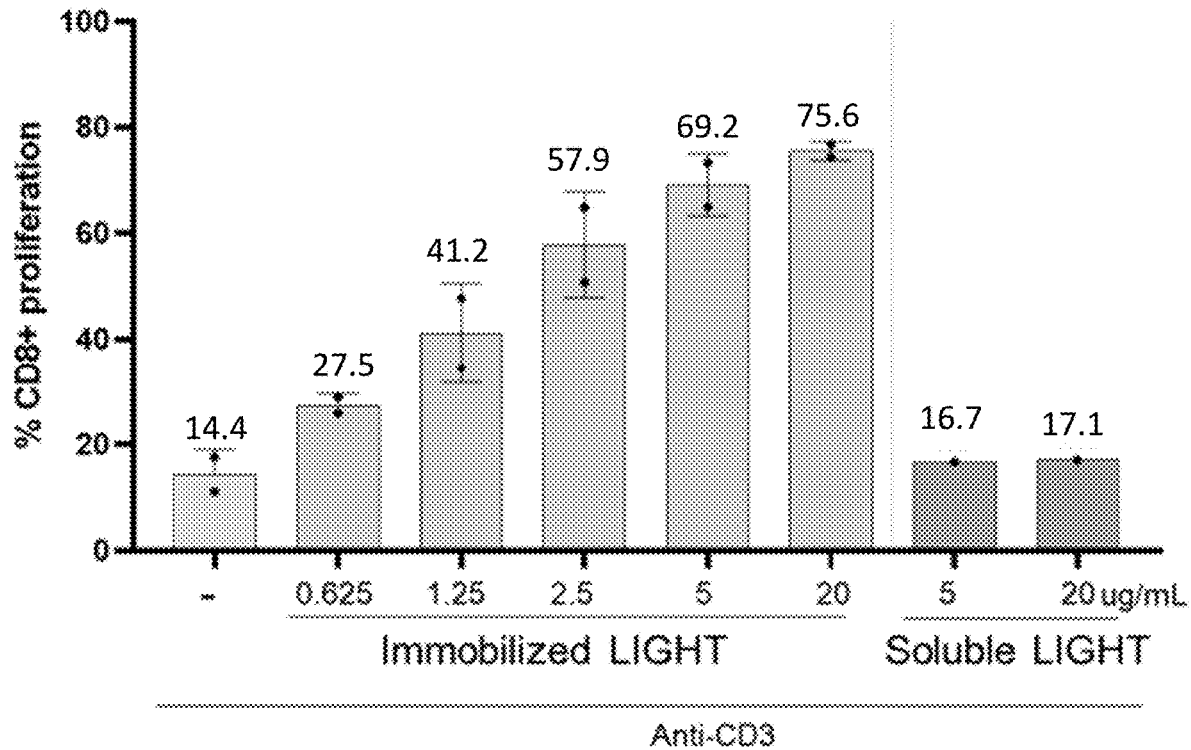
FIGS. 8A and 8B are graphs comparing the CD8 proliferation for soluble LIGHT and membrane-stabilized LIGHT T cells.
Figure 8B:
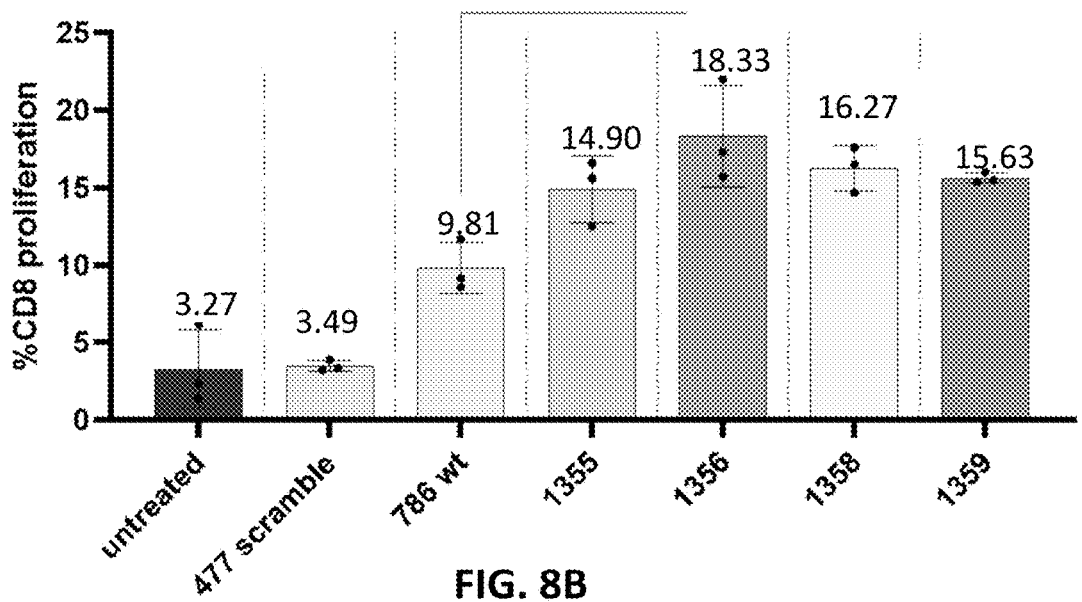
Figure 9A:
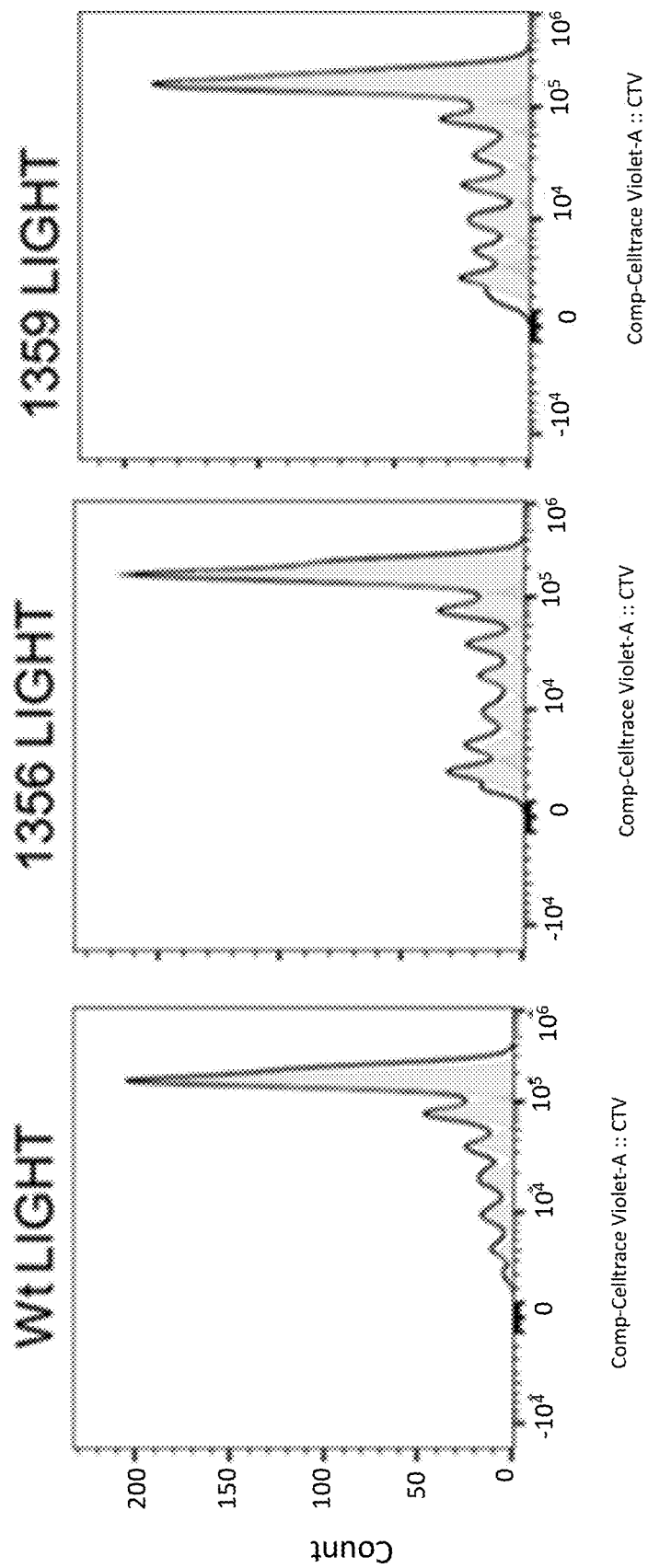
FIGS. 9A and 9B are flow cytometry visualization of T cell proliferations for compositions including soluble LIGHT or membrane-stabilized LIGHT.
Figure 9B:
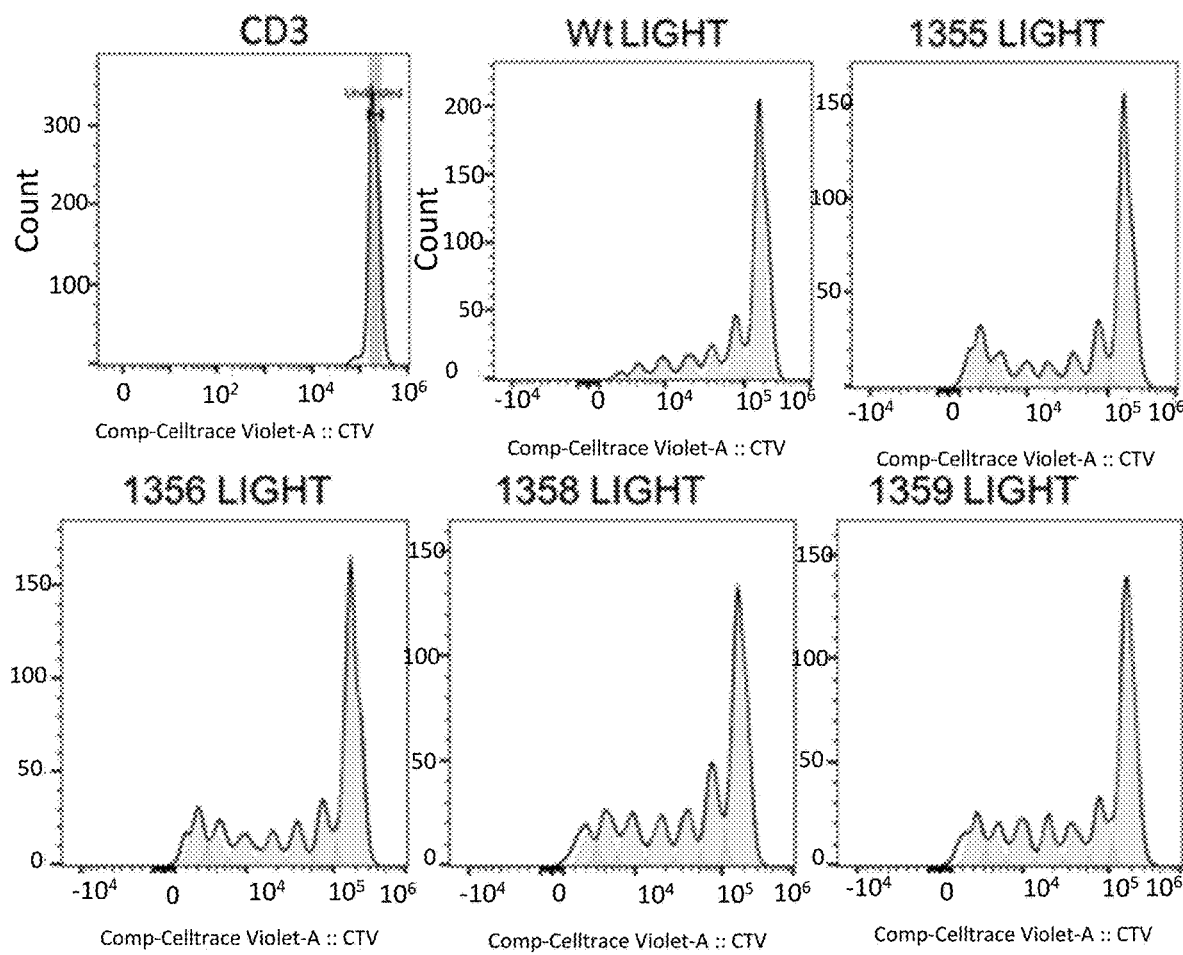

LIGHT variants were formulated in MessengerMax mRNA Transfection Reagent. Human embryonic kidney (HEK) cells were transfected with the LIGHT variant constructs for cell surface expression of LIGHT. CellTrace Violet (Thermo Fischer Scientific) was used to label CD3+ T cells from the resulting peripheral blood mononuclear cells (PBMC). 100 ng/mL of soluble CD3 Antibody was added to the resulting labeled CD3+ T cells. The T cell proliferation and interferon-gamma (IFN-γ) secretion was evaluated about 5 days of co-culture. As shown in FIGS. 8A and 8B, the CD8+ T-cell proliferation for the membrane-stabilized LIGHT is greater than that of the wild type LIGHT. T-cell proliferation induced by soluble (Wt) LIGHT and membrane-stabilized (1356, 1359) LIGHT is depicted in FIGS. 9A and 9B show an increase of T-cell proliferation with membrane-stabilized LIGHT.

Figure 10A:
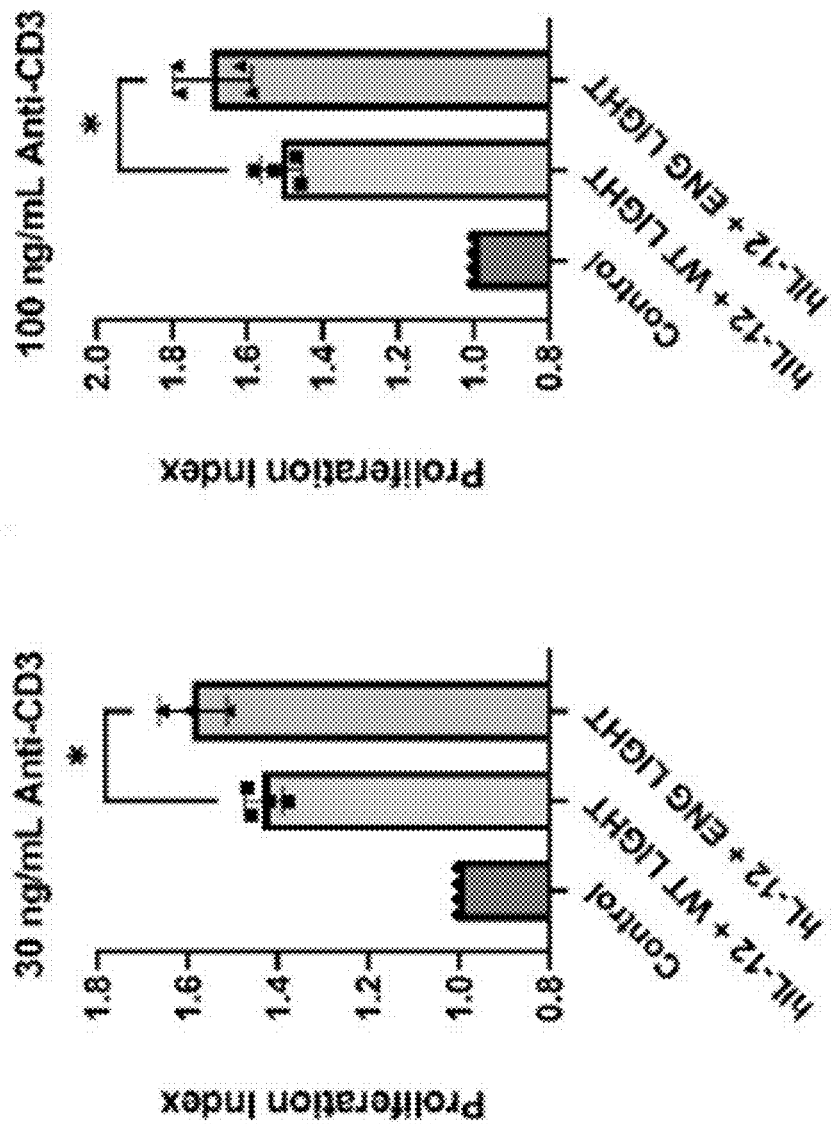
FIGS. 10A and 10B compare T cell proliferations for compositions including soluble LIGHT and IL-12 or membrane-stabilized LIGHT and IL-12. The division index is the total number of divisions/the number of cells at start of culture, the proliferation index is total number of divisions/cells that went into division, the expansion index is total number of cells/cells at start of culture, and the replication index is total number of divided cells/cells that went into division.

Example 1A: Assessment of Human T Cell Proliferation in Response to ENG or WT hLIGHT mRNA with Presence of hIL-12 mRNA in Human PBMCs This study was designed to compare the ability of ENG and WT hLIGHT mRNAs in combination with hIL-12 mRNA to stimulate primary human T cell proliferation. Human T cells were isolated from PBMCs from 1 healthy donor and stained with CellTrace Violet. HEK293 cells were transfected with hIL-12 mRNA (RNA-683) and WT hLIGHT (RNA-786) or ENG hLIGHT (RNA-1359) mRNA formulated in Lipofectamine MessengerMAX (0.5 ng each mRNA per 1000 cells). Control cells were transfected with noncoding mRNA control in the same way. Transfected HEK293 cells were cocultured with the T cells in a 1:5 ratio in the presence of 30 ng/mL or 100 ng/mL anti-CD3 antibody to mimic antigen specific TCR engagement for 4 days at 37° C., 5% $CO_2$. CD8+ T cell proliferation was assessed by flow cytometry and the proliferation index was calculated. Coculture of T cells with HEK293 cells expressing IL-12 and ENG hLIGHT in the presence of anti-CD3 resulted in increased CD8+ T cell proliferation and survival relative to coculture of T cells with HEK293 cells expressing IL-12 and WT hLIGHT in the presence of anti-CD3. The results are shown in FIG. 10A, where ENG=engineered; HEK=human embryonic kidney; IL-12=interleukin-12; PBMC=peripheral blood mononuclear cell; WT=wildtype. The data in FIG. 10A represent mean±standard deviation (n=4). Statistical analysis was performed by unpaired student's t-test (P<0.05).

Figure 10B:
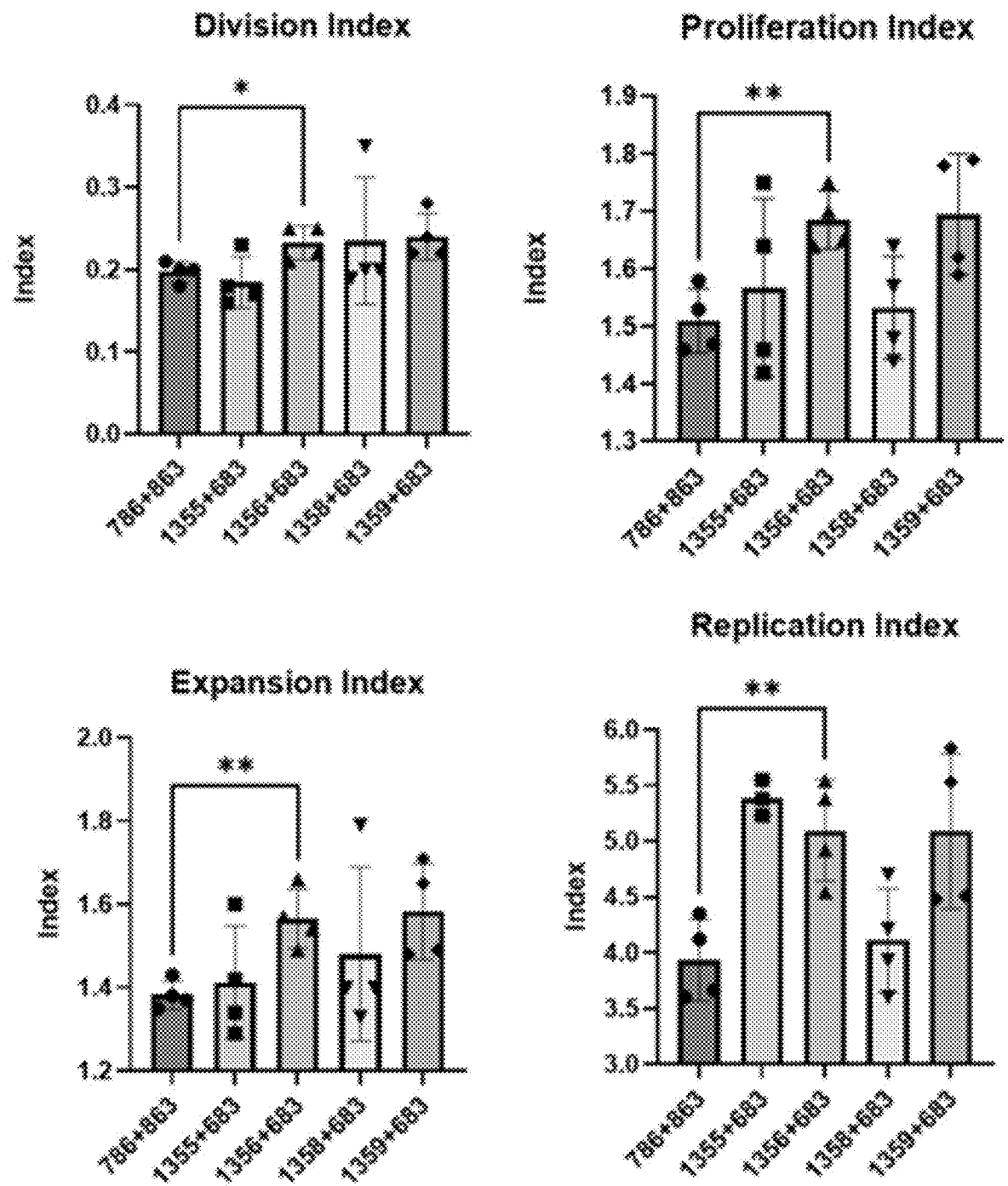
Figure 11:
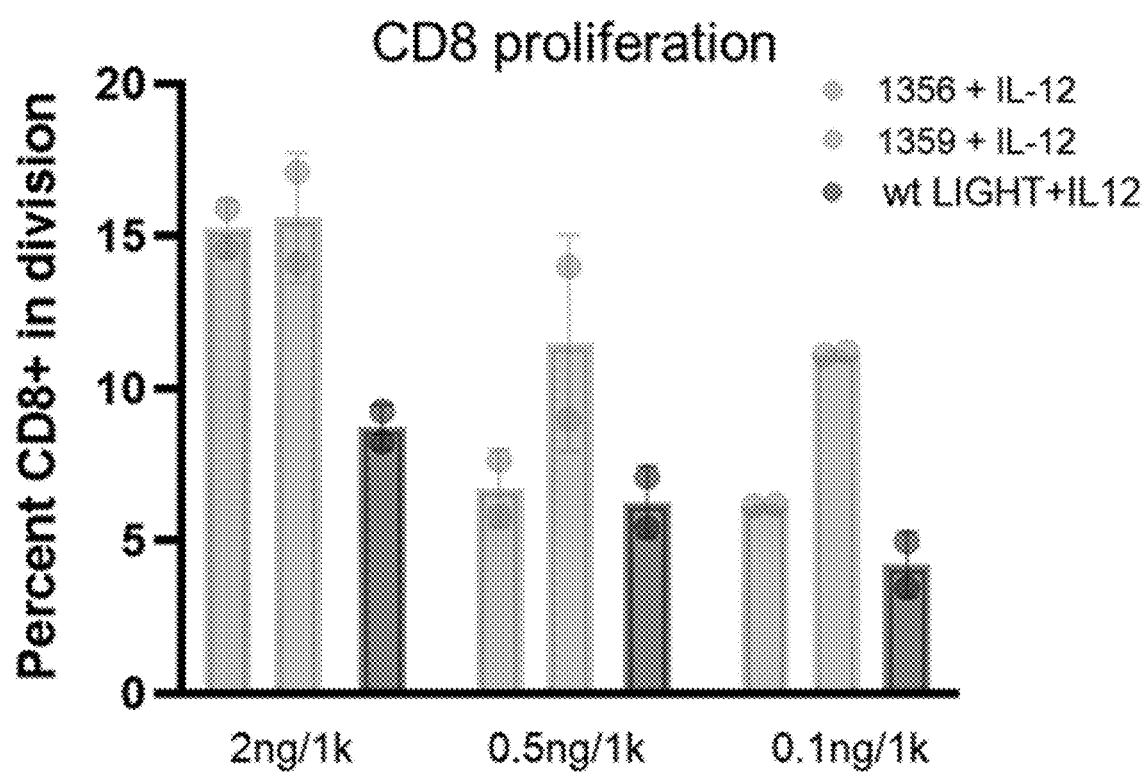
FIG. 11 compares CD8 proliferation for compositions including soluble LIGHT and IL-12 or membrane-stabilized LIGHT and IL-12.

There was a biologically significant increase in the T-cell proliferation with the membrane-stabilized light as compared to the soluble LIGHT. This is further supported by data shown in FIGS. 10B, and 11.

Figure 12:
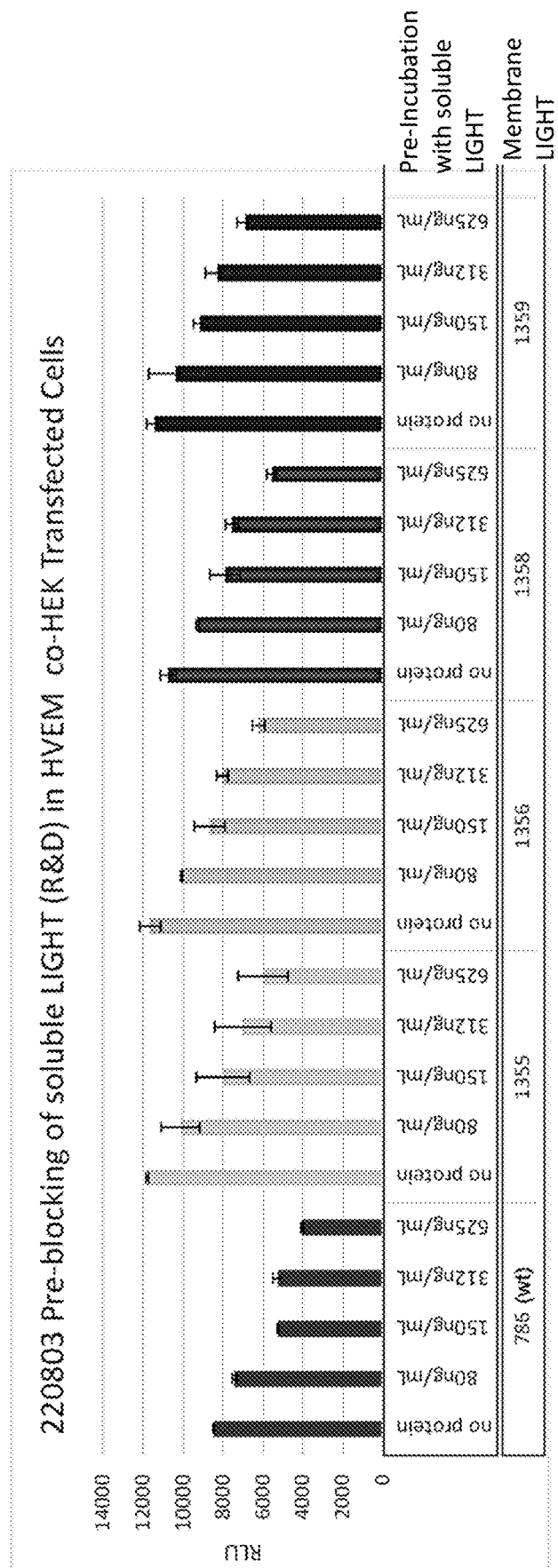
FIG. 12 illustrates pre-blocking of soluble LIGHT in HVEM co-HEK transfected cells.
Figure 13A:
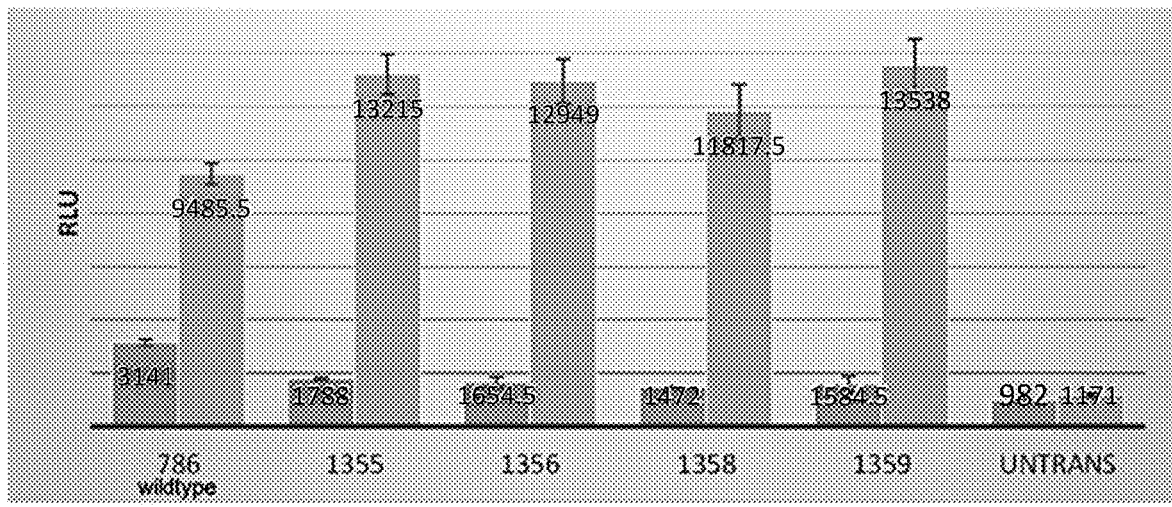
FIGS. 13A-13C are a comparison of HVEM activation with supernatant (blue) or cells (orange) for soluble LIGHT or membrane-stabilized LIGHT.
Figure 13B:
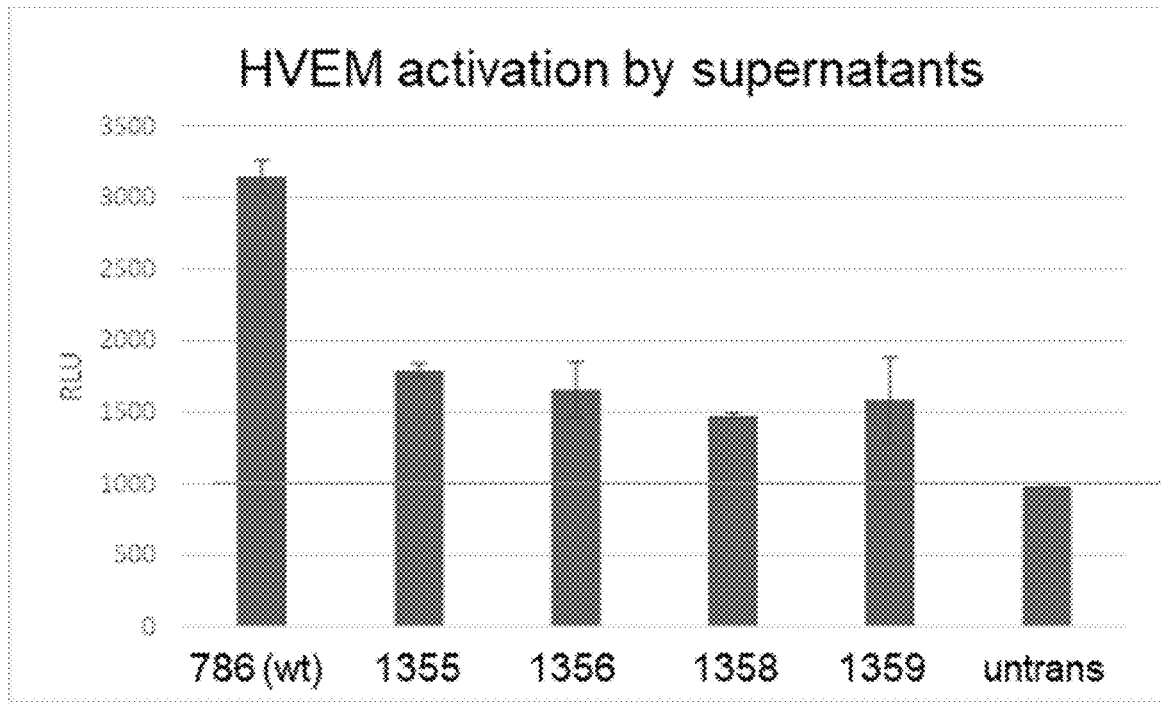
Figure 13C:
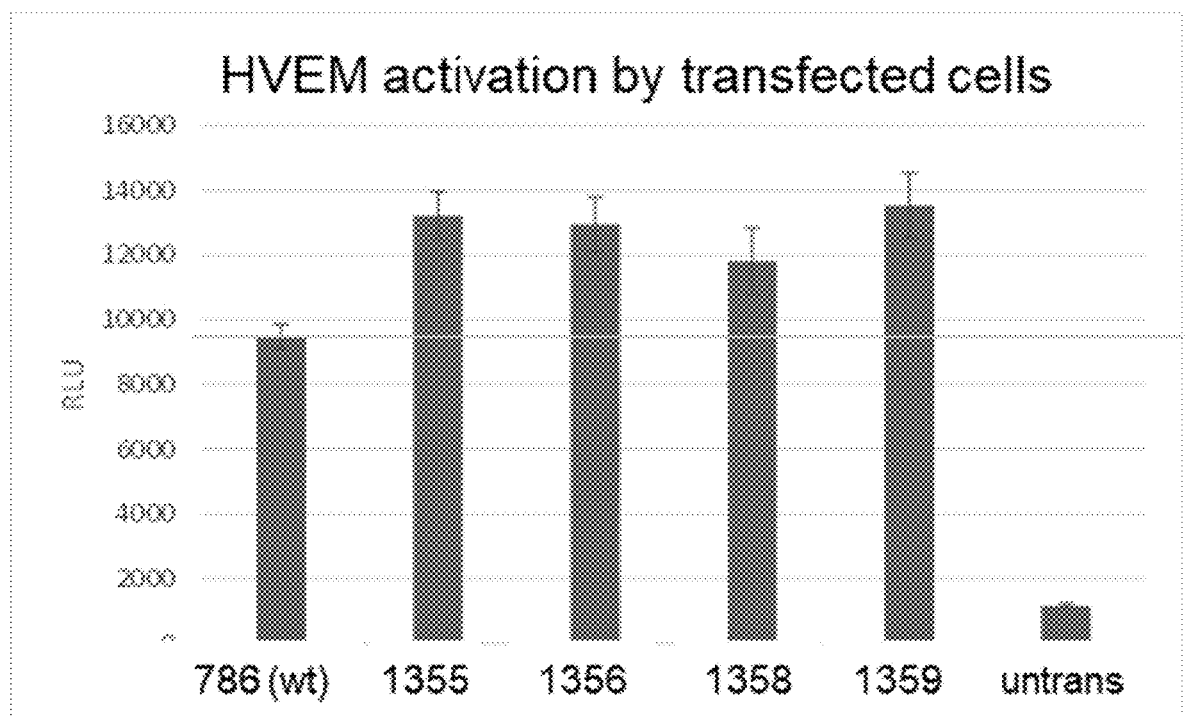
Figure 14A:
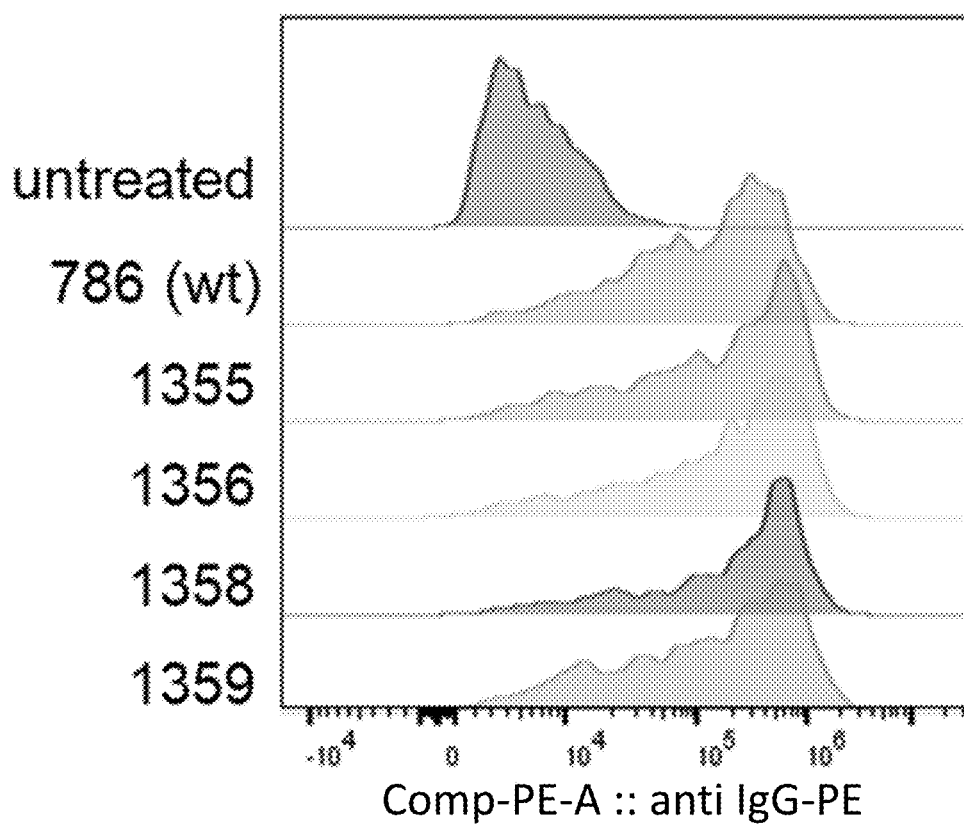
FIGS. 14A and 14B depict the assessment of surface expression of soluble LIGHT or membrane-stabilized LIGHT by flow cytometry using HVEM binding.
Figure 14B:
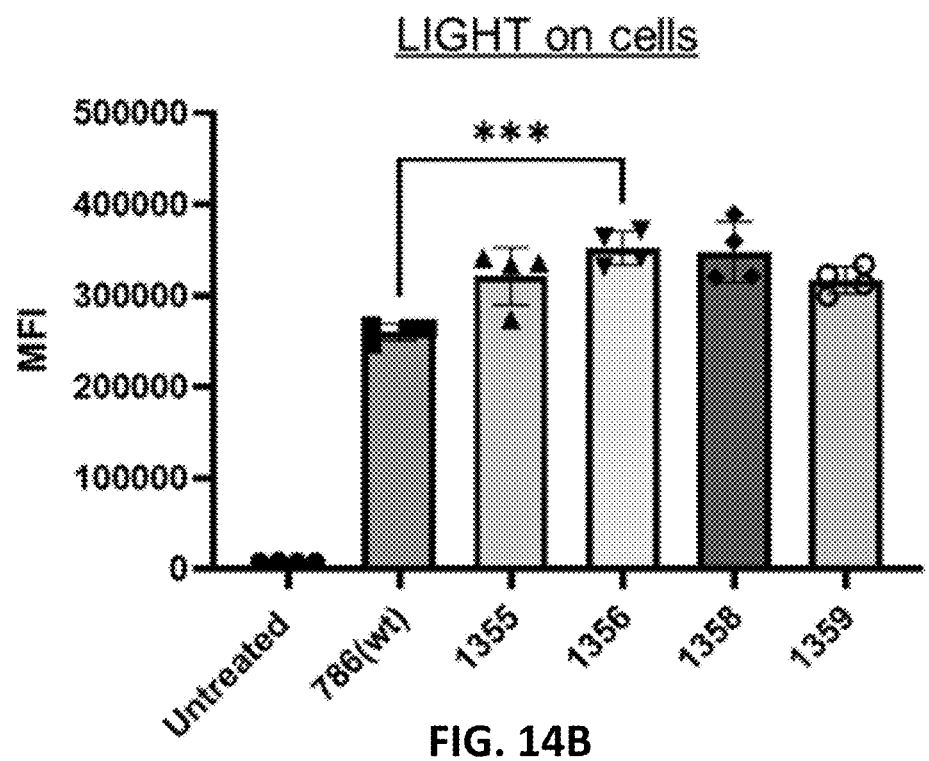

It was also shown that soluble LIGHT competes for HVEM binding and reduces signaling by membrane-stabilized LIGHT. FIGS. 12, while FIGS. 13A-13C show increased function of membrane-stabilized LIGHT on cells with HVEM reporter cell line and FIGS. 14A and 14B show increased cellular expression of membrane-stabilized LIGHT.

Example 2: Tumor Model

The well-established, clinically relevant, C3.43 tumor model (5) was to test an mRNA-based therapeutic composition that included a first isolated mRNA that encodes a membrane-stabilized LIGHT, a second isolated mRNA that encodes HPV16 E6 E7, and a third isolated mRNA that encodes interleukin-12 for preclinical efficacy. C3.43 is a progressive subclone of C3, HPV16-transformed B6 mouse embryo cell line that expresses HPV16 E6 and E7 antigens under the natural promoter (5).

Figure 15:
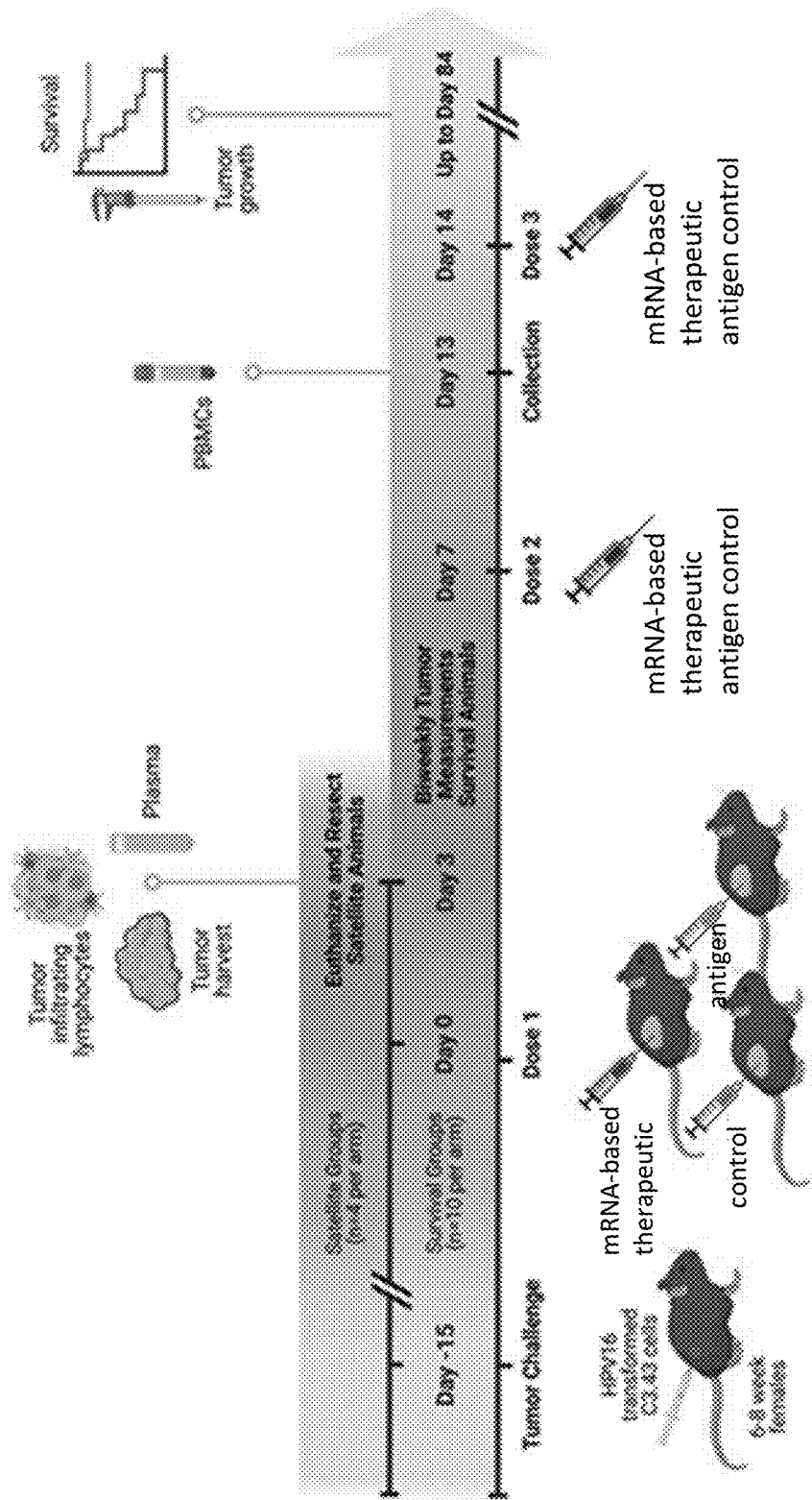
FIG. 15 a study design according to one aspect of the disclosure.

Pathogen-free six to eight week old C57BL/6J female mice were challenged subcutaneously in the right flank with 1×10⁵ C3.43 tumor cells in 100 ml HBSS. Mice with large enough tumors sufficient for intratumoral (IT) injections were randomized into the treatment groups on study day 0, which was 15 days post-tumor challenge. Intratumoral injections occurred 7 days apart for 3 injections total with 20 ml of the assigned treatment. A satellite group of animals from each treatment arm was euthanized on day 3 after dose 1. The tumors of the satellite groups were harvested and processed for isolation of tumor infiltrating lymphocytes (TILs). The remaining animals followed the dosing schedule and were measured for tumor volume on a biweekly basis. A blood draw for PBMC collection occurred on day 13. Survival was analyzed up to day 84. See FIG. 15 for study schematic.

The therapeutic efficacy of the mRNA-based therapeutic was assessed by tracking tumor growth and survival over time between the treatment groups. Tumor growth was measured biweekly with manual calipers to measure tumor volume. A satellite group of animals from each treatment arm was euthanized on day 3 after dose 1 via asphyxiation or cervical dislocation for mechanism studies and immune response profiling. Tumors on the right flank were harvested, with half the tumor formalin fixed and paraffin embedded for tissue analysis, and the other half of the tumor processed for isolation of tumor infiltrating lymphocytes (TILs) for cytokine analysis and flow cytometry. Immunogenicity was evaluated by flow cytometry of peripheral blood mononuclear cells (PBMCs). The frequencies of HPV16 E7-specific CD8+ T cells was compared between all treatment groups. Mechanistic studies were performed by post-treatment tumor microenvironment characterization. The data are shown in FIGS. 4A, 4B, 4C, 4D and 4E.

Example 2A: Repeat-Dose, Intratumoral Injection, Efficacy and Pharmacodynamics Study in the C3.43 Tumor Mouse Model with mNTX-250 Containing mHPV16 and mIL-12 Plus Either ENG or WT mLIGHT mRNA This study compared the in vivo effect of increasing doses of mNTX-250 including mHPV16 antigen, mIL-12, and WT mLIGHT or ENG mLIGHT on tumor growth inhibition (TGI) and the induction of tumor antigen-specific T cells in a syngeneic C3.43 tumor model in female C57BL/6 mice.

C3.43 tumors were implanted in female C57BL/6 mice as described above. When the tumor volume reached approximately 180 mm³, at 18 days post inoculation (Day 0), mice were randomized across treatment groups (n=10 per group) according to the study design in Table 9, below. Mice were treated with increasing doses of mNTX-250 with WT mLIGHT or with ENG mLIGHT formulated in 140-F6.3 in a 20 μL dose volume by IT injection on Day 0 and Day 7. Control mice were administered citrate buffer in the same way. Tumor volume was measured twice weekly using calipers. Blood samples were collected on Day 12 for quantification of HPV16 E7 tetramer-positive T cells by flow cytometry.

TABLE 9

Study Design

| Group | Test Article Description | μg per mRNA | Total mRNA (μg) |
|---|---|---|---|
| 1 | mNTX-250 containing mHPV16 antigen, mIL-12, and WT mLIGHT mRNAs in 140-F6.3 formulation | 0.5 | 1.5 |
| 2 | | 0.15 | 0.45 |
| 3 | | 0.015 | 0.045 |
| 4 | | 0.0015 | 0.0045 |
| 5 | mNTX-250 containing mHPV16 antigen, mIL-12, and ENG mLIGHT mRNAs in 140-F6.3 formulation | 0.5 | 1.5 |
| 6 | | 0.15 | 0.45 |
| 7 | | 0.015 | 0.045 |
| 8 | | 0.0015 | 0.0045 |
| 9 | Control citrate buffer (pH 5.5) | N/A | N/A |

Figure 4A:
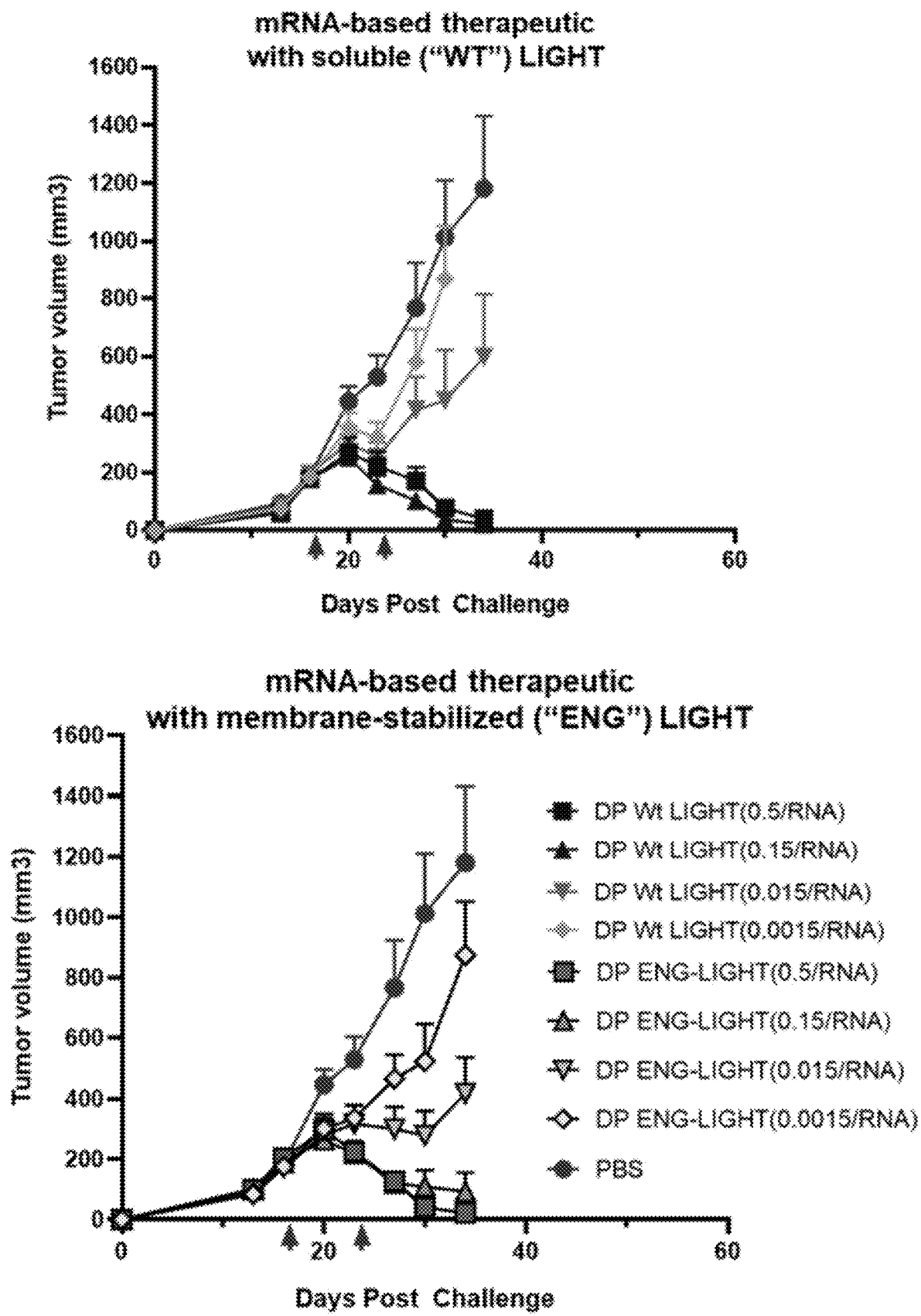
FIGS. 4A-4E are a comparison of anti-tumor efficacy with an mRNA-based therapeutic that includes soluble or membrane-stabilized LIGHT.
Figure 4B:
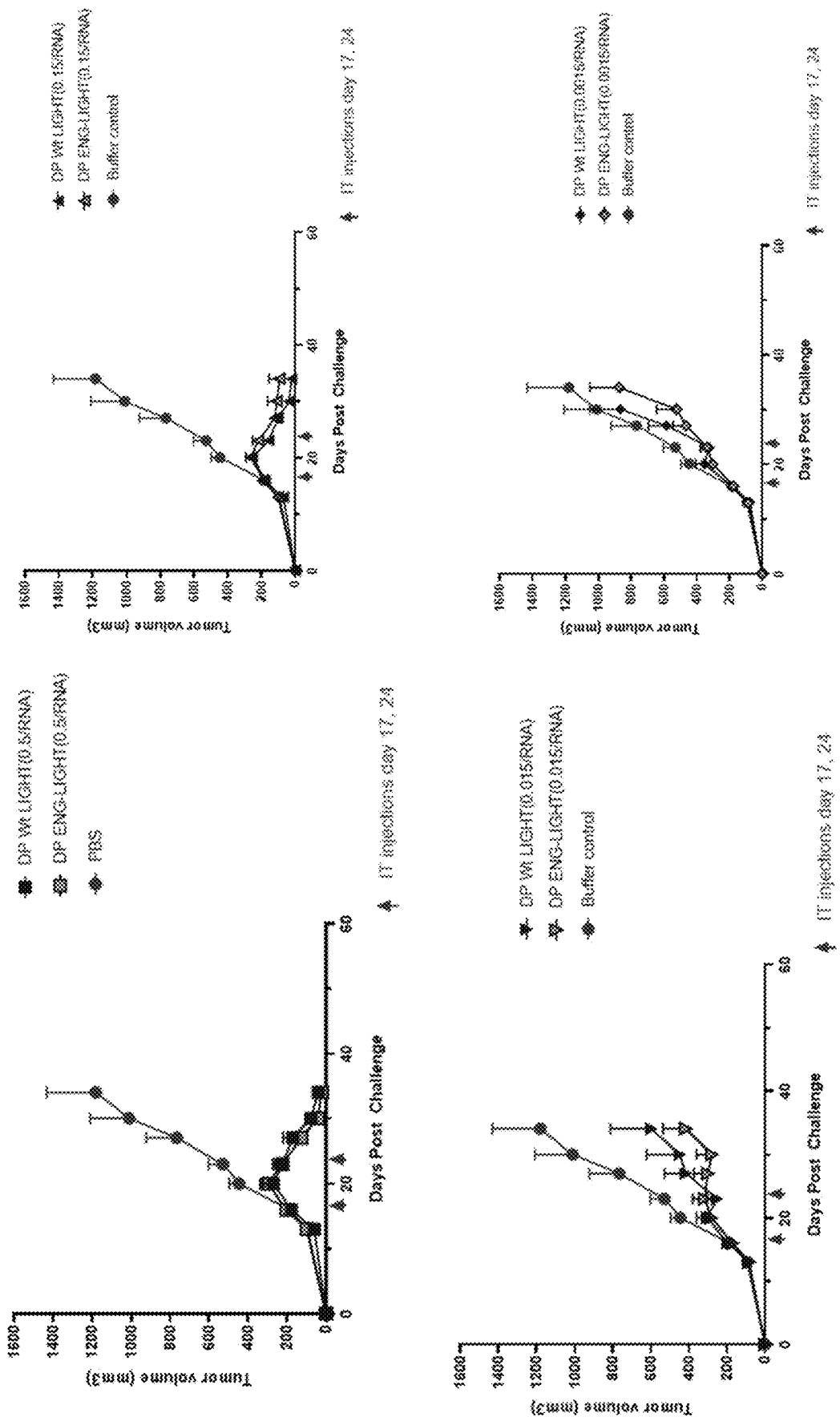
Figure 4C:
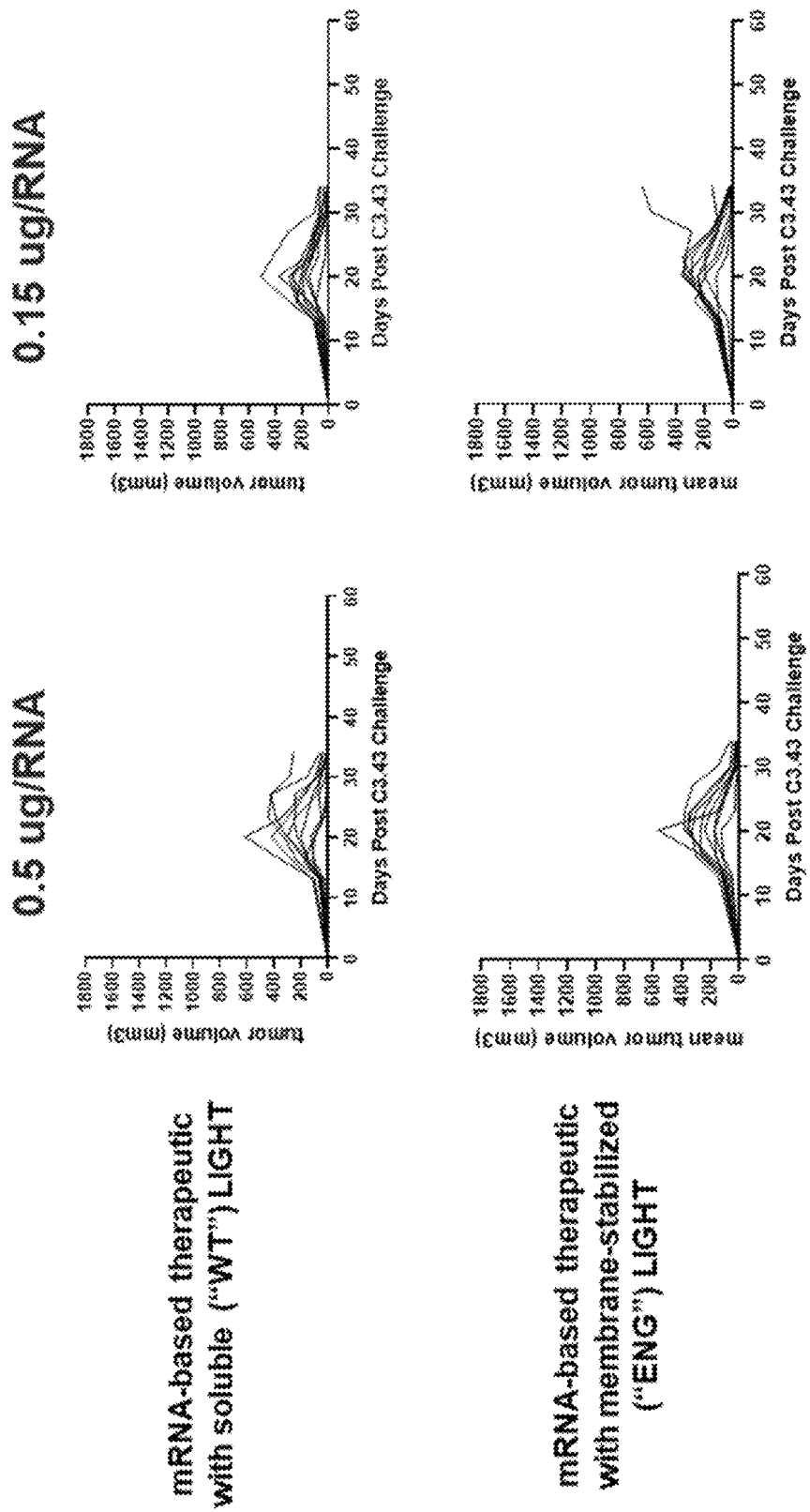
Figure 4D:
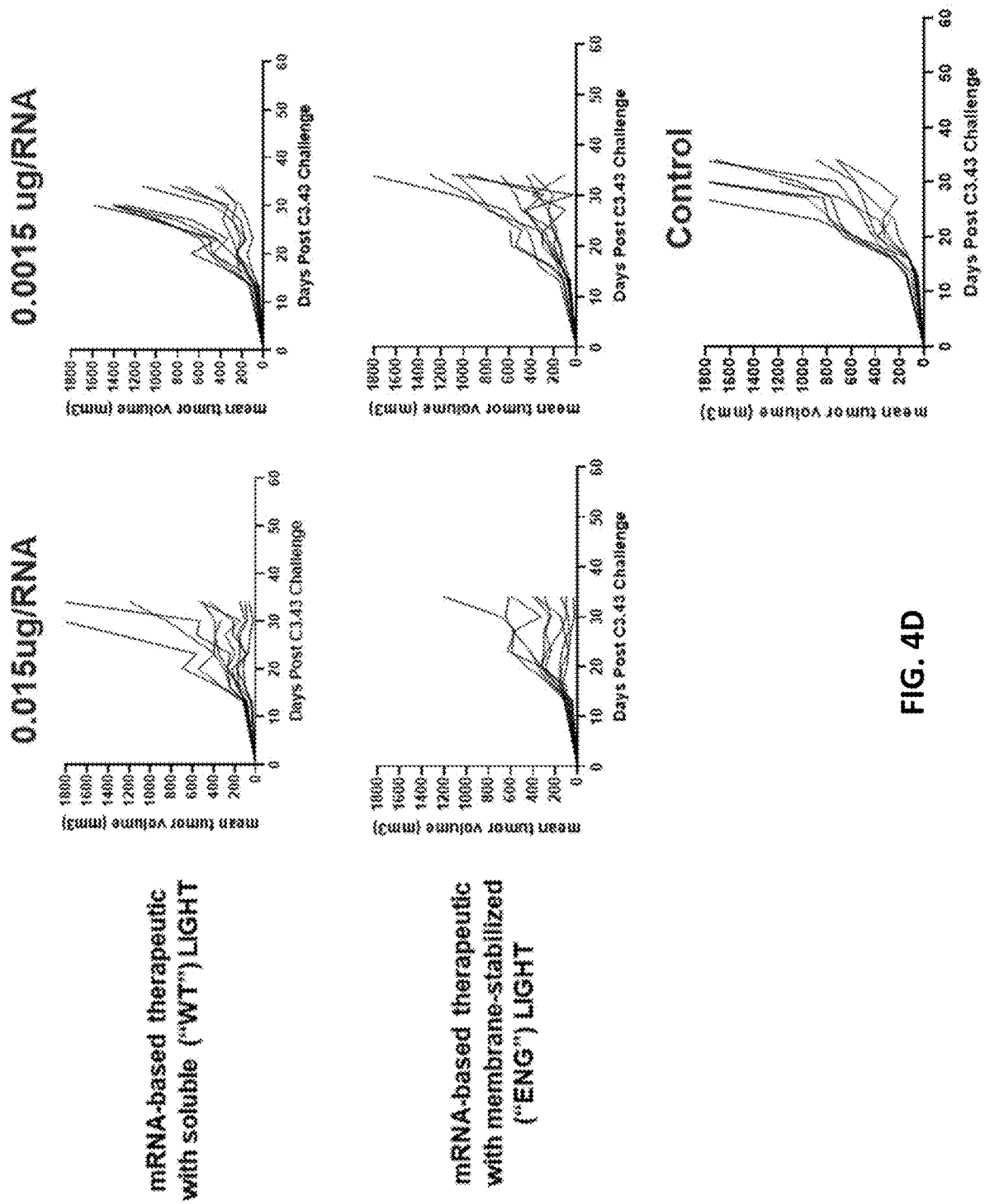
Figure 4E:
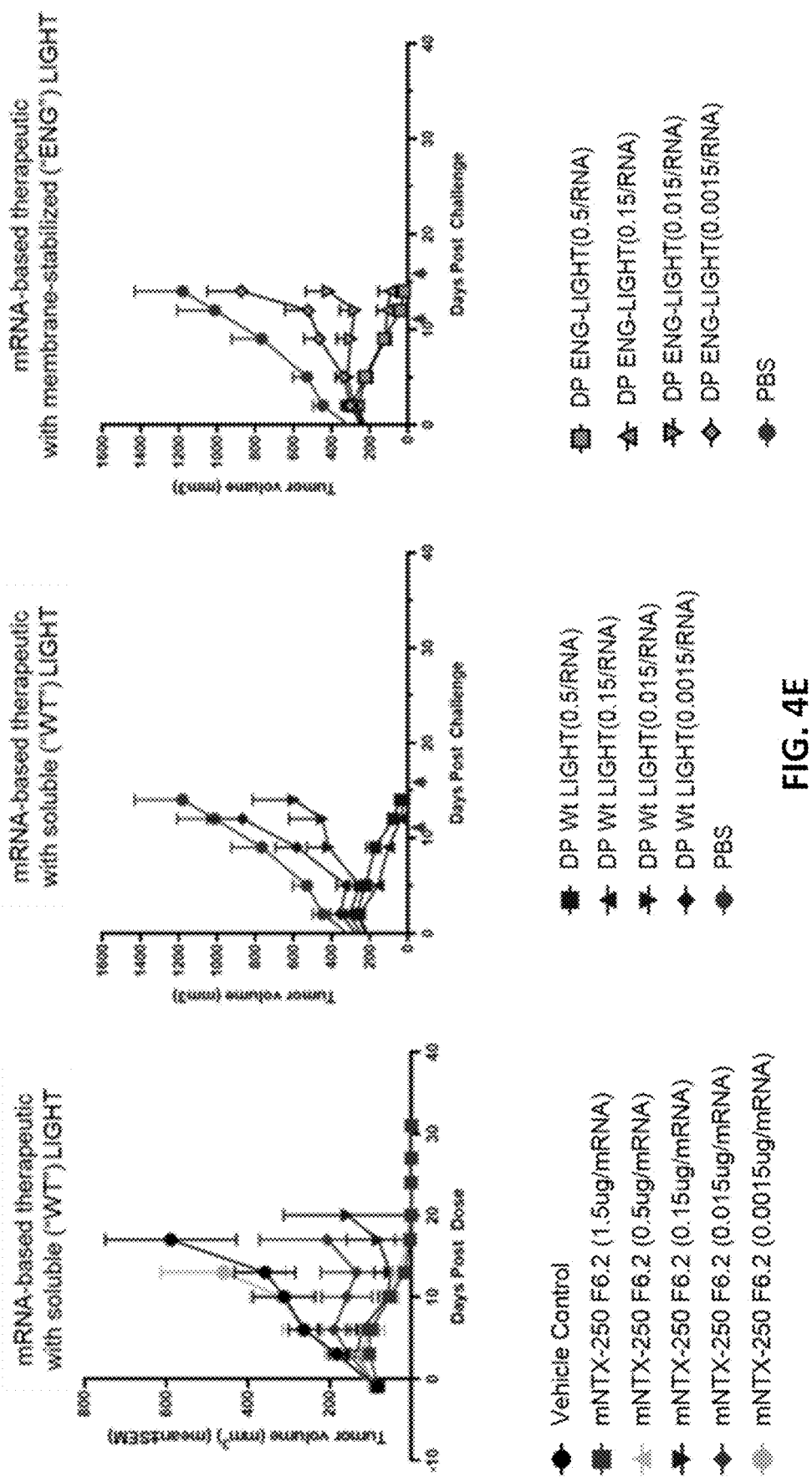
Figure 4F:
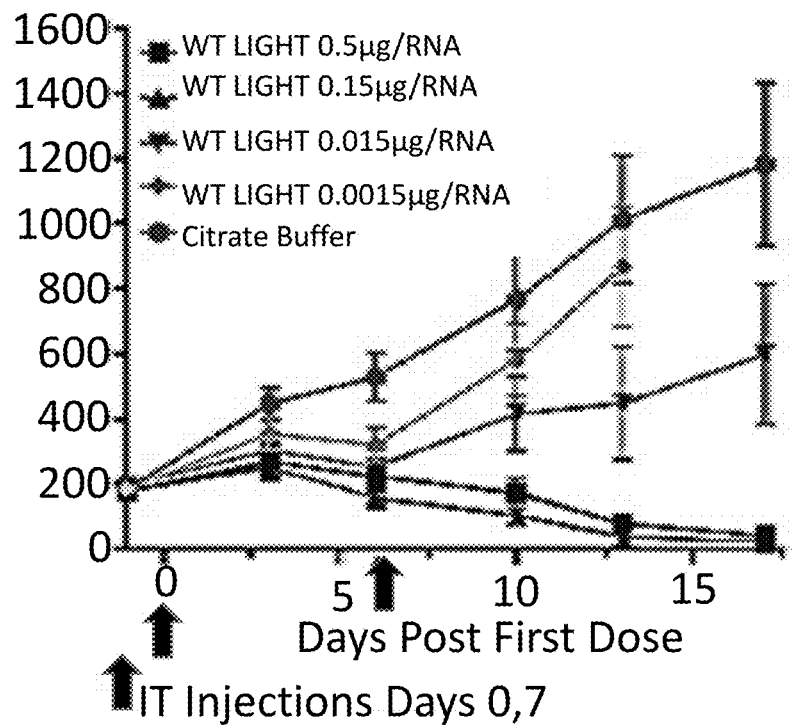
FIGS. 4F and 4G shows the dose-response of mNTX-250 (containing either WT or ENG mLIGHT) on C3.43 tumor growth inhibition in vivo.
Figure 4F:
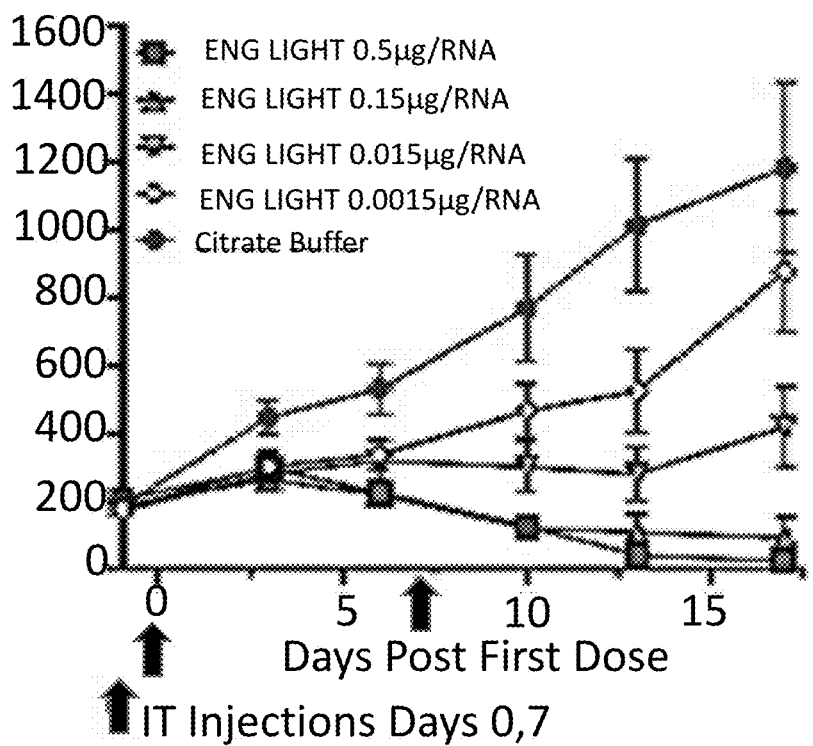
Figure 4G:
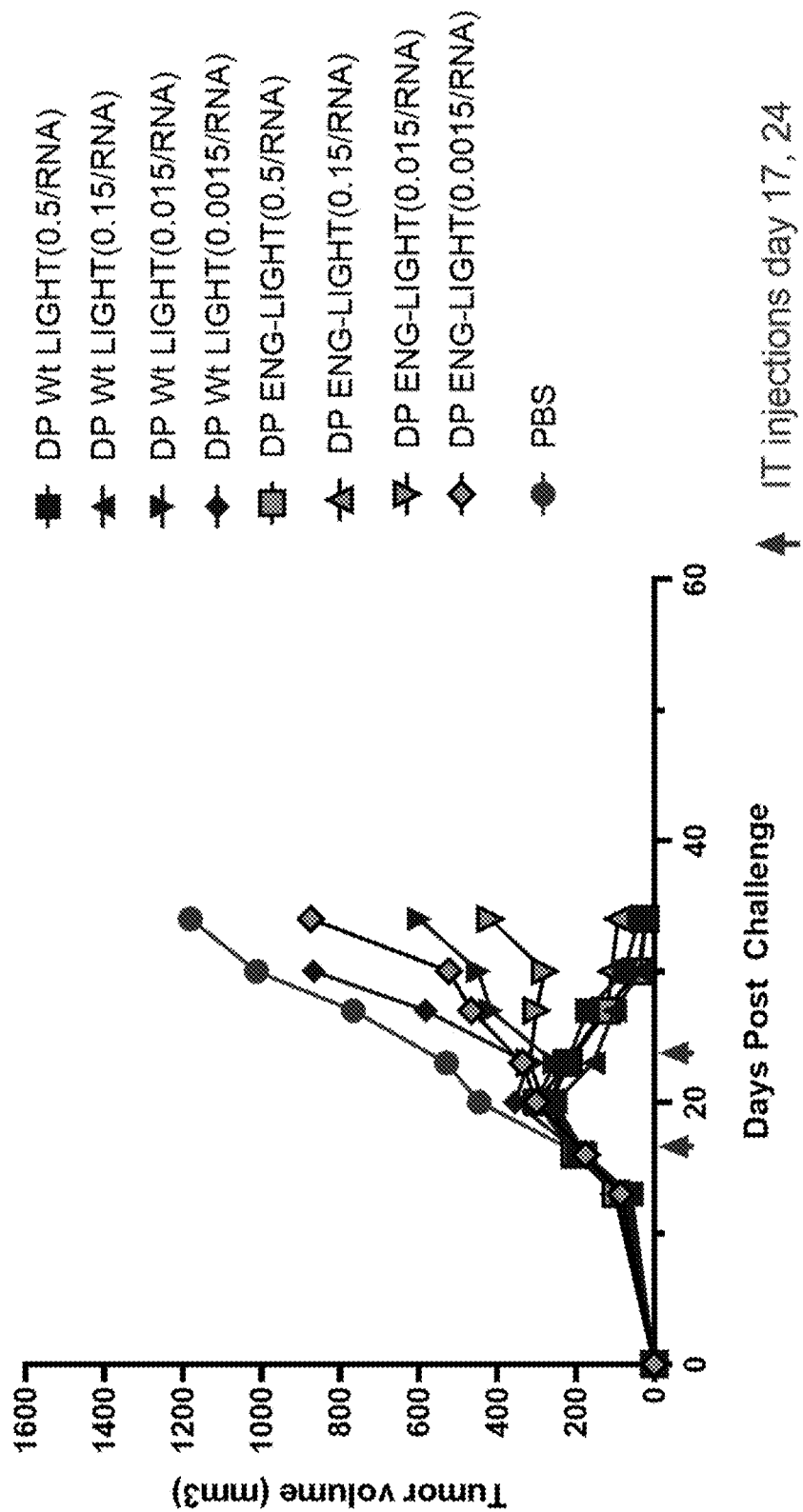
Figure 4H:
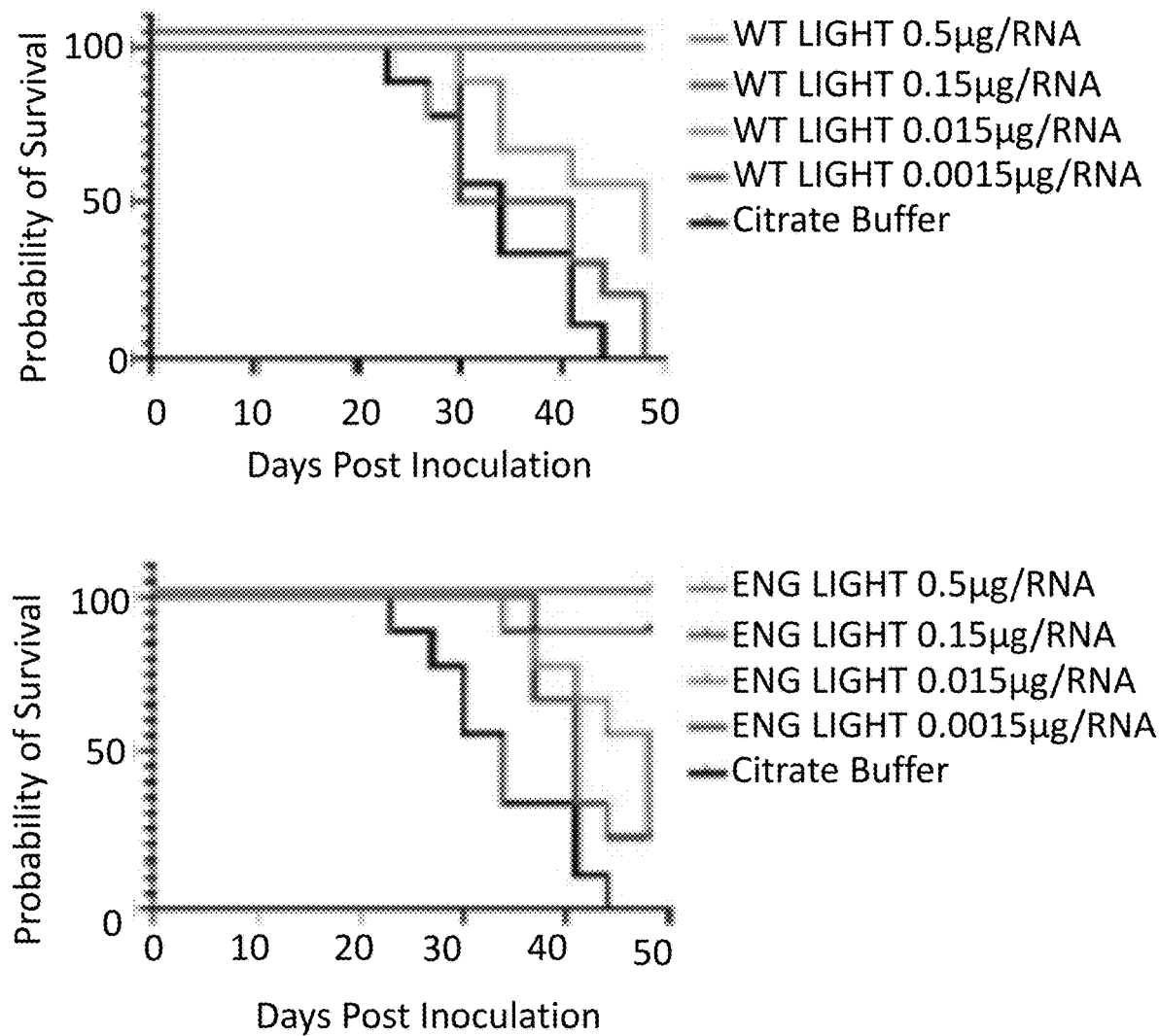
FIG. 4H shows the effect of mNTX-250 (containing either WT or ENG mLIGHT) on survival in the C3.43 tumor mouse model.

ENG = engineered;
mIL-12 = murine surrogate for interleukin-12;
mLIGHT = murine surrogate for LIGHT;
N/A = not applicable;
WT = wild type Treatment with mNTX-250 containing WT or ENG mLIGHT resulted in comparable, dose-dependent TGI (FIGS. 4F and 4G) and improved survival (FIG. 4H) relative to control mice. Similarly, treatment with mNTX-250 containing WT or ENG mLIGHT resulted in comparable, dose-dependent HPV16 tetramer-positive T cell generation (FIG.

5). Together, these results demonstrate comparable efficacy of WT and ENG mLIGHT in the C3.43 syngeneic tumor mouse model.

Example 2B: Comparison of Cytokine Induction in Tumor Microenvironment Using ENG mLIGHT mRNA or WT mLIGHT mRNA in Combination with IL-12 mRNA in an MC38 Transplantable Mouse Tumor Model The objective of this study was to assess the activity of ENG mLIGHT mRNA compared to WT mLIGHT mRNA in combination with mIL-12 mRNA within the TME of a subcutaneous syngeneic MC38 model. MC38 is a murine adenocarcinoma cell line. The MC38 model is an immunoresponsive cancer model with a moderate growth rate (4-day doubling time) that both allows for extended treatment schedules and reflects the complicated TME of adeno- and squamous carcinoma. To establish the MC38 tumor model, $2 \times 10^5$ MC38 tumor cells inoculated into the flanks of female C57BL/6 mice. When the tumor volume reached approximately 100 mm$^3$, mice were injected intratumorally (20 µL) on Day 0 and Day 3 according to the study design in Table 10. At 12 hours post second dose, mice were euthanized, and tumors were harvested for cytokine profiling by Luminex assay.

TABLE 10

Study Design

| Group | N | Treatment | Route | Dose, Volume | Dosing Days |
|---|---|---|---|---|---|
| 1 | 5 | mIL-12 + WT mLIGHT | IT | 1 µg each mRNA, 20 µL | 0, 3 |
| 2 | 5 | mIL-12 + ENG mLIGHT | IT | 1 µg each mRNA, 20 µL | 0, 3 |
| 3 | 5 | mIL-12 | IT | 1 µg mRNA, 20 µL | 0, 3 |
| 4 | 5 | Noncoding mRNA Control | IT | 2 µg mRNA, 20 µL | 0, 3 |

ENG = engineered;
IT = intratumoral;
mIL-12 = murine interleukin-12;
mLIGHT = murine LIGHT;
WT = wildtype.
All mRNAs were formulated in 140-F6.3

Figure 6A:
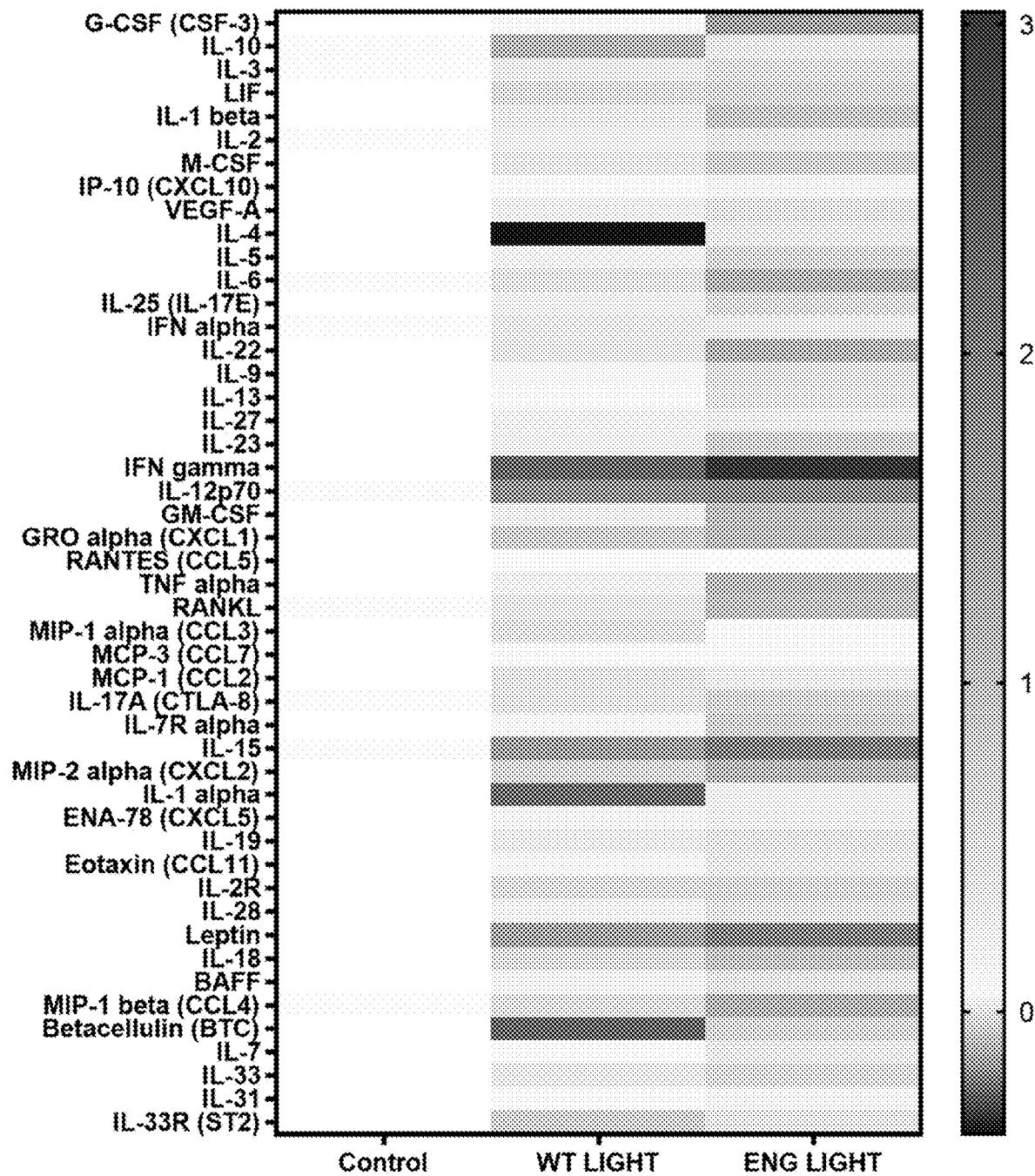
FIGS. 6A-6C show that a composition including membrane-stabilized LIGHT generated according to an aspect of this disclosure and IL-12, promotes the increase of proinflammatory cytokines in tumor microenvironment as compared to soluble mouse LIGHT+IL-12.
Figure 6B:
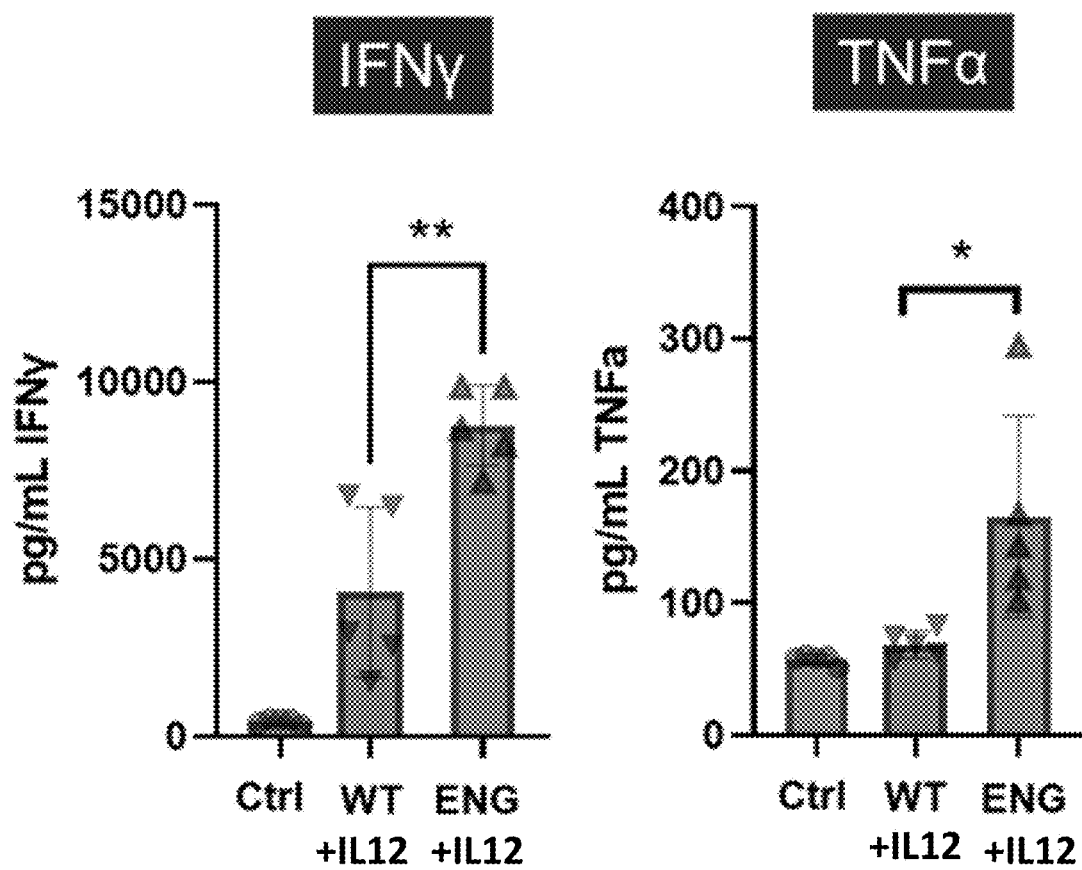
Figure 6C:
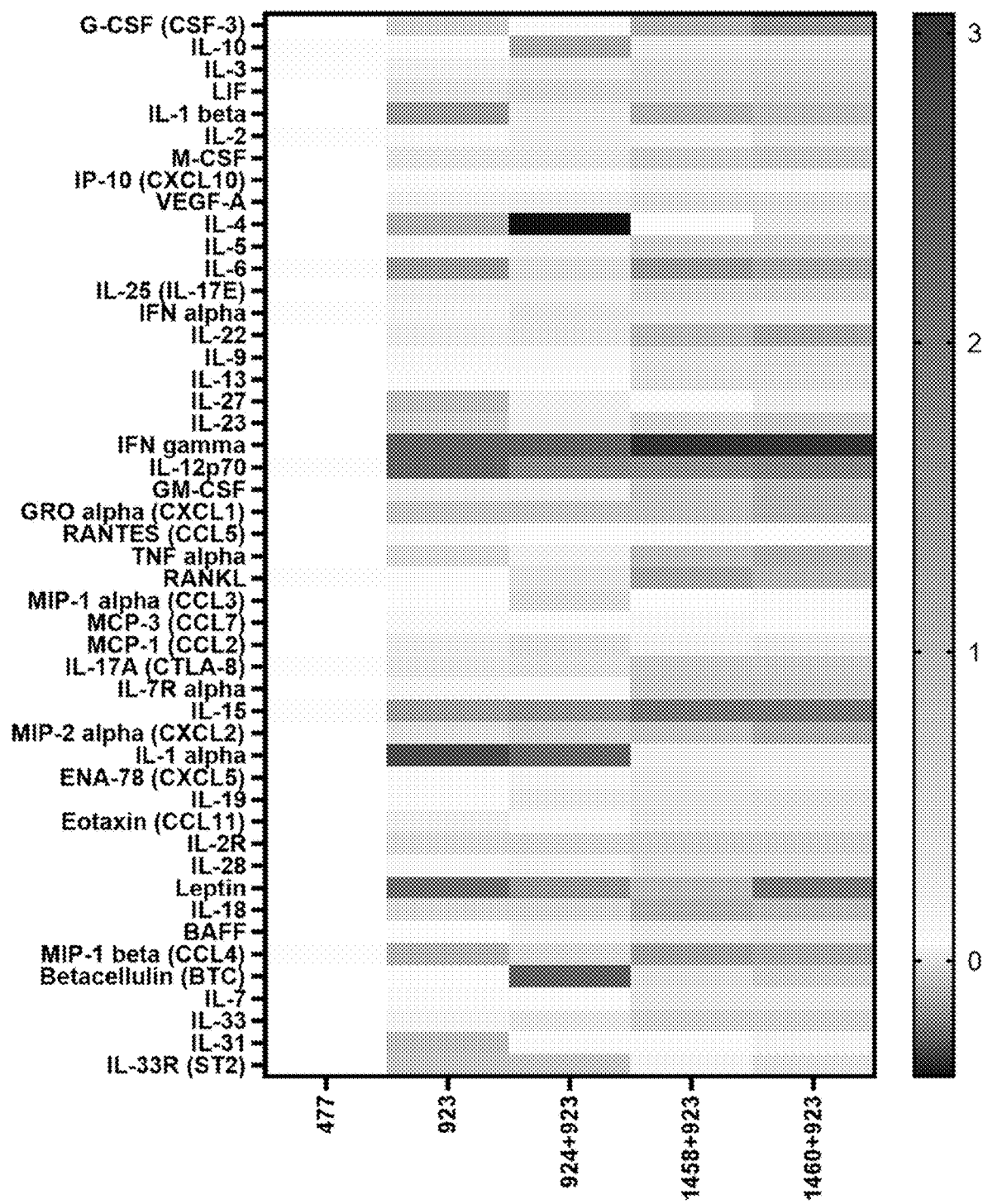
Figure 6D:
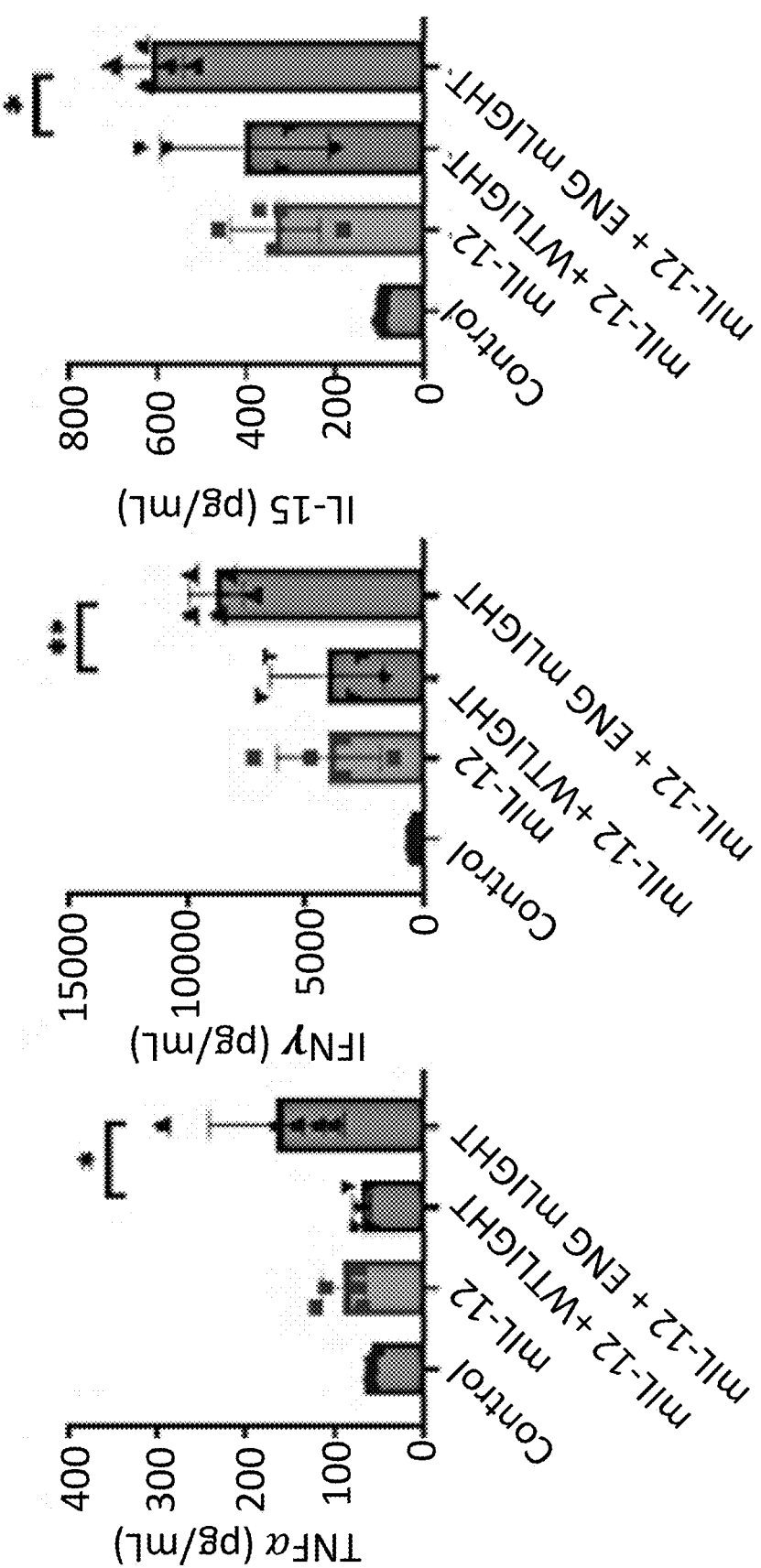
FIG. 6D shows cytokine levels in the tumor microenvironment in mice treated with ENG mLIGHT and mIL-12 versus WT mLIGHT and mIL-12.

Quantification of cytokines induced within the TME revealed that mice treated with mIL-12 plus ENG mLIGHT mRNA had significantly higher levels of TNF-α, IFN-γ, and IL-15 compared to mice treated with mIL-12 mRNA plus WT mLIGHT mRNA (FIG. 6D). An increased T helper 1 and macrophage 1 cytokine-associated response (TNF-α, IFN-γ, and IL-15) has been repeatedly shown to be important for the antitumor immune response (Pan, 2012).

Example 2C: Efficacy in in Cynomolgus Monkeys

The functionality of the mRNA-based therapeutic in nonhuman primates was evaluated in cynomolgus monkeys. Monkeys were randomized to receive either a low dose (n=2) or high dose (n=2) the mRNA-based therapeutic regimen via intramuscular injection. Each animal received 3 injections 7 days apart. Blood draws were taken for collection of PBMCs and evaluation of HPV16 E6 and E7 specific T cell responses via ELISpot assay. The tumor microenvironment was evaluated to shed light on the type of immune response generated by the mRNA-based therapeutic.

Example 3: HPV16+ Donor Proliferation

Figure 16:
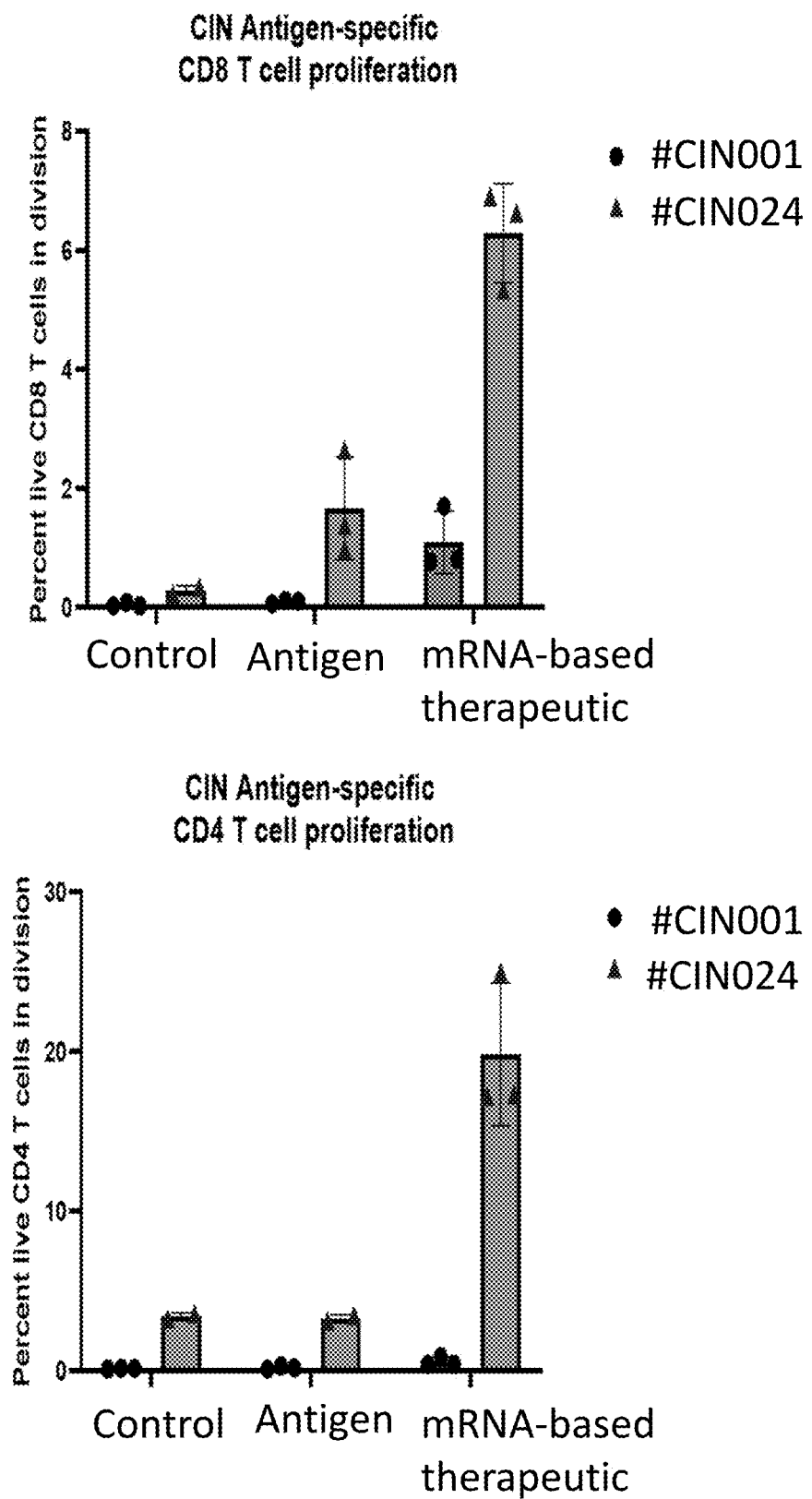
FIG. 16 is a comparison of the percentage of live CD4 and CD8 T cells in proliferation by flow cytometry for control mRNA, antigen mRNA, or an mRNA-based therapeutic mRNA.
Figure 17A:
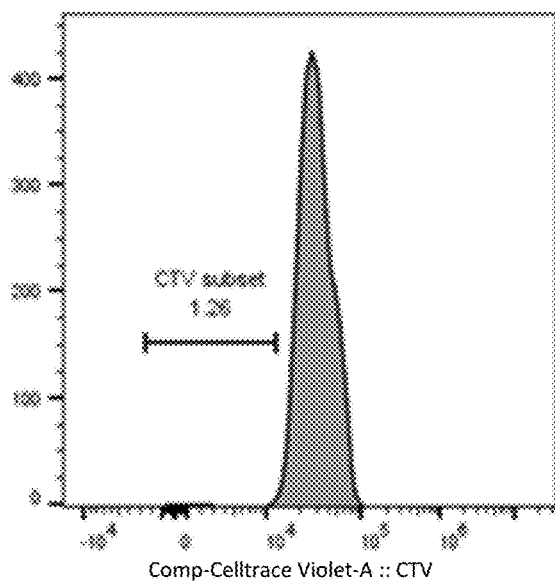
FIGS. 17A-17D depict HPV16+ donor proliferation by flow cytometry.
Figure 17A:
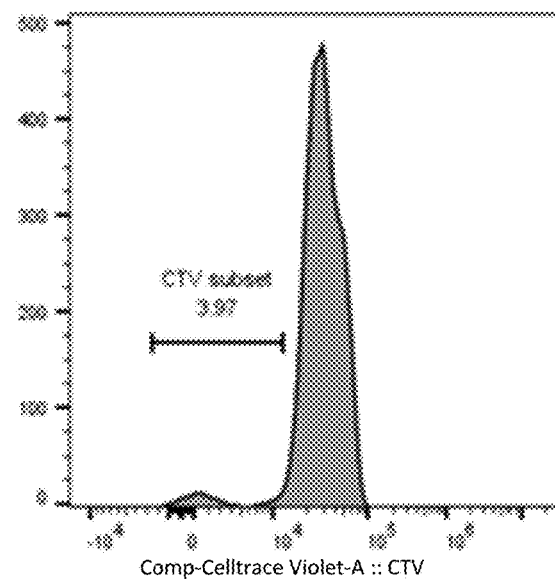
Figure 17A:
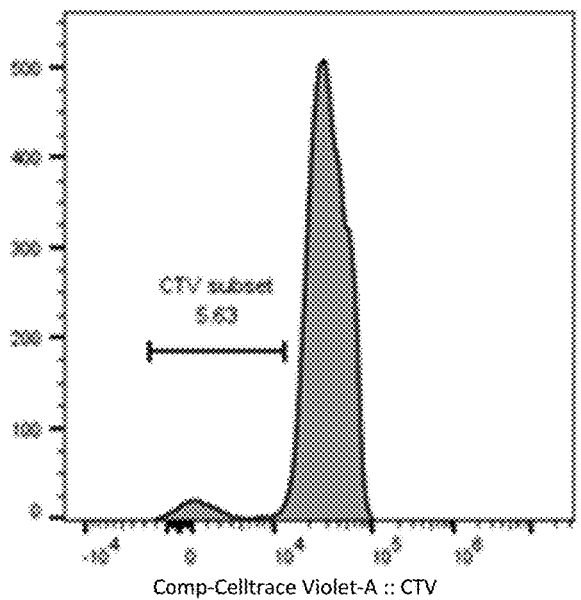
Figure 17A:
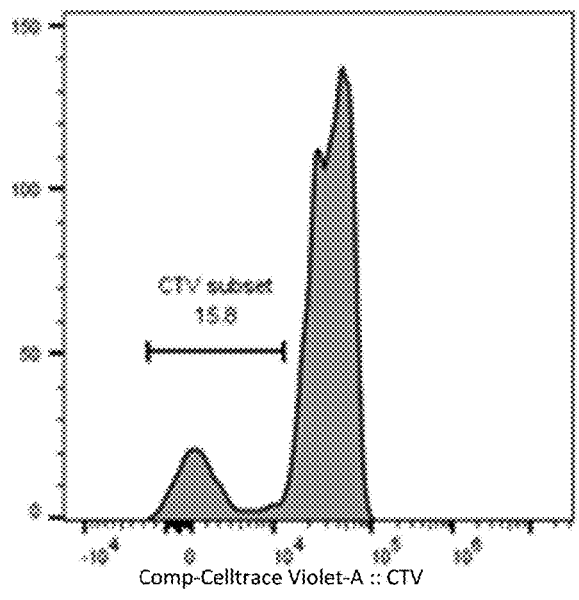
Figure 17B:
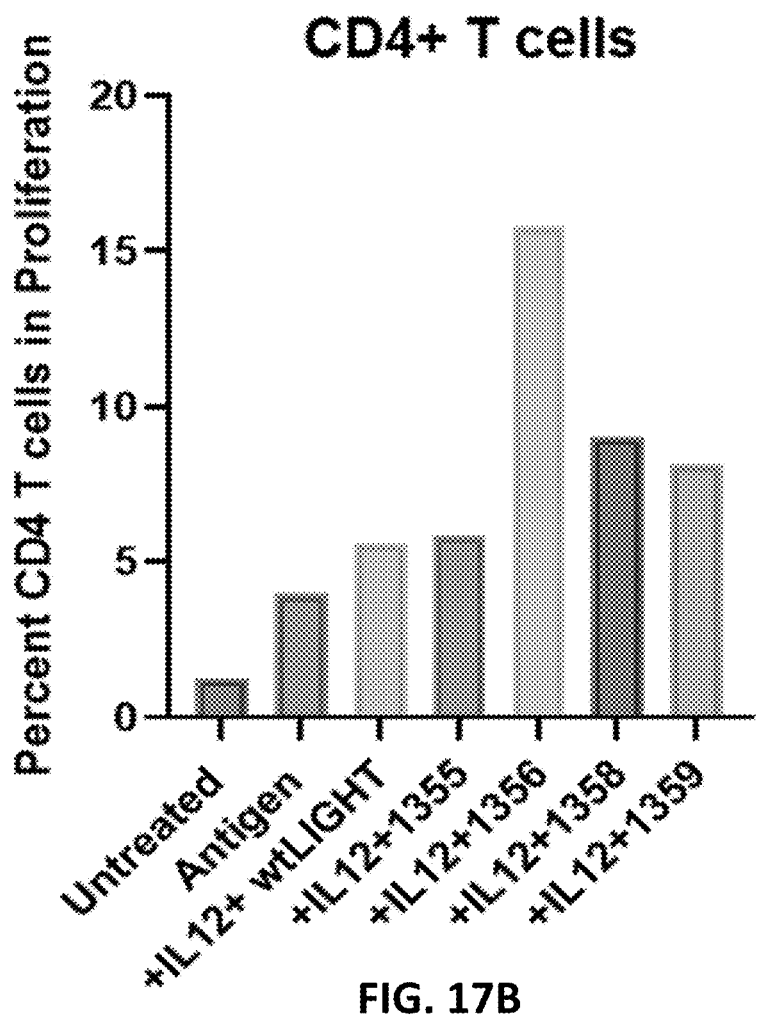
Figure 17D:
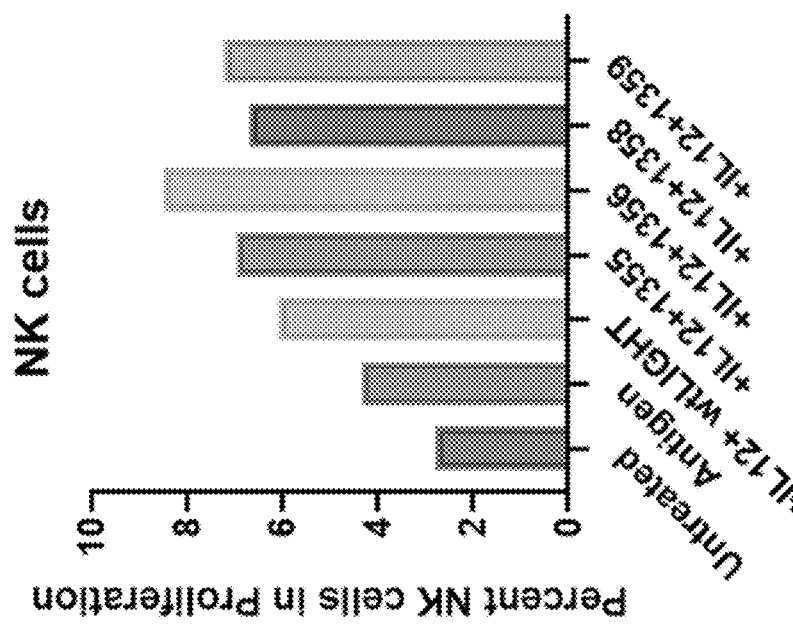
Figure 17C:
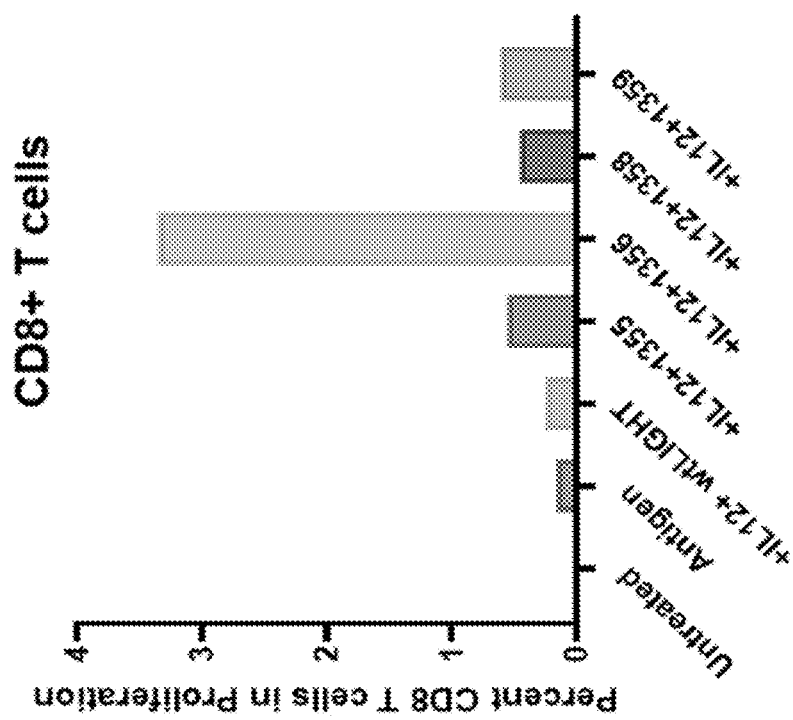

CIN PBMCs form two independent donors were treated with control mRNA, Antigen mRNA or the mRNA-based therapeutic mRNA formulated in a delivery vehicles (n=3). T cell proliferation was measured by dilution of CellTrace Violet dye (VTD) Tracking. Data presented as percentage of live CD4 and CD8 T cells in proliferation by flow cytometry. (FIG. 16). T cell proliferation was measured using the same methods for an independent donor treated with a control, antigen, antigen+soluble LIGHT+IL-12, and several membrane-stabilized LIGHT mRNA-based therapeutics. Data presented as percentage of live CD4 T cells in proliferation by flow cytometry (FIGS. 17A and 17B), CD8 T cells in proliferation by flow cytometry (FIG. 17C), and NK cells in proliferation by flow cytometry (FIG. 17D).

Example 4: General Synthesis of Tertiary Amino Lipidated Cationic Peptoids

General protocols for synthesizing tertiary amino lipidated cationic peptoids disclosed herein can be found in WO2020/069442 and WO2020/069445, each of which is incorporated herein by reference in its entirety. The following example describes the general protocol for synthesis of the tertiary amino lipidated cationic peptoids All polymers were synthesized using bromoacetic acid and primary amines. An Fmoc-Rink amide resin was used as the solid support. The Fmoc group on the resin was deprotected with 20% (v/v) piperidine-dimethylformamide (DMF). The amino resin was then amidated with bromoacetic acid. The amidation was followed by amination of the α-carbon by nucleophilic displacement of the bromide with a primary amine. The two steps were successively repeated to produce the desired cationic peptide sequence.

All reactions and washings were performed at room temperature unless otherwise noted. Washing of the resin refers to the addition of a wash solvent (usually DMF or dimethylsulfoxide (DMSO)) to the resin, agitating the resin so that a uniform slurry was obtained, followed by thorough draining of the solvent from the resin. Solvents were removed by vacuum filtration through the fritted bottom of the reaction vessel until the resin appeared dry. In all the syntheses, resin slurries were agitated via bubbling argon up through the bottom of the fritted vessel.

Initial Resin Deprotection. A fritted reaction vessel was charged with Fmoc-Rink amide resin. DMF was added to the resin and this solution was agitated to swell the resin. The DMF was then drained. The Fmoc group was removed by adding 20% piperidine in DMF to the resin, agitating the resin, and draining the resin. 20% piperidine in DMF was added to the resin and agitated for 15 minutes and then drained. The resin was then washed with DMF, six times.

Acylation/Amidation. The deblocked amine was then acylated by adding bromoacetic acid in DMF to the resin followed by N,N-diisoprooplycarbodiimide (DIC) in DMF. This solution is agitated for 30 minutes at room temperature and then drained. This step was repeated a second time. The resin was then washed with DMF twice and DMSO once. This was one completed reaction cycle.

Nucleophilic Displacement/Amination. The acylated resin was treated with the desired primary or secondary amine to undergo nucleophilic displacement at the bromine leaving group on the α-carbon. This acylation/displacement cycle was repeated until the desired peptide sequence was obtained.

Peptide Cleavage from Resin. The dried resin was placed in a glass scintillation vial containing a teflon-coated micro stir bar, and 95% trifluoroacetic acid (TFA) in water is added. The solution was stirred for 20 minutes and then filtered through solid-phase extraction (SPE) column fitted with a polyethylene frit into a polypropylene conical centrifuge tube. The resin was washed with 1 mL 95% TFA. The combined filtrates were then lyophilized three times from 1:1 acetonitrile:water. The lyophilized peptide was redissolved to a concentration of 5 mM in 5% acetonitrile in water.

Purification and Characterization. The redissolved crude peptide was purified by preparative HPLC. The purified peptide was characterized by LC-MS analysis.

Example 5: Synthesis Hydroxyethyl-Capped Tertiary Amino Lipidated Cationic Peptoids Hydroxyethyl-capped lipidated peptoids were synthesized by the submonomer method described in Example 1 with bromoacetic acid and N,N'-diisopropylcarbodiimide (DIC). Polystyrene-supported MBHA Fmoc-protected Rink amide (200 mg representative scale, 0.64 mmol/g loading, Protein Technologies) resin was used as a solid support. For bromoacetylation, resin was combined with a 1:1 mixture of 0.8 M bromoacetic acid and 0.8 M N,N'-diisopropylcarbodiimide (DIC) for 15 minutes. Amine displacement was carried out using a 1M solution of amine in DMF for 45 minutes. Following synthesis, crude peptoids were cleaved from resin using 5 mL of a mixture of 95:2.5:2.5 trifluoroacetic acid (TFA):water:triisopropylsilane for 40 minutes at room temperature. Resin was removed by filtration and the filtrate concentrated using a vacuum centrifuge. The crude peptoids were further purified by reverse-phase flash chromatography (Biotage Selekt) using a C4 column and a gradient from 60-95% ACN/H2O+0.1% TFA. Purity and identity were assayed with a Waters Acquity UPLC system with Acquity Diode Array UV detector and Waters SQD2 mass spectrometer on a Waters Acquity UPLC Peptide BEH C4 Column over a 5-95% gradient. Select peptoids were further purified by preparative Waters Prep150LC system with Waters 2489 UV/Visible Detector on a Waters XBridge BEH300 Prep C4 column using a 40-85% acetonitrile in water with 0.1% TFA gradient over 30 minutes.

Example 6: Synthesis of Delivery Vehicle Complexes

Synthesis. The hydroxyethyl-capped tertiary amino lipidated peptoids can be combined with polyanionic compounds, such as the mRNA polynucleotides described herein, to form delivery vehicle complexes that can be administered for therapeutic and/or prophylactic purposes in vitro or in vivo. Without being bound to any particular theory, the cationic portion(s) of the amino-lipidated peptoids binds to the negatively-charged phosphodiester backbone of the polyanionic cargo (e.g., nucleic acid cargo) through primarily electrostatic interactions, forming a mixed coacervate complex. Hydrophobic interactions between lipid chains on the hydroxyethyl-capped tertiary amino lipidated peptoids can act to stabilize particle formation and assist with membrane association.

Delivery vehicle complexes can be prepared through any physical and/or chemical methods known in the art to modulate their physical, chemical, and biological properties. These methods typically involve rapid combination of the hydroxyethyl-capped tertiary amino lipidated peptoid in water, or a water-miscible organic solvent, with the oligonucleotide in water or an aqueous buffer solution. These methods can include simple mixing of the components by pipetting, or microfluidic mixing processes such as those involving T-mixers, vortex mixers, or other chaotic mixing structures. Exemplary mixing methods are detailed in, e.g., U.S. Pat. Nos. 11,278,895 and 11,325,122, incorporated herein by reference.

In standard formulations, the hydroxyethyl-capped tertiary amino lipidated peptoid and additional lipids are dissolved in anhydrous ethanol at a concentration of 10 mg/mL to result in solutions that are stable at room temperature. In some aspects, the solutions are stored at −20° C. The nucleic acid cargo is dissolved in DNAse or RNAse-free water at a final concentration of 1-2 mg/mL. These solutions can be stored at −20° C. or −78° C. for extended time periods.

To prepare the delivery vehicle compositions disclosed herein, hydroxyethyl-capped tertiary amino lipidated peptoid and additional lipid components are first pre-mixed in an ethanol phase at the required mass ratios. Nucleic acid cargo(s) are diluted in ethanol and acidic buffer (e.g., 10 mM phosphate/citrate, pH 5.0). Ethanol and aqueous phases were mixed at a 3:1 volume ratio, and then immediately diluted with a 1:1 volume ratio of PBS, resulting in a final mRNA concentration of 0.1 μg/uL. Non-liming exemplary delivery vehicle compositions prepared by the aforementioned method include the compositions listed in Table 8, above (e.g., compositions F2, F6/17, F6/12, and F6/15).

The delivery vehicle compositions were combined with a polyanionic compound, such as the E6/E7 oncogene (e.g., from HPV 16, HPV 18, a functional fragment thereof, and/or a variant thereof) at the ratios indicated in Table 11 to form delivery vehicle complexes. The w/w in Table 11 is the ratio of the indicated component to the mRNA by mass.

TABLE 11

Delivery Vehicle System Components to Polyanionic Cargo

| Mass Ratio | Cationic Component | Anionic or Zwitterionic Component | Neutral Lipid Component | Shielding Component |
|---|---|---|---|---|
| F1A | 5.0 | 0 | 0 | 0.1 |
| F2A | 5.0 | 3.0 | 6.0 | 1.8 |
| F3A | 10 | 2.7 | 5.4 | 1.4 |
| F4A | 5.0 | 0 | 8.0 | 1.8 |
| F5A | 8.5 | 7.0 | 0 | 2.0 |
| F6A | 10 | 0 | 5.4 | 1.4 |
| F1 | 5.0 | 3.0 | 6.0 | 1.8 |
| F2 | 10 | 2.7 | 5.4 | 1.4 |
| F3 | 10 | 2.4 | 6.1 | 1.8 |
| F4 | 10 | 8.0 | 5.6 | 0.69 |
| F5 | 10 | 4.3 | 6.5 | 2.3 |
| F6/12 | 12 | 2.7 | 5.4 | 1.4 |
| F6/15 | 15 | 2.7 | 5.4 | 1.4 |
| F6/17 | 17 | 2.7 | 5.4 | 1.4 |
| F6.1 | 13 | 2.7 | 5.4 | 1.4 |
| F6.2 | 19 | 4.0 | 8.1 | 2.1 |
| F6.3 | 9.7 | 2.7 | 6.7 | 2.1 |

Example 7: RNA-Based Vaccine for Cervical Cancer

The efficacy of the delivery vehicle complexes of the disclosure to act as an RNA-based vaccine for cancer was assessed.

Cellular responses. The efficacy of delivery vehicle complexes described herein in a disease model was evaluated by formulating mRNA coding for either Ovalbumin (OVA) or the HPV E6/E7 oncogene (from HPV16 and/or HPV18) with representative peptoids and administering this vaccine to C57Bl/6 mice. Vaccine candidates were administered twice, with a prime on Day 0 off the study and a boost on Day 7. The resulting immune response to characterized epitopes was determined on Day 14 by measuring levels of antigen-specific CD8+ T-cells in peripheral blood and spleen with a fluorescent MHC-I tetramer conjugate (MBL International). The DV-140-F2 complex elicited a strong cellular response in comparison to other complexes that were tested. See FIG. 18A.

Humoral responses. Humoral responses to the vaccine candidates were evaluated by E7-IgG ELISA. Briefly, MaxiSorp ELISA plates (Thermo Scientific) were coated overnight at 4 C with 1 ug/mL E7-his protein (Abcam). Plates were then washed and blocked with 10% FBS. Plasma samples were diluted in blocking buffer (10% FCS) at a 1:5 dilution with 5 10-fold dilutions down plate. Samples were added to plate and incubated at 4 C overnight. Detection utilized a Donkey anti-mouse IgG-HRP (Jackson Immunology) at 1:1000 in blocking buffer for 1 hour, then detected with HRP substrate and read at 450 nm. The DV-140-F2 complex elicited a strong IgGr response in comparison to other complexes that were tested. See FIG. 18B.

Example 8: Compound 140 Efficacy and Toxicology Studies

Compound 140 was found to be well-tolerated in mouse efficacy and rat toxicology studies. Briefly, Sprague-Dawley rats (n=8) were treated with a control mRNA formulated in DV-140-F2 at 0.03 or 0.3 mg/kg or PBS vehicle. Injections were done 4 times over the course of 13 days and were administered intramuscularly into the hind limb. Whole blood was taken for hematology, and serum taken for clinical chemistry and cytokine analysis at 6 hours post the first dose and final dose, and 2 weeks post the final dose. Additionally, 2 of the animals were sacrificed at 6 hours post the final dose and 2 weeks post final dose and a gross necropsy was performed. Tissue samples were retained and histopathology run on select organs. The results are summarized in Table 12, below.

Cervical Cancer. www.who.int/health-topics/cervical-cancer da Silva, R. L., da Silva Batista, Z., Bastos, G. R. et al. Role of HPV 16 variants among cervical carcinoma samples from Northeastern Brazil. BMC Women's Health 20, 162 (2020).

Tao, L., Han, L., Li, X. et al. Prevalence and risk factors for cervical neoplasia: a cervical cancer screening program in Beijing. BMC Public Health 14, 1185 (2014).

Risk of recurrent high-grade cervical intraepithelial neoplasia after successful treatment: a long-term multi-cohort study. Marielle Kocken 1, Theo J M Helmerhorst, Johannes Berkhof, Jacqueline A Louwers, Marielle A E Nobbenhuis, Aagje G Bais, Cornelis J A Hogewoning, Afra Zaal, Rend H M Verheijen, Peter J F Snijders, Chris J L M Meijer. Lancet Oncol 2011 May; 12 (5): 441-50

Feltkamp M C, Smits H L, Vierboom M P, et al. Vaccination with cytotoxic T lymphocyte epitope-containing peptide protects against a tumor induced by human papillomavirus type 16-transformed cells. Eur J Immunol 1993; 23:2242-9.

Arbyn M, Weiderpass E, Bruni L, et al. Estimates of incidence and mortality of cervical cancer in 2018: a worldwide analysis. Lancet Glob Health 2020; 8: e191-203.

Bjorge T, Skare G B, Bjorge L, et al. Adverse pregnancy outcomes after treatment for cervical intraepithelial neoplasia. Obstet Gynecol. 2016; 128 (6): 1265-1273.

Centers for Disease Control and Prevention (CDC). Estimated number of cases of high-grade cervical lesions diagnosed among women-United States, 2008 and 2016. MMWR Morb Mortal Wkly Rep. 2019; 68 (15): 337-343.

Keytruda® (pembrolizumab) prescribing information. August 2022. dailymed.nlm.nih.gov/dailymed/drugInfo.cfm?setid-9333c79b-d487-4538-a9f0-71b91a02b287.

Loopik D L, IntHout J, Ebisch R M F, et al. The risk of cervical cancer after cervical intraepithelial neoplasia grade 3: A population-based cohort study with 80,442 women. Gynecol Oncol. 2020; 157 (1): 195-201.

TABLE 12

Efficacy and Toxicology Studies dose

| Assessments | Therapeutic dose in mouse | Therapeutic dose scaled for rat | High dose in rat |
|---|---|---|---|
| Regimen | 3 doses 7 days apart; ~1-2 μg RNA IT or IM | 4 doses in 2 weeks; 30 μg RNA IM | 4 doses in 2 weeks; 100 μg RNA IM |
| Body weight | No changes compared to control | No changes compared to control | Reduced weight gain in some animals |
| Injection site reactions or other clinical observations | None observed | None observed | None observed |
| Gross organ pathology | Not assessed | None observed | None observed |
| Hematology parameters | Not assessed | No changes compared to control | Some transient changes in hematology; return to baseline by D30 |
| Clinical chemistries | Not assessed | No meaningful changes in serum chemistries compared to control; majority remain within normal range | No meaningful changes in serum chemistries compared to control; majority remain within normal range |
| Serum cytokines | Not assessed | No changes compared to control | Elevated levels in subset of cytokines; return to baseline by D30 |

Mirabello L., Clarke M. A., Nelson C. W., et al. The intersection of HPV epidemiology, genomics and mechanistic studies of HPV-mediated carcinogenesis. Viruses. 2018; 10 (2).

Moscicki A B, Schiffman M, Kjaer S, et al. Chapter 5: Updating the natural history of HPV and anogenital cancer. Vaccine. 2006; 24 Suppl 3: S3/42-53/51.

Narisawa-Saito M, Kiyono T. Basic mechanisms of high-risk human papillomavirus-induced carcinogenesis: roles of E6 and E7 proteins. Cancer Sci. 2007; 98 (10): 1505-1511.

National Comprehensive Cancer Network (NCCN) Clinical Practice Guidelines in Oncology (NCCN Guidelines®). Cervical Cancer. Version 1. 2022.

Noehr B, Jensen A, Frederiksen K, Tabor A, Kjaer S K. Loop electrosurgical excision of the cervix and subsequent risk for spontaneous preterm delivery: a population-based study of singleton deliveries during a 9-year period. Am J Obstet Gynecol. 2009; 201 (1): 33.el-33.e336.

Pan X Q. The mechanism of the anticancer function of M1 macrophages and their use in the clinic. Chin J Cancer. 2012; 31 (12): 557-563.

Smith J S, Lindsay L, Hoots B, et al. Human papillomavirus type distribution in invasive cervical cancer and high-grade cervical lesions: a meta-analysis update. Int J Cancer. 2007; 121 (3): 621-632.

Spanos W C, Hoover A, Harris G F, et al. The PDZ binding motif of human papillomavirus type 16 E6 induces PTPN13 loss, which allows anchorage-independent growth and synergizes with RAS for invasive growth. J Virol. 2008; 82 (5): 2493-2500.

Walboomers J M, Jacobs M V, Manos M M, et al. Human papillomavirus is a necessary cause of invasive cervical cancer worldwide. J Pathol. 1999; 189 (1): 12-19.

Wieking B G, Vermeer D W, Spanos W C, et al. A non-oncogenic HPV 16 E6/E7 vaccine enhances treatment of HPV expressing tumors. Cancer Gene Ther. 2012; 19 (10): 667-674.

Young N. The effect of loop electrosurgical excision procedure on the subsequent risk of preterm delivery. [scholarly project]. Toledo, OH: The University of Toledo; 2010.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

It will be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The presently described technology is now described in such full, clear, concise and exact terms as to enable any person skilled in the art to which it pertains, to practice the same. It is to be understood that the foregoing describes preferred aspects of the invention and that modifications may be made therein without departing from the spirit or scope of the invention.

The invention claimed is:

1. A composition comprising:
   a first isolated messenger ribonucleic acid (mRNA) encoding a first polypeptide comprising an amino acid sequence selected from the group consisting of SEQ ID NO: 11 and SEQ ID NO: 17, wherein said first polypeptide is a membrane-stabilized human LIGHT polypeptide;
   a second isolated mRNA encoding interleukin-12 (IL-12), wherein the IL-12 comprises the amino acid sequence of SEQ ID NO:21;
   and a third isolated mRNA encoding HPV16 E6 E7, wherein the HPV16 E6 E7 comprises an amino acid sequence selected from the group consisting of SEQ ID NO:24 and SEQ ID NO:27.

2. The composition of claim 1, wherein the first isolated mRNA has at least about 80% nucleic acid sequence identity to SEQ ID NO: 12 or SEQ ID NO: 18.

3. The composition of claim 1, wherein the second isolated mRNA has at least about 80% nucleic acid sequence identity to SEQ ID NO:20.

4. The composition of claim 1, wherein the third isolated mRNA has at least about 80% nucleic acid sequence identity to SEQ ID NO:23 or SEQ ID NO:26.

5. The composition of claim 1, wherein the first isolated mRNA, second isolated mRNA, and/or third isolated mRNA is at least partially encapsulated with a delivery vehicle.

6. The composition of claim 5, wherein the delivery vehicle has a particle size less than or equal to about 200 nm.

7. The composition of claim 5, wherein the delivery vehicle is selected from the group consisting of amphipathic molecules, amino-lipidated peptides, tertiary amino lipidated cationic peptides, a cationic component, a peptoid, a lipoid, a liposome, a lipoplex, a lipid nanoparticle, a cationic lipid nanoparticle, a polymeric compound, and a conjugate.

8. The composition of claim 5, wherein the delivery vehicle comprises at a compound or pharmaceutically acceptable salt of the compound having a having formula (I)

$$\text{HO} \diagup \diagdown \text{N}(\text{R}^1) \diagdown \text{C}(=\text{O}) - [\text{N}(\text{R}^2) - \text{CH}_2 - \text{C}(=\text{O})]_n - \text{NH}_2 \quad (I)$$

wherein n is 1, 2, 3, 4, 5, or 6; $R^1$ is H, $C_{1\text{-}3}$alkyl, or hydroxyethyl; and each $R^2$ independently is $C_{8\text{-}24}$alkyl or $C_{8\text{-}24}$alkenyl.

9. The composition of claim 8, wherein the compound is selected from the group consisting of:

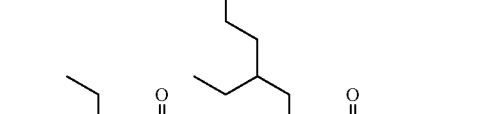

-continued

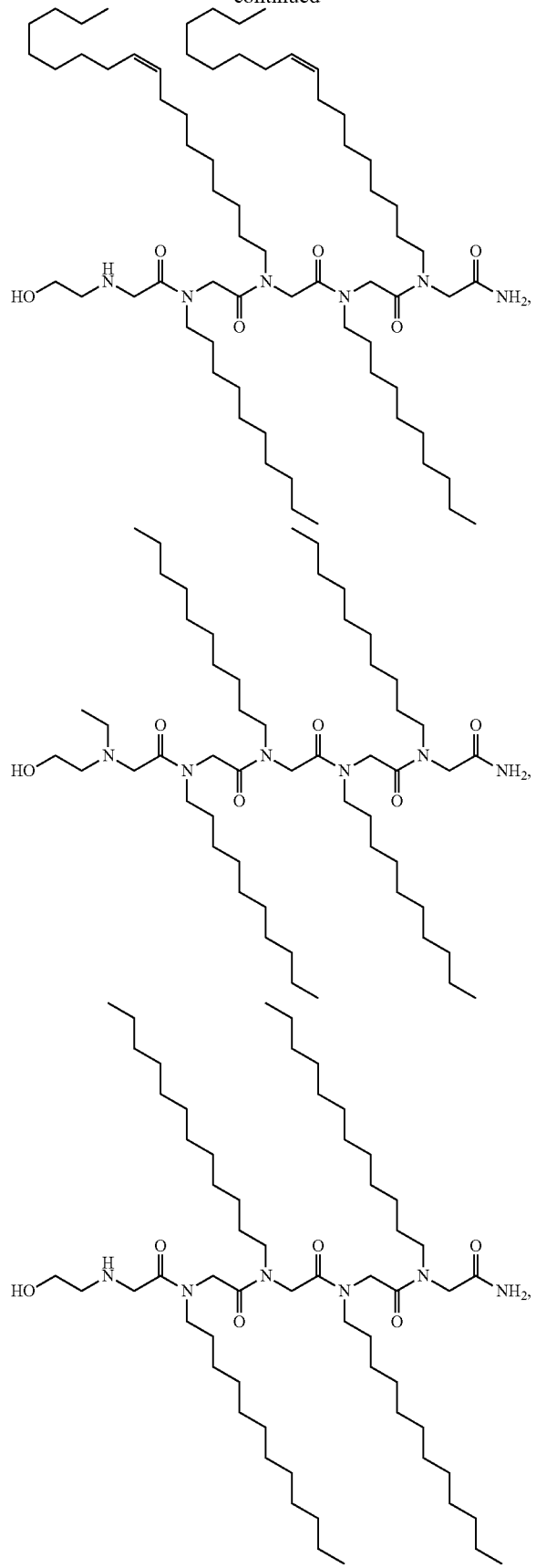

-continued

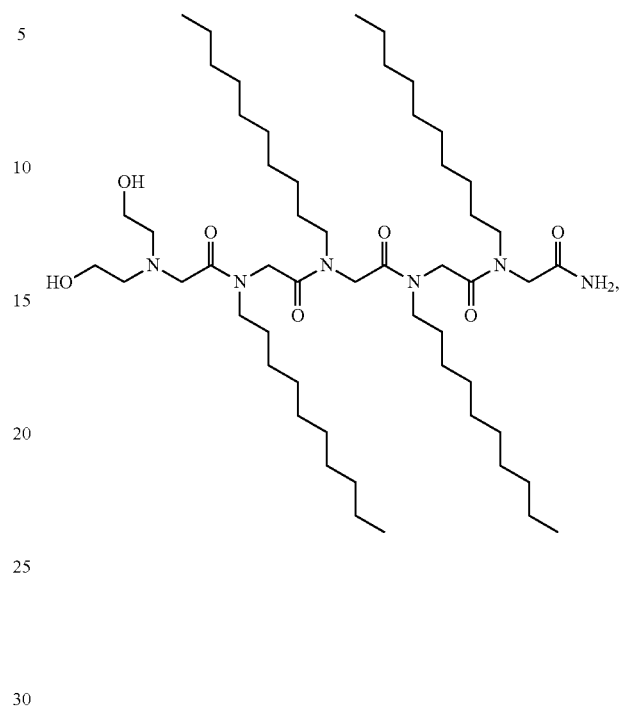

and pharmaceutically acceptable salts of the compound.

10. The composition of claim 1, wherein the composition is a therapeutic composition or a vaccine.

11. The composition of claim 10, wherein the composition is a human papillomavirus (HPV) mRNA vaccine.

12. The composition of claim 10, wherein the composition is configured to be administered to a subject known to have cervical cancer, HPV-driven cancer, or a disease associated with HPV.

13. The composition of claim 10, wherein the composition is configured to be administered as an injectable preparation.

14. The composition of claim 10, wherein the composition is configured to be administered to a subject known to have cervical dysplasia or cervical intraepithelial neoplasia.

15. The composition of claim 14, wherein the composition is configured as an injectable preparation for administration into a cervix of the subject.

16. The composition of claim 10, wherein the composition further comprises one or more one or more therapeutically acceptable carriers, therapeutically acceptable diluents, therapeutically acceptable excipients or other therapeutic agents.

17. The composition of claim 16, wherein the therapeutically acceptable excipients are selected from the group consisting of salts, buffering agents, preservatives, antiadherents, antioxidants, binders, coatings, compression aids, disintegrants, dyes, emollients, emulsifiers, fillers, film formers, coatings, flavors, fragrances, glidants, lubricants, sorbents, suspending or dispersing agents, sweeteners, and waters of hydration.

* * * * *